US012084693B2

(12) United States Patent
Anguela et al.

(10) Patent No.: US 12,084,693 B2
(45) Date of Patent: Sep. 10, 2024

(54) CODON-OPTIMIZED ACID ALPHA-GLUCOSIDASE EXPRESSION CASSETTES AND METHODS OF USING SAME

(71) Applicant: SPARK THERAPEUTICS, INC., Philadelphia, PA (US)

(72) Inventors: Xavier Anguela, Barcelona (ES); Sean Armour, Holland, PA (US); Jayme Nordin, Philadelphia, PA (US)

(73) Assignee: SPARK THERAPEUTICS, INC., Philadelphia, PA (US)

( * ) Notice: Subject to any disclaimer, the term of this patent is extended or adjusted under 35 U.S.C. 154(b) by 920 days.

(21) Appl. No.: 17/055,523

(22) PCT Filed: May 15, 2019

(86) PCT No.: PCT/US2019/032502
§ 371 (c)(1),
(2) Date: Nov. 13, 2020

(87) PCT Pub. No.: WO2019/222411
PCT Pub. Date: Nov. 21, 2019

(65) Prior Publication Data
US 2021/0222141 A1 Jul. 22, 2021

Related U.S. Application Data

(60) Provisional application No. 62/672,419, filed on May 16, 2018, provisional application No. 62/734,454, filed on Sep. 21, 2018.

(51) Int. Cl.
*C12N 9/26* (2006.01)
*A61K 48/00* (2006.01)
*C12N 15/86* (2006.01)

(52) U.S. Cl.
CPC .......... *C12N 9/2408* (2013.01); *A61K 48/005* (2013.01); *C12N 15/86* (2013.01);
(Continued)

(58) Field of Classification Search
CPC .......................... C12N 15/80; C12N 2800/22; C12N 2830/50; C12Y 302/0102; A61P 21/00
See application file for complete search history.

(56) References Cited

U.S. PATENT DOCUMENTS

2013/0259924 A1 10/2013 Bancel et al.
2014/0105965 A1 4/2014 Bancel et al.

FOREIGN PATENT DOCUMENTS

EP 2687597 A1 1/2014
EP 3 293 259 A1 3/2018
(Continued)

OTHER PUBLICATIONS

Puzzo et al. (Sci Transl Med. Nov. 29, 2017; 9(418): pp. 1-27).*
(Continued)

*Primary Examiner* — Terra C Gibbs
(74) *Attorney, Agent, or Firm* — PILLSBURY WINTHROP SHAW PITTMAN LLP; Robert M. Bedgood

(57) ABSTRACT

The invention provides nucleic acids encoding acid α-glucosidase (GAA). In certain embodiments, nucleic acids have greater than about 86% sequence identity to a sequence selected from the group consisting of any of the sequences set forth as SEQ ID NOs:1-5. In certain embodiments, nucleic acids encoding acid α-glucosidase (GAA) contain less than 127 CpG dinucleotides. Expression cassettes, vectors, cells and cell lines and methods of using such nucleic acids encoding acid α-glucosidase (GAA) are also provided.

40 Claims, 15 Drawing Sheets

Specification includes a Sequence Listing.

pAAV-ApoE/hAAT.fixUTR.GAA13.BGH

(52) U.S. Cl.
CPC .................. *C12Y 302/0102* (2013.01); *C12N 2750/14143* (2013.01); *C12N 2750/14152* (2013.01); *C12N 2800/22* (2013.01); *C12N 2830/001* (2013.01); *C12N 2830/50* (2013.01)

(56) References Cited

FOREIGN PATENT DOCUMENTS

| | | | | |
|---|---|---|---|---|
| EP | 3211076 | A4 | 3/2018 | |
| WO | 2013/151666 | A2 | 10/2013 | |
| WO | WO-2013158879 | A1 * | 10/2013 | ............ A61K 48/00 |
| WO | 2018/046772 | A1 | 3/2018 | |
| WO | 2018/046775 | A1 | 3/2018 | |

OTHER PUBLICATIONS

Sun, B., et al., "Correction of glycogen storage disease type II by an adeno-associated virus vector containing a muscle-specific promoter", Molecular Therapy, Elsevier Inc, US, vol. 11, No. 6, Jun. 1, 2005, pp. 889-898, XP004974972, ISSN: 1525-0016, DOI:10.1016/J.YMTHE.2005.01.012.

Sun, B., et al., "Enhanced Efficacy of an AAV vector Encoding Chimeric, Highly Secreted Acid @a-Glucosidase in Glycogen Storage Disease Type II," Molecular Therapy, Elsevier Inc, US, vol. 14, No. 6, Nov. 18, 2006, pp. 822-830, XP005726585, ISSN: 1525-0016, DOI:10.1016/J.YMTHE.2006.08.001.

Broun et al., Catalytic Plasticity of Fatty Acid Modification Enzymes Underlying Chemical Diversity of Plant Lipids, SCIENCE, 1998, v.282, p. 1315-1317, doi: 10.1126/science.282.5392.1315.

Dirks, P. B. Brain Tumor Stem Cells: Bringing Order to the Chaos of Brain Cancer. Journal of Clinical Oncology, 2008, 26(17), 2916-2924. DOI:10.1200/jco.2008.17.6792.

Lopez-Lazaro, M., The migration ability of stem cells can explain the existence of cancer of unknown primary site. Rethinking metastasis. Oncoscience, 2015, 2, 467. doi:10.18632/oncoscience.159.

Mabey, D., Epidemiology of sexually transmitted infections: worldwide, Medicine, 2014, 42(6), p. 287-290.

Seffernick J. L. et al., Melamine Deaminase and Atrazine Chlorohydrolase: 98 Percent Identical but Functionally Different, Journal of Bacteriology, 2001, v.183, No. 8, p. 2405-2410, doi: 10.1128/JB.183.8.2405-2410.2001.

Tran, B., et al.l, Survival comparison between glioblastoma multiforme and other incurable cancers, Journal of Clinical Neuroscience, 2010, vol. 17, Is. 4, p. 417-421.

Whisstock, J. C. et al., Prediction of protein function from protein sequence and structure, Quarterly Reviews of Biophysics 36, 3 2003, p. 307-340. DOI:10.1017/S0033583503003901.

Witkowski, A. et al., Conversion of a ß-Ketoacyl Synthase to a Malonyl Decarboxylase by Replacement of the Active-Site Cysteine with Glutamine, Biochemistry 1999, 38, p. 11643-11650, doi:10.1021/bi990993h.

Russia Application No. 2020141014, Translation of Official Action and Search Report dated Apr. 13, 2023.

* cited by examiner pAAV-ApoE/hAAT.fixUTR.GAA13.BGH pAAV-ApoE/hAAT.GAA13.BGH pAAV-ApoE/hAAT.GAA7.BGH pAAV-ApoE/hAAT.GAA8.BGH pAAV-ApoE/hAAT.GAA2.wtBGH pAAV-ApoE/hAAT.GAA5.wtBGH pAAV-ApoE/hAAT.GAA7.wtBGH pAAV-ApoE/hAAT.GAA8.wtBGH pAAV-ApoE/hAAT.GAA13.wtBGH

SEQUENCE LISTING

```
<160> NUMBER OF SEQ ID NOS: 33

<210> SEQ ID NO 1
<211> LENGTH: 2808
<212> TYPE: DNA
<213> ORGANISM: Artificial Sequence
<220> FEATURE:
<223> OTHER INFORMATION: Modified Nucleic Acid

<400> SEQUENCE: 1

atggctttcc tgtggctgct gagctgctgg gctctgctgg gcaccacctt tgggctgctg      60

gtgcctaggg agctgtctgg gtctagccct gtgctggagg agactcaccc tgcccatcag     120

caggggggcta gcaggcctgg ccccagggat gctcaggccc accctggcag gcccagggct     180

gtgcccaccc agtgtgatgt gccccccaac agcaggtttg actgtgcccc tgacaaggcc     240

attacccagg agcagtgtga ggccaggggc tgctgctaca ttccagctaa gcagggcctg     300

caggggggccc agatgggcca gccctggtgc ttcttccccc ccagctatcc tagctataaa     360

ctggagaacc tgagcagctc tgagatgggc tatactgcca ccctgactag gactactccc     420

acctttttc ctaaggatat cctgaccctg aggctggatg tgatgatgga gactgagaac     480

aggctgcact tcactattaa ggaccctgcc aataggaggt atgaagtgcc tctggagact     540

cctcatgtgc actctagggc cccagcccc ctgtattctg tggagttctc tgaggagccc     600

tttggggtga ttgtgaggag gcagctggat ggcagggtgc tgctgaacac cactgtggcc     660

cccctgttct ttgctgacca gttcctgcag ctgagcacca gcctgcccag ccagtacatc     720

actgggctgg ctgagcatct gagccctctg atgctgagca cctcttggac caggatcacc     780

ctgtggaata gggatctggc cccccacccct ggggctaatc tgtatggctc tcatcccttt     840

tacctggccc tggaggatgg gggctctgcc catggggtgt ttctgctgaa cagcaatgcc     900

atggatgtgg tgctgcagcc ctctcctgcc ctgagctgga ggagcactgg gggcatcctg     960

gatgtgtaca tcttcctggg ccctgagccc aagtctgtgg tccagcagta tctggatgtg    1020

gtgggctacc cctttatgcc cccctattgg ggcctgggct tccacctgtg caggtggggg    1080

tattcttcta ctgctatcac caggcaggtg gtggagaaca tgaccagggc tcacttcccc    1140

ctggatgtgc agtggaatga cctggactat atggactcta ggagggattt caccttcaac    1200

aaggatggct tcagggactt ccctgctatg gtccaggagc tgcatcaggg gggcaggagg    1260

tacatgatga ttgtggaccc tgccatcagc agctctggcc ctgctggcag ctataggccc    1320

tatgatgagg gcctgaggag gggggtgttt atcactaatg aaactgggca gcccctgatt    1380
```

```
ggcaaggtgt ggcctggctc tactgccttc cctgacttca ccaaccccac tgctctggcc   1440

tggtgggagg acatggtggc tgagttccat gaccaggtgc cttttgatgg catgtggatt   1500

gacatgaatg agcccagcaa cttcatcagg ggctctgagg atgggtgccc caataatgag   1560

ctggagaacc cccctatgt gcctggggtg gtgggggca ccctgcaggc tgccactatt   1620

tgtgccagct ctcaccagtt cctgagcacc cactacaacc tgcacaatct gtatggcctg   1680

actgaggcca ttgccagcca cagggccctg gtgaaggcca ggggcactag gccctttgtg   1740

atctctagaa gcacctttgc tggccatggg aggtatgctg gccactggac tggggatgtg   1800

tggagctctt gggagcagct ggccagctct gtgcctgaga tcctgcagtt caacctgctg   1860

ggggtgcccc tggtgggggc tgatgtgtgt ggcttcctgg gcaacacctc tgaagagctg   1920

tgtgtgaggt ggacccagct gggggccttc taccctttca tgaggaacca caacagcctg   1980

ctgagcctgc ctcaggagcc ttactctttc tctgagcctg cccagcaggc catgaggaag   2040

gccctgaccc tgaggtatgc tctgctgccc cacctgtaca ccctgttcca ccaggcccat   2100

gtggctgggg agactgtggc caggcccctg ttcctggagt ttcctaagga tagcagcacc   2160

tggactgtgg accaccagct gctgtggggg gaggccctgc tgattacccc tgtgctgcag   2220

gctggcaagg ctgaggtgac tggctacttc cccctgggca cttggtatga cctgcagact   2280

gtgcctgtgg aagccctggg cagcctgcct cccccccctg ctgcccccag ggagcctgcc   2340

atccactctg agggccagtg ggtgaccctg cctgcccccc tggacaccat taatgtgcat   2400

ctgagggctg ggtatattat ccccctgcag gggcctgggc tgactaccac tgagagcagg   2460

cagcagccta tggccctggc tgtggctctg actaaggggg gggaggccag gggggagctg   2520

ttctgggatg atggggagag cctggaggtg ctggagaggg ggcctacac ccaggtgatt   2580

ttcctggcca ggaacaacac cattgtgaat gagctggtga gggtgacctc tgagggggct   2640

ggcctgcagc tgcagaaagt gactgtgctg gggggtggcca ctgcccccca gcaggtgctg   2700

agcaatgggg tgcctgtgag caacttcacc tacagccctg acaccaaggt gctggatatt   2760

tgtgtgagcc tgctgatggg ggagcagttc ctggtgagct ggtgctga                2808
```

<210> SEQ ID NO 2
<211> LENGTH: 2808
<212> TYPE: DNA
<213> ORGANISM: Artificial Sequence
<220> FEATURE:
<223> OTHER INFORMATION: Modified Nucleic Acid

<400> SEQUENCE: 2

```
atggctttcc tgtggctgct gtcttgctgg gccctgctgg ggactacctt tggcctgctg     60

gtgcccaggg aactgtctgg ctctagccca gtgctggagg agacccaccc tgcccaccag    120

cagggggctt ctaggcctgg ccccagggat gcccaggccc accctggcag gccaagggct    180

gtgcccaccc agtgtgatgt gccccccaac tctagatttg attgtgcccc tgataaggcc    240

atcacccagg agcagtgtga ggctaggggc tgctgctaca tccctgctaa gcagggcctg    300

caggggggctc agatgggcca gccctggtgc ttcttccccc ccagctatcc ctcttacaag    360

ctggagaatc tgagcagctc tgagatgggc tacactgcca ccctgaccag gactactccc    420

accttcttcc ccaaggacat cctgaccctg aggctggatg tgatgatgga gactgagaac    480

aggctgcatt tcaccatcaa ggatcctgcc aacaggaggt atgaggtgcc tctggagacc    540

ccccatgtgc acagcagggc tccttctccc ctgtactctg tggagttctc tgaggaaccc    600

tttggggtga ttgtgaggag gcagctggat ggcagggtcc tgctgaacac cactgtggcc    660
```

-continued

```
cccctgttct ttgctgatca gttcctgcag ctgtccactt ctctgcctag ccagtacatc    720
actgggctgg ctgagcacct gagccctctg atgctgagca cctcttggac taggatcacc    780
ctgtggaaca gggacctggc ccccacccct ggggccaacc tgtatggcag ccaccccttc    840
tatctggccc tggaggatgg gggctctgcc catggggtgt tcctgctgaa tagcaatgct    900
atggatgtgg tgctgcagcc cagccctgcc ctgtcttgga ggagcactgg gggcatcctg    960
gatgtgtaca ttttcctggg gcctgagccc aagtctgtgg tgcagcagta cctggatgtg   1020
gtgggctacc ccttcatgcc tccctactgg ggcctgggct tccacctgtg caggtggggc   1080
tacagctcta ctgccatcac caggcaggtg gtggagaata tgaccagggc ccacttcccc   1140
ctggatgtgc agtggaatga cctggactac atggactcta ggagggactt caccttcaat   1200
aaggatggct tcagagactt ccctgccatg gtgcaggagc tgcatcaggg gggcaggagg   1260
tacatgatga ttgtggaccc tgccatcagc tcttctggcc ctgctggctc ttacaggccc   1320
tatgatgagg gcctgaggag gggggtgttc atcaccaatg agactgggca gcccctgatt   1380
gggaaggtgt ggcctggctc tactgccttc cctgacttca ccaatcctac tgccctggcc   1440
tggtgggagg acatggtggc tgagttccat gaccaggtgc cctttgatgg catgtggatt   1500
gacatgaatg agccctctaa tttcatcagg ggctctgagg atggctgccc caacaatgag   1560
ctggagaacc cccctatgt gcctggggtg gtgggggca ccctgcaggc tgccaccatc   1620
tgtgctagct ctcaccagtt cctgagcacc cactacaatc tgcataacct gtatggcctg   1680
actgaggcca ttgccagcca cagggccctg gtgaaggcta ggggcaccag gcccttttgtg   1740
atttctagga gcacttttgc tggccatggc aggtatgctg ggcactggac tggggatgtg   1800
tggtctagct gggagcagct ggcttcttct gtgcctgaga tcctgcagtt caacctgctg   1860
ggggtgcctc tggtgggggc tgatgtgtgt gggttcctgg gcaacacttc tgaggagctg   1920
tgtgtgaggt ggacccagct gggggccttc taccctttca tgaggaacca caacagcctg   1980
ctgagcctgc cccaggagcc ctacagcttc tctgagcctg cccagcaggc catgaggaag   2040
gccctgaccc tgaggtatgc cctgctgccc cacctgtaca ccctgttcca ccaggcccat   2100
gtggctgggg agactgtggc taggcctctg ttcctggagt tccccaagga ctctagcacc   2160
tggactgtgg accaccagct gctgtggggg gaggccctgc tgatcactcc tgtgctgcag   2220
gctgggaagg ctgaggtgac tggctatttc cccctgggca cctggtatga cctgcagact   2280
gtgcctgtgg aggccctggg gagcctgccc cccccctg ctgcccccag ggagcctgcc   2340
atccactctg agggccagtg ggtgaccctg cctgcccctc tggataccat caatgtgcac   2400
ctgagggctg gctacatcat tcccctgcag ggccctggcc tgaccactac tgagtctagg   2460
cagcagccca tggccctggc tgtggccctg accaaggggg gggaggctag gggggagctg   2520
ttttgggatg atggggagag cctggaggtg ctggagaggg gggcctacac tcaggtgatc   2580
ttcctggcca ggaacaatac cattgtgaat gagctggtga gggtgacctc tgagggggct   2640
ggcctgcagc tgcagaaggt gactgtgctg gggtggcca ctgccccca gcaggtgctg     2700
agcaatgggg tgcctgtgag caacttcacc tatagccctg ataccaaggt gctggatatt   2760
tgtgtgagcc tgctgatggg ggagcagttc ctggtgagct ggtgctga                 2808
```

<210> SEQ ID NO 3
<211> LENGTH: 2808
<212> TYPE: DNA
<213> ORGANISM: Artificial Sequence
<220> FEATURE:

<223> OTHER INFORMATION: Modified Nucleic Acid

<400> SEQUENCE: 3

```
atggctttcc tgtggctgct gtcttgttgg gctctgctgg gcaccacctt tggcctgctg     60
gtgcccaggg agctgtctgg cagcagccct gtgctggagg agacccaccc tgctcatcag    120
caggggggcta gcaggcctgg ccccagggat gcccaggctc accctgggag acccagggct   180
gtgcccactc agtgtgatgt gccccccaac agcaggtttg actgtgctcc tgacaaggct    240
atcacccagg agcagtgtga ggccaggggg tgctgctaca ttcctgctaa gcagggcctg    300
caggggggccc agatgggcca gccctggtgc ttcttccccc cctcttatcc cagctataag   360
ctggagaacc tgagcagctc tgagatgggc tacactgcca ccctgaccag gaccactccc    420
accttctttc ccaaggatat tctgactctg aggctggatg tgatgatgga gactgagaac    480
aggctgcact tcactatcaa ggaccctgcc aataggaggt atgaggtgcc cctggagact    540
cctcatgtgc atagcagggc cccttctcct ctgtattctg tggagttctc tgaggagccc    600
tttggggtga ttgtgaggag gcagctggat ggcagggtgc tgctgaacac cactgtggcc    660
cccctgttct ttgctgacca gttcctgcag ctgagcactt ctctgcccag ccagtacatt    720
actgggctgg ctgagcatct gagccccctg atgctgagca cctcttggac caggatcacc    780
ctgtggaaca gggacctggc cccccactcct ggggctaacc tgtatggctc tcaccccttt   840
tacctggccc tggaggatgg gggctctgcc catggggtgt ttctgctgaa cagcaatgct    900
atggatgtgg tgctgcagcc ctctccagcc ctgtcttgga ggagcactgg gggcattctg    960
gatgtgtaca ttttcctggg gcctgaaccc aagtctgtgg tgcagcagta cctggatgtg   1020
gtgggctacc ccttcatgcc cccctattgg gggctggggt ttcacctgtg caggtggggc   1080
tacagcagca ctgccatcac caggcaggtg gtggagaaca tgaccagggc ccatttcccc   1140
ctggatgtgc agtggaatga cctggactac atggatagca ggagggattt caccttcaac   1200
aaggatggct tcagggactt tcctgccatg gtgcaggagc tgcaccaggg gggcaggagg   1260
tatatgatga ttgtggaccc tgctatcagc agctctggcc ctgctggctc ttacaggccc   1320
tatgatgagg gcctgaggag gggggtgttt atcactaatg aaactggcca gcctctgatt   1380
ggcaaggtct ggcctggctc tactgccttc cctgatttta ctaaccccac tgccctggcc   1440
tggtgggagg acatggtggc tgagttccat gatcaggtgc cttttgatgg catgtggatt   1500
gatatgaatg aaccaagcaa cttcatcaga ggctctgagg atggctgccc caacaatgag   1560
ctggagaacc cccctatgt gcctggggtg gtgggggggca ctctgcaggc tgccaccatt   1620
tgtgctagca gccaccagtt cctgagcacc cactacaatc tgcacaacct gtatggcctg   1680
actgaagcca ttgccagcca tagggccctg gtgaaggcca ggggcactag gccttttgtg   1740
atcagcagga gcacttttgc tggccatggc aggtatgctg gccactggac tggggatgtg   1800
tggagcagct gggagcagct ggccagctct gtgcctgaga ttctgcagtt taacctgctg   1860
ggggtgcccc tggtgggggc tgatgtgtgt ggcttcctgg gcaacacctc tgaggagctg   1920
tgtgtgaggt ggacccagct gggggccttt tatcccttca tgaggaacca caacagcctg   1980
ctgagcctgc ctcaggagcc ctactctttc tctgagcctg cccagcaggc catgaggaag   2040
gccctgaccc tgaggtatgc cctgctgccc cacctgtata ccctgttcca ccaggcccat   2100
gtggctgggg agactgtggc caggcccctg ttcctggagt tccccaagga cagcagcacc   2160
tggactgtgg atcatcagct gctgtggggg gaggccctgc tgatcacccc tgtgctgcag   2220
gctggcaagg ctgaggtcac tggctacttc cctctgggca cctggtatga cctgcagact   2280
```

```
gtgcctgtgg aggctctggg cagcctgccc cccccccctg ctgctcccag ggagcctgcc   2340

atccactctg agggccagtg ggtgaccctg cctgctcccc tggacaccat caatgtgcac   2400

ctgagggctg gctacattat ccccctgcag ggcccagggc tgactaccac tgagagcaga   2460

cagcagccca tggctctggc tgtggccctg accaaggggg gggaagctag gggggagctg   2520

ttctgggatg atggggagag cctggaggtg ctggagaggg gggcctatac ccaggtgatc   2580

ttcctggcta ggaacaacac cattgtcaat gagctggtga gggtgacttc tgagggggct   2640

gggctgcagc tgcagaaggt gactgtgctg gggtggcca ctgctcccca gcaggtgctg    2700

agcaatgggg tgcctgtgag caacttcacc tacagccctg acaccaaggt gctggacatc   2760

tgtgtgtctc tgctgatggg ggagcagttc ctggtgagct ggtgctga                2808
```

<210> SEQ ID NO 4
<211> LENGTH: 2808
<212> TYPE: DNA
<213> ORGANISM: Artificial Sequence
<220> FEATURE:
<223> OTHER INFORMATION: Modified Nucleic Acid

<400> SEQUENCE: 4

```
atggccttcc tgtggctgct gtcttgctgg gctctgctgg ggaccacctt tggcctgctg     60

gtccccaggg agctgtctgg ctcttctcct gtcctggagg agacccaccc tgcccaccag    120

caggggcta gcaggcctgg ccccagggat gcccaggccc accctggcag gcccagggct     180

gtgcccaccc agtgtgatgt gcctcccaac agcaggtttg actgtgcccc tgacaaggcc    240

atcacccagg agcagtgtga ggccaggggc tgctgctata tccctgccaa gcagggcctg    300

caggggctc agatgggcca gccctggtgc ttctttcccc cctcttatcc tagctataag     360

ctggagaacc tgagcagctc tgagatgggg tacactgcca ccctgaccag gaccaccccc    420

actttcttcc ctaaggacat cctgaccctg aggctggatg tgatgatgga gactgagaat    480

aggctgcact ttactatcaa ggaccctgcc aacaggaggt atgaggtgcc tctggagacc    540

ccccatgtgc attctagggc ccccagcccc ctgtactctg tggagttctc tgaggagccc    600

tttggggtga ttgtgaggag acagctggat ggcagggtcc tgctgaacac cactgtggct    660

cccctgtttt ttgctgacca gttcctgcag ctgagcacca gcctgcccag ccagtacatc    720

actgggctgg ctgagcacct gagccccctg atgctgagca ccagctggac caggatcacc    780

ctgtggaaca gggatctggc tcctacccct ggggccaacc tgtatggctc tcaccccttt    840

tacctggccc tggaggatgg gggctctgcc catggggtgt tcctgctgaa cagcaatgct    900

atggatgtgg tgctgcagcc cagccctgcc ctgagctgga ggtctactgg gggcatcctg    960

gatgtgtaca tctttctggg gcctgagccc aagtctgtgg tgcagcagta cctggatgtg   1020

gtgggctatc cttttatgcc ccctattgg ggcctgggct tccacctgtg caggtggggc    1080

tacagcagca ctgccatcac cagacaggtg gtggagaaca tgaccagggc ccacttcccc   1140

ctggatgtgc agtggaatga cctggactac atggacagca ggagggactt cacctttaac   1200

aaggatggct ttagggactt ccctgccatg gtgcaggagc tgcatcaggg gggcaggagg   1260

tacatgatga ttgtggaccc agccatcagc agctctgggc ctgctgggtc ttacaggccc   1320

tatgatgagg gcctgaggag gggggtgttc atcaccaatg agactggcca gcccctgatt   1380

ggcaaggtgt ggcctgggag cactgccttc cctgatttta ccaaccccac tgccctggcc   1440

tggtgggagg atatggtggc tgagtttcat gaccaggtgc cctttgatgg catgtggatt   1500
```

gacatgaatg agcccagcaa tttcatcagg ggctctgagg atggctgccc caacaatgag 1560
ctggagaatc ctccctatgt gcctggggtg gtggggggca ccctgcaggc tgccaccatc 1620
tgtgcctcta gccaccagtt cctgagcacc cactataacc tgcataacct gtatggcctg 1680
actgaggcca ttgccagcca tagagccctg gtgaaggcca gagggaccag gccctttgtg 1740
atctctagga gcacctttgc tggccatggc aggtatgctg gccactggac tggggatgtg 1800
tggagctctt gggagcagct ggccagctct gtgccagaga tcctgcagtt caacctgctg 1860
ggggtgcctc tggtgggggc tgatgtgtgt ggcttcctgg gcaatacctc tgaagagctg 1920
tgtgtgaggt ggactcagct gggggccttc tatcccttca tgaggaacca caacagcctg 1980
ctgtctctgc cccaggagcc ctacagcttc tctgagcctg ctcagcaggc tatgaggaag 2040
gccctgaccc tgaggtatgc cctgctgccc catctgtaca ccctgttcca ccaggcccat 2100
gtggctgggg agactgtggc caggcccctg tttctggagt ttcccaagga cagcagcacc 2160
tggactgtgg accatcagct gctgtggggg gaggctctgc tgattacccc tgtgctgcag 2220
gctggcaagg ctgaggtgac tgggtacttc cccctgggga cttggtatga cctgcagact 2280
gtgcctgtgg aagctctggg cagcctgccc ccaccccctg ctgcccctag ggagcctgcc 2340
atccactctg agggccagtg ggtgaccctg cctgcccctc tggacaccat caatgtgcac 2400
ctgagggctg gctatatcat cccccctgcag ggccctgggc tgaccaccac tgagagcagg 2460
cagcagccca tggccctggc tgtggccctg actaaggggg gggaggccag gggggagctg 2520
ttctgggatg atggggagag cctggaggtg ctggagagag ggcctacac ccaggtgatc 2580 tttctggcca ggaacaacac cattgtgaat gagctggtga gggtgacttc tgagggggct 2640
ggcctgcagc tgcagaaggt gactgtgctg gggtggcca ctgcccccca gcaggtgctg 2700
agcaatgggg tgcctgtgtc taacttcacc tacagccctg atactaaggt gctggatatc 2760
tgtgtgagcc tgctgatggg ggagcagttt ctggtgagct ggtgctga 2808

<210> SEQ ID NO 5
<211> LENGTH: 2808
<212> TYPE: DNA
<213> ORGANISM: Artificial Sequence
<220> FEATURE:
<223> OTHER INFORMATION: Modified Nucleic Acid

<400> SEQUENCE: 5
atggcctttc tgtggctgct gtcctgctgg gccctgctgg ggaccacctt tggcctgctg 60
gtgcccaggg agctgtctgg gagcagccca gtgctggagg agacccaccc tgcccaccag 120
cagggggcca gcaggcctgg ccctagggat gcccaggccc accctggcag gcccagggct 180
gtgcctaccc agtgtgatgt gccacccaat tctaggtttg actgtgctcc tgacaaggcc 240
atcactcagg agcagtgtga agctaggggg tgctgctaca tcccagccaa gcagggcctg 300 caggggggccc agatgggcca gccctggtgc ttcttccccc ccagctaccc tagctacaag 360
ctggagaatc tgagcagctc tgagatgggc tacactgcta ccctgaccag gaccactcct 420
accttcttcc ccaaggacat cctgactctg aggctggatg tcatgatgga gactgaaaat 480
aggctgcact tcaccatcaa ggaccctgcc aataggaggt atgaggtgcc tctggagacc 540
ccccatgtgc atagcagggc tcccagcccc ctgtattctg tggagttctc tgaggagccc 600
tttggggtca ttgtgaggag acagctggat gggagggtgc tgctgaacac tactgtggct 660
cccctgttct ttgctgacca gttcctgcag ctgtctacca gcctgcccag ccagtacatc 720
actgggctgg ctgagcatct gagccccctg atgctgagca ccagctggac caggatcact 780

-continued

```
ctgtggaaca gggatctggc ccccactcct ggggccaacc tgtatgggag ccatcccttc    840
tacctggccc tggaggatgg gggctctgcc catggggtgt tcctgctgaa cagcaatgcc    900
atggatgtgg tgctgcagcc tagccctgcc ctgagctgga ggagcactgg gggcatcctg    960
gatgtctaca tcttcctggg gcctgagccc aagtctgtgg tgcagcagta tctggatgtg   1020
gtggggtatc ccttcatgcc cccctactgg ggcctgggct ttcacctgtg caggtggggc   1080
tacagcagca ctgccatcac caggcaggtg gtggagaaca tgaccagggc ccacttccct   1140
ctggatgtgc agtggaatga cctggactat atggattcta ggagagactt tacttttaac   1200
aaggatggct tcagggattt ccctgccatg gtgcaggagc tgcaccaggg gggcaggagg   1260
tacatgatga ttgtggaccc tgctattagc agctctggcc ctgctgggtc ttacaggcct   1320
tatgatgagg gcctgaggag gggggtgttc atcaccaatg agactggcca gcccctgatt   1380
ggcaaggtgt ggcctggcag cactgccttc cctgacttca ccaaccccac tgccctggcc   1440
tggtgggagg acatggtggc tgagttccat gaccaggtgc cctttgatgg gatgtggatt   1500
gacatgaatg agccctctaa cttcatcagg gggtctgagg atggctgccc caacaatgag   1560
ctggagaacc cccctatgt gcctggggtg gtgggggca ctctgcaggc tgccactatc   1620
tgtgcttctt ctcaccagtt tctgagcacc cactataatc tgcacaacct gtatggcctg   1680
actgaggcca ttgccagcca tagggccctg gtgaaggcca ggggcaccag gccctttgtg   1740
atcagcaggt ctacctttgc tggccatggc aggtatgctg gccactggac tggggatgtg   1800
tggtcttctt gggagcagct ggccagctct gtgcctgaga tcctgcagtt caacctgctg   1860
ggggtgcctc tggtgggggc tgatgtgtgt ggctttctgg gcaacacctc tgaggagctg   1920
tgtgtgaggt ggacccagct gggggccttt taccccttca tgaggaacca caatagcctg   1980
ctgagcctgc cccaggagcc ttactctttc tctgagcctg cccagcaggc catgaggaag   2040
gccctgactc tgaggtatgc cctgctgccc catctgtata ccctgtttca ccaggcccat   2100
gtggctgggg agactgtggc taggcctctg tttctggagt tccctaagga ctctagcacc   2160
tggactgtgg accaccagct gctgtggggg gaggccctgc tgatcacccc tgtgctgcag   2220
gctggcaagg ctgaggtgac tggctacttc cccctgggca cctggtatga cctgcagact   2280
gtgcctgtgg aggccctggg gagcctgcct ccccccctg ctgcccccag ggagcctgcc   2340
attcattctg agggccagtg ggtgaccctg cctgcccctc tggacaccat caatgtgcac   2400
ctgagggctg ggtacatcat ccccctgcag ggccctggcc tgaccaccac tgagagcagg   2460
cagcagccca tggccctggc tgtggctctg accaaggggg gggaggccag gggggagctg   2520
ttctgggatg atggggagtc tctggaggtg ctggagaggg gggcctacac ccaggtgatc   2580
tttctggcca ggaacaatac tattgtgaat gagctggtga gggtgacctc tgagggggct   2640
ggcctgcagc tgcagaaggt gactgtgctg gggtggcca ctgcccccca gcaggtcctg   2700
agcaatgggg tgcctgtgag caacttcacc tactctcctg acaccaaggt gctggacatt   2760
tgtgtgtctc tgctgatggg ggagcagttc ctggtgagct ggtgctga                2808
```

<210> SEQ ID NO 6
<211> LENGTH: 3016
<212> TYPE: DNA
<213> ORGANISM: Artificial Sequence
<220> FEATURE:
<223> OTHER INFORMATION: Modified Nucleic Acid

<400> SEQUENCE: 6

-continued

```
atggctttcc tgtggctgct gagctgctgg gctctgctgg gcaccacctt tgggctgctg     60
gtgcctaggg agctgtctgg gtctagccct gtgctggagg agactcaccc tgcccatcag    120
caggggggcta gcaggcctgg ccccagggat gctcaggccc accctggcag gcccagggct    180
gtgcccaccc agtgtgatgt gcccccccaac agcaggtttg actgtgcccc tgacaaggcc    240
attacccagg agcagtgtga ggccaggggc tgctgctaca ttccagctaa gcagggcctg    300
cagggggccc agatgggcca gccctggtgc ttcttccccc ccagctatcc tagctataaa    360
ctggagaacc tgagcagctc tgagatgggc tatactgcca ccctgactag gactactccc    420
acctttttc ctaaggatat cctgaccctg aggctggatg tgatgatgga gactgagaac    480
aggctgcact tcactattaa ggaccctgcc aataggaggt atgaagtgcc tctggagact    540
cctcatgtgc actctagggc cccccagcccc ctgtattctg tggagttctc tgaggagccc    600
tttggggtga ttgtgaggag gcagctggat ggcagggtgc tgctgaacac cactgtggcc    660
cccctgttct ttgctgacca gttcctgcag ctgagcacca gcctgcccag ccagtacatc    720
actgggctgg ctgagcatct gagccctctg atgctgagca cctcttggac caggatcacc    780
ctgtggaata gggatctggc cccccacccct ggggctaatc tgtatggctc tcatcccttt    840
tacctggccc tggaggatgg gggctctgcc catggggtgt ttctgctgaa cagcaatgcc    900
atggatgtgg tgctgcagcc ctctcctgcc ctgagctgga ggagcactgg gggcatcctg    960
gatgtgtaca tcttcctggg ccctgagccc aagtctgtgg tccagcagta tctggatgtg   1020
gtgggctacc cctttatgcc ccccctattgg ggcctgggct tccacctgtg caggtggggg   1080
tattcttcta ctgctatcac caggcaggtg gtggagaaca tgaccagggc tcacttcccc   1140
ctggatgtgc agtggaatga cctggactat atggactcta ggagggattt caccttcaac   1200
aaggatggct tcagggactt ccctgctatg gtccaggagc tgcatcaggg gggcaggagg   1260
tacatgatga ttgtggaccc tgccatcagc agctctggcc ctgctggcag ctataggccc   1320
tatgatgagg gcctgaggag gggggtgttt atcactaatg aaactgggca gcccctgatt   1380
ggcaaggtgt ggcctggctc tactgccttc cctgacttca ccaaccccac tgctctggcc   1440
tggtgggagg acatggtggc tgagttccat gaccaggtgc cttttgatgg catgtggatt   1500
gacatgaatg agcccagcaa cttcatcagg ggctctgagg atgggtgccc caataatgag   1560
ctggagaacc cccccctatgt gcctggggtg gtggggggca ccctgcaggc tgccactatt   1620
tgtgccagct ctcaccagtt cctgagcacc cactacaacc tgcacaatct gtatggcctg   1680
actgaggcca ttgccagcca cagggccctg gtgaaggcca ggggcactag gccctttgtg   1740
atctctagaa gcacctttgc tggccatggg aggtatgctg gccactggac tggggatgtg   1800
tggagctctt gggagcagct ggccagctct gtgcctgaga tcctgcagtt caacctgctg   1860
ggggtgcccc tggtgggggc tgatgtgtgt ggcttcctgg gcaacacctc tgaagagctg   1920
tgtgtgaggt ggacccagct gggggccttc taccctttca tgaggaacca caacagcctg   1980
ctgagcctgc ctcaggagcc ttactctttc tctgagcctg cccagcaggc catgaggaag   2040
gccctgaccc tgaggtatgc tctgctgccc cacctgtaca ccctgttcca ccaggcccat   2100
gtggctgggg agactgtggc caggcccctg ttcctggagt ttcctaagga tagcagcacc   2160
tggactgtgg accaccagct gctgtggggg gaggccctgc tgattacccc tgtgctgcag   2220
gctggcaagg ctgaggtgac tggctacttc cccctgggca cttggtatga cctgcagact   2280
gtgcctgtgg aagccctggg cagcctgcct cccccccctg ctgcccccag ggagcctgcc   2340
atccactctg agggccagtg ggtgaccctg cctgcccccc tggacaccat taatgtgcat   2400
```

```
ctgagggctg ggtatattat ccccctgcag gggcctgggc tgactaccac tgagagcagg   2460

cagcagccta tggccctggc tgtggctctg actaaggggg gggaggccag gggggagctg   2520

ttctgggatg atggggagag cctggaggtg ctggagaggg gggcctacac ccaggtgatt   2580

ttcctggcca ggaacaacac cattgtgaat gagctggtga gggtgacctc tgagggggct   2640

ggcctgcagc tgcagaaagt gactgtgctg gggggtggcca ctgcccccca gcaggtgctg   2700

agcaatgggg tgcctgtgag caacttcacc tacagccctg acaccaaggt gctggatatt   2760

tgtgtgagcc tgctgatggg ggagcagttc ctggtgagct ggtgctgact cgagagatct   2820

accggtgaat tcaccgcggg tttaaactgt gccttctagt tgccagccat ctgttgtttg   2880

cccctccccc gtgccttcct tgaccctgga aggtgccact cccactgtcc tttcctaata   2940

aaatgaggaa attgcatcgc attgtctgag taggtgtcat tctattctgg ggggtggggt   3000

gggggctagc tctaga                                                 3016
```

```
<210> SEQ ID NO 7
<211> LENGTH: 3016
<212> TYPE: DNA
<213> ORGANISM: Artificial Sequence
<220> FEATURE:
<223> OTHER INFORMATION: Modified Nucleic Acid

<400> SEQUENCE: 7

atggctttcc tgtggctgct gtcttgctgg gccctgctgg ggactacctt tggcctgctg     60

gtgcccaggg aactgtctgg ctctagccca gtgctggagg agacccaccc tgcccaccag    120

cagggggctt ctaggcctgg ccccagggat gcccaggccc accctggcag gccaagggct    180

gtgcccaccc agtgtgatgt gccccccaac tctagatttg attgtgcccc tgataaggcc    240

atcacccagg agcagtgtga ggctaggggc tgctgctaca tccctgctaa gcagggcctg    300

cagggggctc agatgggcca gccctggtgc ttcttccccc ccagctatcc ctcttacaag    360

ctggagaatc tgagcagctc tgagatgggc tacactgcca ccctgaccag gactactccc    420

accttcttcc ccaaggacat cctgaccctg aggctggatg tgatgatgga gactgagaac    480

aggctgcatt tcaccatcaa ggatcctgcc aacaggaggt atgaggtgcc tctggagacc    540

ccccatgtgc acagcagggc tccttctccc ctgtactctg tggagttctc tgaggaaccc    600

tttggggtga ttgtgaggag gcagctggat ggcagggtcc tgctgaacac cactgtggcc    660

cccctgttct ttgctgatca gttcctgcag ctgtccactt ctctgcctag ccagtacatc    720

actgggctgg ctgagcacct gagccctctg atgctgagca cctcttggac taggatcacc    780

ctgtggaaca gggacctggc cccccacccct ggggccaacc tgtatggcag ccacccccttc    840

tatctggccc tggaggatgg gggctctgcc catggggtgt tcctgctgaa tagcaatgct    900

atggatgtgg tgctgcagcc cagccctgcc ctgtcttgga ggagcactgg gggcatcctg    960

gatgtgtaca ttttcctggg gcctgagccc aagtctgtgg tgcagcagta cctggatgtg   1020

gtgggctacc ccttcatgcc tccctactgg ggcctgggct tccacctgtg caggtggggc   1080

tacagctcta ctgccatcac caggcaggtg gtggagaata tgaccagggc ccacttcccc   1140

ctggatgtgc agtggaatga cctggactac atggactcta ggagggactt caccttcaat   1200

aaggatggct tcagagactt ccctgccatg gtgcaggagc tgcatcaggg gggcaggagg   1260

tacatgatga ttgtggaccc tgccatcagc tcttctggcc ctgctggctc ttacaggccc   1320

tatgatgagg gcctgaggag gggggtgttc atcaccaatg agactgggca gcccctgatt   1380
```

-continued gggaaggtgt ggcctggctc tactgccttc cctgacttca ccaatcctac tgccctggcc 1440
tggtgggagg acatggtggc tgagttccat gaccaggtgc cctttgatgg catgtggatt 1500
gacatgaatg agccctctaa tttcatcagg ggctctgagg atggctgccc caacaatgag 1560
ctggagaacc cccccctatgt gcctggggtg gtggggggca ccctgcaggc tgccaccatc 1620
tgtgctagct ctcaccagtt cctgagcacc cactacaatc tgcataacct gtatggcctg 1680
actgaggcca ttgccagcca cagggccctg gtgaaggcta ggggcaccag gccctttgtg 1740
atttctagga gcacttttgc tggccatggc aggtatgctg ggcactggac tggggatgtg 1800
tggtctagct gggagcagct ggcttcttct gtgcctgaga tcctgcagtt caacctgctg 1860
ggggtgcctc tggtgggggc tgatgtgtgt gggttcctgg gcaacacttc tgaggagctg 1920
tgtgtgaggt ggacccagct gggggccttc taccctttca tgaggaacca caacagcctg 1980
ctgagcctgc cccaggagcc ctacagcttc tctgagcctg cccagcaggc catgaggaag 2040
gccctgaccc tgaggtatgc cctgctgccc cacctgtaca ccctgttcca ccaggcccat 2100
gtggctgggg agactgtggc taggcctctg ttcctggagt tccccaagga ctctagcacc 2160
tggactgtgg accaccagct gctgtggggg gaggccctgc tgatcactcc tgtgctgcag 2220
gctgggaagg ctgaggtgac tggctatttc cccctgggca cctggtatga cctgcagact 2280
gtgcctgtgg aggccctggg gagcctgccc ccccccctg ctgcccccag ggagcctgcc 2340
atccactctg agggccagtg ggtgaccctg cctgcccctc tggataccat caatgtgcac 2400
ctgagggctg gctacatcat tcccctgcag ggccctggcc tgaccactac tgagtctagg 2460
cagcagccca tggccctggc tgtggccctg accaaggggg gggaggctag gggggagctg 2520
ttttgggatg atggggagag cctggaggtg ctggagaggg ggcctacac tcaggtgatc 2580 ttcctggcca ggaacaatac cattgtgaat gagctggtga gggtgacctc tgagggggct 2640
ggcctgcagc tgcagaaggt gactgtgctg ggggtggcca ctgcccccca gcaggtgctg 2700
agcaatgggg tgcctgtgag caacttcacc tatagccctg ataccaaggt gctggatatt 2760
tgtgtgagcc tgctgatggg ggagcagttc ctggtgagct ggtgctgact cgagagatct 2820
accggtgaat tcaccgcggg tttaaactgt gccttctagt tgccagccat ctgttgtttg 2880
cccctccccc gtgccttcct tgaccctgga aggtgccact cccactgtcc tttcctaata 2940
aaatgaggaa attgcatcgc attgtctgag taggtgtcat tctattctgg ggggtggggt 3000
gggggctagc tctaga 3016

<210> SEQ ID NO 8
<211> LENGTH: 3016
<212> TYPE: DNA
<213> ORGANISM: Artificial Sequence
<220> FEATURE:
<223> OTHER INFORMATION: Modified Nucleic Acid

<400> SEQUENCE: 8
atggctttcc tgtggctgct gtcttgttgg gctctgctgg gcaccacctt tggcctgctg 60
gtgcccaggg agctgtctgg cagcagccct gtgctggagg agacccaccc tgctcatcag 120
cagggggcta gcaggcctgg ccccagggat gcccaggctc accctgggag acccagggct 180
gtgcccactc agtgtgatgt gcccccccaac agcaggtttg actgtgctcc tgacaaggct 240
atcacccagg agcagtgtga ggccaggggg tgctgctaca ttcctgctaa gcagggcctg 300
cagggggccc agatgggcca gccctggtgc ttcttccccc cctcttatcc cagctataag 360
ctggagaacc tgagcagctc tgagatgggc tacactgcca ccctgaccag gaccactccc 420

```
accttctttc ccaaggatat tctgactctg aggctggatg tgatgatgga gactgagaac    480
aggctgcact tcactatcaa ggaccctgcc aataggaggt atgaggtgcc cctggagact    540
cctcatgtgc atagcagggc cccttctcct ctgtattctg tggagttctc tgaggagccc    600
tttggggtga ttgtgaggag gcagctggat ggcagggtgc tgctgaacac cactgtggcc    660
cccctgttct ttgctgacca gttcctgcag ctgagcactt ctctgcccag ccagtacatt    720
actgggctgg ctgagcatct gagccccctg atgctgagca cctcttggac caggatcacc    780
ctgtggaaca gggacctggc ccccactcct ggggctaacc tgtatggctc tcaccccttt    840
tacctggccc tggaggatgg gggctctgcc catggggtgt ttctgctgaa cagcaatgct    900
atggatgtgg tgctgcagcc ctctccagcc ctgtcttgga ggagcactgg gggcattctg    960
gatgtgtaca ttttcctggg gcctgaaccc aagtctgtgg tgcagcagta cctggatgtg   1020
gtgggctacc ccttcatgcc cccctattgg gggctggggt ttcacctgtg caggtggggc   1080
tacagcagca ctgccatcac caggcaggtg gtggagaaca tgaccagggc ccatttcccc   1140
ctggatgtgc agtggaatga cctggactac atggatagca ggagggattt caccttcaac   1200
aaggatggct tcagggactt tcctgccatg gtgcaggagc tgcaccaggg gggcaggagg   1260
tatatgatga ttgtggaccc tgctatcagc agctctggcc ctgctggctc ttacaggccc   1320
tatgatgagg gcctgaggag gggggtgttt atcactaatg aaactggcca gcctctgatt   1380
ggcaaggtct ggcctggctc tactgccttc cctgatttta ctaaccccac tgccctggcc   1440
tggtgggagg acatggtggc tgagttccat gatcaggtgc cttttgatgg catgtggatt   1500
gatatgaatg aaccaagcaa cttcatcaga ggctctgagg atggctgccc caacaatgag   1560
ctggagaacc ccccctatgt gcctggggtg gtgggggggca ctctgcaggc tgccaccatt  1620
tgtgctagca gccaccagtt cctgagcacc cactacaatc tgcacaacct gtatggcctg   1680
actgaagcca ttgccagcca tagggccctg gtgaaggcca ggggcactag gccttttgtg   1740
atcagcagga gcacttttgc tggccatggc aggtatgctg gccactggac tggggatgtg   1800
tggagcagct gggagcagct ggccagctct gtgcctgaga ttctgcagtt taacctgctg   1860
ggggtgcccc tggtgggggc tgatgtgtgt ggcttcctgg gcaacacctc tgaggagctg   1920
tgtgtgaggt ggacccagct gggggccttt tatcccttca tgaggaacca caacagcctg   1980
ctgagcctgc ctcaggagcc ctactctttc tctgagcctg cccagcaggc catgaggaag   2040
gccctgaccc tgaggtatgc cctgctgccc cacctgtata ccctgttcca ccaggcccat   2100
gtggctgggg agactgtggc caggcccctg ttcctggagt tccccaagga cagcagcacc   2160
tggactgtgg atcatcagct gctgtggggg gaggccctgc tgatcacccc tgtgctgcag   2220
gctggcaagg ctgaggtcac tggctacttc cctctgggca cctggtatga cctgcagact   2280
gtgcctgtgg aggctctggg cagcctgccc ccccccctg ctgctcccag ggagcctgcc   2340
atccactctg agggccagtg ggtgaccctg cctgctcccc tggacaccat caatgtgcac   2400
ctgagggctg gctacattat ccccctgcag ggcccagggc tgactaccac tgagagcaga   2460
cagcagccca tggctctggc tgtggccctg accaaggggg gggaagctag gggggagctg   2520
ttctgggatg atggggagag cctggaggtg ctggagaggg ggcctatac ccaggtgatc   2580
ttcctggcta ggaacaacac cattgtcaat gagctggtga gggtgacttc tgagggggct   2640
gggctgcagc tgcagaaggt gactgtgctg gggtggcca ctgctcccca gcaggtgctg   2700
agcaatgggg tgcctgtgag caacttcacc tacagccctg acaccaaggt gctggacatc   2760
```

-continued

```
tgtgtgtctc tgctgatggg ggagcagttc ctggtgagct ggtgctgact cgagagatct   2820

accggtgaat tcaccgcggg tttaaactgt gccttctagt tgccagccat ctgttgtttg   2880

cccctccccc gtgccttcct tgaccctgga aggtgccact cccactgtcc tttcctaata   2940

aaatgaggaa attgcatcgc attgtctgag taggtgtcat tctattctgg ggggtggggt   3000

gggggctagc tctaga                                                   3016
```

<210> SEQ ID NO 9
<211> LENGTH: 3016
<212> TYPE: DNA
<213> ORGANISM: Artificial Sequence
<220> FEATURE:
<223> OTHER INFORMATION: Modified Nucleic Acid

<400> SEQUENCE: 9

```
atggccttcc tgtggctgct gtcttgctgg gctctgctgg ggaccacctt tggcctgctg     60

gtccccaggg agctgtctgg ctcttctcct gtcctggagg agacccaccc tgcccaccag    120

caggggggcta gcaggcctgg ccccagggat gcccaggccc accctggcag gcccagggct    180

gtgcccaccc agtgtgatgt gcctcccaac agcaggtttg actgtgcccc tgacaaggcc    240

atcacccagg agcagtgtga ggccaggggc tgctgctata tccctgccaa gcagggcctg    300

cagggggctc agatgggcca gccctggtgc ttctttcccc cctcttatcc tagctataag    360

ctggagaacc tgagcagctc tgagatgggg tacactgcca ccctgaccag gaccaccccc    420

actttcttcc ctaaggacat cctgaccctg aggctggatg tgatgatgga gactgagaat    480

aggctgcact ttactatcaa ggaccctgcc aacaggaggt atgaggtgcc tctggagacc    540

ccccatgtgc attctagggc cccagccccc ctgtactctg tggagttctc tgaggagccc    600

tttggggtga ttgtgaggag acagctggat ggcagggtcc tgctgaacac cactgtggct    660

cccctgtttt ttgctgacca gttcctgcag ctgagcacca gcctgcccag ccagtacatc    720

actgggctgg ctgagcacct gagccccctg atgctgagca ccagctggac caggatcacc    780

ctgtggaaca gggatctggc tcctacccct ggggccaacc tgtatggctc tcaccccttt    840

tacctggccc tggaggatgg gggctctgcc catggggtgt tcctgctgaa cagcaatgct    900

atggatgtgg tgctgcagcc cagccctgcc ctgagctgga ggtctactgg gggcatcctg    960

gatgtgtaca tctttctggg gcctgagccc aagtctgtgg tgcagcagta cctggatgtg   1020

gtgggctatc cttttatgcc cccctattgg ggcctgggct tccacctgtg caggtggggc   1080

tacagcagca ctgccatcac cagacaggtg gtggagaaca tgaccagggc ccacttcccc   1140

ctggatgtgc agtggaatga cctggactac atggacagca ggagggactt cacctttaac   1200

aaggatggct ttagggactt ccctgccatg gtgcaggagc tgcatcaggg gggcaggagg   1260

tacatgatga ttgtggaccc agccatcagc agctctgggc ctgctgggtc ttacaggccc   1320

tatgatgagg gcctgaggag gggggtgttc atcaccaatg agactggcca gcccctgatt   1380

ggcaaggtgt ggcctgggag cactgccttc cctgatttta ccaaccccac tgccctggcc   1440

tggtgggagg atatggtggc tgagtttcat gaccaggtgc cctttgatgg catgtggatt   1500

gacatgaatg agcccagcaa tttcatcagg ggctctgagg atggctgccc caacaatgag   1560

ctggagaatc ctccctatgt gcctggggtg gtgggggggca ccctgcaggc tgccaccatc   1620

tgtgcctcta gccaccagtt cctgagcacc cactataacc tgcataacct gtatggcctg   1680

actgaggcca ttgccagcca tagagccctg gtgaaggcca gagggaccag gccctttgtg   1740

atctctagga gcacctttgc tggccatggc aggtatgctg gccactggac tggggatgtg   1800
```

tggagctctt gggagcagct ggccagctct gtgccagaga tcctgcagtt caacctgctg 1860
ggggtgcctc tggtgggggc tgatgtgtgt ggcttcctgg gcaatacctc tgaagagctg 1920
tgtgtgaggt ggactcagct gggggccttc tatcccttca tgaggaacca caacagcctg 1980
ctgtctctgc cccaggagcc ctacagcttc tctgagcctg ctcagcaggc tatgaggaag 2040
gccctgaccc tgaggtatgc cctgctgccc catctgtaca ccctgttcca ccaggcccat 2100
gtggctgggg agactgtggc caggcccctg tttctggagt ttcccaagga cagcagcacc 2160
tggactgtgg accatcagct gctgtggggg gaggctctgc tgattacccc tgtgctgcag 2220
gctggcaagg ctgaggtgac tgggtacttc cccctgggga cttggtatga cctgcagact 2280
gtgcctgtgg aagctctggg cagcctgccc ccaccccctg ctgcccctag ggagcctgcc 2340
atccactctg agggccagtg ggtgaccctg cctgcccctc tggacaccat caatgtgcac 2400
ctgagggctg gctatatcat cccccctgcag ggccctgggc tgaccaccac tgagagcagg 2460
cagcagccca tggccctggc tgtggccctg actaaggggg gggaggccag gggggagctg 2520
ttctgggatg atggggagag cctggaggtg ctggagagag ggcctacac ccaggtgatc 2580 tttctggcca ggaacaacac cattgtgaat gagctggtga gggtgacttc tgagggggct 2640
ggcctgcagc tgcagaaggt gactgtgctg gggtggcca ctgcccccca gcaggtgctg 2700
agcaatgggg tgcctgtgtc taacttcacc tacagccctg atactaaggt gctggatatc 2760
tgtgtgagcc tgctgatggg ggagcagttt ctggtgagct ggtgctgact cgagagatct 2820
accggtgaat tcaccgcggg tttaaactgt gccttctagt tgccagccat ctgttgtttg 2880
cccctccccc gtgccttcct tgaccctgga aggtgccact cccactgtcc tttcctaata 2940
aaatgaggaa attgcatcgc attgtctgag taggtgtcat tctattctgg ggggtggggt 3000
gggggctagc tctaga 3016

<210> SEQ ID NO 10
<211> LENGTH: 3016
<212> TYPE: DNA
<213> ORGANISM: Artificial Sequence
<220> FEATURE:
<223> OTHER INFORMATION: Modified Nucleic Acid

<400> SEQUENCE: 10
atggcctttc tgtggctgct gtcctgctgg gccctgctgg ggaccacctt tggcctgctg 60
gtgcccaggg agctgtctgg gagcagccca gtgctggagg agacccaccc tgcccaccag 120 caggggggcca gcaggcctgg ccctagggat gcccaggccc accctggcag gcccagggct 180
gtgcctaccc agtgtgatgt gccacccaat tctaggtttg actgtgctcc tgacaaggcc 240
atcactcagg agcagtgtga agctaggggg tgctgctaca tcccagccaa gcagggcctg 300 caggggggccc agatgggcca gccctggtgc ttcttccccc ccagctaccc tagctacaag 360
ctggagaatc tgagcagctc tgagatgggc tacactgcta ccctgaccag gaccactcct 420
accttcttcc ccaaggacat cctgactctg aggctggatg tcatgatgga gactgaaaat 480
aggctgcact tcaccatcaa ggaccctgcc aataggaggt atgaggtgcc tctggagacc 540
ccccatgtgc atagcagggc tcccagcccc ctgtattctg tggagttctc tgaggagccc 600
tttggggtca ttgtgaggag acagctggat gggagggtgc tgctgaacac tactgtggct 660
cccctgttct ttgctgacca gttcctgcag ctgtctacca gcctgcccag ccagtacatc 720
actgggctgg ctgagcatct gagccccctg atgctgagca ccagctggac caggatcact 780

```
ctgtggaaca gggatctggc ccccactcct ggggccaacc tgtatgggag ccatcccttc    840
tacctggccc tggaggatgg gggctctgcc catggggtgt tcctgctgaa cagcaatgcc    900
atggatgtgg tgctgcagcc tagccctgcc ctgagctgga ggagcactgg gggcatcctg    960
gatgtctaca tcttcctggg gcctgagccc aagtctgtgg tgcagcagta tctggatgtg   1020
gtggggtatc ccttcatgcc cccctactgg ggcctgggct ttcacctgtg caggtggggc   1080
tacagcagca ctgccatcac caggcaggtg gtggagaaca tgaccagggc ccacttccct   1140
ctggatgtgc agtggaatga cctggactat atggattcta ggagagactt tacttttaac   1200
aaggatggct tcagggattt ccctgccatg gtgcaggagc tgcaccaggg gggcaggagg   1260
tacatgatga ttgtggaccc tgctattagc agctctggcc ctgctgggtc ttacaggcct   1320
tatgatgagg gcctgaggag gggggtgttc atcaccaatg agactggcca gcccctgatt   1380
ggcaaggtgt ggcctggcag cactgccttc cctgacttca ccaaccccac tgccctggcc   1440
tggtgggagg acatggtggc tgagttccat gaccaggtgc cctttgatgg gatgtggatt   1500
gacatgaatg agccctctaa cttcatcagg gggtctgagg atggctgccc caacaatgag   1560
ctggagaacc cccccctatgt gcctggggtg gtggggggca ctctgcaggc tgccactatc   1620
tgtgcttctt ctcaccagtt tctgagcacc cactataatc tgcacaacct gtatggcctg   1680
actgaggcca ttgccagcca tagggccctg gtgaaggcca ggggcaccag gccctttgtg   1740
atcagcaggt ctacctttgc tggccatggc aggtatgctg gccactggac tggggatgtg   1800
tggtcttctt gggagcagct ggccagctct gtgcctgaga tcctgcagtt caacctgctg   1860
ggggtgcctc tggtgggggc tgatgtgtgt ggctttctgg gcaacacctc tgaggagctg   1920
tgtgtgaggt ggacccagct gggggccttt taccccttca tgaggaacca caatagcctg   1980
ctgagcctgc cccaggagcc ttactctttc tctgagcctg cccagcaggc catgaggaag   2040
gccctgactc tgaggtatgc cctgctgccc catctgtata ccctgtttca ccaggcccat   2100
gtggctgggg agactgtggc taggcctctg tttctggagt tccctaagga ctctagcacc   2160
tggactgtgg accaccagct gctgtggggg gaggccctgc tgatcacccc tgtgctgcag   2220
gctggcaagg ctgaggtgac tggctacttc cccctgggca cctggtatga cctgcagact   2280
gtgcctgtgg aggccctggg gagcctgcct cccccccctg ctgcccccag ggagcctgcc   2340
attcattctg agggccagtg ggtgaccctg cctgcccctc tggacaccat caatgtgcac   2400
ctgagggctg ggtacatcat ccccctgcag ggccctggcc tgaccaccac tgagagcagg   2460
cagcagccca tggccctggc tgtggctctg accaaggggg gggaggccag gggggagctg   2520
ttctgggatg atggggagtc tctggaggtg ctggagaggg gggcctacac ccaggtgatc   2580
tttctggcca ggaacaatac tattgtgaat gagctggtga gggtgacctc tgagggggct   2640
ggcctgcagc tgcagaaggt gactgtgctg gggggtggcca ctgcccccca gcaggtcctg   2700
agcaatgggg tgcctgtgag caacttcacc tactctcctg acaccaaggt gctggacatt   2760
tgtgtgtctc tgctgatggg ggagcagttc ctggtgagct ggtgctgact cgagagatct   2820
accggtgaat tcaccgcggg tttaaactgt gccttctagt tgccagccat ctgttgtttg   2880
cccctccccc gtgccttcct tgaccctgga aggtgccact cccactgtcc tttcctaata   2940
aaatgaggaa attgcatcgc attgtctgag taggtgtcat tctattctgg ggggtggggt   3000
gggggctagc tctaga                                                   3016
```

<210> SEQ ID NO 11
<211> LENGTH: 3076

<212> TYPE: DNA
<213> ORGANISM: Artificial Sequence
<220> FEATURE:
<223> OTHER INFORMATION: Modified Nucleic Acid

<400> SEQUENCE: 11

```
atggctttcc tgtggctgct gagctgctgg gctctgctgg gcaccacctt tgggctgctg     60
gtgcctaggg agctgtctgg gtctagccct gtgctggagg agactcaccc tgcccatcag    120
caggggggcta gcaggcctgg ccccagggat gctcaggccc accctggcag gcccagggct    180
gtgcccaccc agtgtgatgt gccccccaac agcaggtttg actgtgcccc tgacaaggcc    240
attacccagg agcagtgtga ggccaggggc tgctgctaca ttccagctaa gcagggcctg    300
caggggggccc agatgggcca gccctggtgc ttcttccccc ccagctatcc tagctataaa    360
ctggagaacc tgagcagctc tgagatgggc tatactgcca ccctgactag gactactccc    420
acctttttttc ctaaggatat cctgaccctg aggctggatg tgatgatgga gactgagaac    480
aggctgcact tcactattaa ggaccctgcc aataggaggt atgaagtgcc tctggagact    540
cctcatgtgc actctagggc ccccagcccc ctgtattctg tggagttctc tgaggagccc    600
tttggggtga ttgtgaggag gcagctggat ggcagggtgc tgctgaacac cactgtggcc    660
cccctgttct ttgctgacca gttcctgcag ctgagcacca gcctgcccag ccagtacatc    720
actgggctgg ctgagcatct gagccctctg atgctgagca cctcttggac caggatcacc    780
ctgtggaata gggatctggc ccccaccccct ggggctaatc tgtatggctc tcatcccttt    840
tacctggccc tggaggatgg gggctctgcc catggggtgt ttctgctgaa cagcaatgcc    900
atggatgtgg tgctgcagcc ctctcctgcc ctgagctgga ggagcactgg gggcatcctg    960
gatgtgtaca tcttcctggg ccctgagccc aagtctgtgg tccagcagta tctggatgtg   1020
gtgggctacc cctttatgcc cccctattgg ggcctgggct tccacctgtg caggtggggg   1080
tattcttcta ctgctatcac caggcaggtg gtggagaaca tgaccagggc tcacttcccc   1140
ctggatgtgc agtggaatga cctggactat atggactcta ggagggattt caccttcaac   1200
aaggatggct tcagggactt ccctgctatg gtccaggagc tgcatcaggg gggcaggagg   1260
tacatgatga ttgtggaccc tgccatcagc agctctggcc ctgctggcag ctataggccc   1320
tatgatgagg gcctgaggag gggggtgttt atcactaatg aaactgggca gcccctgatt   1380
ggcaaggtgt ggcctggctc tactgccttc cctgacttca ccaaccccac tgctctggcc   1440
tggtgggagg acatggtggc tgagttccat gaccaggtgc cttttgatgg catgtggatt   1500
gacatgaatg agcccagcaa cttcatcagg ggctctgagg atgggtgccc caataatgag   1560
ctggagaacc cccctatgt gcctggggtg gtggggggca ccctgcaggc tgccactatt   1620
tgtgccagct ctcaccagtt cctgagcacc cactacaacc tgcacaatct gtatggcctg   1680
actgaggcca ttgccagcca cagggccctg gtgaaggcca ggggcactag gccctttgtg   1740
atctctagaa gcacctttgc tggccatggg aggtatgctg gccactggac tggggatgtg   1800
tggagctctt gggagcagct ggccagctct gtgcctgaga tcctgcagtt caacctgctg   1860
ggggtgcccc tggtgggggc tgatgtgtgt ggcttcctgg gcaacacctc tgaagagctg   1920
tgtgtgaggt ggacccagct gggggccttc taccctttca tgaggaacca caacagcctg   1980
ctgagcctgc ctcaggagcc ttactctttc tctgagcctg cccagcaggc catgaggaag   2040
gccctgaccc tgaggtatgc tctgctgccc cacctgtaca ccctgttcca ccaggcccat   2100
gtggctgggg agactgtggc caggcccctg ttcctggagt ttcctaagga tagcagcacc   2160
```

```
tggactgtgg accaccagct gctgtggggg gaggccctgc tgattacccc tgtgctgcag   2220

gctggcaagg ctgaggtgac tggctacttc cccctgggca cttggtatga cctgcagact   2280

gtgcctgtgg aagccctggg cagcctgcct cccccccctg ctgcccccag ggagcctgcc   2340

atccactctg agggccagtg ggtgaccctg cctgcccccc tggacaccat taatgtgcat   2400

ctgagggctg ggtatattat ccccctgcag gggcctgggc tgactaccac tgagagcagg   2460

cagcagccta tggccctggc tgtggctctg actaaggggg gggaggccag gggggagctg   2520

ttctgggatg atggggagag cctggaggtg ctggagaggg ggcctacac ccaggtgatt   2580

ttcctggcca ggaacaacac cattgtgaat gagctggtga gggtgacctc tgagggggct   2640

ggcctgcagc tgcagaaagt gactgtgctg gggtggcca ctgcccccca gcaggtgctg   2700

agcaatgggg tgcctgtgag caacttcacc tacagccctg acaccaaggt gctggatatt   2760

tgtgtgagcc tgctgatggg ggagcagttc ctggtgagct ggtgctgaag atctagagct   2820

gaattcctgc agccaggggg atcagcctct actgtgcctt ctagttgcca gccatctgtt   2880

gtttgcccct cccccttgcc ttccttgacc ctggaaggtg ccactcccac tgtcctttcc   2940

taataaaatg aggaaattgc atcacattgt ctgagtaggt gtcattctat tctggggggt   3000

ggggtggggc aggacagcaa gggggaggat tgggaagaca atagcaggca tgctggggat   3060

gcagtgggct ctatgg                                                   3076
```

<210> SEQ ID NO 12
<211> LENGTH: 3076
<212> TYPE: DNA
<213> ORGANISM: Artificial Sequence
<220> FEATURE:
<223> OTHER INFORMATION: Modified Nucleic Acid

<400> SEQUENCE: 12

```
atggctttcc tgtggctgct gtcttgctgg gccctgctgg ggactacctt tggcctgctg     60

gtgcccaggg aactgtctgg ctctagccca gtgctggagg agacccaccc tgcccaccag    120

cagggggctt ctaggcctgg ccccagggat gcccaggccc accctggcag gccaagggct    180

gtgcccaccc agtgtgatgt gccccccaac tctagatttg attgtgcccc tgataaggcc    240

atcacccagg agcagtgtga ggctaggggc tgctgctaca tccctgctaa gcagggcctg    300

cagggggctc agatgggcca gccctggtgc ttcttccccc ccagctatcc ctcttacaag    360

ctggagaatc tgagcagctc tgagatgggc tacactgcca ccctgaccag gactactccc    420

accttcttcc ccaaggacat cctgaccctg aggctggatg tgatgatgga gactgagaac    480

aggctgcatt tcaccatcaa ggatcctgcc aacaggaggt atgaggtgcc tctggagacc    540

ccccatgtgc acagcagggc tccttctccc ctgtactctg tggagttctc tgaggaaccc    600

tttggggtga ttgtgaggag gcagctggat ggcagggtcc tgctgaacac cactgtggcc    660

cccctgttct ttgctgatca gttcctgcag ctgtccactt ctctgcctag ccagtacatc    720

actgggctgg ctgagcacct gagccctctg atgctgagca cctcttggac taggatcacc    780

ctgtggaaca gggacctggc ccccacccct ggggccaacc tgtatggcag ccaccccttc    840

tatctggccc tggaggatgg gggctctgcc catggggtgt tcctgctgaa tagcaatgct    900

atggatgtgg tgctgcagcc cagccctgcc ctgtcttgga ggagcactgg gggcatcctg    960

gatgtgtaca ttttcctggg gcctgagccc aagtctgtgg tgcagcagta cctggatgtg   1020

gtgggctacc ccttcatgcc tccctactgg ggcctgggct tccacctgtg caggtggggc   1080

tacagctcta ctgccatcac caggcaggtg gtggagaata tgaccagggc ccacttcccc   1140
```

-continued ctggatgtgc agtggaatga cctggactac atggactcta ggagggactt caccttcaat 1200
aaggatggct tcagagactt ccctgccatg gtgcaggagc tgcatcaggg gggcaggagg 1260
tacatgatga ttgtggaccc tgccatcagc tcttctggcc ctgctggctc ttacaggccc 1320
tatgatgagg gcctgaggag gggggtgttc atcaccaatg agactgggca gcccctgatt 1380
gggaaggtgt ggcctggctc tactgccttc cctgacttca ccaatcctac tgccctggcc 1440
tggtgggagg acatggtggc tgagttccat gaccaggtgc cctttgatgg catgtggatt 1500
gacatgaatg agccctctaa tttcatcagg ggctctgagg atggctgccc caacaatgag 1560
ctggagaacc ccccctatgt gcctggggtg gtggggggca ccctgcaggc tgccaccatc 1620
tgtgctagct ctcaccagtt cctgagcacc cactacaatc tgcataacct gtatggcctg 1680
actgaggcca ttgccagcca cagggccctg gtgaaggcta ggggcaccag gccctttgtg 1740
atttctagga gcacttttgc tggccatggc aggtatgctg ggcactggac tggggatgtg 1800
tggtctagct gggagcagct ggcttcttct gtgcctgaga tcctgcagtt caacctgctg 1860
ggggtgcctc tggtgggggc tgatgtgtgt gggttcctgg gcaacacttc tgaggagctg 1920
tgtgtgaggt ggacccagct gggggccttc taccctttca tgaggaacca caacagcctg 1980
ctgagcctgc cccaggagcc ctacagcttc tctgagcctg cccagcaggc catgaggaag 2040
gccctgaccc tgaggtatgc cctgctgccc cacctgtaca ccctgttcca ccaggcccat 2100
gtggctgggg agactgtggc taggcctctg ttcctggagt tccccaagga ctctagcacc 2160
tggactgtgg accaccagct gctgtggggg gaggccctgc tgatcactcc tgtgctgcag 2220
gctgggaagg ctgaggtgac tggctatttc cccctgggca cctggtatga cctgcagact 2280
gtgcctgtgg aggccctggg gagcctgccc ccccccctg ctgcccccag ggagcctgcc 2340
atccactctg agggccagtg ggtgaccctg cctgcccctc tggataccat caatgtgcac 2400
ctgagggctg gctacatcat tcccctgcag ggccctggcc tgaccactac tgagtctagg 2460
cagcagccca tggccctggc tgtggccctg accaaggggg gggaggctag gggggagctg 2520
ttttgggatg atggggagag cctggaggtg ctggagaggg gggcctacac tcaggtgatc 2580
ttcctggcca ggaacaatac cattgtgaat gagctggtga gggtgacctc tgagggggct 2640
ggcctgcagc tgcagaaggt gactgtgctg ggggtggcca ctgcccccca gcaggtgctg 2700
agcaatgggg tgcctgtgag caacttcacc tatagccctg ataccaaggt gctggatatt 2760
tgtgtgagcc tgctgatggg ggagcagttc ctggtgagct ggtgctgaag atctagagct 2820
gaattcctgc agccaggggg atcagcctct actgtgcctt ctagttgcca gccatctgtt 2880
gtttgcccct cccccttgcc ttccttgacc ctggaaggtg ccactcccac tgtcctttcc 2940
taataaaatg aggaaattgc atcacattgt ctgagtaggt gtcattctat tctggggggt 3000
ggggtggggc aggacagcaa gggggaggat tgggaagaca atagcaggca tgctggggat 3060
gcagtgggct ctatgg 3076

<210> SEQ ID NO 13
<211> LENGTH: 3076
<212> TYPE: DNA
<213> ORGANISM: Artificial Sequence
<220> FEATURE:
<223> OTHER INFORMATION: Modified Nucleic Acid

<400> SEQUENCE: 13
atggctttcc tgtggctgct gtcttgttgg gctctgctgg gcaccacctt tggcctgctg 60

-continued

```
gtgcccaggg agctgtctgg cagcagccct gtgctggagg agacccaccc tgctcatcag    120
caggggggcta gcaggcctgg ccccagggat gcccaggctc accctgggag acccagggct    180
gtgcccactc agtgtgatgt gcccccccaac agcaggtttg actgtgctcc tgacaaggct    240
atcacccagg agcagtgtga ggccaggggg tgctgctaca ttcctgctaa gcagggcctg    300
caggggggccc agatgggcca gccctggtgc ttcttccccc cctcttatcc cagctataag    360
ctggagaacc tgagcagctc tgagatgggc tacactgcca ccctgaccag gaccactccc    420
accttctttc ccaaggatat tctgactctg aggctggatg tgatgatgga gactgagaac    480
aggctgcact tcactatcaa ggaccctgcc aataggaggt atgaggtgcc cctggagact    540
cctcatgtgc atagcagggc cccttctcct ctgtattctg tggagttctc tgaggagccc    600
tttggggtga ttgtgaggag gcagctggat ggcagggtgc tgctgaacac cactgtggcc    660
cccctgttct ttgctgacca gttcctgcag ctgagcactt ctctgcccag ccagtacatt    720
actgggctgg ctgagcatct gagccccctg atgctgagca cctcttggac caggatcacc    780
ctgtggaaca gggacctggc ccccactcct ggggctaacc tgtatggctc tcacccctt    840
tacctggccc tggaggatgg gggctctgcc catggggtgt ttctgctgaa cagcaatgct    900
atggatgtgg tgctgcagcc ctctccagcc ctgtcttgga ggagcactgg gggcattctg    960
gatgtgtaca ttttcctggg gcctgaaccc aagtctgtgg tgcagcagta cctggatgtg   1020
gtgggctacc ccttcatgcc cccctattgg gggctggggt ttcacctgtg caggtggggc   1080
tacagcagca ctgccatcac caggcaggtg gtggagaaca tgaccagggc ccatttcccc   1140
ctggatgtgc agtggaatga cctggactac atggatagca ggagggattt caccttcaac   1200
aaggatggct tcagggactt tcctgccatg gtgcaggagc tgcaccaggg gggcaggagg   1260
tatatgatga ttgtggaccc tgctatcagc agctctggcc ctgctggctc ttacaggccc   1320
tatgatgagg gcctgaggag gggggtgttt atcactaatg aaactggcca gcctctgatt   1380
ggcaaggtct ggcctggctc tactgccttc cctgatttta ctaaccccac tgccctggcc   1440
tggtgggagg acatggtggc tgagttccat gatcaggtgc cttttgatgg catgtggatt   1500
gatatgaatg aaccaagcaa cttcatcaga ggctctgagg atggctgccc caacaatgag   1560
ctggagaacc cccctatgt gcctggggtg gtgggggggca ctctgcaggc tgccaccatt   1620
tgtgctagca gccaccagtt cctgagcacc cactacaatc tgcacaacct gtatggcctg   1680
actgaagcca ttgccagcca tagggccctg gtgaaggcca ggggcactag gccttttgtg   1740
atcagcagga gcacttttgc tggccatggc aggtatgctg gccactggac tggggatgtg   1800
tggagcagct gggagcagct ggccagctct gtgcctgaga ttctgcagtt taacctgctg   1860
ggggtgcccc tggtgggggc tgatgtgtgt ggcttcctgg gcaacacctc tgaggagctg   1920
tgtgtgaggt ggacccagct gggggccttt tatcccttca tgaggaacca caacagcctg   1980
ctgagcctgc ctcaggagcc ctactctttc tctgagcctg cccagcaggc catgaggaag   2040
gccctgaccc tgaggtatgc cctgctgccc cacctgtata ccctgttcca ccaggcccat   2100
gtggctgggg agactgtggc caggcccctg ttcctggagt tccccaagga cagcagcacc   2160
tggactgtgg atcatcagct gctgtggggg gaggccctgc tgatcacccc tgtgctgcag   2220
gctggcaagg ctgaggtcac tggctacttc cctctgggca cctggtatga cctgcagact   2280
gtgcctgtgg aggctctggg cagcctgccc cccccccctg ctgctcccag ggagcctgcc   2340
atccactctg agggccagtg ggtgaccctg cctgctcccc tggacaccat caatgtgcac   2400
ctgagggctg gctacattat ccccctgcag ggcccagggc tgactaccac tgagagcaga   2460
```

```
cagcagccca tggctctggc tgtggccctg accaaggggg gggaagctag gggggagctg   2520

ttctgggatg atggggagag cctggaggtg ctggagaggg gggcctatac ccaggtgatc   2580

ttcctggcta ggaacaacac cattgtcaat gagctggtga gggtgacttc tgagggggct   2640

gggctgcagc tgcagaaggt gactgtgctg gggtggcca ctgctcccca gcaggtgctg   2700

agcaatgggg tgcctgtgag caacttcacc tacagccctg acaccaaggt gctggacatc   2760

tgtgtgtctc tgctgatggg ggagcagttc ctggtgagct ggtgctgaag atctagagct   2820

gaattcctgc agccaggggg atcagcctct actgtgcctt ctagttgcca gccatctgtt   2880

gtttgcccct cccccttgcc ttccttgacc ctggaaggtg ccactcccac tgtcctttcc   2940

taataaaatg aggaaattgc atcacattgt ctgagtaggt gtcattctat tctggggggt   3000

ggggtggggc aggacagcaa gggggaggat tgggaagaca atagcaggca tgctggggat   3060

gcagtgggct ctatgg                                                   3076
```

```
<210> SEQ ID NO 14
<211> LENGTH: 3076
<212> TYPE: DNA
<213> ORGANISM: Artificial Sequence
<220> FEATURE:
<223> OTHER INFORMATION: Modified Nucleic Acid

<400> SEQUENCE: 14
```

```
atggccttcc tgtggctgct gtcttgctgg gctctgctgg ggaccacctt tggcctgctg     60

gtccccaggg agctgtctgg ctcttctcct gtcctggagg agacccaccc tgcccaccag    120

cagggggcta gcaggcctgg ccccagggat gcccaggccc accctggcag gcccagggct    180

gtgcccaccc agtgtgatgt gcctcccaac agcaggtttg actgtgcccc tgacaaggcc    240

atcacccagg agcagtgtga ggccaggggc tgctgctata tccctgccaa gcagggcctg    300

cagggggctc agatgggcca gccctggtgc ttctttcccc cctcttatcc tagctataag    360

ctggagaacc tgagcagctc tgagatgggg tacactgcca ccctgaccag gaccaccccc    420

actttcttcc ctaaggacat cctgaccctg aggctggatg tgatgatgga gactgagaat    480

aggctgcact ttactatcaa ggaccctgcc aacaggaggt atgaggtgcc tctggagacc    540

ccccatgtgc attctagggc cccccagcccc ctgtactctg tggagttctc tgaggagccc    600

tttggggtga ttgtgaggag acagctggat ggcagggtcc tgctgaacac cactgtggct    660

cccctgtttt ttgctgacca gttcctgcag ctgagcacca gcctgcccag ccagtacatc    720

actgggctgg ctgagcacct gagcccccctg atgctgagca ccagctggac caggatcacc    780

ctgtggaaca gggatctggc tcctacccct ggggccaacc tgtatggctc tcacccctttt    840

tacctggccc tggaggatgg gggctctgcc catggggtgt tcctgctgaa cagcaatgct    900

atggatgtgg tgctgcagcc cagccctgcc ctgagctgga ggtctactgg gggcatcctg    960

gatgtgtaca tctttctggg gcctgagccc aagtctgtgg tgcagcagta cctggatgtg   1020

gtgggctatc cttttatgcc cccctattgg ggcctgggct tccacctgtg caggtggggc   1080

tacagcagca ctgccatcac cagacaggtg gtggagaaca tgaccagggc ccacttcccc   1140

ctggatgtgc agtggaatga cctggactac atggacagca ggagggactt cacctttaac   1200

aaggatggct ttagggactt ccctgccatg gtgcaggagc tgcatcaggg gggcaggagg   1260

tacatgatga ttgtggaccc agccatcagc agctctgggc ctgctgggtc ttacaggccc   1320

tatgatgagg gcctgaggag gggggtgttc atcaccaatg agactggcca gcccctgatt   1380
```

-continued

```
ggcaaggtgt ggcctgggag cactgccttc cctgatttta ccaaccccac tgccctggcc   1440

tggtgggagg atatggtggc tgagtttcat gaccaggtgc cctttgatgg catgtggatt   1500

gacatgaatg agcccagcaa tttcatcagg ggctctgagg atggctgccc caacaatgag   1560

ctggagaatc ctccctatgt gcctggggtg gtggggggca ccctgcaggc tgccaccatc   1620

tgtgcctcta gccaccagtt cctgagcacc cactataacc tgcataacct gtatggcctg   1680

actgaggcca ttgccagcca tagagccctg gtgaaggcca gagggaccag gccctttgtg   1740

atctctagga gcacctttgc tggccatggc aggtatgctg gccactggac tggggatgtg   1800

tggagctctt gggagcagct ggccagctct gtgccagaga tcctgcagtt caacctgctg   1860

ggggtgcctc tggtgggggc tgatgtgtgt ggcttcctgg gcaatacctc tgaagagctg   1920

tgtgtgaggt ggactcagct gggggccttc tatcccttca tgaggaacca caacagcctg   1980

ctgtctctgc cccaggagcc ctacagcttc tctgagcctg ctcagcaggc tatgaggaag   2040

gccctgaccc tgaggtatgc cctgctgccc catctgtaca ccctgttcca ccaggcccat   2100

gtggctgggg agactgtggc caggcccctg tttctggagt ttcccaagga cagcagcacc   2160

tggactgtgg accatcagct gctgtggggg gaggctctgc tgattacccc tgtgctgcag   2220

gctggcaagg ctgaggtgac tgggtacttc cccctgggga cttggtatga cctgcagact   2280

gtgcctgtgg aagctctggg cagcctgccc ccaccccctg ctgcccctag ggagcctgcc   2340

atccactctg agggccagtg ggtgaccctg cctgcccctc tggacaccat caatgtgcac   2400

ctgagggctg gctatatcat ccccctgcag ggccctgggc tgaccaccac tgagagcagg   2460

cagcagccca tggccctggc tgtggccctg actaaggggg gggaggccag gggggagctg   2520

ttctgggatg atggggagag cctggaggtg ctggagagag ggcctacacc ccaggtgatc   2580

tttctggcca ggaacaacac cattgtgaat gagctggtga gggtgacttc tgagggggct   2640

ggcctgcagc tgcagaaggt gactgtgctg gggtggccca ctgcccccca gcaggtgctg   2700

agcaatgggg tgcctgtgtc taacttcacc tacagccctg atactaaggt gctggatatc   2760

tgtgtgagcc tgctgatggg ggagcagttt ctggtgagct ggtgctgaag atctagagct   2820

gaattcctgc agccaggggg atcagcctct actgtgcctt ctagttgcca gccatctgtt   2880

gtttgcccct cccccttgcc ttccttgacc ctggaaggtg ccactcccac tgtcctttcc   2940

taataaaatg aggaaattgc atcacattgt ctgagtaggt gtcattctat tctggggggt   3000

ggggtggggc aggacagcaa gggggaggat tgggaagaca atagcaggca tgctggggat   3060

gcagtgggct ctatgg                                                   3076
```

```
<210> SEQ ID NO 15
<211> LENGTH: 3076
<212> TYPE: DNA
<213> ORGANISM: Artificial Sequence
<220> FEATURE:
<223> OTHER INFORMATION: Modified Nucleic Acid

<400> SEQUENCE: 15

atggcctttc tgtggctgct gtcctgctgg gccctgctgg ggaccacctt tggcctgctg     60

gtgcccaggg agctgtctgg gagcagccca gtgctggagg agacccaccc tgcccaccag    120

cagggggcca gcaggcctgg ccctagggat gcccaggccc accctggcag gcccagggct    180

gtgcctaccc agtgtgatgt gccacccaat tctaggtttg actgtgctcc tgacaaggcc    240

atcactcagg agcagtgtga agctaggggg tgctgctaca tcccagccaa gcagggcctg    300

cagggggccc agatgggcca gccctggtgc ttcttccccc ccagctaccc tagctacaag    360
```

-continued ctggagaatc tgagcagctc tgagatgggc tacactgcta ccctgaccag gaccactcct 420
accttcttcc ccaaggacat cctgactctg aggctggatg tcatgatgga gactgaaaat 480
aggctgcact tcaccatcaa ggaccctgcc aataggaggt atgaggtgcc tctggagacc 540
ccccatgtgc atagcagggc tcccagcccc ctgtattctg tggagttctc tgaggagccc 600
tttggggtca ttgtgaggag acagctggat gggagggtgc tgctgaacac tactgtggct 660
cccctgttct ttgctgacca gttcctgcag ctgtctacca gcctgcccag ccagtacatc 720
actgggctgg ctgagcatct gagccccctg atgctgagca ccagctggac caggatcact 780
ctgtggaaca gggatctggc ccccactcct ggggccaacc tgtatgggag ccatcccttc 840
tacctggccc tggaggatgg gggctctgcc catggggtgt tcctgctgaa cagcaatgcc 900
atggatgtgg tgctgcagcc tagccctgcc ctgagctgga ggagcactgg gggcatcctg 960
gatgtctaca tcttcctggg gcctgagccc aagtctgtgg tgcagcagta tctggatgtg 1020
gtggggtatc ccttcatgcc cccctactgg ggcctgggct ttcacctgtg caggtggggc 1080
tacagcagca ctgccatcac caggcaggtg gtggagaaca tgaccagggc ccacttccct 1140
ctggatgtgc agtggaatga cctggactat atggattcta ggagagactt tacttttaac 1200
aaggatggct tcagggattt ccctgccatg gtgcaggagc tgcaccaggg gggcaggagg 1260
tacatgatga ttgtggaccc tgctattagc agctctggcc ctgctgggtc ttacaggcct 1320
tatgatgagg gcctgaggag gggggtgttc atcaccaatg agactggcca gcccctgatt 1380
ggcaaggtgt ggcctggcag cactgccttc cctgacttca ccaaccccac tgccctggcc 1440
tggtgggagg acatggtggc tgagttccat gaccaggtgc cctttgatgg gatgtggatt 1500
gacatgaatg agccctctaa cttcatcagg gggtctgagg atggctgccc caacaatgag 1560
ctggagaacc cccccctatgt gcctggggtg gtgggggggca ctctgcaggc tgccactatc 1620
tgtgcttctt ctcaccagtt tctgagcacc cactataatc tgcacaacct gtatggcctg 1680
actgaggcca ttgccagcca tagggccctg gtgaaggcca ggggcaccag gcccttttgtg 1740
atcagcaggt ctacctttgc tggccatggc aggtatgctg gccactggac tggggatgtg 1800
tggtcttctt gggagcagct ggccagctct gtgcctgaga tcctgcagtt caacctgctg 1860
ggggtgcctc tggtgggggc tgatgtgtgt ggctttctgg gcaacacctc tgaggagctg 1920
tgtgtgaggt ggacccagct gggggccttt taccccttca tgaggaacca caatagcctg 1980
ctgagcctgc cccaggagcc ttactctttc tctgagcctg cccagcaggc catgaggaag 2040
gccctgactc tgaggtatgc cctgctgccc catctgtata ccctgtttca ccaggcccat 2100
gtggctgggg agactgtggc taggcctctg tttctggagt tccctaagga ctctagcacc 2160
tggactgtgg accaccagct gctgtggggg gaggccctgc tgatcacccc tgtgctgcag 2220
gctggcaagg ctgaggtgac tggctacttc cccctgggca cctggtatga cctgcagact 2280
gtgcctgtgg aggccctggg gagcctgcct cccccccctg ctgcccccag ggagcctgcc 2340
attcattctg agggccagtg ggtgaccctg cctgcccctc tggacaccat caatgtgcac 2400
ctgagggctg ggtacatcat ccccctgcag ggccctggcc tgaccaccac tgagagcagg 2460
cagcagccca tggccctggc tgtggctctg accaaggggg gggaggccag gggggagctg 2520
ttctgggatg atggggagtc tctggaggtg ctggagaggg gggcctacac ccaggtgatc 2580
tttctggcca ggaacaatac tattgtgaat gagctggtga gggtgacctc tgagggggct 2640
ggcctgcagc tgcagaaggt gactgtgctg gggggtggcca ctgcccccca gcaggtcctg 2700
agcaatgggg tgcctgtgag caacttcacc tactctcctg acaccaaggt gctggacatt 2760
tgtgtgtctc tgctgatggg ggagcagttc ctggtgagct ggtgctgaag atctagagct 2820
gaattcctgc agccaggggg atcagcctct actgtgcctt ctagttgcca gccatctgtt 2880
gtttgcccct cccccttgcc ttccttgacc ctggaaggtg ccactcccac tgtcctttcc 2940
taataaaatg aggaaattgc atcacattgt ctgagtaggt gtcattctat tctggggggt 3000
ggggtggggc aggacagcaa gggggaggat tgggaagaca atagcaggca tgctggggat 3060
gcagtgggct ctatgg 3076

<210> SEQ ID NO 16
<211> LENGTH: 4730
<212> TYPE: DNA
<213> ORGANISM: Artificial Sequence
<220> FEATURE:
<223> OTHER INFORMATION: Modified Nucleic Acid

<400> SEQUENCE: 16
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggcctag taggctcaga ggcacacagg agtttctggg 180
ctcaccctgc cccttccaa cccctcagtt cccatcctcc agcagctgtt tgtgtgctgc 240
ctctgaagtc cacactgaac aaacttcagc ctactcatgt ccctaaaatg ggcaaacatt 300
gcaagcagca aacagcaaac acacagccct ccctgcctgc tgaccttgga gctggggcag 360
aggtcagaga cctctctggg cccatgccac ctccaacatc cactcgaccc cttggaattt 420
cggtggagag gagcagaggt tgtcctggcg tggtttaggt agtgtgagag gggtacccgg 480
ggatcttgct accagtggaa cagccactaa ggattctgca gtgagagcag agggccagct 540
aagtggtact ctcccagaga ctgtctgact cacgccaccc cctccacctt ggacacagga 600
cgctgtggtt tctgagccag gtacaatgac tcctttcggt aagtgcagtg gaagctgtac 660
actgcccagg caaagcgtcc gggcagcgta ggcgggcgac tcagatccca gccagtggac 720
ttagcccctg tttgctcctc cgataactgg ggtgaccttg gttaatattc accagcagcc 780
tcccccgttg cccctctgga tccactgctt aaatacggac gaggacaggg ccctgtctcc 840
tcagcttcag gcaccaccac tgacctggga cagtgaatac cactttcaca atctgctagc 900
gtttaaacga tcctgagaac ttcagggtga gtctatggga cccttgatgt tttctttccc 960
cttcttttct atggttaagt tcatgtcata ggaaggggag aagtaacagg gtacacatat 1020
tgaccaaatc agggtaattt tgcatttgta attttaaaaa atgctttctt cttttaatat 1080 actttttgt ttatcttatt tctaatactt tccctaatct ctttctttca gggcaataat 1140
gatacaatgt atcatgcctc tttgcaccat tctaaagaat aacagtgata atttctgggt 1200
taaggcaata gcaatatttc tgcatataaa tatttctgca tataaattgt aactgatgta 1260
agaggtttca tattgctaat agcagctaca atccagctac cattctgctt ttattttctg 1320
gttgggataa ggctggatta ttctgagtcc aagctaggcc cttttgctaa tcttgttcat 1380
acctcttatc ttcctcccac agctcctggg caacctgctg gtctctctgc tggcccatca 1440
ctttggcaaa gcacgcgtgc caccatggcc tttctgtggc tgctgtcctg ctgggccctg 1500
ctggggacca cctttggcct gctggtgccc agggagctgt ctgggagcag cccagtgctg 1560
gaggagaccc accctgccca ccagcagggg gccagcaggc ctggccctag ggatgcccag 1620
gcccaccctg gcaggcccag ggctgtgcct acccagtgtg atgtgccacc caattctagg 1680

```
tttgactgtg ctcctgacaa ggccatcact caggagcagt gtgaagctag ggggtgctgc   1740
tacatcccag ccaagcaggg cctgcagggg gcccagatgg gccagccctg gtgcttcttc   1800
ccccccagct accctagcta caagctggag aatctgagca gctctgagat gggctacact   1860
gctaccctga ccaggaccac tcctaccttc ttccccaagg acatcctgac tctgaggctg   1920
gatgtcatga tggagactga aaataggctg cacttcacca tcaaggaccc tgccaatagg   1980
aggtatgagg tgcctctgga gaccccccat gtgcatagca gggctcccag cccccctgtat   2040
tctgtggagt tctctgagga gccctttggg gtcattgtga ggagacagct ggatgggagg   2100
gtgctgctga acactactgt ggctcccctg ttctttgctg accagttcct gcagctgtct   2160
accagcctgc ccagccagta catcactggg ctggctgagc atctgagccc cctgatgctg   2220
agcaccagct ggaccaggat cactctgtgg aacagggatc tggcccccac tcctggggcc   2280
aacctgtatg ggagccatcc cttctacctg gccctggagg atgggggctc tgcccatggg   2340
gtgttcctgc tgaacagcaa tgccatggat gtggtgctgc agcctagccc tgccctgagc   2400
tggaggagca ctgggggcat cctggatgtc tacatcttcc tggggcctga gcccaagtct   2460
gtggtgcagc agtatctgga tgtggtgggg tatcccttca tgccccccta ctggggcctg   2520
ggctttcacc tgtgcaggtg ggctacagc agcactgcca tcaccaggca ggtggtggag   2580
aacatgacca gggcccactt ccctctggat gtgcagtgga atgacctgga ctatatggat   2640
tctaggagag actttacttt taacaaggat ggcttcaggg atttccctgc catggtgcag   2700
gagctgcacc agggggggcag gaggtacatg atgattgtgg accctgctat tagcagctct   2760
ggccctgctg ggtcttacag gccttatgat gagggcctga ggaggggggt gttcatcacc   2820
aatgagactg gccagcccct gattggcaag gtgtggcctg gcagcactgc cttccctgac   2880
ttcaccaacc ccactgccct ggcctggtgg gaggacatgg tggctgagtt ccatgaccag   2940
gtgccctttg atgggatgtg gattgacatg aatgagccct ctaacttcat caggggggtct   3000
gaggatggct gccccaacaa tgagctggag aacccccct atgtgcctgg ggtggtgggg   3060
ggcactctgc aggctgccac tatctgtgct tcttctcacc agtttctgag cacccactat   3120
aatctgcaca acctgtatgg cctgactgag gccattgcca gccatagggc cctggtgaag   3180
gccaggggca ccaggccctt tgtgatcagc aggtctacct ttgctggcca tggcaggtat   3240
gctggccact ggactgggga tgtgtggtct tcttgggagc agctggccag ctctgtgcct   3300
gagatcctgc agttcaacct gctgggggtg cctctggtgg gggctgatgt gtgtggcttt   3360
ctgggcaaca cctctgagga gctgtgtgtg aggtggaccc agctgggggc cttttacccc   3420
ttcatgagga accacaatag cctgctgagc ctgccccagg agccttactc tttctctgag   3480
cctgcccagc aggccatgag gaaggccctg actctgaggt atgccctgct gccccatctg   3540
tataccctgt ttcaccaggc ccatgtggct ggggagactg tggctaggcc tctgtttctg   3600
gagttcccta aggactctag cacctggact gtggaccacc agctgctgtg gggggaggcc   3660
ctgctgatca cccctgtgct gcaggctggc aaggctgagg tgactggcta cttcccccctg   3720
ggcacctggt atgacctgca gactgtgcct gtggaggccc tggggagcct gcctccccccc   3780
cctgctgccc ccagggagcc tgccattcat tctgagggcc agtgggtgac cctgcctgcc   3840
cctctggaca ccatcaatgt gcacctgagg gctgggtaca tcatcccccct gcagggccct   3900
ggcctgacca ccactgagag caggcagcag cccatggccc tggctgtggc tctgaccaag   3960
ggggggggagg ccagggggga gctgttctgg gatgatgggg agtctctgga ggtgctggag   4020
```

```
agggggggcct acacccaggt gatctttctg gccaggaaca atactattgt gaatgagctg   4080

gtgagggtga cctctgaggg ggctggcctg cagctgcaga aggtgactgt gctgggggtg   4140

gccactgccc cccagcaggt cctgagcaat ggggtgcctg tgagcaactt cacctactct   4200

cctgacacca aggtgctgga catttgtgtg tctctgctga tgggggagca gttcctggtg   4260

agctggtgct gaagatctag agctgaattc ctgcagccag gggatcagc ctctactgtg   4320

ccttctagtt gccagccatc tgttgtttgc ccctcccccct tgccttcctt gaccctggaa   4380

ggtgccactc ccactgtcct ttcctaataa aatgaggaaa ttgcatcaca ttgtctgagt   4440

aggtgtcatt ctattctggg gggtggggtg gggcaggaca gcaaggggga ggattgggaa   4500

gacaatagca ggcatgctgg ggatgcagtg ggctctatgg cttctgaggc agaaagaacc   4560

agctggggct cgagatccac tagggccgca ggaacccta gtgatggagt tggccactcc   4620

ctctctgcgc gctcgctcgc tcactgaggc cgggcgacca aaggtcgccc gacgcccggg   4680

ctttgcccgg gcggcctcag tgagcgagcg agcgcgcagc tgcctgcagg              4730
```

<210> SEQ ID NO 17
<211> LENGTH: 4701
<212> TYPE: DNA
<213> ORGANISM: Artificial Sequence
<220> FEATURE:
<223> OTHER INFORMATION: Modified Nucleic Acid

<400> SEQUENCE: 17

```
cctgcaggca gctgcgcgct cgctcgctca ctgaggccgc ccgggcaaag cccgggcgtc     60

gggcgacctt tggtcgcccg gcctcagtga gcgagcgagc gcgcagagag ggagtggcca    120

actccatcac taggggttcc tgcggcctag taggctcaga ggcacacagg agtttctggg    180

ctcaccctgc cccctccaa cccctcagtt cccatcctcc agcagctgtt tgtgtgctgc    240

ctctgaagtc cacactgaac aaacttcagc ctactcatgt ccctaaaatg ggcaaacatt    300

gcaagcagca aacagcaaac acacagccct ccctgcctgc tgaccttgga gctggggcag    360

aggtcagaga cctctctggg cccatgccac ctccaacatc cactcgaccc cttggaattt    420

cggtggagag gagcagaggt tgtcctggcg tggtttaggt agtgtgagag gggtacccgg    480

ggatcttgct accagtggaa cagccactaa ggattctgca gtgagagcag agggccagct    540

aagtggtact ctcccagaga ctgtctgact cacgccaccc cctccacctt ggacacagga    600

cgctgtggtt tctgagccag gtacaatgac tcctttcggt aagtgcagtg gaagctgtac    660

actgcccagg caaagcgtcc gggcagcgta ggcgggcgac tcagatccca gccagtggac    720

ttagcccctg tttgctcctc cgataactgg ggtgaccttg gttaatattc accagcagcc    780

tcccccgttg cccctctgga tccactgctt aaatacggac gaggacaggg ccctgtctcc    840

tcagcttcag gcaccaccac tgacctggga cagtgaatag atcctgagaa cttcagggtg    900

agtctatggg acccttgatg ttttctttcc ccttcttttc tatggttaag ttcatgtcat    960

aggaagggga gaagtaacag ggtacacata ttgaccaaat cagggtaatt ttgcatttgt   1020

aattttaaaa aatgctttct tcttttaata tactttttttg tttatcttat ttctaatact   1080

ttccctaatc tctttctttc agggcaataa tgatacaatg tatcatgcct ctttgcacca   1140

ttctaaagaa taacagtgat aatttctggg ttaaggcaat agcaatattt ctgcatataa   1200

atatttctgc atataaattg taactgatgt aagaggtttc atattgctaa tagcagctac   1260

aatccagcta ccattctgct tttattttct ggttgggata aggctggatt attctgagtc   1320

caagctaggc ccttttgcta atcttgttca tacctcttat cttcctccca cagctcctgg   1380
```

-continued

```
gcaacctgct ggtctctctg ctggcccatc actttggcaa agcacgcgtg ccaccatggc   1440
ctttctgtgg ctgctgtcct gctgggccct gctggggacc acctttggcc tgctggtgcc   1500
cagggagctg tctgggagca gcccagtgct ggaggagacc caccctgccc accagcaggg   1560
ggccagcagg cctggcccta gggatgccca ggcccaccct ggcaggccca gggctgtgcc   1620
tacccagtgt gatgtgccac ccaattctag gtttgactgt gctcctgaca aggccatcac   1680
tcaggagcag tgtgaagcta gggggtgctg ctacatccca gccaagcagg gcctgcaggg   1740
ggcccagatg ggccagccct ggtgcttctt cccccccagc taccctagct acaagctgga   1800
gaatctgagc agctctgaga tgggctacac tgctaccctg accaggacca ctcctacctt   1860
cttccccaag gacatcctga ctctgaggct ggatgtcatg atggagactg aaaataggct   1920
gcacttcacc atcaaggacc ctgccaatag gaggtatgag gtgcctctgg agaccccccca   1980
tgtgcatagc agggctccca gcccccctgta ttctgtggag ttctctgagg agccctttgg   2040
ggtcattgtg aggagacagc tggatgggag ggtgctgctg aacactactg tggctcccct   2100
gttctttgct gaccagttcc tgcagctgtc taccagcctg cccagccagt acatcactgg   2160
gctggctgag catctgagcc ccctgatgct gagcaccagc tggaccagga tcactctgtg   2220
gaacagggat ctggccccca ctcctggggc caacctgtat gggagccatc ccttctacct   2280
ggccctggag gatgggggct ctgcccatgg ggtgttcctg ctgaacagca atgccatgga   2340
tgtggtgctg cagcctagcc ctgccctgag ctggaggagc actgggggca tcctggatgt   2400
ctacatcttc ctggggcctg agcccaagtc tgtggtgcag cagtatctgg atgtggtggg   2460
gtatcccttc atgccccccct actggggcct gggctttcac ctgtgcaggt ggggctacag   2520
cagcactgcc atcaccaggc aggtggtgga gaacatgacc agggcccact tccctctgga   2580
tgtgcagtgg aatgacctgg actatatgga ttctaggaga gactttactt ttaacaagga   2640
tggcttcagg gatttccctg ccatggtgca ggagctgcac caggggggca ggaggtacat   2700
gatgattgtg gaccctgcta ttagcagctc tggccctgct gggtcttaca ggccttatga   2760
tgagggcctg aggagggggg tgttcatcac caatgagact ggccagcccc tgattggcaa   2820
ggtgtggcct ggcagcactg ccttccctga cttcaccaac cccactgccc tggcctggtg   2880
ggaggacatg gtggctgagt tccatgacca ggtgcccttt gatgggatgt ggattgacat   2940
gaatgagccc tctaacttca tcagggggtc tgaggatggc tgccccaaca atgagctgga   3000
gaaccccccc tatgtgcctg ggtggtgggg gggcactctg caggctgcca ctatctgtgc   3060
ttcttctcac cagtttctga gcacccacta taatctgcac aacctgtatg gcctgactga   3120
ggccattgcc agccataggg ccctggtgaa ggccaggggc accaggccct ttgtgatcag   3180
caggtctacc tttgctggcc atggcaggta tgctggccac tggactgggg atgtgtggtc   3240
ttcttgggag cagctggcca gctctgtgcc tgagatcctg cagttcaacc tgctgggggt   3300
gcctctggtg gggggctgatg tgtgtggctt tctgggcaac acctctgagg agctgtgtgt   3360
gaggtggacc cagctggggg ccttttaccc cttcatgagg aaccacaata gcctgctgag   3420
cctgccccag gagccttact ctttctctga gcctgcccag caggccatga ggaaggccct   3480
gactctgagg tatgccctgc tgccccatct gtataccctg tttcaccagg cccatgtggc   3540
tggggagact gtggctaggc ctctgtttct ggagttccct aaggactcta gcacctggac   3600
tgtggaccac cagctgctgt ggggggaggc cctgctgatc acccctgtgc tgcaggctgg   3660
caaggctgag gtgactggct acttccccct gggcacctgg tatgacctgc agactgtgcc   3720
```

```
tgtggaggcc ctggggagcc tgcctccccc ccctgctgcc cccagggagc ctgccattca   3780
ttctgagggc cagtgggtga ccctgcctgc ccctctggac accatcaatg tgcacctgag   3840
ggctgggtac atcatccccc tgcagggccc tggcctgacc accactgaga gcaggcagca   3900
gcccatggcc ctggctgtgg ctctgaccaa gggggggag gccagggggg agctgttctg   3960
ggatgatggg gagtctctgg aggtgctgga gaggggggcc tacacccagg tgatctttct   4020
ggccaggaac aatactattg tgaatgagct ggtgagggtg acctctgagg gggctggcct   4080
gcagctgcag aaggtgactg tgctgggggt ggccactgcc ccccagcagg tcctgagcaa   4140
tggggtgcct gtgagcaact tcacctactc tcctgacacc aaggtgctgg acatttgtgt   4200
gtctctgctg atgggggagc agttcctggt gagctggtgc tgaagatcta gagctgaatt   4260
cctgcagcca gggggatcag cctctactgt gccttctagt tgccagccat ctgttgtttg   4320
cccctccccc ttgccttcct tgaccctgga aggtgccact cccactgtcc tttcctaata   4380
aaatgaggaa attgcatcac attgtctgag taggtgtcat tctattctgg ggggtggggt   4440
ggggcaggac agcaaggggg aggattggga agacaatagc aggcatgctg gggatgcagt   4500
gggctctatg gcttctgagg cagaaagaac cagctggggc tcgagatcca ctagggccgc   4560
aggaacccct agtgatggag ttggccactc cctctctgcg cgctcgctcg ctcactgagg   4620
ccgggcgacc aaaggtcgcc cgacgcccgg gctttgcccg ggcggcctca gtgagcgagc   4680
gagcgcgcag ctgcctgcag g                                              4701
```

<210> SEQ ID NO 18
<211> LENGTH: 4701
<212> TYPE: DNA
<213> ORGANISM: Artificial Sequence
<220> FEATURE:
<223> OTHER INFORMATION: Modified Nucleic Acid

<400> SEQUENCE: 18

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggcctag taggctcaga ggcacacagg agtttctggg    180
ctcaccctgc cccccttccaa cccctcagtt cccatcctcc agcagctgtt tgtgtgctgc   240
ctctgaagtc cacactgaac aaacttcagc ctactcatgt ccctaaaatg ggcaaacatt    300
gcaagcagca aacagcaaac acacagccct ccctgcctgc tgaccttgga gctggggcag    360
aggtcagaga cctctctggg cccatgccac ctccaacatc cactcgaccc cttggaattt    420
cggtggagag gagcagaggt tgtcctggcg tggtttaggt agtgtgagag gggtacccgg    480
ggatcttgct accagtggaa cagccactaa ggattctgca gtgagagcag agggccagct    540
aagtggtact ctcccagaga ctgtctgact cacgccaccc cctccacctt ggacacagga    600
cgctgtggtt tctgagccag gtacaatgac tcctttcggt aagtgcagtg gaagctgtac    660
actgcccagg caaagcgtcc gggcagcgta ggcgggcgac tcagatccca gccagtggac    720
ttagcccctg tttgctcctc cgataactgg ggtgaccttg gttaatattc accagcagcc    780
tcccccgttg cccctctgga tccactgctt aaatacggac gaggacaggg ccctgtctcc    840
tcagcttcag gcaccaccac tgacctggga cagtgaatag atcctgagaa cttcagggtg    900
agtctatggg acccttgatg ttttctttcc ccttcttttc tatggttaag ttcatgtcat    960
aggaagggga gaagtaacag ggtacacata ttgaccaaat cagggtaatt ttgcatttgt   1020
aattttaaaa aatgctttct tcttttaata tactttttttg tttatcttat ttctaatact  1080
```

-continued

```
ttccctaatc tctttctttc agggcaataa tgatacaatg tatcatgcct ctttgcacca   1140
ttctaaagaa taacagtgat aatttctggg ttaaggcaat agcaatattt ctgcatataa   1200
atatttctgc atataaattg taactgatgt aagaggtttc atattgctaa tagcagctac   1260
aatccagcta ccattctgct tttattttct ggttgggata aggctggatt attctgagtc   1320
caagctaggc ccttttgcta atcttgttca tacctcttat cttcctccca cagctcctgg   1380
gcaacctgct ggtctctctg ctggcccatc actttggcaa agcacgcgtg ccaccatggc   1440
tttcctgtgg ctgctgtctt gttgggctct gctgggcacc acctttggcc tgctggtgcc   1500
cagggagctg tctggcagca gccctgtgct ggaggagacc caccctgctc atcagcaggg   1560
ggctagcagg cctggcccca gggatgccca ggctcaccct gggagaccca gggctgtgcc   1620
cactcagtgt gatgtgcccc ccaacagcag gtttgactgt gctcctgaca aggctatcac   1680
ccaggagcag tgtgaggcca gggggtgctg ctacattcct gctaagcagg gcctgcaggg   1740
ggcccagatg ggccagccct ggtgcttctt ccccccctct tatcccagct ataagctgga   1800
gaacctgagc agctctgaga tgggctacac tgccaccctg accaggacca ctcccacctt   1860
ctttcccaag gatattctga ctctgaggct ggatgtgatg atggagactg agaacaggct   1920
gcacttcact atcaaggacc ctgccaatag gaggtatgag gtgcccctgg agactcctca   1980
tgtgcatagc agggcccctt ctcctctgta ttctgtggag ttctctgagg agccctttgg   2040
ggtgattgtg aggaggcagc tggatggcag ggtgctgctg aacaccactg tggccccccct   2100
gttctttgct gaccagttcc tgcagctgag cacttctctg cccagccagt acattactgg   2160
gctggctgag catctgagcc ccctgatgct gagcacctct tggaccagga tcaccctgtg   2220
gaacagggac ctggccccca ctcctggggc taacctgtat ggctctcacc ccttttacct   2280
ggccctggag gatgggggct ctgcccatgg ggtgtttctg ctgaacagca atgctatgga   2340
tgtggtgctg cagccctctc cagccctgtc ttggaggagc actgggggca ttctggatgt   2400
gtacattttc ctggggcctg aacccaagtc tgtggtgcag cagtacctgg atgtggtggg   2460
ctaccccttc atgcccccct attgggggct ggggtttcac ctgtgcaggt ggggctacag   2520
cagcactgcc atcaccaggc aggtggtgga gaacatgacc agggcccatt tcccccctgga   2580
tgtgcagtgg aatgacctgg actacatgga tagcaggagg gatttcacct tcaacaagga   2640
tggcttcagg gactttcctg ccatggtgca ggagctgcac caggggggca ggaggtatat   2700
gatgattgtg gaccctgcta tcagcagctc tggccctgct ggctcttaca ggccctatga   2760
tgagggcctg aggagggggg tgtttatcac taatgaaact ggccagcctc tgattggcaa   2820
ggtctggcct ggctctactg ccttccctga ttttactaac ccccactgccc tggcctggtg   2880
ggaggacatg gtggctgagt tccatgatca ggtgcctttt gatggcatgt ggattgatat   2940
gaatgaacca agcaacttca tcagaggctc tgaggatggc tgccccaaca atgagctgga   3000
gaaccccccc tatgtgcctg ggtggtgggg gggcactctg caggctgcca ccatttgtgc   3060
tagcagccac cagttcctga gcacccacta caatctgcac aacctgtatg gcctgactga   3120
agccattgcc agccataggg ccctggtgaa ggccaggggc actaggcctt ttgtgatcag   3180
caggagcact tttgctggcc atggcaggta tgctggccac tggactgggg atgtgtggag   3240
cagctgggag cagctggcca gctctgtgcc tgagattctg cagtttaacc tgctgggggt   3300
gcccctggtg gggggctgatg tgtgtggcttt cctgggcaac acctctgagg agctgtgtgt   3360
gaggtggacc cagctggggg ccttttatcc cttcatgagg aaccacaaca gcctgctgag   3420
```

```
cctgcctcag gagccctact ctttctctga gcctgcccag caggccatga ggaaggccct   3480
gaccctgagg tatgccctgc tgccccacct gtataccctg ttccaccagg cccatgtggc   3540
tggggagact gtggccaggc ccctgttcct ggagttcccc aaggacagca gcacctggac   3600
tgtggatcat cagctgctgt ggggggaggc cctgctgatc accccctgtgc tgcaggctgg  3660
caaggctgag gtcactggct acttccctct gggcacctgg tatgacctgc agactgtgcc   3720
tgtggaggct ctgggcagcc tgcccccccc ccctgctgct cccagggagc ctgccatcca   3780
ctctgagggc cagtgggtga ccctgcctgc tcccctggac accatcaatg tgcacctgag   3840
ggctggctac attatccccc tgcagggccc agggctgact accactgaga gcagacagca   3900
gcccatggct ctggctgtgg ccctgaccaa gggggggggaa gctagggggg agctgttctg  3960
ggatgatggg gagagcctgg aggtgctgga gaggggggcc tatacccagg tgatcttcct   4020
ggctaggaac aacaccattg tcaatgagct ggtgagggtg acttctgagg gggctgggct   4080
gcagctgcag aaggtgactg tgctgggggt ggccactgct ccccagcagg tgctgagcaa   4140
tggggtgcct gtgagcaact tcacctacag ccctgacacc aaggtgctgg acatctgtgt   4200
gtctctgctg atgggggagc agttcctggt gagctggtgc tgaagatcta gagctgaatt   4260
cctgcagcca gggggatcag cctctactgt gccttctagt tgccagccat ctgttgtttg   4320
cccctccccc ttgccttcct tgaccctgga aggtgccact cccactgtcc tttcctaata   4380
aaatgaggaa attgcatcac attgtctgag taggtgtcat tctattctgg ggggtggggt   4440
ggggcaggac agcaaggggg aggattggga agacaatagc aggcatgctg gggatgcagt   4500
gggctctatg gcttctgagg cagaaagaac cagctggggc tcgagatcca ctagggccgc   4560
aggaacccct agtgatggag ttggccactc cctctctgcg cgctcgctcg ctcactgagg   4620
ccgggcgacc aaaggtcgcc cgacgcccgg gctttgcccg ggcggcctca gtgagcgagc   4680
gagcgcgcag ctgcctgcag g                                             4701
```

```
<210> SEQ ID NO 19
<211> LENGTH: 4701
<212> TYPE: DNA
<213> ORGANISM: Artificial Sequence
<220> FEATURE:
<223> OTHER INFORMATION: Modified Nucleic Acid

<400> SEQUENCE: 19
```

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggcctag taggctcaga ggcacacagg agtttctggg    180
ctcaccctgc cccttccaa ccccctcagtt cccatcctcc agcagctgtt tgtgtgctgc    240
ctctgaagtc cacactgaac aaacttcagc ctactcatgt ccctaaaatg ggcaaacatt    300
gcaagcagca aacagcaaac acacagccct ccctgcctgc tgaccttgga gctggggcag    360
aggtcagaga cctctctggg cccatgccac ctccaacatc cactcgaccc cttggaattt    420
cggtggagag gagcagaggt tgtcctggcg tggtttaggt agtgtgagag gggtacccgg    480
ggatcttgct accagtggaa cagccactaa ggattctgca gtgagagcag agggccagct    540
aagtggtact ctcccagaga ctgtctgact cacgccaccc cctccacctt ggacacagga    600
cgctgtggtt tctgagccag gtacaatgac tcctttcggt aagtgcagtg gaagctgtac    660
actgcccagg caaagcgtcc gggcagcgta ggcgggcgac tcagatccca gccagtggac    720
ttagcccctg tttgctcctc cgataactgg ggtgaccttg gttaatattc accagcagcc    780
```

```
tcccccgttg cccctctgga tccactgctt aaatacggac gaggacaggg ccctgtctcc    840
tcagcttcag gcaccaccac tgacctggga cagtgaatag atcctgagaa cttcagggtg    900
agtctatggg acccttgatg ttttctttcc ccttcttttc tatggttaag ttcatgtcat    960
aggaagggga gaagtaacag ggtacacata ttgaccaaat cagggtaatt ttgcatttgt   1020
aattttaaaa aatgctttct tcttttaata tactttttg tttatcttat ttctaatact    1080
ttccctaatc tctttctttc agggcaataa tgatacaatg tatcatgcct ctttgcacca   1140
ttctaaagaa taacagtgat aatttctggg ttaaggcaat agcaatattt ctgcatataa   1200
atatttctgc atataaattg taactgatgt aagaggtttc atattgctaa tagcagctac   1260
aatccagcta ccattctgct tttattttct ggttgggata aggctggatt attctgagtc   1320
caagctaggc ccttttgcta atcttgttca tacctcttat cttcctccca cagctcctgg   1380
gcaacctgct ggtctctctg ctggcccatc actttggcaa agcacgcgtg ccaccatggc   1440
cttcctgtgg ctgctgtctt gctgggctct gctggggacc acctttggcc tgctggtccc   1500
cagggagctg tctggctctt ctcctgtcct ggaggagacc caccctgccc accagcaggg   1560
ggctagcagg cctggcccca gggatgccca ggcccacct ggcaggccca gggctgtgcc    1620
cacccagtgt gatgtgcctc ccaacagcag gtttgactgt gcccctgaca aggccatcac   1680
ccaggagcag tgtgaggcca ggggctgctg ctatatccct gccaagcagg gcctgcaggg   1740
ggctcagatg ggccagccct ggtgcttctt tcccccctct tatcctagct ataagctgga   1800
gaacctgagc agctctgaga tggggtacac tgccaccctg accaggacca cccccacttt   1860
cttccctaag gacatcctga ccctgaggct ggatgtgatg atggagactg agaataggct   1920
gcactttact atcaaggacc ctgccaacag gaggtatgag gtgcctctgg agaccccca    1980
tgtgcattct agggccccca gccccctgta ctctgtggag ttctctgagg agccctttgg   2040
ggtgattgtg aggagacagc tggatggcag ggtcctgctg aacaccactg tggctcccct   2100
gtttttgct gaccagttcc tgcagctgag caccagcctg cccagccagt acatcactgg    2160
gctggctgag cacctgagcc ccctgatgct gagcaccagc tggaccagga tcaccctgtg   2220
gaacagggat ctggctccta cccctggggc caacctgtat ggctctcacc ccttttacct   2280
ggccctggag gatgggggct ctgcccatgg ggtgttcctg ctgaacagca atgctatgga   2340
tgtggtgctg cagcccagcc ctgccctgag ctggaggtct actgggggca tcctggatgt   2400
gtacatcttt ctggggcctg agcccaagtc tgtggtgcag cagtacctgg atgtggtggg   2460
ctatcctttt atgcccccct attggggcct gggcttccac ctgtgcaggt ggggctacag   2520
cagcactgcc atcaccagac aggtggtgga gaacatgacc agggcccact tcccccctgga   2580
tgtgcagtgg aatgacctgg actacatgga cagcaggagg gacttcacct ttaacaagga   2640
tggctttagg gacttccctg ccatggtgca ggagctgcat caggggggca ggaggtacat   2700
gatgattgtg gacccagcca tcagcagctc tgggcctgct gggtcttaca ggccctatga   2760
tgagggcctg aggagggggg tgttcatcac caatgagact ggccagcccc tgattggcaa   2820
ggtgtggcct gggagcactg ccttccctga ttttaccaac cccactgccc tggcctggtg   2880
ggaggatatg gtggctgagt ttcatgacca ggtgcccttt gatggcatgt ggattgacat   2940
gaatgagccc agcaatttca tcaggggctc tgaggatggc tgccccaaca atgagctgga   3000
gaatcctccc tatgtgcctg ggtggtgggg gggcaccctg caggctgcca ccatctgtgc   3060
ctctagccac cagttcctga gcacccacta taacctgcat aacctgtatg gcctgactga   3120
```

ggccattgcc agccatagag ccctggtgaa ggccagaggg accaggccct ttgtgatctc 3180
taggagcacc tttgctggcc atggcaggta tgctggccac tggactgggg atgtgtggag 3240
ctcttgggag cagctggcca gctctgtgcc agagatcctg cagttcaacc tgctgggggt 3300
gcctctggtg gggctgatg tgtgtggctt cctgggcaat acctctgaag agctgtgtgt 3360
gaggtggact cagctggggg ccttctatcc cttcatgagg aaccacaaca gcctgctgtc 3420
tctgccccag gagccctaca gcttctctga gcctgctcag caggctatga ggaaggccct 3480
gaccctgagg tatgccctgc tgccccatct gtacaccctg ttccaccagg cccatgtggc 3540
tggggagact gtggccaggc ccctgtttct ggagtttccc aaggacagca gcacctggac 3600
tgtggaccat cagctgctgt ggggggaggc tctgctgatt acccctgtgc tgcaggctgg 3660
caaggctgag gtgactgggt acttcccccct ggggacttgg tatgacctgc agactgtgcc 3720
tgtggaagct ctgggcagcc tgcccccacc ccctgctgcc cctagggagc ctgccatcca 3780
ctctgagggc cagtgggtga ccctgcctgc ccctctggac accatcaatg tgcacctgag 3840
ggctggctat atcatccccc tgcagggccc tgggctgacc accactgaga gcaggcagca 3900
gcccatggcc ctggctgtgg ccctgactaa gggggggag gccagggggg agctgttctg 3960
ggatgatggg gagagcctgg aggtgctgga gagaggggcc tacacccagg tgatctttct 4020
ggccaggaac aacaccattg tgaatgagct ggtgagggtg acttctgagg gggctggcct 4080
gcagctgcag aaggtgactg tgctgggggt ggccactgcc ccccagcagg tgctgagcaa 4140
tggggtgcct gtgtctaact tcacctacag ccctgatact aaggtgctgg atatctgtgt 4200
gagcctgctg atgggggagc agtttctggt gagctggtgc tgaagatcta gagctgaatt 4260
cctgcagcca gggggatcag cctctactgt gccttctagt tgccagccat ctgttgtttg 4320
cccctccccc ttgccttcct tgaccctgga aggtgccact cccactgtcc tttcctaata 4380
aaatgaggaa attgcatcac attgtctgag taggtgtcat tctattctgg ggggtggggt 4440
ggggcaggac agcaaggggg aggattggga agacaatagc aggcatgctg gggatgcagt 4500
gggctctatg gcttctgagg cagaaagaac cagctggggc tcgagatcca ctagggccgc 4560
aggaacccct agtgatggag ttggccactc cctctctgcg cgctcgctcg ctcactgagg 4620
ccgggcgacc aaaggtcgcc cgacgcccgg gctttgcccg ggcggcctca gtgagcgagc 4680
gagcgcgcag ctgcctgcag g 4701

<210> SEQ ID NO 20
<211> LENGTH: 4611
<212> TYPE: DNA
<213> ORGANISM: Artificial Sequence
<220> FEATURE:
<223> OTHER INFORMATION: Modified Nucleic Acid

<400> SEQUENCE: 20
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca ggctcagagg cacacaggag tttctgggct 180
caccctgccc ccttccaacc cctcagttcc catcctccag cagctgtttg tgtgctgcct 240
ctgaagtcca cactgaacaa acttcagcct actcatgtcc ctaaaatggg caaacattgc 300
aagcagcaaa cagcaaacac acagccctcc ctgcctgctg accttggagc tggggcagag 360
gtcagagacc tctctgggcc catgccacct ccaacatcca ctcgacccct tggaatttcg 420
gtggagagga gcagaggttg tcctggcgtg gtttaggtag tgtgagaggg gtacccgggg 480

```
atcttgctac cagtggaaca gccactaagg attctgcagt gagagcagag ggccagctaa    540
gtggtactct cccagagact gtctgactca cgccaccccc tccaccttgg acacaggacg    600
ctgtggtttc tgagccaggt acaatgactc ctttcggtaa gtgcagtgga agctgtacac    660
tgcccaggca aagcgtccgg gcagcgtagg cgggcgactc agatcccagc cagtggactt    720
agcccctgtt tgctcctccg ataactgggg tgaccttggt taatattcac cagcagcctc    780
ccccgttgcc cctctggatc cactgcttaa atacggacga ggacagggcc ctgtctcctc    840
agcttcaggc accaccactg acctgggaca gtgaatagat cctgagaact tcagggtgag    900
tctatgggac ccttgatgtt ttctttcccc ttcttttcta tggttaagtt catgtcatag    960
gaaggggaga agtaacaggg tacacatatt gaccaaatca gggtaatttt gcatttgtaa   1020
ttttaaaaaa tgctttcttc ttttaatata cttttttgtt tatcttattt ctaatacttt   1080
ccctaatctc tttctttcag ggcaataatg atacaatgta tcatgcctct ttgcaccatt   1140
ctaaagaata acagtgataa tttctgggtt aaggcaatag caatatttct gcatataaat   1200
atttctgcat ataaattgta actgatgtaa gaggtttcat attgctaata gcagctacaa   1260
tccagctacc attctgcttt tattttctgg ttgggataag gctggattat tctgagtcca   1320
agctaggccc ttttgctaat cttgttcata cctcttatct tcctcccaca gctcctgggc   1380
aacctgctgg tctctctgct ggcccatcac tttggcaaag cacgcgtgcc accatggctt   1440
tcctgtggct gctgagctgc tgggctctgc tgggcaccac ctttgggctg ctggtgccta   1500
gggagctgtc tgggtctagc cctgtgctgg aggagactca ccctgcccat cagcaggggg   1560
ctagcaggcc tggccccagg gatgctcagg cccaccctgg caggcccagg gctgtgccca   1620
cccagtgtga tgtgcccccc aacagcaggt ttgactgtgc ccctgacaag gccattaccc   1680
aggagcagtg tgaggccagg ggctgctgct acattccagc taagcagggc ctgcaggggg   1740
cccagatggg ccagccctgg tgcttcttcc cccccagcta tcctagctat aaactggaga   1800
acctgagcag ctctgagatg ggctatactg ccaccctgac taggactact cccacctttt   1860
ttcctaagga tatcctgacc ctgaggctgg atgtgatgat ggagactgag aacaggctgc   1920
acttcactat taaggaccct gccaatagga ggtatgaagt gcctctggag actcctcatg   1980
tgcactctag ggcccccagc cccctgtatt ctgtggagtt ctctgaggag ccctttgggg   2040
tgattgtgag gaggcagctg gatggcaggg tgctgctgaa caccactgtg gccccccctgt  2100
tctttgctga ccagttcctg cagctgagca ccagcctgcc cagccagtac atcactgggc   2160
tggctgagca tctgagccct ctgatgctga gcacctcttg gaccaggatc accctgtgga   2220
atagggatct ggcccccacc cctggggcta atctgtatgg ctctcatccc ttttacctgg   2280
ccctggagga tgggggctct gcccatgggg tgtttctgct gaacagcaat gccatggatg   2340
tggtgctgca gccctctcct gccctgagct ggaggagcac tgggggcatc ctggatgtgt   2400
acatcttcct gggccctgag cccaagtctg tggtccagca gtatctggat gtggtgggct   2460
acccctttat gcccccctat tggggcctgg gcttccacct gtgcaggtgg gggtattctt   2520
ctactgctat caccaggcag gtggtggaga acatgaccag ggctcacttc cccctggatg   2580
tgcagtggaa tgacctggac tatatggact ctaggaggga tttcaccttc aacaaggatg   2640
gcttcaggga cttccctgct atggtccagg agctgcatca ggggggcagg aggtacatga   2700
tgattgtgga ccctgccatc agcagctctg gccctgctgg cagctatagg ccctatgatg   2760
agggcctgag gagggggtg tttatcacta atgaaactgg gcagcccctg attggcaagg    2820
```

tgtggcctgg ctctactgcc ttccctgact tcaccaaccc cactgctctg gcctggtggg 2880
aggacatggt ggctgagttc catgaccagg tgccttttga tggcatgtgg attgacatga 2940
atgagcccag caacttcatc aggggctctg aggatgggtg ccccaataat gagctggaga 3000 accccccccta tgtgcctggg gtggtggggg gcaccctgca ggctgccact atttgtgcca 3060
gctctcacca gttcctgagc acccactaca acctgcacaa tctgtatggc ctgactgagg 3120
ccattgccag ccacagggcc ctggtgaagg ccaggggcac taggcccttt gtgatctcta 3180
gaagcacctt tgctggccat gggaggtatg ctggccactg gactggggat gtgtggagct 3240
cttgggagca gctggccagc tctgtgcctg agatcctgca gttcaacctg ctgggggtgc 3300
ccctggtggg ggctgatgtg tgtggcttcc tgggcaacac ctctgaagag ctgtgtgtga 3360
ggtggaccca gctgggggcc ttctaccctt tcatgaggaa ccacaacagc ctgctgagcc 3420
tgcctcagga gccttactct ttctctgagc ctgcccagca ggccatgagg aaggccctga 3480
ccctgaggta tgctctgctg ccccacctgt acaccctgtt ccaccaggcc catgtggctg 3540
gggagactgt ggccaggccc ctgttcctgg agtttcctaa ggatagcagc acctggactg 3600
tggaccacca gctgctgtgg ggggaggccc tgctgattac ccctgtgctg caggctggca 3660
aggctgaggt gactggctac ttcccccctgg gcacttggta tgacctgcag actgtgcctg 3720
tggaagccct gggcagcctg cctccccccc ctgctgcccc cagggagcct gccatccact 3780
ctgagggcca gtgggtgacc ctgcctgccc ccctggacac cattaatgtg catctgaggg 3840
ctgggtatat tatcccccctg caggggcctg ggctgactac cactgagagc aggcagcagc 3900
ctatggccct ggctgtggct ctgactaagg ggggggaggc caggggggag ctgttctggg 3960
atgatgggga gagcctggag gtgctggaga gggggcccta cacccaggtg attttcctgg 4020
ccaggaacaa caccattgtg aatgagctgg tgagggtgac ctctgagggg gctggcctgc 4080
agctgcagaa agtgactgtg ctgggggtgg ccactgcccc ccagcaggtg ctgagcaatg 4140
gggtgcctgt gagcaacttc acctacagcc ctgacaccaa ggtgctggat atttgtgtga 4200
gcctgctgat gggggagcag ttcctggtga gctggtgctg actcgagaga tctaccggtg 4260
aattcaccgc gggtttaaac tgtgccttct agttgccagc catctgttgt ttgcccctcc 4320
cccgtgcctt ccttgaccct ggaaggtgcc actcccactg tcctttccta ataaaatgag 4380
gaaattgcat cgcattgtct gagtaggtgt cattctattc tggggggtgg ggtgggggct 4440
agctctagac tcgagatcca ctagggccgc aggaacccct agtgatggag ttggccactc 4500
cctctctgcg cgctcgctcg ctcactgagg ccgggcgacc aaaggtcgcc cgacgcccgg 4560
gctttgcccg ggcggcctca gtgagcgagc gagcgcgcag ctgcctgcag g 4611

<210> SEQ ID NO 21
<211> LENGTH: 4611
<212> TYPE: DNA
<213> ORGANISM: Artificial Sequence
<220> FEATURE:
<223> OTHER INFORMATION: Modified Nucleic Acid

<400> SEQUENCE: 21
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca ggctcagagg cacacaggag tttctgggct 180
caccctgccc ccttccaacc cctcagttcc catcctccag cagctgtttg tgtgctgcct 240
ctgaagtcca cactgaacaa acttcagcct actcatgtcc ctaaaatggg caaacattgc 300
aagcagcaaa cagcaaacac acagccctcc ctgcctgctg accttggagc tggggcagag 360
gtcagagacc tctctgggcc catgccacct ccaacatcca ctcgacccct tggaatttcg 420
gtggagagga gcagaggttg tcctggcgtg gtttaggtag tgtgagaggg gtacccgggg 480
atcttgctac cagtggaaca gccactaagg attctgcagt gagagcagag ggccagctaa 540
gtggtactct cccagagact gtctgactca cgccaccccc tccaccttgg acacaggacg 600
ctgtggtttc tgagccaggt acaatgactc ctttcggtaa gtgcagtgga agctgtacac 660
tgcccaggca aagcgtccgg gcagcgtagg cgggcgactc agatcccagc cagtggactt 720
agcccctgtt tgctcctccg ataactgggg tgaccttggt taatattcac cagcagcctc 780
ccccgttgcc cctctggatc cactgcttaa atacggacga ggacagggcc ctgtctcctc 840
agcttcaggc accaccactg acctgggaca gtgaatagat cctgagaact tcagggtgag 900
tctatgggac ccttgatgtt ttctttcccc ttcttttcta tggttaagtt catgtcatag 960
gaaggggaga agtaacaggg tacacatatt gaccaaatca gggtaatttt gcatttgtaa 1020
ttttaaaaaa tgctttcttc ttttaatata cttttttgtt tatcttattt ctaatacttt 1080
ccctaatctc tttctttcag ggcaataatg atacaatgta tcatgcctct ttgcaccatt 1140
ctaaagaata acagtgataa tttctgggtt aaggcaatag caatatttct gcatataaat 1200
atttctgcat ataaattgta actgatgtaa gaggtttcat attgctaata gcagctacaa 1260
tccagctacc attctgcttt tattttctgg ttgggataag gctggattat tctgagtcca 1320
agctaggccc ttttgctaat cttgttcata cctcttatct tcctcccaca gctcctgggc 1380
aacctgctgg tctctctgct ggcccatcac tttggcaaag cacgcgtgcc accatggctt 1440
tcctgtggct gctgtcttgc tgggccctgc tggggactac ctttggcctg ctggtgccca 1500
gggaactgtc tggctctagc ccagtgctgg aggagaccca ccctgcccac cagcaggggg 1560
cttctaggcc tggccccagg gatgcccagg cccaccctgg caggccaagg gctgtgccca 1620
cccagtgtga tgtgcccccc aactctagat ttgattgtgc ccctgataag gccatcaccc 1680
aggagcagtg tgaggctagg ggctgctgct acatccctgc taagcagggc ctgcaggggg 1740
ctcagatggg ccagccctgg tgcttcttcc cccccagcta tccctcttac aagctggaga 1800
atctgagcag ctctgagatg ggctacactg ccaccctgac caggactact cccaccttct 1860
tccccaagga catcctgacc ctgaggctgg atgtgatgat ggagactgag aacaggctgc 1920
atttcaccat caaggatcct gccaacagga ggtatgaggt gcctctggag accccccatg 1980
tgcacagcag ggctccttct cccctgtact ctgtggagtt ctctgaggaa ccctttgggg 2040
tgattgtgag gaggcagctg gatggcaggg tcctgctgaa caccactgtg gccccccctgt 2100
tctttgctga tcagttcctg cagctgtcca cttctctgcc tagccagtac atcactgggc 2160
tggctgagca cctgagccct ctgatgctga gcacctcttg gactaggatc accctgtgga 2220
acagggacct ggcccccacc cctggggcca acctgtatgg cagccacccc ttctatctgg 2280
ccctggagga tgggggctct gcccatgggg tgttcctgct gaatagcaat gctatggatg 2340
tggtgctgca gcccagccct gccctgtctt ggaggagcac tgggggcatc ctggatgtgt 2400
acattttcct ggggcctgag cccaagtctg tggtgcagca gtacctggat gtggtgggct 2460
acccccttcat gcctccctac tggggcctgg gcttccacct gtgcaggtgg ggctacagct 2520
ctactgccat caccaggcag gtggtggaga atatgaccag ggcccacttc cccctggatg 2580
tgcagtggaa tgacctggac tacatggact ctaggaggga cttcaccttc aataaggatg 2640

-continued

```
gcttcagaga cttccctgcc atggtgcagg agctgcatca ggggggcagg aggtacatga   2700
tgattgtgga ccctgccatc agctcttctg gccctgctgg ctcttacagg ccctatgatg   2760
agggcctgag gaggggggtg ttcatcacca atgagactgg gcagcccctg attgggaagg   2820
tgtggcctgg ctctactgcc ttccctgact tcaccaatcc tactgccctg gcctggtggg   2880
aggacatggt ggctgagttc catgaccagg tgccctttga tggcatgtgg attgacatga   2940
atgagccctc taatttcatc aggggctctg aggatggctg ccccaacaat gagctggaga   3000
acccccccta tgtgcctggg gtggtggggg gcaccctgca ggctgccacc atctgtgcta   3060
gctctcacca gttcctgagc acccactaca atctgcataa cctgtatggc ctgactgagg   3120
ccattgccag ccacagggcc ctggtgaagg ctaggggcac caggcccttt gtgatttcta   3180
ggagcacttt tgctggccat ggcaggtatg ctgggcactg gactggggat gtgtggtcta   3240
gctgggagca gctggcttct tctgtgcctg agatcctgca gttcaacctg ctgggggtgc   3300
ctctggtggg ggctgatgtg tgtgggttcc tgggcaacac ttctgaggag ctgtgtgtga   3360
ggtggaccca gctgggggcc ttctaccctt tcatgaggaa ccacaacagc ctgctgagcc   3420
tgccccagga gccctacagc ttctctgagc ctgcccagca ggccatgagg aaggccctga   3480
ccctgaggta tgccctgctg ccccacctgt acaccctgtt ccaccaggcc catgtggctg   3540
gggagactgt ggctaggcct ctgttcctgg agttccccaa ggactctagc acctggactg   3600
tggaccacca gctgctgtgg ggggaggccc tgctgatcac tcctgtgctg caggctggga   3660
aggctgaggt gactggctat ttccccctgg gcacctggta tgacctgcag actgtgcctg   3720
tggaggccct ggggagcctg cccccccccc ctgctgcccc cagggagcct gccatccact   3780
ctgagggcca gtgggtgacc ctgcctgccc ctctggatac catcaatgtg cacctgaggg   3840
ctggctacat cattcccctg cagggccctg gcctgaccac tactgagtct aggcagcagc   3900
ccatggccct ggctgtggcc ctgaccaagg ggggggaggc tagggggggag ctgttttggg   3960
atgatgggga gagcctggag gtgctggaga gggggggccta cactcaggtg atcttcctgg   4020
ccaggaacaa taccattgtg aatgagctgg tgagggtgac ctctgagggg gctggcctgc   4080
agctgcagaa ggtgactgtg ctgggggtgg ccactgcccc ccagcaggtg ctgagcaatg   4140
gggtgcctgt gagcaacttc acctatagcc ctgataccaa ggtgctggat atttgtgtga   4200
gcctgctgat gggggagcag ttcctggtga gctggtgctg actcgagaga tctaccggtg   4260
aattcaccgc gggtttaaac tgtgccttct agttgccagc catctgttgt ttgcccctcc   4320
cccgtgcctt ccttgaccct ggaaggtgcc actcccactg tcctttccta ataaaatgag   4380
gaaattgcat cgcattgtct gagtaggtgt cattctattc tggggggtgg ggtgggggct   4440
agctctagac tcgagatcca ctagggccgc aggaacccct agtgatggag ttggccactc   4500
cctctctgcg cgctcgctcg ctcactgagg ccgggcgacc aaaggtcgcc cgacgcccgg   4560
gctttgcccg ggcggcctca gtgagcgagc gagcgcgcag ctgcctgcag g            4611
```

<210> SEQ ID NO 22
<211> LENGTH: 4611
<212> TYPE: DNA
<213> ORGANISM: Artificial Sequence
<220> FEATURE:
<223> OTHER INFORMATION: Modified Nucleic Acid

<400> SEQUENCE: 22

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
```

-continued

```
actccatcac taggggttcc tgcggccgca ggctcagagg cacacaggag tttctgggct    180
caccctgccc ccttccaacc cctcagttcc catcctccag cagctgtttg tgtgctgcct    240
ctgaagtcca cactgaacaa acttcagcct actcatgtcc ctaaaatggg caaacattgc    300
aagcagcaaa cagcaaacac acagccctcc ctgcctgctg accttggagc tggggcagag    360
gtcagagacc tctctgggcc catgccacct ccaacatcca ctcgacccct tggaatttcg    420
gtggagagga gcagaggttg tcctggcgtg gtttaggtag tgtgagaggg gtacccgggg    480
atcttgctac cagtggaaca gccactaagg attctgcagt gagagcagag ggccagctaa    540
gtggtactct cccagagact gtctgactca cgccaccccc tccaccttgg acacaggacg    600
ctgtggtttc tgagccaggt acaatgactc ctttcggtaa gtgcagtgga agctgtacac    660
tgcccaggca aagcgtccgg gcagcgtagg cgggcgactc agatcccagc cagtggactt    720
agcccctgtt tgctcctccg ataactgggg tgaccttggt taatattcac cagcagcctc    780
ccccgttgcc cctctggatc cactgcttaa atacggacga ggacagggcc ctgtctcctc    840
agcttcaggc accaccactg acctgggaca gtgaatagat cctgagaact tcagggtgag    900
tctatgggac ccttgatgtt ttctttcccc ttcttttcta tggttaagtt catgtcatag    960
gaaggggaga agtaacaggg tacacatatt gaccaaatca gggtaatttt gcatttgtaa   1020
ttttaaaaaa tgctttcttc ttttaatata ctttttttgtt tatcttattt ctaatacttt  1080
ccctaatctc tttctttcag ggcaataatg atacaatgta tcatgcctct ttgcaccatt   1140
ctaaagaata acagtgataa tttctgggtt aaggcaatag caatatttct gcatataaat   1200
atttctgcat ataaattgta actgatgtaa gaggtttcat attgctaata gcagctacaa   1260
tccagctacc attctgcttt tattttctgg ttgggataag gctggattat tctgagtcca   1320
agctaggccc ttttgctaat cttgttcata cctcttatct tcctcccaca gctcctgggc   1380
aacctgctgg tctctctgct ggcccatcac tttggcaaag cacgcgtgcc accatggctt   1440
tcctgtggct gctgtcttgt tgggctctgc tgggcaccac ctttggcctg ctggtgccca   1500
gggagctgtc tggcagcagc cctgtgctgg aggagaccca ccctgctcat cagcaggggg   1560
ctagcaggcc tggccccagg gatgcccagg ctcaccctgg gagacccagg gctgtgccca   1620
ctcagtgtga tgtgcccccc aacagcaggt ttgactgtgc tcctgacaag gctatcaccc   1680
aggagcagtg tgaggccagg gggtgctgct acattcctgc taagcagggc ctgcaggggg   1740
cccagatggg ccagccctgg tgcttcttcc ccccctctta tcccagctat aagctggaga   1800
acctgagcag ctctgagatg ggctacactg ccaccctgac caggaccact cccaccttct   1860
ttcccaagga tattctgact ctgaggctgg atgtgatgat ggagactgag aacaggctgc   1920
acttcactat caaggaccct gccaatagga ggtatgaggt gcccctggag actcctcatg   1980
tgcatagcag ggccccttct cctctgtatt ctgtggagtt ctctgaggag ccctttgggg   2040
tgattgtgag gaggcagctg gatggcaggg tgctgctgaa caccactgtg gccccccctgt  2100
tctttgctga ccagttcctg cagctgagca cttctctgcc cagccagtac attactgggc   2160
tggctgagca tctgagcccc ctgatgctga gcacctcttg gaccaggatc accctgtgga   2220
acagggacct ggcccccact cctggggcta acctgtatgg ctctcacccc ttttacctgg   2280
ccctggagga tgggggctct gcccatgggg tgtttctgct gaacagcaat gctatggatg   2340
tggtgctgca gccctctcca gccctgtctt ggaggagcac tgggggcatt ctggatgtgt   2400
acattttcct ggggcctgaa cccaagtctg tggtgcagca gtacctggat gtggtgggct   2460
```

-continued

```
accccttcat gcccccctat tgggggctgg ggtttcacct gtgcaggtgg ggctacagca   2520
gcactgccat caccaggcag gtggtggaga acatgaccag ggcccatttc cccctggatg   2580
tgcagtggaa tgacctggac tacatggata gcaggaggga tttcaccttc aacaaggatg   2640
gcttcaggga ctttcctgcc atggtgcagg agctgcacca ggggggcagg aggtatatga   2700
tgattgtgga ccctgctatc agcagctctg gccctgctgg ctcttacagg ccctatgatg   2760
agggcctgag gagggggtg tttatcacta atgaaactgg ccagcctctg attggcaagg   2820
tctggcctgg ctctactgcc ttccctgatt ttactaaccc cactgccctg gcctggtggg   2880
aggacatggt ggctgagttc catgatcagg tgccttttga tggcatgtgg attgatatga   2940
atgaaccaag caacttcatc agaggctctg aggatggctg ccccaacaat gagctggaga   3000
acccccccta tgtgcctggg gtggtggggg gcactctgca ggctgccacc atttgtgcta   3060
gcagccacca gttcctgagc acccactaca atctgcacaa cctgtatggc ctgactgaag   3120
ccattgccag ccatagggcc ctggtgaagg ccaggggcac taggcctttt gtgatcagca   3180
ggagcacttt tgctggccat ggcaggtatg ctggccactg gactggggat gtgtggagca   3240
gctgggagca gctggccagc tctgtgcctg agattctgca gtttaacctg ctgggggtgc   3300
ccctggtggg ggctgatgtg tgtggcttcc tgggcaacac ctctgaggag ctgtgtgtga   3360
ggtggaccca gctgggggcc ttttatccct tcatgaggaa ccacaacagc ctgctgagcc   3420
tgcctcagga gccctactct ttctctgagc ctgcccagca ggccatgagg aaggccctga   3480
ccctgaggta tgccctgctg ccccacctgt ataccctgtt ccaccaggcc catgtggctg   3540
gggagactgt ggccaggccc ctgttcctgg agttccccaa ggacagcagc acctggactg   3600
tggatcatca gctgctgtgg ggggaggccc tgctgatcac ccctgtgctg caggctggca   3660
aggctgaggt cactggctac ttccctctgg gcacctggta tgacctgcag actgtgcctg   3720
tggaggctct gggcagcctg cccccccccc ctgctgctcc cagggagcct gccatccact   3780
ctgagggcca gtgggtgacc ctgcctgctc ccctggacac catcaatgtg cacctgaggg   3840
ctggctacat tatccccctg cagggcccag ggctgactac cactgagagc agacagcagc   3900
ccatggctct ggctgtggcc ctgaccaagg gggggaagc taggggggag ctgttctggg    3960
atgatgggga gagcctggag gtgctggaga gggggccta tacccaggtg atcttcctgg    4020
ctaggaacaa caccattgtc aatgagctgg tgagggtgac ttctgagggg gctgggctgc   4080
agctgcagaa ggtgactgtg ctgggggtgg ccactgctcc ccagcaggtg ctgagcaatg   4140
gggtgcctgt gagcaacttc acctacagcc ctgacaccaa ggtgctggac atctgtgtgt   4200
ctctgctgat gggggagcag ttcctggtga gctggtgctg actcgagaga tctaccggtg   4260
aattcaccgc gggtttaaac tgtgccttct agttgccagc catctgttgt ttgcccctcc   4320
cccgtgcctt ccttgaccct ggaaggtgcc actcccactg tcctttccta ataaaatgag   4380
gaaattgcat cgcattgtct gagtaggtgt cattctattc tggggggtgg ggtgggggct   4440
agctctagac tcgagatcca ctagggccgc aggaacccct agtgatggag ttggccactc   4500
cctctctgcg cgctcgctcg ctcactgagg ccgggcgacc aaaggtcgcc cgacgcccgg   4560
gctttgcccg ggcggcctca gtgagcgagc gagcgcgcag ctgcctgcag g            4611
```

<210> SEQ ID NO 23
<211> LENGTH: 4611
<212> TYPE: DNA
<213> ORGANISM: Artificial Sequence
<220> FEATURE:
<223> OTHER INFORMATION: Modified Nucleic Acid

<400> SEQUENCE: 23

```
cctgcaggca gctgcgcgct cgctcgctca ctgaggccgc ccgggcaaag cccgggcgtc     60
gggcgacctt tggtcgcccg gcctcagtga gcgagcgagc gcgcagagag ggagtggcca    120
actccatcac taggggttcc tgcggccgca ggctcagagg cacacaggag tttctgggct    180
caccctgccc ccttccaacc cctcagttcc catcctccag cagctgtttg tgtgctgcct    240
ctgaagtcca cactgaacaa acttcagcct actcatgtcc ctaaaatggg caaacattgc    300
aagcagcaaa cagcaaacac acagccctcc ctgcctgctg accttggagc tggggcagag    360
gtcagagacc tctctgggcc catgccacct ccaacatcca ctcgacccct tggaatttcg    420
gtggagagga gcagaggttg tcctggcgtg gtttaggtag tgtgagaggg gtacccgggg    480
atcttgctac cagtggaaca gccactaagg attctgcagt gagagcagag ggccagctaa    540
gtggtactct cccagagact gtctgactca cgccaccccc tccaccttgg acacaggacg    600
ctgtggtttc tgagccaggt acaatgactc ctttcggtaa gtgcagtgga agctgtacac    660
tgcccaggca aagcgtccgg gcagcgtagg cgggcgactc agatcccagc cagtggactt    720
agcccctgtt tgctcctccg ataactgggg tgaccttggt taatattcac cagcagcctc    780
ccccgttgcc cctctggatc cactgcttaa atacggacga ggacagggcc ctgtctcctc    840
agcttcaggc accaccactg acctgggaca gtgaatagat cctgagaact tcagggtgag    900
tctatgggac ccttgatgtt ttctttcccc ttcttttcta tggttaagtt catgtcatag    960
gaaggggaga agtaacaggg tacacatatt gaccaaatca gggtaatttt gcatttgtaa   1020
ttttaaaaaa tgctttcttc ttttaatata ctttttgtt tatcttattt ctaatacttt   1080
ccctaatctc tttctttcag ggcaataatg atacaatgta tcatgcctct ttgcaccatt   1140
ctaaagaata acagtgataa tttctgggtt aaggcaatag caatatttct gcatataaat   1200
atttctgcat ataaattgta actgatgtaa gaggtttcat attgctaata gcagctacaa   1260
tccagctacc attctgcttt tattttctgg ttgggataag gctggattat tctgagtcca   1320
agctaggccc ttttgctaat cttgttcata cctcttatct tcctcccaca gctcctgggc   1380
aacctgctgg tctctctgct ggcccatcac tttggcaaag cacgcgtgcc accatggcct   1440
tcctgtggct gctgtcttgc tgggctctgc tggggaccac ctttggcctg ctggtcccca   1500
gggagctgtc tggctcttct cctgtcctgg aggagaccca ccctgcccac cagcaggggg   1560
ctagcaggcc tggccccagg gatgcccagg cccaccctgg caggcccagg gctgtgccca   1620
cccagtgtga tgtgcctccc aacagcaggt ttgactgtgc ccctgacaag gccatcaccc   1680
aggagcagtg tgaggccagg ggctgctgct atatccctgc caagcagggc ctgcaggggg   1740
ctcagatggg ccagccctgg tgcttctttc ccccctctta tcctagctat aagctggaga   1800
acctgagcag ctctgagatg ggtacactg ccaccctgac caggaccacc cccactttct   1860
tccctaagga catcctgacc ctgaggctgg atgtgatgat ggagactgag aataggctgc   1920
actttactat caaggaccct gccaacagga ggtatgaggt gcctctggag accccccatg   1980
tgcattctag ggcccccagc cccctgtact ctgtggagtt ctctgaggag cccctttggg   2040
tgattgtgag gagacagctg gatggcaggg tcctgctgaa caccactgtg gctcccctgt   2100
tttttgctga ccagttcctg cagctgagca ccagcctgcc cagccagtac atcactgggc   2160
tggctgagca cctgagcccc ctgatgctga gcaccagctg gaccaggatc accctgtgga   2220
acagggatct ggctcctacc cctggggcca acctgtatgg ctctcacccc ttttacctgg   2280
```

-continued

```
ccctggagga tgggggctct gcccatgggg tgttcctgct gaacagcaat gctatggatg   2340
tggtgctgca gcccagccct gccctgagct ggaggtctac tgggggcatc ctggatgtgt   2400
acatctttct ggggcctgag cccaagtctg tggtgcagca gtacctggat gtggtgggct   2460
atccttttat gcccccctat tggggcctgg gcttccacct gtgcaggtgg ggctacagca   2520
gcactgccat caccagacag gtggtggaga acatgaccag ggcccacttc cccctggatg   2580
tgcagtggaa tgacctggac tacatggaca gcaggaggga cttcaccttt aacaaggatg   2640
gctttaggga cttccctgcc atggtgcagg agctgcatca gggggcagg aggtacatga    2700
tgattgtgga cccagccatc agcagctctg gccctgctgg gtcttacagg ccctatgatg   2760
agggcctgag gaggggggtg ttcatcacca atgagactgg ccagcccctg attggcaagg   2820
tgtggcctgg gagcactgcc ttccctgatt ttaccaaccc cactgccctg gcctggtggg   2880
aggatatggt ggctgagttt catgaccagg tgcccttga tggcatgtgg attgacatga    2940
atgagcccag caatttcatc aggggctctg aggatggctg ccccaacaat gagctggaga   3000
atcctcccta tgtgcctggg gtggtggggg gcaccctgca ggctgccacc atctgtgcct   3060
ctagccacca gttcctgagc acccactata acctgcataa cctgtatggc ctgactgagg   3120
ccattgccag ccatagagcc ctggtgaagg ccagagggac caggcccttt gtgatctcta   3180
ggagcacctt tgctggccat ggcaggtatg ctggccactg gactggggat gtgtggagct   3240
cttgggagca gctggccagc tctgtgccag agatcctgca gttcaacctg ctgggggtgc   3300
ctctggtggg ggctgatgtg tgtggcttcc tgggcaatac ctctgaagag ctgtgtgtga   3360
ggtggactca gctgggggcc ttctatccct tcatgaggaa ccacaacagc ctgctgtctc   3420
tgccccagga gccctacagc ttctctgagc ctgctcagca ggctatgagg aaggccctga   3480
ccctgaggta tgccctgctg ccccatctgt acaccctgtt ccaccaggcc catgtggctg   3540
gggagactgt ggccaggccc ctgtttctgg agtttcccaa ggacagcagc acctggactg   3600
tggaccatca gctgctgtgg ggggaggctc tgctgattac ccctgtgctg caggctggca   3660
aggctgaggt gactgggtac ttccccctgg ggacttggta tgacctgcag actgtgcctg   3720
tggaagctct gggcagcctg cccccacccc ctgctgcccc tagggagcct gccatccact   3780
ctgagggcca gtgggtgacc ctgcctgccc ctctggacac catcaatgtg cacctgaggg   3840
ctggctatat catccccctg cagggccctg ggctgaccac cactgagagc aggcagcagc   3900
ccatggccct ggctgtggcc ctgactaagg gggggaggc caggggggag ctgttctggg     3960
atgatgggga gagcctggag gtgctggaga gaggggccta cacccaggtg atctttctgg   4020
ccaggaacaa caccattgtg aatgagctgg tgagggtgac ttctgagggg gctggcctgc   4080
agctgcagaa ggtgactgtg ctgggggtgg ccactgcccc ccagcaggtg ctgagcaatg   4140
gggtgcctgt gtctaacttc acctacagcc ctgatactaa ggtgctggat atctgtgtga   4200
gcctgctgat gggggagcag tttctggtga gctggtgctg actcgagaga tctaccggtg   4260
aattcaccgc gggtttaaac tgtgccttct agttgccagc catctgttgt ttgcccctcc   4320
cccgtgcctt ccttgaccct ggaaggtgcc actcccactg tcctttccta ataaaatgag   4380
gaaattgcat cgcattgtct gagtaggtgt cattctattc tggggggtgg ggtgggggct   4440
agctctagac tcgagatcca ctagggccgc aggaacccct agtgatggag ttggccactc   4500
cctctctgcg cgctcgctcg ctcactgagg ccgggcgacc aaaggtcgcc cgacgcccgg   4560
gctttgcccg ggcggcctca gtgagcgagc gagcgcgcag ctgcctgcag g             4611
```

<210> SEQ ID NO 24
<211> LENGTH: 4611
<212> TYPE: DNA
<213> ORGANISM: Artificial Sequence
<220> FEATURE:
<223> OTHER INFORMATION: Modified Nucleic Acid

<400> SEQUENCE: 24
cctgcaggca gctgcgcgct cgctcgctca ctgaggccgc ccgggcaaag cccgggcgtc 60
gggcgacctt tggtcgcccg gcctcagtga gcgagcgagc gcgcagagag ggagtggcca 120
actccatcac taggggttcc tgcggccgca ggctcagagg cacacaggag tttctgggct 180
caccctgccc ccttccaacc cctcagttcc catcctccag cagctgtttg tgtgctgcct 240
ctgaagtcca cactgaacaa acttcagcct actcatgtcc ctaaaatggg caaacattgc 300
aagcagcaaa cagcaaacac acagccctcc ctgcctgctg accttggagc tggggcagag 360
gtcagagacc tctctgggcc catgccacct ccaacatcca ctcgacccct tggaatttcg 420
gtggagagga gcagaggttg tcctggcgtg gtttaggtag tgtgagaggg gtacccgggg 480
atcttgctac cagtggaaca gccactaagg attctgcagt gagagcagag ggccagctaa 540
gtggtactct cccagagact gtctgactca cgccaccccc tccaccttgg acacaggacg 600
ctgtggtttc tgagccaggt acaatgactc ctttcggtaa gtgcagtgga agctgtacac 660
tgcccaggca aagcgtccgg gcagcgtagg cgggcgactc agatcccagc cagtggactt 720
agcccctgtt tgctcctccg ataactgggg tgaccttggt taatattcac cagcagcctc 780
ccccgttgcc cctctggatc cactgcttaa atacggacga ggacagggcc ctgtctcctc 840
agcttcaggc accaccactg acctgggaca gtgaatagat cctgagaact tcagggtgag 900
tctatgggac ccttgatgtt ttctttcccc ttcttttcta tggttaagtt catgtcatag 960
gaaggggaga agtaacaggg tacacatatt gaccaaatca gggtaatttt gcatttgtaa 1020
ttttaaaaaa tgctttcttc ttttaatata cttttttgtt tatcttattt ctaatacttt 1080
ccctaatctc tttctttcag ggcaataatg atacaatgta tcatgcctct ttgcaccatt 1140
ctaaagaata acagtgataa tttctgggtt aaggcaatag caatatttct gcatataaat 1200
atttctgcat ataaattgta actgatgtaa gaggtttcat attgctaata gcagctacaa 1260
tccagctacc attctgcttt tattttctgg ttgggataag gctggattat tctgagtcca 1320
agctaggccc ttttgctaat cttgttcata cctcttatct tcctcccaca gctcctgggc 1380
aacctgctgg tctctctgct ggcccatcac tttggcaaag cacgcgtgcc accatggcct 1440
ttctgtggct gctgtcctgc tgggccctgc tggggaccac ctttggcctg ctggtgccca 1500
gggagctgtc tgggagcagc ccagtgctgg aggagaccca ccctgcccac cagcaggggg 1560
ccagcaggcc tggccctagg gatgcccagg cccaccctgg caggcccagg gctgtgccta 1620
cccagtgtga tgtgccaccc aattctaggt ttgactgtgc tcctgacaag gccatcactc 1680
aggagcagtg tgaagctagg gggtgctgct acatcccagc caagcagggc ctgcaggggg 1740
cccagatggg ccagccctgg tgcttcttcc cccccagcta ccctagctac aagctggaga 1800
atctgagcag ctctgagatg ggctacactg ctaccctgac caggaccact cctaccttct 1860
tccccaagga catcctgact ctgaggctgg atgtcatgat ggagactgaa aataggctgc 1920
acttcaccat caaggaccct gccaatagga ggtatgaggt gcctctggag acccccccatg 1980 tgcatagcag ggctcccagc cccctgtatt ctgtggagtt ctctgaggag ccctttgggg 2040
tcattgtgag gagacagctg gatgggaggg tgctgctgaa cactactgtg gctcccctgt 2100

-continued

```
tctttgctga ccagttcctg cagctgtcta ccagcctgcc cagccagtac atcactgggc   2160
tggctgagca tctgagcccc ctgatgctga gcaccagctg gaccaggatc actctgtgga   2220
acagggatct ggcccccact cctggggcca acctgtatgg gagccatccc ttctacctgg   2280
ccctggagga tgggggctct gcccatgggg tgttcctgct gaacagcaat gccatggatg   2340
tggtgctgca gcctagccct gccctgagct ggaggagcac tgggggcatc ctggatgtct   2400
acatcttcct ggggcctgag cccaagtctg tggtgcagca gtatctggat gtggtggggt   2460
atcccttcat gcccccctac tggggcctgg gctttcacct gtgcaggtgg ggctacagca   2520
gcactgccat caccaggcag gtggtggaga acatgaccag ggcccacttc cctctggatg   2580
tgcagtggaa tgacctggac tatatggatt ctaggagaga ctttactttt aacaaggatg   2640
gcttcaggga tttccctgcc atggtgcagg agctgcacca gggggggcagg aggtacatga   2700
tgattgtgga ccctgctatt agcagctctg gccctgctgg gtcttacagg ccttatgatg   2760
agggcctgag gagggggggtg ttcatcacca atgagactgg ccagcccctg attggcaagg   2820
tgtggcctgg cagcactgcc ttccctgact tcaccaaccc cactgccctg gcctggtggg   2880
aggacatggt ggctgagttc catgaccagg tgccctttga tgggatgtgg attgacatga   2940
atgagccctc taacttcatc agggggtctg aggatggctg ccccaacaat gagctggaga   3000
acccccccta tgtgcctggg gtggtggggg gcactctgca ggctgccact atctgtgctt   3060
cttctcacca gtttctgagc acccactata atctgcacaa cctgtatggc ctgactgagg   3120
ccattgccag ccatagggcc ctggtgaagg ccaggggcac caggcccttt gtgatcagca   3180
ggtctacctt tgctggccat ggcaggtatg ctggccactg gactggggat gtgtggtctt   3240
cttgggagca gctggccagc tctgtgcctg agatcctgca gttcaacctg ctgggggtgc   3300
ctctggtggg ggctgatgtg tgtggctttc tgggcaacac ctctgaggag ctgtgtgtga   3360
ggtggaccca gctgggggcc ttttacccct tcatgaggaa ccacaatagc ctgctgagcc   3420
tgccccagga gccttactct ttctctgagc ctgcccagca ggccatgagg aaggccctga   3480
ctctgaggta tgccctgctg ccccatctgt ataccctgtt tcaccaggcc catgtggctg   3540
gggagactgt ggctaggcct ctgtttctgg agttccctaa ggactctagc acctggactg   3600
tggaccacca gctgctgtgg ggggaggccc tgctgatcac ccctgtgctg caggctggca   3660
aggctgaggt gactggctac ttccccctgg gcacctggta tgacctgcag actgtgcctg   3720
tggaggccct ggggagcctg cctccccccc ctgctgcccc cagggagcct gccattcatt   3780
ctgagggcca gtgggtgacc ctgcctgccc ctctggacac catcaatgtg cacctgaggg   3840
ctgggtacat catcccccctg cagggccctg gcctgaccac cactgagagc aggcagcagc   3900
ccatggccct ggctgtggct ctgaccaagg ggggggaggc caggggggag ctgttctggg   3960
atgatgggga gtctctggag gtgctggaga gggggggccta cacccaggtg atctttctgg   4020
ccaggaacaa tactattgtg aatgagctgg tgagggtgac ctctgagggg gctggcctgc   4080
agctgcagaa ggtgactgtg ctgggggtgg ccactgcccc ccagcaggtc ctgagcaatg   4140
ggtgcctgt gagcaacttc acctactctc ctgacaccaa ggtgctggac atttgtgtgt   4200
ctctgctgat gggggagcag ttcctggtga gctggtgctg actcgagaga tctaccggtg   4260
aattcaccgc gggtttaaac tgtgccttct agttgccagc catctgttgt ttgcccctcc   4320
cccgtgcctt ccttgaccct ggaaggtgcc actcccactg tcctttccta ataaaatgag   4380
gaaattgcat cgcattgtct gagtaggtgt cattctattc tggggggtgg ggtgggggct   4440
agctctagac tcgagatcca ctagggccgc aggaacccct agtgatggag ttggccactc   4500
```

cctctctgcg cgctcgctcg ctcactgagg ccgggcgacc aaaggtcgcc cgacgcccgg 4560
gctttgcccg ggcggcctca gtgagcgagc gagcgcgcag ctgcctgcag g 4611

<210> SEQ ID NO 25
<211> LENGTH: 935
<212> TYPE: PRT
<213> ORGANISM: Artificial Sequence
<220> FEATURE:
<223> OTHER INFORMATION: GAA peptide

<400> SEQUENCE: 25

Met Ala Phe Leu Trp Leu Leu Ser Cys Trp Ala Leu Leu Gly Thr Thr
1 5 10 15

Phe Gly Leu Leu Val Pro Arg Glu Leu Ser Gly Ser Ser Pro Val Leu
20 25 30

Glu Glu Thr His Pro Ala His Gln Gln Gly Ala Ser Arg Pro Gly Pro
35 40 45

Arg Asp Ala Gln Ala His Pro Gly Arg Pro Arg Ala Val Pro Thr Gln
50 55 60

Cys Asp Val Pro Pro Asn Ser Arg Phe Asp Cys Ala Pro Asp Lys Ala
65 70 75 80

Ile Thr Gln Glu Gln Cys Glu Ala Arg Gly Cys Cys Tyr Ile Pro Ala
85 90 95

Lys Gln Gly Leu Gln Gly Ala Gln Met Gly Gln Pro Trp Cys Phe Phe
100 105 110

Pro Pro Ser Tyr Pro Ser Tyr Lys Leu Glu Asn Leu Ser Ser Ser Glu
115 120 125

Met Gly Tyr Thr Ala Thr Leu Thr Arg Thr Thr Pro Thr Phe Phe Pro
130 135 140

Lys Asp Ile Leu Thr Leu Arg Leu Asp Val Met Met Glu Thr Glu Asn
145 150 155 160

Arg Leu His Phe Thr Ile Lys Asp Pro Ala Asn Arg Arg Tyr Glu Val
165 170 175

Pro Leu Glu Thr Pro His Val His Ser Arg Ala Pro Ser Pro Leu Tyr
180 185 190

Ser Val Glu Phe Ser Glu Glu Pro Phe Gly Val Ile Val Arg Arg Gln
195 200 205

Leu Asp Gly Arg Val Leu Leu Asn Thr Thr Val Ala Pro Leu Phe Phe
210 215 220

Ala Asp Gln Phe Leu Gln Leu Ser Thr Ser Leu Pro Ser Gln Tyr Ile
225 230 235 240

Thr Gly Leu Ala Glu His Leu Ser Pro Leu Met Leu Ser Thr Ser Trp
245 250 255

Thr Arg Ile Thr Leu Trp Asn Arg Asp Leu Ala Pro Thr Pro Gly Ala
260 265 270

Asn Leu Tyr Gly Ser His Pro Phe Tyr Leu Ala Leu Glu Asp Gly Gly
275 280 285

Ser Ala His Gly Val Phe Leu Leu Asn Ser Asn Ala Met Asp Val Val
290 295 300

Leu Gln Pro Ser Pro Ala Leu Ser Trp Arg Ser Thr Gly Gly Ile Leu
305 310 315 320

Asp Val Tyr Ile Phe Leu Gly Pro Glu Pro Lys Ser Val Val Gln Gln
325 330 335

Tyr Leu Asp Val Val Gly Tyr Pro Phe Met Pro Pro Tyr Trp Gly Leu

-continued

```
            340                 345                 350

Gly Phe His Leu Cys Arg Trp Gly Tyr Ser Ser Thr Ala Ile Thr Arg
        355                 360                 365

Gln Val Val Glu Asn Met Thr Arg Ala His Phe Pro Leu Asp Val Gln
    370                 375                 380

Trp Asn Asp Leu Asp Tyr Met Asp Ser Arg Arg Asp Phe Thr Phe Asn
385                 390                 395                 400

Lys Asp Gly Phe Arg Asp Phe Pro Ala Met Val Gln Glu Leu His Gln
                405                 410                 415

Gly Gly Arg Arg Tyr Met Met Ile Val Asp Pro Ala Ile Ser Ser Ser
            420                 425                 430

Gly Pro Ala Gly Ser Tyr Arg Pro Tyr Asp Glu Gly Leu Arg Arg Gly
        435                 440                 445

Val Phe Ile Thr Asn Glu Thr Gly Gln Pro Leu Ile Gly Lys Val Trp
    450                 455                 460

Pro Gly Ser Thr Ala Phe Pro Asp Phe Thr Asn Pro Thr Ala Leu Ala
465                 470                 475                 480

Trp Trp Glu Asp Met Val Ala Glu Phe His Asp Gln Val Pro Phe Asp
                485                 490                 495

Gly Met Trp Ile Asp Met Asn Glu Pro Ser Asn Phe Ile Arg Gly Ser
            500                 505                 510

Glu Asp Gly Cys Pro Asn Asn Glu Leu Glu Asn Pro Pro Tyr Val Pro
        515                 520                 525

Gly Val Val Gly Gly Thr Leu Gln Ala Ala Thr Ile Cys Ala Ser Ser
    530                 535                 540

His Gln Phe Leu Ser Thr His Tyr Asn Leu His Asn Leu Tyr Gly Leu
545                 550                 555                 560

Thr Glu Ala Ile Ala Ser His Arg Ala Leu Val Lys Ala Arg Gly Thr
                565                 570                 575

Arg Pro Phe Val Ile Ser Arg Ser Thr Phe Ala Gly His Gly Arg Tyr
            580                 585                 590

Ala Gly His Trp Thr Gly Asp Val Trp Ser Ser Trp Glu Gln Leu Ala
        595                 600                 605

Ser Ser Val Pro Glu Ile Leu Gln Phe Asn Leu Leu Gly Val Pro Leu
    610                 615                 620

Val Gly Ala Asp Val Cys Gly Phe Leu Gly Asn Thr Ser Glu Glu Leu
625                 630                 635                 640

Cys Val Arg Trp Thr Gln Leu Gly Ala Phe Tyr Pro Phe Met Arg Asn
                645                 650                 655

His Asn Ser Leu Leu Ser Leu Pro Gln Glu Pro Tyr Ser Phe Ser Glu
            660                 665                 670

Pro Ala Gln Gln Ala Met Arg Lys Ala Leu Thr Leu Arg Tyr Ala Leu
        675                 680                 685

Leu Pro His Leu Tyr Thr Leu Phe His Gln Ala His Val Ala Gly Glu
    690                 695                 700

Thr Val Ala Arg Pro Leu Phe Leu Glu Phe Pro Lys Asp Ser Ser Thr
705                 710                 715                 720

Trp Thr Val Asp His Gln Leu Leu Trp Gly Glu Ala Leu Leu Ile Thr
                725                 730                 735

Pro Val Leu Gln Ala Gly Lys Ala Glu Val Thr Gly Tyr Phe Pro Leu
            740                 745                 750

Gly Thr Trp Tyr Asp Leu Gln Thr Val Pro Val Glu Ala Leu Gly Ser
        755                 760                 765
```

```
Leu Pro Pro Pro Pro Ala Ala Pro Arg Glu Pro Ala Ile His Ser Glu
    770                 775                 780

Gly Gln Trp Val Thr Leu Pro Ala Pro Leu Asp Thr Ile Asn Val His
785                 790                 795                 800

Leu Arg Ala Gly Tyr Ile Ile Pro Leu Gln Gly Pro Gly Leu Thr Thr
                805                 810                 815

Thr Glu Ser Arg Gln Gln Pro Met Ala Leu Ala Val Ala Leu Thr Lys
            820                 825                 830

Gly Gly Glu Ala Arg Gly Glu Leu Phe Trp Asp Asp Gly Glu Ser Leu
        835                 840                 845

Glu Val Leu Glu Arg Gly Ala Tyr Thr Gln Val Ile Phe Leu Ala Arg
    850                 855                 860

Asn Asn Thr Ile Val Asn Glu Leu Val Arg Val Thr Ser Glu Gly Ala
865                 870                 875                 880

Gly Leu Gln Leu Gln Lys Val Thr Val Leu Gly Val Ala Thr Ala Pro
                885                 890                 895

Gln Gln Val Leu Ser Asn Gly Val Pro Val Ser Asn Phe Thr Tyr Ser
            900                 905                 910

Pro Asp Thr Lys Val Leu Asp Ile Cys Val Ser Leu Leu Met Gly Glu
        915                 920                 925

Gln Phe Leu Val Ser Trp Cys
    930                 935
```

<210> SEQ ID NO 26
<211> LENGTH: 268
<212> TYPE: DNA
<213> ORGANISM: Artificial Sequence
<220> FEATURE:
<223> OTHER INFORMATION: Modified Nucleic Acid

<400> SEQUENCE: 26

```
agatctagag ctgaattcct gcagccaggg ggatcagcct ctactgtgcc ttctagttgc     60

cagccatctg ttgtttgccc ctcccccttg ccttccttga ccctggaagg tgccactccc    120

actgtccttt cctaataaaa tgaggaaatt gcatcacatt gtctgagtag gtgtcattct    180

attctggggg gtggggtggg gcaggacagc aagggggagg attgggaaga caatagcagg    240

catgctgggg atgcagtggg ctctatgg                                        268
```

<210> SEQ ID NO 27
<211> LENGTH: 202
<212> TYPE: DNA
<213> ORGANISM: Bos taurus

<400> SEQUENCE: 27

```
agatctaccg gtgaattcac cgcgggttta aactgtgcct tctagttgcc agccatctgt     60

tgtttgcccc tcccccgtgc cttccttgac cctggaaggt gccactccca ctgtcctttc    120

ctaataaaat gaggaaattg catcgcattg tctgagtagg tgtcattcta ttctgggggg    180

tggggtgggg gctagctcta ga                                              202
```

<210> SEQ ID NO 28
<211> LENGTH: 456
<212> TYPE: DNA
<213> ORGANISM: Homo sapiens

<400> SEQUENCE: 28

```
gggcccatgc cacctccaac atccactcga ccccttggaa tttcggtgga gaggagcaga     60
```

```
ggttgtcctg gcgtggttta ggtagtgtga gaggggtacc cggggatctt gctaccagtg    120

gaacagccac taaggattct gcagtgagag cagagggcca gctaagtggt actctcccag    180

agactgtctg actcacgcca ccccctccac cttggacaca ggacgctgtg gtttctgagc    240

caggtacaat gactcctttc ggtaagtgca gtggaagctg tacactgccc aggcaaagcg    300

tccgggcagc gtaggcgggc gactcagatc ccagccagtg gacttagccc ctgtttgctc    360

ctccgataac tggggtgacc ttggttaata ttcaccagca gcctcccccg ttgcccctct    420

ggatccactg cttaaatacg gacgaggaca gggccc                              456


<210> SEQ ID NO 29
<211> LENGTH: 444
<212> TYPE: DNA
<213> ORGANISM: Homo sapiens

<400> SEQUENCE: 29

atgccacctc caacatccac tcgacccctt ggaatttcgg tggagaggag cagaggttgt     60

cctggcgtgg tttaggtagt gtgagagggg tacccgggga tcttgctacc agtggaacag    120

ccactaagga ttctgcagtg agagcagagg gccagctaag tggtactctc ccagagactg    180

tctgactcac gccaccccct ccaccttgga cacaggacgc tgtggtttct gagccaggta    240

caatgactcc tttcggtaag tgcagtggaa gctgtacact gcccaggcaa agcgtccggg    300

cagcgtaggc gggcgactca gatcccagcc agtggactta gcccctgttt gctcctccga    360

taactggggt gaccttggtt aatattcacc agcagcctcc cccgttgccc ctctggatcc    420

actgcttaaa tacggacgag gaca                                           444


<210> SEQ ID NO 30
<211> LENGTH: 738
<212> TYPE: PRT
<213> ORGANISM: Artificial Sequence
<220> FEATURE:
<223> OTHER INFORMATION: AAV vector capsid

<400> SEQUENCE: 30

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160
```

-continued

```
Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
```

```
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 31
<211> LENGTH: 601
<212> TYPE: PRT
<213> ORGANISM: Artificial Sequence
<220> FEATURE:
<223> OTHER INFORMATION: AAV vector capsid

<400> SEQUENCE: 31

Thr Ala Pro Gly Lys Lys Arg Pro Val Glu Pro Ser Pro Gln Arg Ser
1               5                   10                  15

Pro Asp Ser Ser Thr Gly Ile Gly Lys Lys Gly Gln Gln Pro Ala Lys
            20                  25                  30

Lys Arg Leu Asn Phe Gly Gln Thr Gly Asp Ser Glu Ser Val Pro Asp
        35                  40                  45

Pro Gln Pro Ile Gly Glu Pro Pro Ala Gly Pro Ser Gly Leu Gly Ser
    50                  55                  60

Gly Thr Met Ala Ala Gly Gly Gly Ala Pro Met Ala Asp Asn Asn Glu
65                  70                  75                  80

Gly Ala Asp Gly Val Gly Ser Ser Ser Gly Asn Trp His Cys Asp Ser
                85                  90                  95

Thr Trp Leu Gly Asp Arg Val Ile Thr Thr Ser Thr Arg Thr Trp Ala
            100                 105                 110

Leu Pro Thr Tyr Asn Asn His Leu Tyr Lys Gln Ile Ser Asn Gly Thr
        115                 120                 125

Ser Gly Gly Ser Thr Asn Asp Asn Thr Tyr Phe Gly Tyr Ser Thr Pro
    130                 135                 140

Trp Gly Tyr Phe Asp Phe Asn Arg Phe His Cys His Phe Ser Pro Arg
145                 150                 155                 160

Asp Trp Gln Arg Leu Ile Asn Asn Asn Trp Gly Phe Arg Pro Lys Arg
                165                 170                 175

Leu Asn Phe Lys Leu Phe Asn Ile Gln Val Lys Glu Val Thr Gln Asn
            180                 185                 190

Glu Gly Thr Lys Thr Ile Ala Asn Asn Leu Thr Ser Thr Ile Gln Val
        195                 200                 205
```

```
Phe Thr Asp Ser Glu Tyr Gln Leu Pro Tyr Val Leu Gly Ser Ala His
    210                 215                 220

Gln Gly Cys Leu Pro Pro Phe Pro Ala Asp Val Phe Met Ile Pro Gln
225                 230                 235                 240

Tyr Gly Tyr Leu Thr Leu Asn Asn Gly Ser Gln Ala Val Gly Arg Ser
                245                 250                 255

Ser Phe Tyr Cys Leu Glu Tyr Phe Pro Ser Gln Met Leu Arg Thr Gly
            260                 265                 270

Asn Asn Phe Glu Phe Ser Tyr Asn Phe Glu Asp Val Pro Phe His Ser
        275                 280                 285

Ser Tyr Ala His Ser Gln Ser Leu Asp Arg Leu Met Asn Pro Leu Ile
    290                 295                 300

Asp Gln Tyr Leu Tyr Tyr Leu Ser Arg Thr Gln Ser Thr Gly Gly Thr
305                 310                 315                 320

Ala Gly Thr Gln Gln Leu Leu Phe Ser Gln Ala Gly Pro Asn Asn Met
                325                 330                 335

Ser Ala Gln Ala Lys Asn Trp Leu Pro Gly Pro Cys Tyr Arg Gln Gln
            340                 345                 350

Arg Val Ser Thr Thr Leu Ser Gln Asn Asn Asn Ser Asn Phe Ala Trp
        355                 360                 365

Thr Gly Ala Thr Lys Tyr His Leu Asn Gly Arg Asp Ser Leu Val Asn
    370                 375                 380

Pro Gly Val Ala Met Ala Thr His Lys Asp Asp Glu Glu Arg Phe Phe
385                 390                 395                 400

Pro Ser Ser Gly Val Leu Met Phe Gly Lys Gln Gly Ala Gly Lys Asp
                405                 410                 415

Asn Val Asp Tyr Ser Ser Val Met Leu Thr Ser Glu Glu Glu Ile Lys
            420                 425                 430

Thr Thr Asn Pro Val Ala Thr Glu Gln Tyr Gly Val Val Ala Asp Asn
        435                 440                 445

Leu Gln Gln Gln Asn Ala Ala Pro Ile Val Gly Ala Val Asn Ser Gln
    450                 455                 460

Gly Ala Leu Pro Gly Met Val Trp Gln Asn Arg Asp Val Tyr Leu Gln
465                 470                 475                 480

Gly Pro Ile Trp Ala Lys Ile Pro His Thr Asp Gly Asn Phe His Pro
                485                 490                 495

Ser Pro Leu Met Gly Gly Phe Gly Leu Lys His Pro Pro Pro Gln Ile
            500                 505                 510

Leu Ile Lys Asn Thr Pro Val Pro Ala Asp Pro Pro Thr Thr Phe Asn
        515                 520                 525

Gln Ala Lys Leu Ala Ser Phe Ile Thr Gln Tyr Ser Thr Gly Gln Val
    530                 535                 540

Ser Val Glu Ile Glu Trp Glu Leu Gln Lys Glu Asn Ser Lys Arg Trp
545                 550                 555                 560

Asn Pro Glu Ile Gln Tyr Thr Ser Asn Tyr Tyr Lys Ser Thr Asn Val
                565                 570                 575

Asp Phe Ala Val Asn Thr Glu Gly Thr Tyr Ser Glu Pro Arg Pro Ile
            580                 585                 590

Gly Thr Arg Tyr Leu Thr Arg Asn Leu
        595                 600
```

<210> SEQ ID NO 32
<211> LENGTH: 535

<212> TYPE: PRT
<213> ORGANISM: Artificial Sequence
<220> FEATURE:
<223> OTHER INFORMATION: AAV vector capsid

<400> SEQUENCE: 32

```
Met Ala Ala Gly Gly Gly Ala Pro Met Ala Asp Asn Asn Glu Gly Ala
1               5                   10                  15

Asp Gly Val Gly Ser Ser Ser Gly Asn Trp His Cys Asp Ser Thr Trp
            20                  25                  30

Leu Gly Asp Arg Val Ile Thr Thr Ser Thr Arg Thr Trp Ala Leu Pro
        35                  40                  45

Thr Tyr Asn Asn His Leu Tyr Lys Gln Ile Ser Asn Gly Thr Ser Gly
    50                  55                  60

Gly Ser Thr Asn Asp Asn Thr Tyr Phe Gly Tyr Ser Thr Pro Trp Gly
65                  70                  75                  80

Tyr Phe Asp Phe Asn Arg Phe His Cys His Phe Ser Pro Arg Asp Trp
                85                  90                  95

Gln Arg Leu Ile Asn Asn Asn Trp Gly Phe Arg Pro Lys Arg Leu Asn
            100                 105                 110

Phe Lys Leu Phe Asn Ile Gln Val Lys Glu Val Thr Gln Asn Glu Gly
        115                 120                 125

Thr Lys Thr Ile Ala Asn Asn Leu Thr Ser Thr Ile Gln Val Phe Thr
    130                 135                 140

Asp Ser Glu Tyr Gln Leu Pro Tyr Val Leu Gly Ser Ala His Gln Gly
145                 150                 155                 160

Cys Leu Pro Pro Phe Pro Ala Asp Val Phe Met Ile Pro Gln Tyr Gly
                165                 170                 175

Tyr Leu Thr Leu Asn Asn Gly Ser Gln Ala Val Gly Arg Ser Ser Phe
            180                 185                 190

Tyr Cys Leu Glu Tyr Phe Pro Ser Gln Met Leu Arg Thr Gly Asn Asn
        195                 200                 205

Phe Glu Phe Ser Tyr Asn Phe Glu Asp Val Pro Phe His Ser Ser Tyr
    210                 215                 220

Ala His Ser Gln Ser Leu Asp Arg Leu Met Asn Pro Leu Ile Asp Gln
225                 230                 235                 240

Tyr Leu Tyr Tyr Leu Ser Arg Thr Gln Ser Thr Gly Gly Thr Ala Gly
                245                 250                 255

Thr Gln Gln Leu Leu Phe Ser Gln Ala Gly Pro Asn Asn Met Ser Ala
            260                 265                 270

Gln Ala Lys Asn Trp Leu Pro Gly Pro Cys Tyr Arg Gln Gln Arg Val
        275                 280                 285

Ser Thr Thr Leu Ser Gln Asn Asn Asn Ser Asn Phe Ala Trp Thr Gly
    290                 295                 300

Ala Thr Lys Tyr His Leu Asn Gly Arg Asp Ser Leu Val Asn Pro Gly
305                 310                 315                 320

Val Ala Met Ala Thr His Lys Asp Asp Glu Glu Arg Phe Phe Pro Ser
                325                 330                 335

Ser Gly Val Leu Met Phe Gly Lys Gln Gly Ala Gly Lys Asp Asn Val
            340                 345                 350

Asp Tyr Ser Ser Val Met Leu Thr Ser Glu Glu Glu Ile Lys Thr Thr
        355                 360                 365

Asn Pro Val Ala Thr Glu Gln Tyr Gly Val Val Ala Asp Asn Leu Gln
    370                 375                 380
```

```
Gln Gln Asn Ala Ala Pro Ile Val Gly Ala Val Asn Ser Gln Gly Ala
385                 390                 395                 400

Leu Pro Gly Met Val Trp Gln Asn Arg Asp Val Tyr Leu Gln Gly Pro
                405                 410                 415

Ile Trp Ala Lys Ile Pro His Thr Asp Gly Asn Phe His Pro Ser Pro
            420                 425                 430

Leu Met Gly Gly Phe Gly Leu Lys His Pro Pro Pro Gln Ile Leu Ile
        435                 440                 445

Lys Asn Thr Pro Val Pro Ala Asp Pro Pro Thr Thr Phe Asn Gln Ala
    450                 455                 460

Lys Leu Ala Ser Phe Ile Thr Gln Tyr Ser Thr Gly Gln Val Ser Val
465                 470                 475                 480

Glu Ile Glu Trp Glu Leu Gln Lys Glu Asn Ser Lys Arg Trp Asn Pro
                485                 490                 495

Glu Ile Gln Tyr Thr Ser Asn Tyr Tyr Lys Ser Thr Asn Val Asp Phe
            500                 505                 510

Ala Val Asn Thr Glu Gly Thr Tyr Ser Glu Pro Arg Pro Ile Gly Thr
        515                 520                 525

Arg Tyr Leu Thr Arg Asn Leu
    530                 535


<210> SEQ ID NO 33
<211> LENGTH: 736
<212> TYPE: PRT
<213> ORGANISM: Artificial Sequence
<220> FEATURE:
<223> OTHER INFORMATION: AAV vector capsid

<400> SEQUENCE: 33

Met Ala Ala Asp Gly Tyr Leu Pro Asp Trp Leu Glu Asp Asn Leu Ser
1               5                   10                  15

Glu Gly Ile Arg Glu Trp Trp Ala Leu Gln Pro Gly Ala Pro Lys Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140

Pro Val Asp Gln Ser Pro Gln Glu Pro Asp Ser Ser Ser Gly Val Gly
145                 150                 155                 160

Lys Ser Gly Lys Gln Pro Ala Arg Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Ala Pro Thr Ser Leu Gly Ser Asn Thr Met Ala Ser Gly Gly Gly
        195                 200                 205
```

-continued

```
Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly His Phe His Pro Ser Pro Leu Met Gly Gly Phe Gly Leu
```

-continued

```
625                 630                 635                 640

Lys His Pro Pro Pro Gln Ile Met Ile Lys Asn Thr Pro Val Pro Ala
                645                 650                 655

Asn Pro Pro Thr Thr Phe Ser Pro Ala Lys Phe Ala Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Asn Lys Ser Val Asn Val Asp Phe Thr Val Asp Thr Asn Gly Val
705                 710                 715                 720

Tyr Ser Glu Pro Arg Pro Ile Gly Thr Arg Tyr Leu Thr Arg Pro Leu
                725                 730                 735
```

CODON-OPTIMIZED ACID ALPHA-GLUCOSIDASE EXPRESSION CASSETTES AND METHODS OF USING SAME

RELATED APPLICATIONS

This patent application is the National Phase of International Application No. PCT/US2019/032502, filed May 15, 2019, which designated the U.S. and that International Application was published under PCT Article 21(2) in English, which claims the benefit of priority to U.S. Provisional Patent Application No. 62/672,419, filed May 16, 2018, and U.S. Provisional Patent Application No. 62/734,454, filed Sep. 21, 2018. The entire contents of the foregoing applications are incorporated herein by reference, including all text, tables, sequence listing and drawings.

SEQUENCE LISTING

The instant application contains a Sequence Listing which has been submitted electronically in ASCII format and is hereby incorporated by reference in its entirety. Said ASCII copy, created on Nov. 13, 2020, is named "Spark0515886_ST25.txt" and is 145 KB in size.

INTRODUCTION

Glycogen storage disease type II, also called Pompe disease, is an autosomal recessive disorder caused by mutations in the gene encoding the lysosomal enzyme acid α-glucosidase (GAA), which catalyzes the degradation of glycogen. The resulting enzyme deficiency leads to pathological accumulation of glycogen and lysosomal alterations in all tissues of the body, resulting in cardiac, respiratory, and skeletal muscle dysfunction (van der Ploeg & Reuser, 2008 Lancet, 372:1342-1353). Traditionally, Pompe disease has been separated into two major phenotypes—infantile-onset Pompe disease (IOPD) (also referred to as infantile Pompe disease (IPD) or early-onset Pompe disease) and late-onset Pompe disease (LOPD)-based on residual GAA enzyme activity, age of onset, organ involvement (i.e., presence of cardiomyopathy), severity, and rate of progression. Enzyme replacement therapy (ERT) is available for Pompe disease; however, it has several limitations (i.e., limited biodistribution and high immunogenicity) leading to treatment failures and limited long-term efficacy (van der Ploeg & Reuser, 2008).

SUMMARY

Disclosed herein are optimized cassettes for liver-directed expression of a secretable version of human GAA. These optimizations to the cassettes lead to an increase in GAA secretion from liver and enable hepatic gene transfer to achieve circulating levels of GAA sufficient to cross-correct GAA deficiency systemically in subjects. These cassettes achieve increased transgene expression, improved safety characteristics and potentially reduced immunogenicity. These cassettes will be useful as a gene therapy treatment of subjects with Pompe disease and other diseases and disorders treatable with GAA.

Codon optimization of GAA expression cassette was undertaken to improve expression of GAA. In one embodiment, nucleic acid sequences encoding GAA were modified to eliminate CpG dinucleotides. In total, 20 new codon optimized transgene sequences were created (GAA1-

GAA20). Based on in vitro comparison of GAA activity, 5 codon-optimized sequences were selected (GAA 2, 5, 7, 8 and 13) for further optimization. The GAA13 sequence was used to analyze the differences in expression of GAA after addition of a 29-base pair polynucleotide sequence to the 5' untranslated region (UTR). Two different polyadenylation sequences derived from bovine growth hormone (bGH or BGH) (wild-type and CpG-reduced) were also evaluated for GAA7, 8 and 13. The resulting 9 expression cassettes (Table 1) were packaged within the SEQ ID NOs:30-32 capsid; one was also packaged into AAV6 capsid.

In accordance with the invention, there are provided nucleic acids encoding an acid α-glucosidase (GAA), expression cassettes comprising the nucleic acids encoding an acid α-glucosidase (GAA) and viral vectors comprising the nucleic acids encoding an acid α-glucosidase (GAA).

In one embodiment, a nucleic acid encoding a GAA has greater than 86% sequence identity to any of the sequences set forth as SEQ ID NOs:1-5. In additional aspects, a nucleic acid encoding a GAA has greater than 87% sequence identity to any of the sequences set forth as SEQ ID NOs:1-5.

In another embodiment, a nucleic acid encoding a GAA has greater than 87% sequence identity to any of the sequences set forth as SEQ ID NOs:6-15. In particular aspects, a nucleic acid encoding a GAA has greater than 88% sequence identity to any of the sequences set forth as SEQ ID NOs:6-15. In additional particular aspects, a nucleic acid encoding a GAA has greater than 89% sequence identity to any of the sequences set forth as SEQ ID NOs:6-15. In further particular aspects, a nucleic acid encoding a GAA has greater than 90% sequence identity to any of the sequences set forth as SEQ ID NOs:6-15. In yet additional particular aspects, a nucleic acid encoding a GAA has greater than 91% sequence identity to any of the sequences set forth as SEQ ID NOs:6-15.

In another embodiment, a nucleic acid encoding a GAA has greater than 91% sequence identity to any of the sequences set forth as SEQ ID NOs:16-24.

In another embodiment, a nucleic acid encoding a GAA has greater than 92% sequence identity to any of the sequences set forth as SEQ ID NOs:1-24.

In another embodiment, a nucleic acid encoding a GAA has greater than 93% sequence identity to any of the sequences set forth as SEQ ID NOs:1-24.

In another embodiment, a nucleic acid encoding a GAA has greater than 94% sequence identity to any of the sequences set forth as SEQ ID NOs:1-24.

In another embodiment, a nucleic acid encoding a GAA has greater than 95% sequence identity to any of the sequences set forth as SEQ ID NOs:1-24.

In another embodiment, a nucleic acid encoding a GAA has greater than 96% sequence identity to any of the sequences set forth as SEQ ID NOs:1-24.

In another embodiment, a nucleic acid encoding a GAA has greater than 97% sequence identity to any of the sequences set forth as SEQ ID NOs:1-24.

In another embodiment, a nucleic acid encoding a GAA has greater than 98% sequence identity to any of the sequences set forth as SEQ ID NOs:1-24.

In another embodiment, a nucleic acid encoding a GAA has greater than 99% sequence identity to any of the sequences set forth as SEQ ID NOs:1-24.

In another embodiment, a nucleic acid encoding a GAA has greater than 99.5% sequence identity to any of the sequences set forth as SEQ ID NOs:1-24.

In another embodiment, a nucleic acid encoding a GAA has 100% sequence identity to any of the sequences set forth as SEQ ID NOs:1-24.

In another embodiment, a nucleic acid encoding a GAA contains less than 127 CpG dinucleotides.

In another embodiment, a nucleic acid encoding a GAA contains less than 126 CpG dinucleotides.

In another embodiment, a nucleic acid encoding a GAA contains from about 126-120 CpG dinucleotides.

In another embodiment, a nucleic acid encoding a GAA contains from about 120-110 CpG dinucleotides.

In another embodiment, a nucleic acid encoding a GAA contains from about 110-100 CpG dinucleotides.

In another embodiment, a nucleic acid encoding a GAA contains from about 100-90 CpG dinucleotides.

In another embodiment, a nucleic acid encoding a GAA contains from about 90-80 CpG dinucleotides.

In another embodiment, a nucleic acid encoding a GAA contains from about 80-70 CpG dinucleotides.

In another embodiment, a nucleic acid encoding a GAA contains from about 70-60 CpG dinucleotides.

In another embodiment, a nucleic acid encoding a GAA contains from about 60-50 CpG dinucleotides.

In another embodiment, a nucleic acid encoding a GAA contains from about 50-40 CpG dinucleotides.

In another embodiment, a nucleic acid encoding a GAA contains from about 40-30 CpG dinucleotides.

In another embodiment, a nucleic acid encoding a GAA contains from about 30-20 CpG dinucleotides.

In another embodiment, a nucleic acid encoding a GAA contains less than 20 CpG dinucleotides.

In another embodiment, a nucleic acid encoding a GAA contains from about 20-10 CpG dinucleotides.

In another embodiment, a nucleic acid encoding a GAA contains less than 10 CpG dinucleotides.

In another embodiment, a nucleic acid encoding a GAA contains from about 10-5 CpG dinucleotides.

In another embodiment, a nucleic acid encoding a GAA contains 5 CpG dinucleotides.

In another embodiment, a nucleic acid encoding a GAA contains 4 CpG dinucleotides.

In another embodiment, a nucleic acid encoding a GAA contains 3 CpG dinucleotides.

In another embodiment, a nucleic acid encoding a GAA contains 2 CpG dinucleotides.

In another embodiment, a nucleic acid encoding a GAA contains 1 CpG dinucleotide.

In another embodiment, a nucleic acid encoding a GAA contains 0 CpG dinucleotides.

The invention also provides expression cassettes comprising the nucleic acids encoding GAA as set forth herein, operably linked to an expression control element.

In one embodiment, an expression cassette comprises a nucleic acid encoding a GAA with greater than 86% sequence identity (e.g., 87%-100% identity) to any of the sequences set forth as SEQ ID NOs:1-5.

In another embodiment, an expression cassette comprises a nucleic acid encoding a GAA with greater than 87% sequence identity (e.g., 88%-100% identity) to any of the sequences set forth as SEQ ID NOs:6-15.

In another embodiment, an expression cassette comprises a nucleic acid encoding a GAA with less than 127 CpG dinucleotides, less than 127 CpG dinucleotides, less than 127 CpG dinucleotides, less than 126 CpG dinucleotides, less than 125 CpG dinucleotides, less than 124 CpG dinucleotides, less than 123 CpG dinucleotides, less than 122 CpG dinucleotides, less than 121 CpG dinucleotides, less than 120 CpG dinucleotides, less than 119 CpG dinucleotides, less than 118 CpG dinucleotides, less than 117 CpG dinucleotides, less than 116 CpG dinucleotides, less than 115 CpG dinucleotides, less than 114 CpG dinucleotides, less than 113 CpG dinucleotides, less than 112 CpG dinucleotides, less than 111 CpG dinucleotides, less than 110 CpG dinucleotides, less than 109 CpG dinucleotides, less than 108 CpG dinucleotides, less than 107 CpG dinucleotides, less than 106 CpG dinucleotides, less than 105 CpG dinucleotides, less than 104 CpG dinucleotides, less than 103 CpG dinucleotides, less than 102 CpG dinucleotides, less than 101 CpG dinucleotides, less than 101 CpG dinucleotides, and so forth all the way down to zero (0) CpG dinucleotides.

In one embodiment, an expression control element is positioned 5' of a nucleic acid encoding a GAA.

In another embodiment, an expression cassette includes a poly-adenylation (polyA) sequence positioned 3' of a nucleic acid encoding a GAA.

In another embodiment, an expression control element or poly-adenylation sequence is CpG reduced compared to wild-type expression control element or poly-adenylation sequence.

In another embodiment, an expression control element comprises an ApoE/hAAT enhancer/promoter sequence.

In another embodiment, a poly-adenylation sequence comprises a bovine growth hormone (bGH) polyadenylation sequence.

In another embodiment, an ApoE/hAAT enhancer/promoter sequence or bGH polyadenylation sequence is CpG reduced compared to wild-type ApoE/hAAT enhancer/promoter sequence or bGH polyadenylation sequence.

In one aspect, a wild-type bGH polyadenylation sequence comprises the sequence of SEQ ID NO:27.

In another aspect, a wild-type ApoE/hAAT enhancer/promoter sequence comprises the sequence of SEQ ID NO:28 or 29.

In another aspect, a CpG reduced bGH polyadenylation sequence comprises the sequence of SEQ ID NO:26.

In another embodiment, an expression cassette further comprises an intron positioned between the 3' end of the expression control element and the 5' end of the nucleic acid encoding a GAA.

In another embodiment, a GAA comprises or consists of the sequence set forth as SEQ ID NO:25.

The invention further provides viral vectors such as adenovirus-associated virus (AAV) vectors comprising the nucleic acids encoding GAA as set forth herein.

In one embodiment, a viral vector such as an adenovirus-associated virus (AAV) vector comprises any of the nucleic acids encoding GAA as set forth herein operably linked to an expression control element.

In another embodiment, a viral vector such as an adenovirus-associated virus (AAV) vector comprises any of the expression cassettes comprising the nucleic acids encoding GAA as set forth herein.

In another embodiment, an AAV vector comprises: one or more of an AAV capsid; and one or more AAV inverted terminal repeats (ITRs), wherein the AAV ITR(s) flanks the 5' or 3' terminus of the nucleic acid or the expression cassette.

In additional embodiments, an AAV vector further comprises an intron positioned 5' or 3' of one or more ITRs.

In additional embodiments, an AAV vector comprising at least one or more ITRs or an intron has the one or more ITRs or intron modified to have reduced CpGs.

In additional embodiments, an AAV vector has a capsid serotype comprising a modified or variant AAV VP1, VP2 and/or VP3 capsid having 90% or more sequence identity to AAV1, AAV2, AAV3, AAV4, AAV5, AAV6, AAV7, AAV8, AAV9, AAV10, AAV11, Rh10, Rh74, AAV3B, AAV-2i8 or SEQ ID NO:30, 31 or 32 VP1, VP2 and/or VP3 sequences, or a capsid having 95% or more sequence identity to AAV1, AAV2, AAV3, AAV4, AAV5, AAV6, AAV7, AAV8, AAV9, AAV10, AAV11, AAV12, Rh10, Rh74, AAV3B, AAV-2i8, or SEQ ID NO:30, 31 or 32 VP1, VP2 and/or VP3 sequences, or a capsid having 100% sequence identity to AAV1, AAV2, AAV3, AAV4, AAV5, AAV6, AAV7, AAV8, AAV9, AAV10, AAV11, Rh10, Rh74, AAV3B, AAV-2i8, or SEQ ID NO:30, 31 or 32 VP1, VP2 and/or VP3 sequences.

In additional embodiments, an AAV vector comprising one or more ITRs as one or more ITRs of any of: AAV1, AAV2, AAV3, AAV4, AAV5, AAV6, AAV7, AAV8, AAV9, AAV10, AAV11, Rh10, Rh74, or AAV3B AAV serotypes, or a combination thereof.

The invention additionally provides pharmaceutical compositions comprising any of the nucleic acids encoding GAA, expression cassettes comprising nucleic acids encoding GAA or viral vectors such as AAV vectors comprising nucleic acids encoding GAA or expression cassettes comprising nucleic acids encoding GAA as set forth herein.

In one embodiment, a pharmaceutical composition comprises a plurality of AAV vectors as set forth herein in a biologically compatible carrier or excipient.

In another embodiment, a pharmaceutical composition comprising any of the AAV vectors as set forth herein, further comprises empty AAV capsids.

In particular embodiments, in a pharmaceutical composition comprising AAV vectors and empty AAV capsids, the ratio of the empty AAV capsids to the AAV vector is within or between about 100:1-50:1, from about 50:1-25:1, from about 25:1-10:1, from about 10:1-1:1, from about 1:1-1:10, from about 1:10-1:25, from about 1:25-1:50, or from about 1:50-1:100.

In particular aspects, in a pharmaceutical composition comprising AAV vectors and empty AAV capsids, the ratio of the of the empty AAV capsids to the AAV vector is about 2:1, 3:1, 4:1, 5:1, 6:1, 7:1, 8:1, 9:1, or 10:1.

In another embodiment, a pharmaceutical composition includes a surfactant.

The invention still further provides methods of treating a human in need of acid α-glucosidase (GAA) by administering or delivering any of the nucleic acids encoding GAA, expression cassettes comprising nucleic acids encoding GAA, or viral vectors such as AAV vectors comprising the nucleic acids encoding GAA or expression cassettes comprising the nucleic acids encoding GAA to the human.

In one embodiment, a method of treating a human in need of acid α-glucosidase (GAA), includes: (a) providing a nucleic acid, expression cassette or viral vector such as AAV vector as set forth herein, or any pharmaceutical composition as set forth herein; and (b) administering an amount of the nucleic acid, expression cassette, viral (e.g., AAV) vector, or pharmaceutical composition to redo human, where the GAA is expressed in the human.

In particular embodiments, a human has Pompe disease, such as infantile onset Pompe disease or late onset Pompe disease.

In another embodiment, a human has a glycogen storage disease (GSD).

In particular aspects, a GSD is any of: GSD type I (von Gierke's disease), GSD type III (Forbes-Cori disease), GSD type IV (Anderson disease, amylopectinosis), GSD type V (McArdle disease), GSD type VI (Hers disease), GSD type VII (Tarui disease), or a congenital GSD of the heart (e.g., lethal congenital GSD of the heart).

In particular embodiments, a nucleic acid encoding a GAA, an expression cassette comprising a nucleic acid encoding a GAA, or an AAV vector is administered to a human intravenously, intraarterially, intra-cavity, intracavitary, intramucosally, or via catheter.

In particular embodiments, in a method GAA is expressed at increased levels, optionally greater than 1% of the levels of GAA found in a human not in need of GAA.

In particular embodiments, an AAV vector is administered in a range from about $1\times10^8$ to about $1\times10^{14}$ vector genomes per kilogram (vg/kg) of the weight of the human.

In particular embodiments, a method reduces, decreases or inhibits one or more symptoms of the need of GAA or the disease; or prevents or reduces progression or worsening of one or more symptoms of the need of GAA or the disease; or stabilizes one or more symptoms of the need of GAA or the disease; or improves one or more symptoms of the need of GAA or the disease.

In particular aspects, a symptom treatable in accordance with the invention can be one or more of the following: difficulty eating and/or not gaining weight; poor head and/or neck control; breathing problems and/or lung infections; enlarged and/or thickening heart; heart defects; enlarged tongue; difficulty swallowing; enlarged liver; poor muscle strength; weak muscle tone; weakness in the legs, waist and/or arms; shortness of breath; difficulty exercising; difficulty breathing while sleeping; curvature of the spine; and/or stiff joints.

The invention yet additionally provides cells comprising nucleic acids encoding GAA, cells comprising expression cassettes comprising the nucleic acids encoding GAA and cells comprising viral vectors such as AAV vectors comprising nucleic acids encoding GAA or expression cassettes comprising nucleic acids encoding GAA.

In one embodiment, a cell produces a viral vector.

In another embodiment, a cell produces an AAV vector as set forth herein.

Still further, the invention also provides methods of producing viral vectors such as AAV vectors as set forth herein.

In one embodiment, a method of producing AAV vectors include: introducing an AAV vector genome comprising a nucleic acid encoding GAA or expression cassette comprising a nucleic acid encoding GAA as set forth herein into a packaging helper cell; and culturing the helper cell under conditions to produce the AAV vectors.

In another embodiment, a method of producing AAV vector errors includes: introducing a nucleic acid encoding GAA or expression cassette comprising a nucleic acid encoding GAA as set forth herein into a packaging helper cell; and culturing the helper cells under conditions to produce the AAV vector.

In additional embodiments, cells are mammalian cells.

In additional embodiments, cells for vector production provide helper functions, such as AAV helper functions, that package the vector into a viral particle. In a particular aspect, the helper functions are Rep and/or Cap proteins for AAV vector packaging.

In additional embodiments, cells for vector production may be stably or transiently transfected with polynucleotide(s) encoding Rep and/or Cap protein sequence(s).

In additional embodiments, cells for vector production provide Rep78 and/or Rep68 proteins. In such cells, the cells may be stably or transiently transfected with Rep78 and/or Rep68 proteins polynucleotide encoding sequence(s).

In particular embodiments, cells for vector production are human embryonic kidney cells. In a particular aspect, cells for vector production are HEK-293 cells.

DETAILED DESCRIPTION

Figure 1:
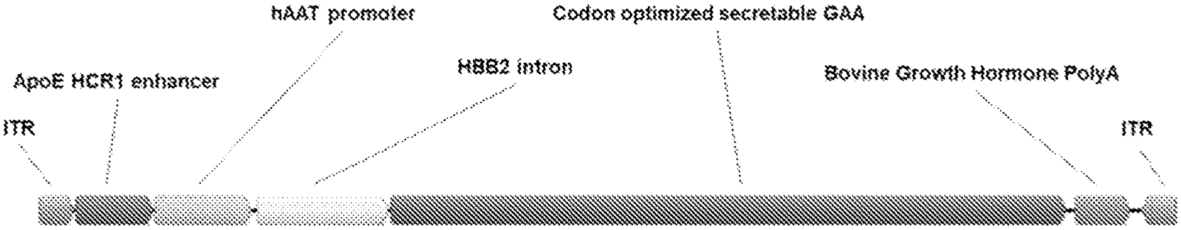
FIG. 1 shows a schematic of pAAV-ApoE/hAAT.fixUTR.GAA13.BGH (SEQ ID NO:16).
Figure 2:
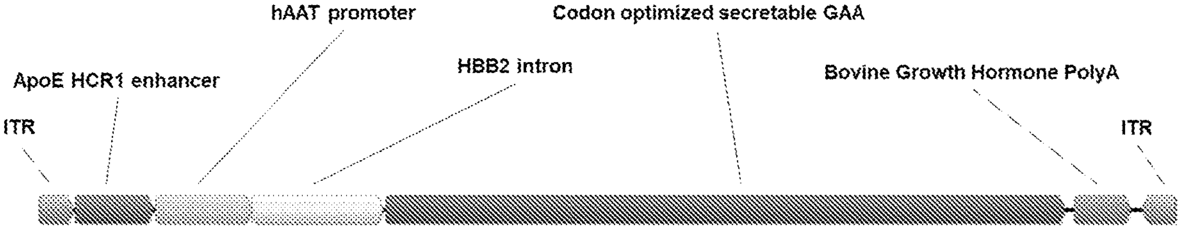
FIG. 2 shows a schematic of pAAV-ApoE/hAAT.GAA13.BGH (SEQ ID NO:17).
Figure 3:
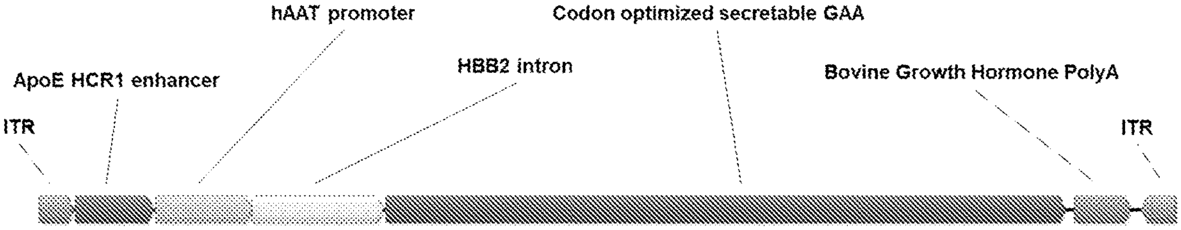
FIG. 3 shows a schematic of pAAV-ApoE/hAAT.GAA7.BGH (SEQ ID NO:18).
Figure 4:
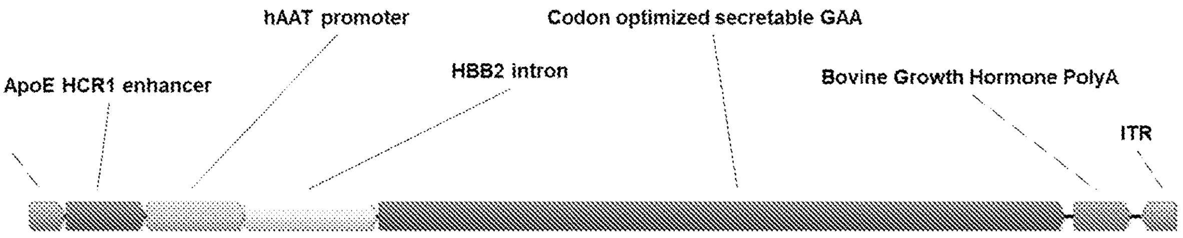
FIG. 4 shows a schematic of pAAV-ApoE/hAAT.GAA8.BGH (SEQ ID NO:19).
Figure 5:
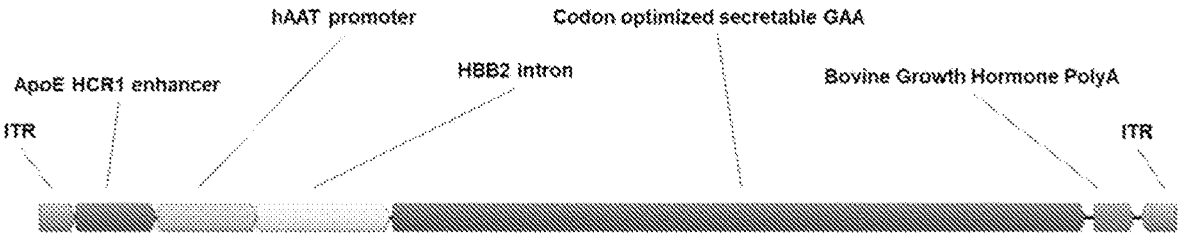
FIG. 5 shows a schematic of pAAV-ApoE/hAAT.GAA2.wtBGH (SEQ ID NO:20).
Figure 6:
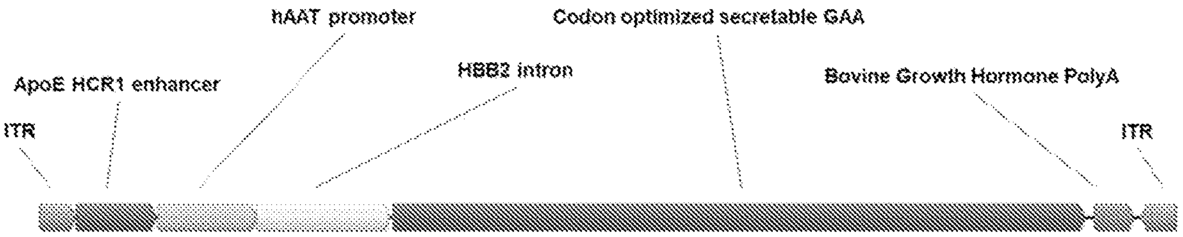
FIG. 6 shows a schematic of pAAV-ApoE/hAAT.GAA5.wtBGH (SEQ ID NO:21).
Figure 7:
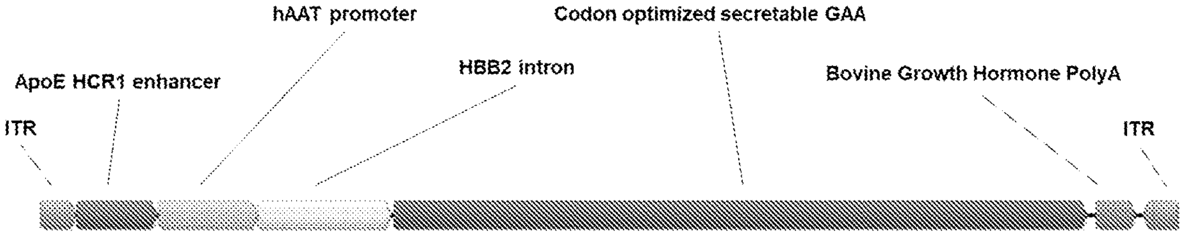
FIG. 7 shows a schematic of pAAV-ApoE/hAAT.GAA7.wtBGH (SEQ ID NO:22).
Figure 8:
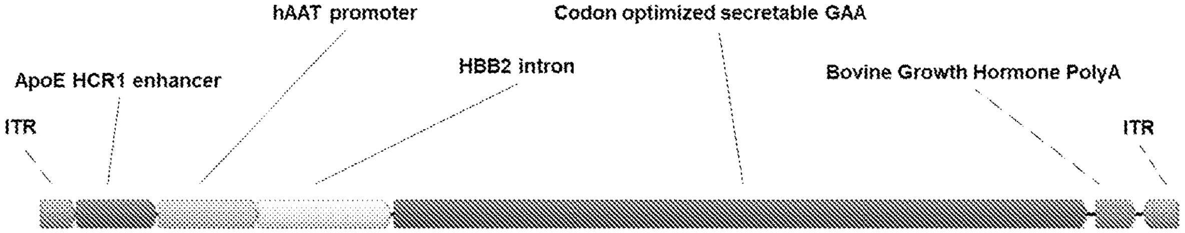
FIG. 8 shows a schematic of pAAV-ApoE/hAAT.GAA8.wtBGH (SEQ ID NO:23).
Figure 9:
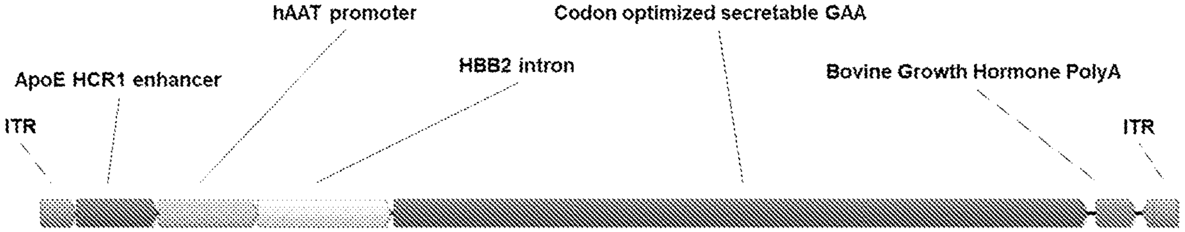
FIG. 9 shows a schematic of pAAV-ApoE/hAAT.GAA13.wtBGH. (SEQ ID NO:24)

The invention provides modified nucleic acids encoding GAA, expression cassettes comprising modified nucleic acids encoding GAA, AAV vector genomes comprising modified nucleic acids encoding GAA, and recombinant AAV vectors and particles comprising the modified nucleic acids encoding GAA. The invention modified nucleic acids encoding GAA, expression cassettes comprising modified nucleic acids encoding GAA, AAV vector genomes comprising modified nucleic acids encoding GAA, and recombinant AAV vectors and particles are useful for treating Pompe disease as well as other glycogen storage diseases (GSDs).

As used herein, the terms "modify" and grammatical variations thereof, mean that a nucleic acid or protein deviates from a reference or parental sequence. A modified nucleic acid encoding GAA has been altered compared to reference (e.g., wild-type) or parental nucleic acid. Modified nucleic acids may therefore have substantially the same, greater or less activity or function than a reference or parental nucleic acid, but at least retain partial activity, function and or sequence identity to the reference or parental nucleic acid. The modified nucleic acid may be genetically modified to encode a modified or variant GAA.

A "modified nucleic acid encoding GAA" means that the GAA nucleic acid has alteration compared the parental unmodified nucleic acid encoding GAA. A particular example of a modification is a nucleotide substitution. The terms "modification" herein need not appear in each instance of a reference made to a nucleic acid encoding GAA.

In particular embodiments, for a modified nucleic acid encoding GAA, the GAA protein retains at least part of a function or activity of wild type GAA protein. The function or activity of GAA protein includes acid alpha glucosidase activity, a lysosomal hydrolase which degrades glycogen, maltose and isomaltose. Accordingly, the modified nucleic acids encoding GAA include modified forms so long as the encoded GAA retains some degree or aspect of lysosomal hydrolase activity of GAA.

As set forth herein, modified nucleic acids encoding GAA can exhibit different features or characteristics compared to a reference or parental nucleic acid. For example, modified nucleic acids include sequences with 100% identity to a reference nucleic acid encoding GAA as set forth herein, as well as sequences with less than 100% identity to a reference nucleic acid encoding GAA.

The term "identity," "homology" and grammatical variations thereof, mean that two or more referenced entities are the same, when they are "aligned" sequences. Thus, by way of example, when two nucleic acids are identical, they have the same sequence, at least within the referenced region or portion. The identity can be over a defined area (region or domain) of the sequence.

An "area" or "region" of identity refers to a portion of two or more referenced entities that are the same. Thus, where two protein or nucleic acid sequences are identical over one or more sequence areas or regions they share identity within that region. An "aligned" sequence refers to multiple protein (amino acid) or nucleic acid sequences, often containing corrections for missing or additional bases or amino acids (gaps) as compared to a reference sequence.

The identity can extend over the entire length or a portion of the sequence. In certain embodiments, the length of the sequence sharing the percent identity is 2, 3, 4, 5 or more contiguous amino acids or nucleic acids, e.g., 6, 7, 8, 9, 10, 11, 12, 13, 14, 15, 16, 17, 18, 19, 20, etc. contiguous nucleic acids or amino acids. In additional embodiments, the length of the sequence sharing identity is 21 or more contiguous amino acids or nucleic acids, e.g., 21, 22, 23, 24, 25, 26, 27, 28, 29, 30, 31, 32, 33, 34, 35, 36, 37, 38, 39, 40, etc. contiguous amino acids or nucleic acids. In further embodiments, the length of the sequence sharing identity is 41 or more contiguous amino acids or nucleic acids, e.g., 42, 43, 44, 45, 45, 47, 48, 49, 50, etc., contiguous amino acids or nucleic acids. In yet further embodiments, the length of the sequence sharing identity is 50 or more contiguous amino acids or nucleic acids, e.g., 50-55, 55-60, 60-65, 65-70, 70-75, 75-80, 80-85, 85-90, 90-95, 95-100, 100-150, 150-200, 200-250, 250-300, 300-500, 500-1,000, etc. contiguous amino acids or nucleic acids.

As set forth herein, modified nucleic acids encoding GAA can be distinct from or exhibit 100% identity or less than 100% identity to a reference nucleic acid encoding GAA.

In particular embodiments, nucleic acids of the invention encoding GAA can be more than 86% identical to any nucleic acid set forth in SEQ ID NOs:1-5.

In particular embodiments, nucleic acids of the invention encoding GAA can be more than 87% identical to any nucleic acid set forth in SEQ ID NOs:6-14.

In particular embodiments, nucleic acids of the invention encoding GAA can be more than 91% identical to any nucleic acid set forth in SEQ ID NOs:16-24.

Such modified nucleic acids encoding GAA can even exhibits greater identity, for example, more than 87% identical; more than 88% identical, more than 89% identical, more than 90% identical, more than 91% identical, more than 92% identical, more than 93% identical, more than 94% identical, more than 95% identical, more than 96% identical, more than 97%, more than 98% identical, more than 99% identical or 100% identical to any of SEQ ID NOs:1-24.

The extent of identity (homology) or "percent identity" between two sequences can be ascertained using a computer program and/or mathematical algorithm. For purposes of this invention comparisons of nucleic acid sequences are performed using the GCG Wisconsin Package version 9.1, available from the Genetics Computer Group in Madison, Wisconsin. For convenience, the default parameters (gap creation penalty=12, gap extension penalty=4) specified by that program are intended for use herein to compare sequence identity. Alternately, the Blastn 2.0 program provided by the National Center for Biotechnology Information (found on the world wide web at ncbi.nlm.nih.gov/blast/; Altschul et al., 1990, J Mol Biol 215:403-410) using a gapped alignment with default parameters, may be used to determine the level of identity and similarity between nucleic acid sequences and amino acid sequences. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate extent of identity (Pearson et al., *Proc. Natl. Acad. Sci. USA* 85:2444 (1988); *Pearson, Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Modified nucleic acids encoding GAA that exhibit different features or characteristics compared to a reference or parental nucleic acid include substitutions of nucleotides. For example, modified nucleic acids encoding GAA include nucleic acids with a reduced number of CpG dinucleotides compared to a reference nucleic acid encoding GAA.

In certain embodiments, a nucleic acid encoding GAA contains less than 127 CpG dinucleotides.

In certain embodiments, a nucleic acid encoding GAA contains less than 126 CpG dinucleotides.

In certain embodiments, a nucleic acid encoding GAA contains less than 125 CpG dinucleotides.

In certain embodiments, a nucleic acid encoding GAA contains less than 124 CpG dinucleotides.

In certain embodiments, a nucleic acid encoding GAA contains less than 123 CpG dinucleotides.

In certain embodiments, a nucleic acid encoding GAA contains less than 122 CpG dinucleotides.

In certain embodiments, a nucleic acid encoding GAA contains less than 121 CpG dinucleotides.

In certain embodiments, a nucleic acid encoding GAA contains less than 120 CpG dinucleotides.

In certain embodiments, a nucleic acid encoding GAA contains less than 119 CpG dinucleotides.

In certain embodiments, a nucleic acid encoding GAA contains less than 118 CpG dinucleotides.

In certain embodiments, a nucleic acid encoding GAA contains less than 117 CpG dinucleotides.

In certain embodiments, a nucleic acid encoding GAA contains less than 116 CpG dinucleotides.

In certain embodiments, a nucleic acid encoding GAA contains less than 115 CpG dinucleotides.

In certain embodiments, a nucleic acid encoding GAA contains less than 114 CpG dinucleotides.

In certain embodiments, a nucleic acid encoding GAA contains less than 113 CpG dinucleotides.

In certain embodiments, a nucleic acid encoding GAA contains less than 112 CpG dinucleotides.

In certain embodiments, a nucleic acid encoding GAA contains less than 111 CpG dinucleotides.

In certain embodiments, a nucleic acid encoding GAA contains less than 110 CpG dinucleotides.

In certain embodiments, a nucleic acid encoding GAA contains less than 109 CpG dinucleotides.

In certain embodiments, a nucleic acid encoding GAA contains less than 108 CpG dinucleotides.

In certain embodiments, a nucleic acid encoding GAA contains less than 107 CpG dinucleotides.

In certain embodiments, a nucleic acid encoding GAA contains less than 106 CpG dinucleotides.

In certain embodiments, a nucleic acid encoding GAA contains less than 105 CpG dinucleotides.

In certain embodiments, a nucleic acid encoding GAA contains less than 104 CpG dinucleotides.

In certain embodiments, a nucleic acid encoding GAA contains less than 103 CpG dinucleotides.

In certain embodiments, a nucleic acid encoding GAA contains less than 102 CpG dinucleotides.

In certain embodiments, a nucleic acid encoding GAA contains less than 101 CpG dinucleotides.

In certain embodiments, a nucleic acid encoding GAA contains less than 100 CpG dinucleotides.

In certain embodiments, a nucleic acid encoding GAA contains less than 99 CpG dinucleotides.

In certain embodiments, a nucleic acid encoding GAA contains less than 98 CpG dinucleotides.

In certain embodiments, a nucleic acid encoding GAA contains less than 97 CpG dinucleotides.

In certain embodiments, a nucleic acid encoding GAA contains less than 96 CpG dinucleotides.

In certain embodiments, a nucleic acid encoding GAA contains less than 95 CpG dinucleotides.

In certain embodiments, a nucleic acid encoding GAA contains less than 94 CpG dinucleotides.

In certain embodiments, a nucleic acid encoding GAA contains less than 93 CpG dinucleotides.

In certain embodiments, a nucleic acid encoding GAA contains less than 92 CpG dinucleotides.

In certain embodiments, a nucleic acid encoding GAA contains less than 91 CpG dinucleotides.

In certain embodiments, a nucleic acid encoding GAA contains less than 90 CpG dinucleotides.

In certain embodiments, a nucleic acid encoding GAA contains less than 89 CpG dinucleotides.

In certain embodiments, a nucleic acid encoding GAA contains less than 88 CpG dinucleotides.

In certain embodiments, a nucleic acid encoding GAA contains less than 87 CpG dinucleotides.

In certain embodiments, a nucleic acid encoding GAA contains less than 86 CpG dinucleotides.

In certain embodiments, a nucleic acid encoding GAA contains less than 85 CpG dinucleotides.

In certain embodiments, a nucleic acid encoding GAA contains less than 84 CpG dinucleotides.

In certain embodiments, a nucleic acid encoding GAA contains less than 83 CpG dinucleotides.

In certain embodiments, a nucleic acid encoding GAA contains less than 82 CpG dinucleotides.

In certain embodiments, a nucleic acid encoding GAA contains less than 81 CpG dinucleotides.

In certain embodiments, a nucleic acid encoding GAA contains less than 80 CpG dinucleotides.

In certain embodiments, a nucleic acid encoding GAA contains less than 79 CpG dinucleotides.

In certain embodiments, a nucleic acid encoding GAA contains less than 78 CpG dinucleotides.

In certain embodiments, a nucleic acid encoding GAA contains less than 77 CpG dinucleotides.

In certain embodiments, a nucleic acid encoding GAA contains less than 76 CpG dinucleotides.

In certain embodiments, a nucleic acid encoding GAA contains less than 75 CpG dinucleotides.

In certain embodiments, a nucleic acid encoding GAA contains less than 74 CpG dinucleotides.

In certain embodiments, a nucleic acid encoding GAA contains less than 73 CpG dinucleotides.

In certain embodiments, a nucleic acid encoding GAA contains less than 72 CpG dinucleotides.

In certain embodiments, a nucleic acid encoding GAA contains less than 71 CpG dinucleotides.

In certain embodiments, a nucleic acid encoding GAA contains less than 70 CpG dinucleotides.

In certain embodiments, a nucleic acid encoding GAA contains less than 69 CpG dinucleotides.

In certain embodiments, a nucleic acid encoding GAA contains less than 68 CpG dinucleotides.

In certain embodiments, a nucleic acid encoding GAA contains less than 67 CpG dinucleotides.

In certain embodiments, a nucleic acid encoding GAA contains less than 66 CpG dinucleotides.

In certain embodiments, a nucleic acid encoding GAA contains less than 65 CpG dinucleotides.

In certain embodiments, a nucleic acid encoding GAA contains less than 64 CpG dinucleotides.

In certain embodiments, a nucleic acid encoding GAA contains less than 63 CpG dinucleotides.

In certain embodiments, a nucleic acid encoding GAA contains less than 62 CpG dinucleotides.

In certain embodiments, a nucleic acid encoding GAA contains less than 61 CpG dinucleotides.

In certain embodiments, a nucleic acid encoding GAA contains less than 60 CpG dinucleotides.

In certain embodiments, a nucleic acid encoding GAA contains less than 59 CpG dinucleotides.

In certain embodiments, a nucleic acid encoding GAA contains less than 58 CpG dinucleotides.

In certain embodiments, a nucleic acid encoding GAA contains less than 57 CpG dinucleotides.

In certain embodiments, a nucleic acid encoding GAA contains less than 56 CpG dinucleotides.

In certain embodiments, a nucleic acid encoding GAA contains less than 55 CpG dinucleotides.

In certain embodiments, a nucleic acid encoding GAA contains less than 54 CpG dinucleotides.

In certain embodiments, a nucleic acid encoding GAA contains less than 53 CpG dinucleotides.

In certain embodiments, a nucleic acid encoding GAA contains less than 52 CpG dinucleotides.

In certain embodiments, a nucleic acid encoding GAA contains less than 51 CpG dinucleotides.

In certain embodiments, a nucleic acid encoding GAA contains less than 50 CpG dinucleotides.

In certain embodiments, a nucleic acid encoding GAA contains less than 49 CpG dinucleotides.

In certain embodiments, a nucleic acid encoding GAA contains less than 48 CpG dinucleotides.

In certain embodiments, a nucleic acid encoding GAA contains less than 47 CpG dinucleotides.

In certain embodiments, a nucleic acid encoding GAA contains less than 46 CpG dinucleotides.

In certain embodiments, a nucleic acid encoding GAA contains less than 45 CpG dinucleotides.

In certain embodiments, a nucleic acid encoding GAA contains less than 44 CpG dinucleotides.

In certain embodiments, a nucleic acid encoding GAA contains less than 43 CpG dinucleotides.

In certain embodiments, a nucleic acid encoding GAA contains less than 42 CpG dinucleotides.

In certain embodiments, a nucleic acid encoding GAA contains less than 41 CpG dinucleotides.

In certain embodiments, a nucleic acid encoding GAA contains less than 40 CpG dinucleotides.

In certain embodiments, a nucleic acid encoding GAA contains less than 39 CpG dinucleotides.

In certain embodiments, a nucleic acid encoding GAA contains less than 38 CpG dinucleotides.

In certain embodiments, a nucleic acid encoding GAA contains less than 37 CpG dinucleotides.

In certain embodiments, a nucleic acid encoding GAA contains less than 36 CpG dinucleotides.

In certain embodiments, a nucleic acid encoding GAA contains less than 35 CpG dinucleotides.

In certain embodiments, a nucleic acid encoding GAA contains less than 34 CpG dinucleotides.

In certain embodiments, a nucleic acid encoding GAA contains less than 33 CpG dinucleotides.

In certain embodiments, a nucleic acid encoding GAA contains less than 32 CpG dinucleotides.

In certain embodiments, a nucleic acid encoding GAA contains less than 31 CpG dinucleotides.

In certain embodiments, a nucleic acid encoding GAA contains less than 30 CpG dinucleotides.

In certain embodiments, a nucleic acid encoding GAA contains less than 29 CpG dinucleotides.

In certain embodiments, a nucleic acid encoding GAA contains less than 28 CpG dinucleotides.

In certain embodiments, a nucleic acid encoding GAA contains less than 27 CpG dinucleotides.

In certain embodiments, a nucleic acid encoding GAA contains less than 26 CpG dinucleotides.

In certain embodiments, a nucleic acid encoding GAA contains less than 25 CpG dinucleotides.

In certain embodiments, a nucleic acid encoding GAA contains less than 24 CpG dinucleotides.

In certain embodiments, a nucleic acid encoding GAA contains less than 23 CpG dinucleotides.

In certain embodiments, a nucleic acid encoding GAA contains less than 22 CpG dinucleotides.

In certain embodiments, a nucleic acid encoding GAA contains less than 21 CpG dinucleotides.

In certain embodiments, a nucleic acid encoding GAA contains less than 20 CpG dinucleotides.

In certain embodiments, a nucleic acid encoding GAA contains less than 19 CpG dinucleotides.

In certain embodiments, a nucleic acid encoding GAA contains less than 18 CpG dinucleotides.

In certain embodiments, a nucleic acid encoding GAA contains less than 17 CpG dinucleotides.

In certain embodiments, a nucleic acid encoding GAA contains less than 16 CpG dinucleotides.

In certain embodiments, a nucleic acid encoding GAA contains less than 15 CpG dinucleotides.

In certain embodiments, a nucleic acid encoding GAA contains less than 14 CpG dinucleotides.

In certain embodiments, a nucleic acid encoding GAA contains less than 13 CpG dinucleotides.

In certain embodiments, a nucleic acid encoding GAA contains less than 12 CpG dinucleotides.

In certain embodiments, a nucleic acid encoding GAA contains less than 11 CpG dinucleotides.

In certain embodiments, a nucleic acid encoding GAA contains less than 10 CpG dinucleotides.

In certain embodiments, a nucleic acid encoding GAA contains less than 9 CpG dinucleotides.

In certain embodiments, a nucleic acid encoding GAA contains less than 8 CpG dinucleotides.

In certain embodiments, a nucleic acid encoding GAA contains less than 7 CpG dinucleotides.

In certain embodiments, a nucleic acid encoding GAA contains less than 6 CpG dinucleotides.

In certain embodiments, a nucleic acid encoding GAA contains less than 5 CpG dinucleotides.

In certain embodiments, a nucleic acid encoding GAA contains less than 4 CpG dinucleotides.

In certain embodiments, a nucleic acid encoding GAA contains less than 3 CpG dinucleotides.

In certain embodiments, a nucleic acid encoding GAA contains less than 2 CpG dinucleotides.

In certain embodiments, a nucleic acid encoding GAA contains less than 1 CpG dinucleotides.

The term "vector" refers to small carrier nucleic acid molecule, a plasmid, virus (e.g., AAV vector), or other vehicle that can be manipulated by insertion or incorporation of a nucleic acid. Such vectors can be used for genetic manipulation (i.e., "cloning vectors"), to introduce/transfer polynucleotides into cells, and to transcribe or translate the inserted polynucleotide in cells. An "expression vector" is a specialized vector that contains a gene or nucleic acid sequence with the necessary regulatory regions needed for expression in a host cell.

A vector nucleic acid sequence generally contains at least an origin of replication for propagation in a cell and optionally additional elements, such as a heterologous polynucleotide sequence, expression control element (e.g., a promoter, enhancer), intron, an inverted terminal repeat (ITR), selectable marker (e.g., antibiotic resistance), polyadenylation signal.

A viral vector is derived from or based upon one or more nucleic acid elements that comprise a viral genome. Particular viral vectors include lentiviral and adeno-associated virus (AAV) vectors.

The term "recombinant," as a modifier of vector, such as recombinant AAV (rAAV) vector, as well as a modifier of sequences such as recombinant polynucleotides and polypeptides, means that the compositions have been manipulated (i.e., engineered) in a fashion that generally does not occur in nature. A particular example of a recombinant AAV vector would be where a click acid sequence that is not normally present in the wild-type AAV genome is inserted within the AAV genome. Although the term "recombinant" is not always used herein in reference to AAV vectors, as well as sequences such as polynucleotides, recombinant forms including polynucleotides, are expressly included in spite of any such omission.

A "recombinant AAV vector" or "rAAV" is derived from the wild type genome of AAV by using molecular methods to remove the wild type genome from the AAV genome, and replacing with a non-native nucleic acid sequence, referred to as a heterologous nucleic acid. Typically, for AAV one or both inverted terminal repeat (ITR) sequences of AAV genome are retained in the AAV vector. rAAV is distinguished from an AAV genome, since all or a part of the AAV genome has been replaced with a non-native sequence with respect to the AAV genomic nucleic acid. Incorporation of a non-native sequence therefore defines the AAV vector as a "recombinant" vector, which can be referred to as a "rAAV vector."

A rAAV sequence can be packaged—referred to herein as a "particle"—for subsequent infection (transduction) of a cell, ex vivo, in vitro or in vivo. Where a recombinant AAV vector sequence is encapsidated or packaged into an AAV particle, the particle can also be referred to as a "rAAV vector" or "rAAV particle." Such rAAV particles include proteins that encapsidate or package the vector genome and in the case of AAV, they are referred to as capsid proteins.

A vector "genome" refers to the portion of the recombinant plasmid sequence that is ultimately packaged or encapsidated to form a viral (e.g., rAAV) particle. In cases where recombinant plasmids are used to construct or manufacture recombinant vectors, the vector genome does not include the portion of the "plasmid" that does not correspond to the vector genome sequence of the recombinant plasmid. This non vector genome portion of the recombinant plasmid can be referred to as the "plasmid backbone," which is important for cloning and amplification of the plasmid, a process that is needed for propagation and recombinant virus production, but is not itself packaged or encapsidated into virus (e.g., AAV) particles. Thus, a vector "genome" refers to the nucleic acid that is packaged or encapsidated by virus (e.g., AAV).

Host cells for producing recombinant AAV particles include but are not limited to microorganisms, yeast cells, insect cells, and mammalian cells that can be, or have been, used as recipients of a heterologous rAAV vectors. Cells from the stable human cell line, HEK293 (readily available through, e.g., the American Type Culture Collection under Accession Number ATCC CRL1573) can be used. In certain embodiments a modified human embryonic kidney cell line (e.g., HEK293), which is transformed with adenovirus type-5 DNA fragments, and expresses the adenoviral E1a and E1b genes is used to generate recombinant AAV particles. The modified HEK293 cell line is readily transfected, and provides a particularly convenient platform in which to produce rAAV particles. Other host cell lines appropriate for recombinant AAV production are described in International Application PCT/2017/024951.

In certain embodiments, AAV helper functions are introduced into the host cell by transfecting the host cell with an AAV helper construct either prior to, or concurrently with, the transfection of an AAV expression vector. A host cell having AAV helper functions can be referred to as a "helper cell" or "packaging helper cell." AAV helper constructs are thus sometimes used to provide at least transient expression of AAV rep and/or cap genes to complement missing AAV functions necessary for productive AAV transduction. AAV helper constructs often lack AAV ITRs and can neither replicate nor package themselves. These constructs can be in the form of a plasmid, phage, transposon, cosmid, virus, or virion. A number of AAV helper constructs have been described, such as the commonly used plasmids pAAV/Ad and pIM29+45 which encode both Rep and Cap expression products. A number of other vectors are known which encode Rep and/or Cap expression products.

Methods of generating recombinant AAV particles capable of transducing mammalian cells are known in the art. For example, recombinant AAV particles can be produced as described in U.S. Pat. No. 9,408,904; and International Applications PCT/US2017/025396 and PCT/US2016/064414.

The terms "nucleic acid" and "polynucleotide" are used interchangeably herein to refer to all forms of nucleic acid, oligonucleotides, including deoxyribonucleic acid (DNA) and ribonucleic acid (RNA). Nucleic acids include genomic DNA, cDNA and antisense DNA, and spliced or unspliced mRNA, rRNA tRNA and inhibitory DNA or RNA (RNAi, e.g., small or short hairpin (sh)RNA, microRNA (miRNA), small or short interfering (si)RNA, trans-splicing RNA, or antisense RNA). Nucleic acids include naturally occurring, synthetic, and intentionally modified or altered polynucleotides (e.g., variant nucleic acid). The nucleic acids such as cDNA, genomic DNA, RNA, and fragments thereof which may be single- or double-stranded.

Polynucleotides can be single, double, or triplex, linear or circular, and can be of any length. In discussing polynucleotides, a sequence or structure of a particular polynucleotide may be described herein according to the convention of providing the sequence in the 5' to 3' direction.

A "transgene" is used herein to conveniently refer to a heterologous nucleic acid that is intended or has been introduced into a cell or organism. Transgenes include any heterologous nucleic acid, such as a modified nucleic acid encoding GAA.

The term "transduce" and grammatical variations thereof refer to introduction of a molecule such as an rAAV vector into a cell or host organism. The heterologous nucleic acid/transgene may or may not be integrated into genomic nucleic acid of the recipient cell. The introduced heterologous nucleic acid may also exist in the recipient cell or host organism extrachromosomally, or only transiently.

A "transduced cell" is a cell into which the transgene has been introduced. Accordingly, a "transduced" cell (e.g., in a mammal, such as a cell or tissue or organ cell), means a genetic change in a cell following incorporation, for example, of a nucleic acid (e.g., a transgene) into the cell. Thus, a "transduced" cell is a cell into which, or a progeny thereof in which an exogenous nucleic acid has been introduced. The cell(s) can be propagated and the introduced protein expressed. For gene therapy uses and methods, a transduced cell can be in a subject.

An "expression control element" refers to nucleic acid sequence(s) that influence expression of an operably linked nucleic acid. Expression control elements as set forth herein include promoters and enhancers. Vector sequences including AAV vectors can include one or more "expression control elements." Typically, such elements are included to facilitate proper heterologous polynucleotide transcription and as appropriate translation (e.g., a promoter, enhancer, splicing signal for introns, maintenance of the correct reading frame of the gene to permit in-frame translation of mRNA and, stop codons etc.). Such elements typically act in cis, referred to as a "cis acting" element, but may also act in trans.

Expression control can be effected at the level of transcription, translation, splicing, message stability, etc. Typically, an expression control element that modulates transcription is juxtaposed near the 5' end (i.e., "upstream") of a transcribed nucleic acid. Expression control elements can also be located at the 3' end (i.e., "downstream") of the transcribed sequence or within the transcript (e.g., in an intron). Expression control elements can be located adjacent to or at a distance away from the transcribed sequence (e.g., 1-10, 10-25, 25-50, 50-100, 100 to 500, or more nucleotides from the polynucleotide), even at considerable distances. Nevertheless, owing to the length limitations of AAV vectors, expression control elements will typically be within 1 to 1000 nucleotides from the transcription start site of the heterologous nucleic acid.

Functionally, expression of operably linked nucleic acid is at least in part controllable by the element (e.g., promoter) such that the element modulates transcription of the nucleic acid and, as appropriate, translation of the transcript. A specific example of an expression control element is a promoter, which is usually located 5' of the transcribed nucleic acid sequence. A promoter typically increases an amount expressed from operably linked nucleic acid as compared to an amount expressed when no promoter exists.

An "enhancer" as used herein can refer to a sequence that is located adjacent to the heterologous nucleic acid. Enhancer elements are typically located upstream of a promoter element but also function and can be located downstream of or within a sequence. Hence, an enhancer element can be located 10-50 base pairs, 50-100 base pairs, 100-200 base pairs, or 200-300 base pairs, or more base pairs upstream or downstream of a heterologous nucleic acid sequence. Enhancer elements typically increase expressed of an operably linked nucleic acid above expression afforded by a promoter element.

An expression construct may comprise regulatory elements which serve to drive expression in a particular cell or tissue type. Expression control elements (e.g., promoters) include those active in a particular tissue or cell type, referred to herein as a "tissue-specific expression control elements/promoters." Tissue-specific expression control elements are typically active in specific cell or tissue (e.g., liver). Expression control elements are typically active in particular cells, tissues or organs because they are recognized by transcriptional activator proteins, or other regulators of transcription, that are unique to a specific cell, tissue or organ type. Such regulatory elements are known to those of skill in the art (see, e.g., Sambrook et al. (1989) and Ausubel et al. (1992)).

The incorporation of tissue specific regulatory elements in the expression constructs provides for at least partial tissue tropism for the expression of a heterologous nucleic acid encoding a protein or inhibitory RNA. Examples of promoters that are active in liver are the transthyretin (TTR) gene promoter; human alpha 1-antitrypsin (hAAT) promoter; albumin, Miyatake, et al., *J. Virol.,* 71:5124-32 (1997); hepatitis B virus core promoter, Sandig, et al., *Gene Ther.* 3:1002-9 (1996); alpha-fetoprotein (AFP), Arbuthnot, et al., *Hum. Gene. Ther.,* 7:1503-14 (1996), among others. An example of an enhancer active in liver is apolipoprotein E (apoE) HCR-1 and HCR-2 (Allan et al., *J. Biol. Chem.,* 272:29113-19 (1997)).

Expression control elements also include ubiquitous or promiscuous promoters/enhancers which are capable of driving expression of a polynucleotide in many different cell types. Such elements include, but are not limited to the cytomegalovirus (CMV) immediate early promoter/enhancer sequences, the Rous sarcoma virus (RSV) promoter/enhancer sequences and the other viral promoters/enhancers active in a variety of mammalian cell types, or synthetic elements that are not present in nature (see, e.g., Boshart et al., *Cell,* 41:521-530 (1985)), the SV40 promoter, the dihydrofolate reductase promoter, the cytoplasmic β-actin promoter and the phosphoglycerol kinase (PGK) promoter.

Expression control elements also can confer expression in a manner that is regulatable, that is, a signal or stimuli increases or decreases expression of the operably linked heterologous polynucleotide. A regulatable element that increases expression of the operably linked polynucleotide in response to a signal or stimuli is also referred to as an "inducible element" (i.e., is induced by a signal). Particular examples include, but are not limited to, a hormone (e.g., steroid) inducible promoter. Typically, the amount of increase or decrease conferred by such elements is proportional to the amount of signal or stimuli present; the greater the amount of signal or stimuli, the greater the increase or decrease in expression. Particular non-limiting examples include zinc-inducible sheep metallothionine (MT) promoter; the steroid hormone-inducible mouse mammary tumor virus (MMTV) promoter; the T7 polymerase promoter system (WO 98/10088); the tetracycline-repressible system (Gossen, et al., *Proc. Natl. Acad. Sci. USA,* 89:5547-5551 (1992)); the tetracycline-inducible system (Gossen, et al., *Science.* 268:1766-1769 (1995); see also Harvey, et al., *Curr. Opin. Chem. Biol.* 2:512-518 (1998)); the RU486-inducible system (Wang, et al., *Nat. Biotech.* 15:239-243 (1997) and Wang, et al., *Gene Ther.* 4:432-441 (1997)]; and the rapamycin-inducible system (Magari, et al., *J. Clin. Invest.* 100:2865-2872 (1997); Rivera, et al., *Nat. Medicine.* 2:1028-1032 (1996)). Other regulatable control elements which may be useful in this context are those which are regulated by a specific physiological state, e.g., temperature, acute phase, development.

Expression control elements also include the native elements(s) for the heterologous polynucleotide. A native control element (e.g., promoter) may be used when it is desired that expression of the heterologous polynucleotide should mimic the native expression. The native element may be used when expression of the heterologous polynucleotide is to be regulated temporally or developmentally, or in a tissue-specific manner, or in response to specific transcriptional stimuli. Other native expression control elements, such as introns, polyadenylation sites or Kozak consensus sequences may also be used.

The term "operably linked" means that the regulatory sequences necessary for expression of a nucleic acid sequence are placed in the appropriate positions relative to the sequence so as to effect expression of the nucleic acid sequence. This same definition is sometimes applied to the arrangement of nucleic acid sequences and transcription control elements (e.g., promoters, enhancers, and termination elements) in an expression vector, e.g., rAAV vector.

In the example of an expression control element in operable linkage with a nucleic acid, the relationship is such that the control element modulates expression of the nucleic acid. More specifically, for example, two DNA sequences operably linked means that the two DNAs are arranged (cis or trans) in such a relationship that at least one of the DNA sequences is able to exert a physiological effect upon the other sequence.

Accordingly, additional elements for vectors include, without limitation, an expression control (e.g., promoter/enhancer) element, a transcription termination signal or stop codon, 5' or 3' untranslated regions (e.g., polyadenylation (polyA) sequences) which flank a sequence, such as one or more copies of an AAV ITR sequence, or an intron.

Further elements include, for example, filler or stuffer polynucleotide sequences, for example to improve packaging and reduce the presence of contaminating nucleic acid. AAV vectors typically accept inserts of DNA having a size range which is generally about 4 kb to about 5.2 kb, or slightly more. Thus, for shorter sequences, inclusion of a stuffer or filler in order to adjust the length to near or at the normal size of the virus genomic sequence acceptable for AAV vector packaging into virus particle. In various embodiments, a filler/stuffer nucleic acid sequence is an untranslated (non-protein encoding) segment of nucleic acid. For a nucleic acid sequence less than 4.7 kb, the filler or stuffer polynucleotide sequence has a length that when combined (e.g., inserted into a vector) with the sequence has a total length between about 3.0-5.5 kb, or between about 4.0-5.0 kb, or between about 4.3-4.8 kb.

The term "isolated," when used as a modifier of a composition, means that the compositions are made by the hand of man or are separated, completely or at least in part, from their naturally occurring in vivo environment. Generally, isolated compositions are substantially free of one or more materials with which they normally associate with in nature, for example, one or more protein, nucleic acid, lipid, carbohydrate, cell membrane.

The term "isolated" does not exclude combinations produced by the hand of man, for example, a rAAV sequence, or rAAV particle that packages or encapsidates an AAV vector genome and a pharmaceutical formulation. The term "isolated" also does not exclude alternative physical forms of the composition, such as hybrids/chimeras, multimers/oligomers, modifications (e.g., phosphorylation, glycosylation, lipidation) or derivatized forms, or forms expressed in host cells produced by the hand of man.

The term "substantially pure" refers to a preparation comprising at least 50-60% by weight the compound of interest (e.g., nucleic acid, oligonucleotide, protein, etc.). The preparation can comprise at least 75% by weight, or at least 85% by weight, or about 90-99% by weight, of the compound of interest. Purity is measured by methods appropriate for the compound of interest (e.g., chromatographic methods, agarose or polyacrylamide gel electrophoresis, HPLC analysis, and the like).

The phrase "consisting essentially of" when referring to a particular nucleotide sequence or amino acid sequence means a sequence having the properties of a given SEQ ID NO. For example, when used in reference to an amino acid sequence, the phrase includes the sequence per se and molecular modifications that would not affect the basic and novel characteristics of the sequence.

Nucleic acids, expression vectors (e.g., AAV vector genomes), plasmids, including modified nucleic acids encoding GAA of the invention may be prepared by using recombinant DNA technology methods. The availability of nucleotide sequence information enables preparation of isolated nucleic acid molecules of the invention by a variety of means. Nucleic acids encoding GAA can be made using various standard cloning, recombinant DNA technology, via cell expression or in vitro translation and chemical synthesis techniques. Purity of polynucleotides can be determined through sequencing, gel electrophoresis and the like. For example, nucleic acids can be isolated using hybridization or computer-based database screening techniques. Such techniques include, but are not limited to: (1) hybridization of genomic DNA or cDNA libraries with probes to detect homologous nucleotide sequences; (2) antibody screening to detect polypeptides having shared structural features, for example, using an expression library; (3) polymerase chain reaction (PCR) on genomic DNA or cDNA using primers capable of annealing to a nucleic acid sequence of interest; (4) computer searches of sequence databases for related sequences; and (5) differential screening of a subtracted nucleic acid library.

Nucleic acids may be maintained as DNA in any convenient cloning vector. In one embodiment, clones are maintained in a plasmid cloning/expression vector, such as pBluescript (Stratagene, La Jolla, CA), which is propagated in a suitable *E. coli* host cell. Alternatively, nucleic acids may be maintained in vector suitable for expression in mammalian cells, for example, an AAV vector. In cases where post-translational modification affects protein function, nucleic acid molecule can be expressed in mammalian cells.

As disclosed herein, rAAV vectors may optionally comprise regulatory elements necessary for expression of the heterologous nucleic acid in a cell positioned in such a manner as to permit expression of the encoded protein in the host cell. Such regulatory elements required for expression include, but are not limited to, promoter sequences, enhancer sequences and transcription initiation sequences as set forth herein and known to the skilled artisan.

Methods and uses of the invention include delivering (transducing) nucleic acid (transgene) into host cells, including dividing and/or non-dividing cells. The nucleic acids, rAAV vector, methods, uses and pharmaceutical formulations of the invention are additionally useful in a method of delivering, administering or providing sequence encoded by heterologous nucleic acid to a subject in need thereof, as a method of treatment. In this manner, the nucleic acid is transcribed and a protein produced in vivo in a subject. The subject may benefit from or be in need of the protein because the subject has a deficiency of the protein, or because production of the protein in the subject may impart some therapeutic effect, as a method of treatment or otherwise.

The invention is useful in animals including human and veterinary medical applications. Suitable subjects therefore include mammals, such as humans, as well as non-human mammals. The term "subject" refers to an animal, typically a mammal, such as humans, non-human primates (apes, gibbons, gorillas, chimpanzees, orangutans, macaques), a domestic animal (dogs and cats), a farm animal (poultry such as chickens and ducks, horses, cows, goats, sheep, pigs), and experimental animals (mouse, rat, rabbit, guinea pig). Human subjects include fetal, neonatal, infant, juvenile and adult subjects. Subjects include animal disease models, for example, mouse and other animal models of protein/enzyme deficiencies such as Pompe disease, and glycogen storage diseases (GSDs) and others known to those of skill in the art.

Subjects appropriate for treatment in accordance with the invention include those having or at risk of producing an insufficient amount of GAA, or produce an aberrant, partially functional or non-functional GAA. Subjects can be tested for GAA activity to determine if such subjects are appropriate for treatment according to a method of the invention. Subjects appropriate for treatment in accordance with the invention also include those subjects that would benefit from GAA. Such subjects that may benefit from GAA include those having a glycogen storage disease (GSD). Treated subjects can be monitored after treatment periodically, e.g., every 1-4 weeks, 1-6 months, 6-12 months, or 1, 2, 3, 4, 5 or more years.

Subjects can be tested for an immune response, e.g., antibodies against AAV. Candidate subjects can therefore be screened prior to treatment according to a method of the invention. Subjects also can be tested for antibodies against AAV after treatment, and optionally monitored for a period of time after treatment. Subjects having pre-existing or developing AAV antibodies can be treated with an immunosuppressive agent, or other regimen as set forth herein.

Subjects appropriate for treatment in accordance with the invention also include those having or at risk of producing antibodies against AAV. rAAV vectors can be administered or delivered to such subjects using several techniques. For example, AAV empty capsid (i.e., AAV lacking a modified nucleic acid encoding GAA) can be delivered to bind to the AAV antibodies in the subject thereby allowing the rAAV vector comprising the heterologous nucleic acid to transduce cells of the subject.

The modified nucleic acids, expression cassettes and rAAV vectors of the invention can be used for treatment of a GAA deficiency. Accordingly, in various embodiments, modified nucleic acids encoding GAA, expression cassettes comprising modified nucleic acids encoding GAA and rAAV vectors of the invention can be used as a therapeutic and/or prophylactic agent.

In particular embodiments, the modified nucleic acids encoding GAA, expression cassettes comprising modified nucleic acids encoding GAA and rAAV vectors of the invention can be used for treatment of Pompe disease as well as other glycogen storage diseases. Administration of modified nucleic acids encoding GAA, expression cassettes comprising modified nucleic acids encoding GAA and rAAV vectors of the invention to a patient with Pompe or another glycogen storage disease leads to the expression of the GAA protein which serves to suppress, inhibit or reduce the accumulation of glycogen, prevent the accumulation of glycogen or degrade glycogen, which in turn can reduce or decrease one or more adverse effects or symptoms of Pompe disease.

Subjects, animals or patients administered the modified nucleic acids encoding GAA, expression cassettes comprising modified nucleic acids encoding GAA and rAAV vectors of the invention can be evaluated by a variety of tests, assays and functional assessments to demonstrate, measure and/or assess efficacy of the modified nucleic acids encoding GAA, expression cassettes comprising modified nucleic acids encoding GAA and rAAV vectors of the invention as therapeutic and/or prophylactic agents. Such tests and assays include, but are not limited to, measurement of GAA activity (such as by use of standard GAA activity assays) and or GAA amount (such as by western blot with anti-GAA antibody) in a biological sample such as blood or plasma; measurement of glycogen content in tissues, such as muscle samples; histological evaluation of muscle (such as muscle from triceps brachii, quadriceps femoris, diaphragm and heart), spinal cord (including examination and counting of ChAT-positive motor neurons in the ventral horn of the cervical thoracic and lumbar spinal cord segments, and evaluation of astroglial reaction and microglial activation); assessment of respiratory function during quiet breathing; forelimbs wire-hanging test; measurement of grip strength;

rotarod testing of motor coordination (such as by rotarod protocol); chest x-ray which can show cardiomegaly; electrocardiogram (ECG) to examine heart function; electromyogram (EMG) which can show myopathy; measurement of GAA activity in skin fibroblasts; assays of GAA activity in dried blood samples; blood/serum tests for serum creatine kinase, which when elevated is a nonspecific marker of Pompe disease; blood/serum tests for or aminotransferase, alanine aminotransferase, or lactate dehydrogenase, which may be elevated as indicator of release from muscle in Pompe disease; test for glucose tetrasaccharide in urine (a sensitive, nonspecific marker for Pompe disease; analysis of peak and steady-state vector-derived GAA enzyme levels assessed by total GAA protein and activity in plasma; testing of pulmonary function; testing of muscle function; muscle biopsy and staining for presence of glycogen in cell vacuoles; biomarkers of liver health; examination of lysosomal health; testing for immune responses against AAV capsid; testing for immune responses against the GAA transgene protein product; six-minute walk test (6MWT); forced vital capacity test; peak and steady-state AAV vector-derived GAA enzyme levels (assessed by total GAA protein and activity measured in plasma; gait, stairs, gower, and chair (GSGC) testing; muscle strength testing using Rasch-built Medical Research Council (MRC) grading scale; patient-reported life activity/social participation; quantitative sleep and sleep breathing measures from polysomnography (PSG); patient-reported measures of fatigue, daytime sleepiness, and sleep quality; Walton and Gardner-Medwin (WGM) score; respiratory function tests, including, but not limited to sniff nasal inspiratory pressure (SNIP) and maximum inspiratory and expiratory pressures (MIP and MEP, respectively); liver biomarkers; βhexosaminidase (βHexo) testing; health outcome measurements, including but not limited to short form-36 health survey (SF-36); Rasch-built Pompe-specific activity (R-PAct) scale; fatigue severity score (FSS); and patient reported outcomes measurement information system (PROMIS) item banks.

Additionally, the modified nucleic acids encoding GAA, expression cassettes comprising modified nucleic acids encoding GAA and rAAV vectors of the invention can be used for treatment of a glycogen storage disease (GSD). Glycogen storage diseases include, for example, GSD type I (von Gierke's disease), GSD type II (Pompe disease), GSD type III (Forbes-Cori disease), GSD type IV (Anderson disease, amylopectinosis), GSD type V (McArdle disease), GSD type VI (Hers disease), GSD type VII (Tarui disease), or a lethal congenital glycogen storage disease of the heart.

As set forth herein, rAAV are useful as gene therapy vectors as they can penetrate cells and introduce nucleic acid/genetic material into the cells. Because AAV are not associated with pathogenic disease in humans, rAAV vectors are able to deliver heterologous polynucleotide sequences (e.g., therapeutic proteins and agents) to human patients without causing substantial AAV pathogenesis or disease.

rAAV vectors possess a number of desirable features for such applications, including tropism for dividing and non-dividing cells. Early clinical experience with these vectors also demonstrated no sustained toxicity and immune responses are typically minimal or undetectable. AAV are known to infect a wide variety of cell types in vivo by receptor-mediated endocytosis or by transcytosis. These vector systems have been tested in humans targeting many tissues, such as, retinal epithelium, liver, skeletal muscle, airways, brain, joints and hematopoietic stem cells.

It may be desirable to introduce a rAAV vector that can provide, for example, multiple copies of GAA and hence greater amounts of GAA protein. Improved rAAV vectors and methods for producing these vectors have been described in detail in a number of references, patents, and patent applications, including: Wright J. F. (Hum. Gene Ther., 20:698-706, 2009).

Direct delivery of rAAV vectors or ex vivo transduction of human cells followed by infusion into the body will result in expression of the heterologous nucleic acid thereby exerting a beneficial therapeutic effect on hemostasis. In the context of modified nucleic acids encoding GAA, administration suppresses, inhibits or reduces the amount or accumulation of glycogen, prevents accumulation of glycogen or degrades glycogen. This, in turn, can suppress, inhibit, reduce or decrease one or more adverse effects of Pompe disease such as promoting or improving muscle tone and/or muscle strength and/or reducing or decreasing enlarged liver.

Recombinant AAV vector, as well as methods and uses thereof, include any viral strain or serotype. As a non-limiting example, a recombinant AAV vector can be based upon any AAV genome, such as AAV (SEQ ID NOs:30-32), LK03 (SEQ ID NO:33), AAV1, AAV2, AAV3, AAV4, AAV5, AAV6, AAV7, AAV8, AAV9, AAV10, AAV11, AAV12, Rh10, Rh74, AAV3B or AAV-2i8, for example. Such vectors can be based on the same strain or serotype (or subgroup or variant), or be different from each other. As a non-limiting example, a recombinant AAV vector based upon a particular serotype genome can be identical to the serotype of the capsid proteins that package the vector. In addition, a recombinant AAV vector genome can be based upon an AAV serotype genome distinct from the serotype of the AAV capsid proteins that package the vector. For example, the AAV vector genome can be based upon AAV2, whereas at least one of the three capsid proteins could be an AAV (SEQ ID NOs:30-32), LK03 (SEQ ID NO:33), AAV1, AAV3, AAV4, AAV5, AAV6, AAV7, AAV8, AAV9, AAV10, AAV11, AAV12, Rh10, Rh74, AAV3B or AAV-2i8 or variant thereof, for example.

In particular embodiments, adeno-associated virus (AAV) vectors include AAV (SEQ ID NOs:30-32), LK03 (SEQ ID NO:33), AAV1, AAV2, AAV3, AAV4, AAV5, AAV6, AAV7, AAV8, AAV9, AAV10, AAV11, AAV12, Rh10, Rh74, AAV3B and AAV-2i8, as well as variants (e.g., capsid variants, such as amino acid insertions, additions, substitutions and deletions) thereof, for example, as set forth in WO 2013/158879 (International Application PCT/US2013/037170), WO 2015/013313 (International Application PCT/US2014/047670) and US 2013/0059732 (U.S. Pat. No. 9,169,299, discloses LK01, LK02, LK03, etc.).

As used herein, the term "serotype" is a distinction used to refer to an AAV having a capsid that is serologically distinct from other AAV serotypes. Serologic distinctiveness is determined on the basis of the lack of cross-reactivity between antibodies to one AAV as compared to another AAV. Such cross-reactivity differences are usually due to differences in capsid protein sequences/antigenic determinants (e.g., due to VP1, VP2, and/or VP3 sequence differences of AAV serotypes). Despite the possibility that AAV variants including capsid variants may not be serologically distinct from a reference AAV or other AAV serotype, they differ by at least one nucleotide or amino acid residue compared to the reference or other AAV serotype.

Under the traditional definition, a serotype means that the virus of interest has been tested against serum specific for all existing and characterized serotypes for neutralizing activity and no antibodies have been found that neutralize the virus of interest. As more naturally occurring virus isolates of are discovered and/or capsid mutants generated, there may or may not be serological differences with any of the currently existing serotypes. Thus, in cases where the new virus (e.g., AAV) has no serological difference, this new virus (e.g., AAV) would be a subgroup or variant of the corresponding serotype. In many cases, serology testing for neutralizing activity has yet to be performed on mutant viruses with capsid sequence modifications to determine if they are of another serotype according to the traditional definition of serotype. Accordingly, for the sake of convenience and to avoid repetition, the term "serotype" broadly refers to both serologically distinct viruses (e.g., AAV) as well as viruses (e.g., AAV) that are not serologically distinct that may be within a subgroup or a variant of a given serotype.

As set forth herein, AAV capsid proteins can exhibit less than 100% sequence identity to a reference or parental AAV serotype such as AAV (SEQ ID NOs:30-32), LK03 (SEQ ID NO:33), AAV1, AAV2, AAV3, AAV4, AAV5, AAV6, AAV7, AAV8, AAV9, AAV10, AAV11, AAV12, Rh10, Rh74, AAV3B or AAV-2i8, but are distinct from and not identical to known AAV genes or proteins, such as AAV1, AAV2, AAV3, AAV4, AAV5, AAV6, AAV7, AAV8, AAV9, AAV10, AAV11, AAV12, Rh10, Rh74, AAV3B or AAV-2i8. In one embodiment, a modified/variant AAV capsid protein includes or consists of a sequence at least 80%, 85%, 85%, 87%, 88%, 89%, 90%, 91%, 92%, 93%, 94%, 95%, 96%, 97%, 98%, 99%, 99.1%, 99.2%, 99.3%, 99.4%, 99.5%, etc., up to 99.9% identical to a reference or parental AAV capsid protein, such as AAV (SEQ ID NOs:30-32), LK03 (SEQ ID NO:33), AAV1, AAV2, AAV3, AAV4, AAV5, AAV6, AAV7, AAV8, AAV9, AAV10, AAV11, AAV12, Rh10, Rh74, AAV3B or AAV-2i8.

rAAV vectors may be administered to a patient via infusion in a biologically compatible carrier, for example, via intravenous injection. rAAV vectors may be administered alone or in combination with other molecules. Accordingly, rAAV vectors and other compositions, agents, drugs, biologics (proteins) can be incorporated into pharmaceutical compositions. Such pharmaceutical compositions are useful for, among other things, administration and delivery to a subject in vivo or ex vivo.

In particular embodiments, pharmaceutical compositions also contain a pharmaceutically acceptable carrier or excipient. Such excipients include any pharmaceutical agent that does not itself induce an immune response harmful to the individual receiving the composition, and which may be administered without undue toxicity.

As used herein the term "pharmaceutically acceptable" and "physiologically acceptable" mean a biologically acceptable formulation, gaseous, liquid or solid, or mixture thereof, which is suitable for one or more routes of administration, in vivo delivery or contact. A "pharmaceutically acceptable" or "physiologically acceptable" composition is a material that is not biologically or otherwise undesirable, e.g., the material may be administered to a subject without causing substantial undesirable biological effects. Thus, such a pharmaceutical composition may be used, for example in administering a nucleic acid, vector, viral particle or protein to a subject.

Pharmaceutically acceptable excipients include, but are not limited to, liquids such as water, saline, glycerol, sugars and ethanol. Pharmaceutically acceptable salts can also be included therein, for example, mineral acid salts such as hydrochlorides, hydrobromides, phosphates, sulfates, and the like; and the salts of organic acids such as acetates, propionates, malonates, benzoates, and the like. Excipients also include proteins such as albumin. Additionally, auxiliary substances, such as wetting or emulsifying agents, pH buffering substances, and the like, may be present in such vehicles.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding, free base forms. In other cases, a preparation may be a lyophilized powder which may contain any or all of the following: 1-50 mM histidine, 0.1%-2% sucrose, and 2-7% mannitol, at a pH range of 4.5 to 5.5, that is combined with buffer prior to use.

Pharmaceutical compositions include solvents (aqueous or non-aqueous), solutions (aqueous or non-aqueous), emulsions (e.g., oil-in-water or water-in-oil), suspensions, syrups, elixirs, dispersion and suspension media, coatings, isotonic and absorption promoting or delaying agents, compatible with pharmaceutical administration or in vivo contact or delivery. Aqueous and non-aqueous solvents, solutions and suspensions may include suspending agents and thickening agents. Such pharmaceutically acceptable carriers include tablets (coated or uncoated), capsules (hard or soft), microbeads, powder, granules and crystals. Supplementary active compounds (e.g., preservatives, antibacterial, antiviral and antifungal agents) can also be incorporated into the compositions.

Pharmaceutical compositions can be formulated to be compatible with a particular route of administration or delivery, as set forth herein or known to one of skill in the art. Thus, pharmaceutical compositions include carriers, diluents, or excipients suitable for administration by various routes.

Compositions suitable for parenteral administration comprise aqueous and non-aqueous solutions, suspensions or emulsions of the active compound, which preparations are typically sterile and can be isotonic with the blood of the intended recipient. Non-limiting illustrative examples include water, buffered saline, Hanks' solution, Ringer's solution, dextrose, fructose, ethanol, animal, vegetable or synthetic oils. Aqueous injection suspensions may contain substances which increase the viscosity of the suspension, such as sodium carboxymethyl cellulose, sorbitol, or dextran.

Additionally, suspensions of the active compounds may be prepared as appropriate oil injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

Cosolvents and adjuvants may be added to the formulation. Non-limiting examples of cosolvents contain hydroxyl groups or other polar groups, for example, alcohols, such as isopropyl alcohol; glycols, such as propylene glycol, polyethyleneglycol, polypropylene glycol, glycol ether; glycerol; polyoxyethylene alcohols and polyoxyethylene fatty acid esters. Adjuvants include, for example, surfactants such as, soya lecithin and oleic acid; sorbitan esters such as sorbitan trioleate; and polyvinylpyrrolidone.

After pharmaceutical compositions have been prepared, they may be placed in an appropriate container and labeled for treatment. Such labeling could include amount, frequency, and method of administration.

Pharmaceutical compositions and delivery systems appropriate for the compositions, methods and uses of the invention are known in the art (see, e.g., *Remington: The Science and Practice of Pharmacy* (2003) $20^{th}$ ed., Mack Publishing Co., Easton, PA; *Remington's Pharmaceutical Sciences* (1990) $18^{th}$ ed., Mack Publishing Co., Easton, PA; The Merck Index (1996) $12^{th}$ ed., Merck Publishing Group, Whitehouse, NJ; *Pharmaceutical Principles of Solid Dosage Forms* (1993), Technomic Publishing Co., Inc., Lancaster, Pa.; Ansel and Stoklosa, *Pharmaceutical Calculations* (2001) $11^{th}$ ed., Lippincott Williams & Wilkins, Baltimore, MD; and Poznansky et al., *Drug Delivery Systems* (1980), R. L. Juliano, ed., Oxford, N.Y., pp. 253-315).

An "effective amount" or "sufficient amount" refers to an amount that provides, in single or multiple doses, alone or in combination, with one or more other compositions (therapeutic or immunosuppressive agents such as a drug), treatments, protocols, or therapeutic regimens agents, a detectable response of any duration of time (long or short term), an expected or desired outcome in or a benefit to a subject of any measurable or detectable degree or for any duration of time (e.g., for minutes, hours, days, months, years, or cured).

Doses can vary and depend upon the type, onset, progression, severity, frequency, duration, or probability of the disease to which treatment is directed, the clinical endpoint desired, previous or simultaneous treatments, the general health, age, gender, race or immunological competency of the subject and other factors that will be appreciated by the skilled artisan. The dose amount, number, frequency or duration may be proportionally increased or reduced, as indicated by any adverse side effects, complications or other risk factors of the treatment or therapy and the status of the subject. The skilled artisan will appreciate the factors that may influence the dosage and timing required to provide an amount sufficient for providing a therapeutic or prophylactic benefit.

The dose to achieve a therapeutic effect, e.g., the dose in vector genomes/per kilogram of body weight (vg/kg), will vary based on several factors including, but not limited to: route of administration, the level of heterologous polynucleotide expression required to achieve a therapeutic effect, the specific disease treated, any host immune response to the viral vector, a host immune response to the heterologous polynucleotide or expression product (protein), and the stability of the protein expressed. One skilled in the art can determine a rAAV/vector genome dose range to treat a patient having a particular disease or disorder based on the aforementioned factors, as well as other factors.

Generally, doses will range from at least $1\times10^8$ vector genomes per kilogram (vg/kg) of the weight of the subject, or more, for example, $1\times10^9$, $1\times10^{10}$, $1\times10^{11}$, $1\times10^{12}$, $1\times10^{13}$ or $1\times10^{14}$, or more, vector genomes per kilogram (vg/kg) of the weight of the subject, to achieve a therapeutic effect. An rAAV dose in the range of $1\times10^{10}$-$1\times10^{11}$ vg/kg in mice, and $1\times10^{12}$-$1\times10^{13}$ vg/kg in dogs have been effective. Doses can be less, for example, a dose of less than $6\times10^{12}$ vg/kg. More particularly, a dose of $5\times10^{11}$ vg/kg or $1\times10^{12}$ vg/kg.

rAAV vector doses can be at a level, typically at the lower end of the dose spectrum, such that there is not a substantial immune response against the heterologous nucleic acid sequence, the encoded protein or inhibitory nucleic acid, or rAAV vector. More particularly, a dose of up to but less than $6\times10^{12}$ vg/kg, such as about $5\times10^{11}$ to about $5\times10^{12}$ vg/kg, or more particularly, about $5\times10^{11}$ vg/kg or about $1\times10^{12}$ vg/kg.

A "unit dosage form" as used herein refers to physically discrete units suited as unitary dosages for the subject to be treated; each unit containing a predetermined quantity optionally in association with a pharmaceutical carrier (excipient, diluent, vehicle or filling agent) which, when administered in one or more doses, is calculated to produce a desired effect (e.g., prophylactic or therapeutic effect). Unit dosage forms may be within, for example, ampules and vials, which may include a liquid composition, or a composition in a freeze-dried or lyophilized state; a sterile liquid carrier, for example, can be added prior to administration or delivery in vivo. Individual unit dosage forms can be included in multi-dose kits or containers. rAAV particles, and pharmaceutical compositions thereof can be packaged in single or multiple unit dosage form for ease of administration and uniformity of dosage.

The doses of an "effective amount" or "sufficient amount" for treatment (e.g., to ameliorate or to provide a therapeutic benefit or improvement) typically are effective to provide a response to one, multiple or all adverse symptoms, consequences or complications of the disease, one or more adverse symptoms, disorders, illnesses, pathologies, or complications, for example, caused by or associated with the disease, to a measurable extent, although decreasing, reducing, inhibiting, suppressing, limiting or controlling progression or worsening of the disease is a satisfactory outcome.

An effective amount or a sufficient amount can but need not be provided in a single administration, may require multiple administrations, and, can but need not be, administered alone or in combination with another composition (e.g., agent), treatment, protocol or therapeutic regimen. For example, the amount may be proportionally increased as indicated by the need of the subject, type, status and severity of the disease treated or side effects (if any) of treatment. In addition, an effective amount or a sufficient amount need not be effective or sufficient if given in single or multiple doses without a second composition (e.g., another drug or agent), treatment, protocol or therapeutic regimen, since additional doses, amounts or duration above and beyond such doses, or additional compositions (e.g., drugs or agents), treatments, protocols or therapeutic regimens may be included in order to be considered effective or sufficient in a given subject. Amounts considered effective also include amounts that result in a reduction of the use of another treatment, therapeutic regimen or protocol, such as administration of modified nucleic acid encoding GAA for treatment of a GAA deficiency (e.g., Pompe disease) or another glycogen storage disease.

Accordingly, methods and uses of the invention also include, among other things, methods and uses that result in a reduced need or use of another compound, agent, drug, therapeutic regimen, treatment protocol, process, or remedy. For example, for GAA deficiency, a method or use of the invention has a therapeutic benefit if in a given subject a less frequent or reduced dose or elimination of administration of a recombinant GAA to supplement for the deficient or defective GAA in the subject. Thus, in accordance with the invention, methods and uses of reducing need or use of another treatment or therapy are provided.

An effective amount or a sufficient amount need not be effective in each and every subject treated, nor a majority of treated subjects in a given group or population. An effective amount or a sufficient amount means effectiveness or sufficiency in a particular subject, not a group or the general population. As is typical for such methods, some subjects will exhibit a greater response, or less or no response to a given treatment method or use.

Administration or in vivo delivery to a subject can be performed prior to development of an adverse symptom, condition, complication, etc. caused by or associated with the disease. For example, a screen (e.g., genetic) can be used to identify such subjects as candidates for invention compositions, methods and uses. Such subjects therefore include those screened positive for an insufficient amount or a deficiency in a functional gene product (e.g., GAA or a protein deficiency that leads to a GSD), or that produce an aberrant, partially functional or non-functional gene product (e.g., GAA or a protein implicated in a GSD).

Administration or in vivo delivery to a subject in accordance with the methods and uses of the invention as disclosed herein can be practiced within 1-2, 2-4, 4-12, 12-24 or 24-72 hours after a subject has been identified as having the disease targeted for treatment, has one or more symptoms of the disease, or has been screened and is identified as positive as set forth herein even though the subject does not have one or more symptoms of the disease. Of course, methods and uses of the invention can be practiced 1-7, 7-14, 14-24, 24-48, 48-64 or more days, months or years after a subject has been identified as having the disease targeted for treatment, has one or more symptoms of the disease, or has been screened and is identified as positive as set forth herein.

The term "ameliorate" means a detectable or measurable improvement in a subject's disease or symptom thereof, or an underlying cellular response. A detectable or measurable improvement includes a subjective or objective decrease, reduction, inhibition, suppression, limit or control in the occurrence, frequency, severity, progression, or duration of the disease, or complication caused by or associated with the disease, or an improvement in a symptom or an underlying cause or a consequence of the disease, or a reversal of the disease.

For Pompe disease, an effective amount would be an amount that inhibits or reduces glycogen production or accumulation, enhances or increases glycogen degradation or removal, for example. An effective amount would also be an amount that improves or ameliorates difficulty eating and/or not gaining weight; poor head and/or neck control; breathing problems and/or lung infections; enlarged and/or thickening heart; heart defects; enlarged tongue; difficulty swallowing; enlarged liver; poor muscle strength; week muscle tone; weakness in the legs, waist and/or arms; shortness of breath; difficulty exercising; difficulty breathing while sleeping; curvature of the spine; and/or stiff joints; week muscle tone and/or lack of muscle strength. An effective amount would also be an amount that decreases or inhibits one or more symptoms, or prevents or reduces the progression or worsening of one or more symptoms, or stabilizes one or more symptoms, or improves one or more symptoms in a patient or subject in need of GAA or having Pompe disease.

Therapeutic doses will depend on, among other factors, the age and general condition of the subject, the severity of the disease or disorder. A therapeutically effective amount in humans will fall in a relatively broad range that may be determined by a medical practitioner based on the response of an individual patient.

Compositions such as pharmaceutical compositions may be delivered to a subject, so as to allow production of the encoded protein. In a particular embodiment, pharmaceutical compositions comprise sufficient genetic material to enable a recipient to produce a therapeutically effective amount of a protein in the subject.

Compositions may be formulated and/or administered in any sterile, biocompatible pharmaceutical carrier, including, but not limited to, saline, buffered saline, dextrose, and water. The compositions may be formulated and/or administered to a patient alone, or in combination with other agents (e.g., co-factors) which influence hemostasis.

Methods and uses of the invention include delivery and administration systemically, regionally or locally, or by any route, for example, by injection or infusion. Delivery of the pharmaceutical compositions in vivo may generally be accomplished via injection using a conventional syringe, although other delivery methods such as convection-enhanced delivery are envisioned (See e.g., U.S. Pat. No. 5,720,720). For example, compositions may be delivered subcutaneously, epidermally, intradermally, intrathecally, intraorbitally, intramucosally, intranasally, intraperitoneally, intravenously, intra-pleurally, intraarterially, intracavitary, orally, intrahepatically, via the portal vein, or intramuscularly. Other modes of administration include oral and pulmonary administration, suppositories, and transdermal applications. A clinician specializing in the treatment of patients with Pompe or other glycogen storage diseases may determine the optimal route for administration of the adenoviral-associated vectors based on a number of criteria, including, but not limited to: the condition of the patient and the purpose of the treatment (e.g., enhanced or reduced GAA levels).

The compositions may be administered alone. In certain embodiments, a rAAV particle provides a therapeutic effect without an immunosuppressive agent. The therapeutic effect optionally is sustained for a period of time, e.g., 2-4, 4-6, 6-8, 8-10, 10-14, 14-20, 20-25, 25-30, or 30-50 days or more, for example, 50-75, 75-100, 100-150, 150-200 days or more without administering an immunosuppressive agent. Accordingly, a therapeutic effect is provided for a period of time.

Invention rAAV vectors, methods and uses can be combined with any compound, agent, drug, treatment or other therapeutic regimen or protocol having a desired therapeutic, beneficial, additive, synergistic or complementary activity or effect. Exemplary combination compositions and treatments include second actives, such as, biologics (proteins), agents (e.g., immunosuppressive agents) and drugs. Such biologics (proteins), agents, drugs, treatments and therapies can be administered or performed prior to, substantially contemporaneously with or following any other method or use of the invention.

The compound, agent, drug, treatment or other therapeutic regimen or protocol can be administered as a combination composition, or administered separately, such as concurrently or in series or sequentially (prior to or following) delivery or administration of a nucleic acid, vector, or rAAV particle. The invention therefore provides combinations in which a method or use of the invention is in a combination with any compound, agent, drug, therapeutic regimen, treatment protocol, process, remedy or composition, set forth herein or known to one of skill in the art. The compound, agent, drug, therapeutic regimen, treatment protocol, process, remedy or composition can be administered or performed prior to, substantially contemporaneously with or following administration of a nucleic acid, vector or rAAV particle of the invention, to a subject.

In certain embodiments, nucleic acid, vector, or rAAV particle of the invention is administered to a patient in combination with an immunosuppressive agent or regimen where the patient has or is at risk of developing an immune response against the rAAV particle and/or the GAA protein. Such immunosuppressive agent or regimen can be administered prior to, substantially at the same time or after administering a nucleic acid, vector, or rAAV vector of the invention In some embodiments, a subject or patient, such as a human patient, with Pompe disease has developed inhibitors to the GAA protein (including anti-GAA antibodies and/or anti-GAA T-cells), which can occur following treatment with traditional enzyme replacement therapy (e.g., following administration of recombinantly produced GAA protein). The development of such GAA inhibitors can occur in patients that receive enzyme replacement therapy, particularly where the patient has undetectable GAA levels (as can be the case in infantile Pompe disease), leading the patient's immune system to see the replacement GAA protein as "foreign." In certain embodiments, a Pompe patient having GAA inhibitors is administered one or more regimen intended to achieve immune tolerance or mitigate the immune response to the GAA protein in the patient, prior to, substantially at the same time or after administering an rAAV vector of the invention. Such regimens to achieve immune tolerance or mitigate the immune response to the GAA protein can include administration of one or more immunosuppressive agent, including but not limited to methotrexate, rituximab, intravenous gamma globulin (IVIG), omalizumab, and synthetic vaccine particle (SVP™)-rapamycin (rapamycin encapsulated in a biodegradable nanoparticle) and/or administration of one or more immunosuppressive protocol or procedure, such as B-cell depletion, immunoadsorption, and plasmapheresis.

In certain embodiments, rAAV vector is administered in conjunction with one or more immunosuppressive agents prior to, substantially at the same time or after administering a rAAV vector. In certain embodiments, e.g., 1-12, 12-24 or 24-48 hours, or 2-4, 4-6, 6-8, 8-10, 10-14, 14-20, 20-25, 25-30, 30-50, or more than 50 days following administering rAAV vector. Such administration of immunosuppressive agents after a period of time following administering rAAV vector if there is a decrease in the encoded protein or inhibitory nucleic acid after the initial expression levels for a period of time, e.g., 20-25, 25-30, 30-50, 50-75, 75-100, 100-150, 150-200 or more than 200 days following rAAV vector.

In certain embodiments, an immunosuppressive agent is an anti-inflammatory agent. In certain embodiments, an immunosuppressive agent is a steroid, e.g., a corticosteroid. In certain embodiments, an immunosuppressive agent is prednisone, prednisolone, cyclosporine (e.g., cyclosporine A), mycophenolate, a B cell targeting antibody, e.g., rituximab; a proteasome inhibitor, e.g., bortezomib; a mammalian target of rapamycin (mTOR) inhibitor, e.g., rapamycin; a tyrosine kinase inhibitor, e.g., ibrutinib; an inhibitor of B-cell activating factor (BAFF); or an inhibitor of a proliferation-inducing ligand (APRIL) or a derivative thereof. In certain embodiments, the immunosuppressive agent is an anti-IL-1 β agent (e.g., anti-IL-1β monoclonal antibody canakinumab (Ilaris®)) or an anti-IL-6 agent (e.g., anti-IL-6 antibody sirukumab or anti-IL-6 receptor antibody tocilizumab (Actemra®)), or a combination thereof.

Immune-suppression protocols, including the use of rapamycin, alone or in combination with IL-10, can be used to decrease, reduce, inhibit, prevent or block humoral and cellular immune responses to the GAA protein. Hepatic gene transfer with AAV vectors of the invention can be used to induce immune tolerance to the GAA protein through induction of regulatory T cells (Tregs) and other mechanisms. Strategies to reduce (overcome) or avoid humoral immunity to AAV in systemic gene transfer include, administering high vector doses, use of AAV empty capsids as decoys to adsorb anti-AAV antibodies, administration of immunosuppressive drugs to decrease, reduce, inhibit, prevent or eradicate the humoral immune response to AAV, changing the AAV capsid serotype or engineering the AAV capsid to be less susceptible to neutralizing antibodies, use of plasma exchange cycles to adsorb anti-AAV immunoglobulins, thereby reducing anti-AAV antibody titer, and use of delivery techniques such as balloon catheters followed by saline flushing. Such strategies are described in Mingozzi et al., 2013, Blood, 122:23-36. Procedures and approaches to induce tolerance to GAA in Pompe patients in order to improve therapeutic treatment are reviewed in Doerfler et al., 2016, Mol. Ther., 3:15053.

Ratio of AAV empty capsids to the rAAV vector can be within or between about 100:1-50:1, from about 50:1-25:1, from about 25:1-10:1, from about 10:1-1:1, from about 1:1-1:10, from about 1:10-1:25, from about 1:25-1:50, or from about 1:50-1:100. Ratios can also be about 2:1, 3:1, 4:1, 5:1, 6:1, 7:1, 8:1, 9:1, or 10:1.

Amounts of AAV empty capsids to administer can be calibrated based upon the amount (titer) of AAV antibodies produced in a particular subject. AAV empty capsids can be of any serotype, for example, AAV (SEQ ID NOs:30-32), LK03 (SEQ ID NO:33), AAV1, AAV2, AAV3, AAV4, AAV5, AAV6, AAV7, AAV8, AAV9, AAV10, AAV11, AAV12, Rh10, Rh74, AAV3B or AAV-2i8.

Alternatively, or in addition to, rAAV vector can be delivered by direct intramuscular injection (e.g., one or more slow-twitch fibers of a muscle). In another alternative, a catheter introduced into the femoral artery can be used to delivery rAAV vectors to liver via the hepatic artery. Non-surgical means can also be employed, such as endoscopic retrograde cholangiopancreatography (ERCP), to deliver rAAV vectors directly to the liver, thereby bypassing the bloodstream and AAV antibodies. Other ductal systems, such as the ducts of the submandibular gland, can also be used as portals for delivering rAAV vectors into a subject that develops or has preexisting anti-AAV antibodies.

Additional strategies to reduce humoral immunity to AAV include methods to remove, deplete, capture, and/or inactivate AAV antibodies, commonly referred to as apheresis and more particularly, plasmapheresis where blood products are involved. Apheresis or plasmapheresis, is a process in which a human subject's plasma is circulated ex vivo (extracorporal) through a device that modifies the plasma through addition, removal and/or replacement of components before its return to the patient. Plasmapheresis can be used to remove human immunoglobulins (e.g., IgG, IgE, IgA, IgD) from a blood product (e.g., plasma). This procedure depletes, captures, inactivates, reduces or removes immunoglobulins (antibodies) that bind AAV thereby reducing the titer of AAV antibodies in the treated subject that may contribute to AAV vector neutralization. An example is a device composed of an AAV capsid affinity matrix column. Passing blood product (e.g., plasma) through an AAV capsid affinity matrix would result in binding only of AAV antibodies, and of all isotypes (including IgG, IgM, etc.).

A sufficient amount of plasmapheresis using an AAV capsid affinity matrix is predicted to substantially remove AAV capsid antibodies, and reduce the AAV capsid antibody titer (load) in the human. In certain embodiments, titer in a treated subject is reduced substantially to low levels (to $<1:5$, or less, such as $<1:4$, or $<1:3$, or $<1:2$, or $<1:1$). A reduction in antibody titer will be temporary because the B lymphocytes that produce the AAV capsid antibodies would be expected to gradually cause the AAV capsid antibody titer to rebound to the steady state level prior to plasmapheresis.

In the case where a pre-existing AAV antibody titer was reduced from 1:100 to 1:1, AAV antibody titer rebounds of approximately 0.15% (corresponding to a titer of 1:1.2) 0.43% (1:1.4), 0.9% (1:1.9), 1.7% (1:2.7), and 3.4% (1:4.4), occur at 1 hour, 3 hours, 6 hours, 12 hours and 24 hours, respectively, after completion of the plasmapheresis method. Temporary removal of AAV antibodies from such a subject would correspond to a window of time (for example, of about 24 hours or less, such as 12 hours or less, or 6 hours or less, or 3 hours or less, or 2 hours or less, or 1 hour or less) during which an AAV vector could be administered to the subject and predicted to efficiently transduce target tissues without substantial neutralization of the AAV vector with the AAV antibodies.

In the case where a pre-existing AAV antibody titer was reduced from 1:1000 to 1:1, AAV antibody titer rebounds of approximately 0.15% (corresponding to a titer of 1:2.5) 0.4% (1:5.3), 0.9% (1:9.7), 1.7% (1:18), and 3.4% (1:35), occur at 1 hour, 3 hours, 6 hours, 12 hours and 24 hours, respectively, after completion of the plasmapheresis method. Thus, a window for administration of AAV vector will be comparatively shorter.

AAV antibodies may be preexisting and may be present at levels that reduce or block therapeutic GAA gene transfer vector transduction of target cells. Alternatively, AAV antibodies may develop after exposure to AAV or administration of an AAV vector. If such antibodies develop after administration of an AAV vector, these subjects can also be treated via apheresis, more particularly, plasmapheresis.

In some embodiments, the nucleic acids, expression cassettes and AAV vectors of the invention can be used in combination with symptomatic and support therapies, including, for example, respiratory support (including mechanical ventilation), physical therapy to strengthen muscles, physiotherapy to improve strength and physical ability, occupational therapy, including use of canes, walkers and wheelchairs, speech therapy to improve articulation and speech, use of orthopedic devices, including braces, and dietary therapy and feeding tubes to ensure proper nutrition and weight gain.

In some embodiments, the nucleic acids, expression cassettes and AAV vectors of the invention can be used in combination with pharmacological chaperone therapy (also known as enzyme enhancement therapy), where one or more pharmacological chaperones is administered before, concomitant with, or after administration of the nucleic acid, expression cassette or AAV vectors of the invention, for the treatment of a GSD, such as Pompe disease.

In some embodiments, the nucleic acids, expression cassettes and AAV vectors of the invention can be used in combination with one or more pharmacological chaperone, which may stabilize GAA protein. Pharmacological chaperones that can be used in combination with the nucleic acids, expression cassettes and AAV vectors of the invention include 1-deoxynojirimycin (1-DNJ, also known as duvoglustat), N-butyl-1-deoxynojirimycin (also known as miglustat), N-methyl-DNJ, N-ethyl-DNJ, N-propyl-DNJ, N-pentyl-DNJ, N-hexyl-DNJ, N-heptyl-DNJ, N-octyl-DNJ, N-nonyl-DNJ, N-methylcyclopropyl-DNJ, N-methylcyclopentyl-DNJ, N-2-hydroxyethyl-DNJ, 5-N-carboxypentyl DNJ, and pharmacological chaperones described in U.S. Pat. Nos. 6,599,919 and 9,181,184, and in International Patent Application publication WO/2013/182652.

In some embodiments, the nucleic acids, expression cassettes and AAV vectors of the invention can be used in combination with adjunctive therapy, with one or more 32 agonist, including, for example, clenbuterol, albuterol, formoterol and salmeterol, and as described in International Patent Application publication WO/2017/049161.

In particular embodiments, the nucleic acids, and expression cassettes of the invention are delivered or administered via AAV vector particles. In other embodiments, the nucleic acids and expression cassettes of the invention can be delivered or administered via other types of viral particles, including retroviral, adenoviral, helper-dependent adenoviral, hybrid adenoviral, herpes simplex virus, lentiviral, poxvirus, Epstein-Barr virus, vaccinia virus, and human cytomegalovirus particles.

In other embodiments, the nucleic acids and expression cassettes of the invention are delivered or administered with a non-viral delivery system. Non-viral delivery systems include for example, chemical methods, such as liposomes, nanoparticles, lipid nanoparticles, polymers, microparticles, microcapsules, micelles, or extracellular vesicles and physical methods, such as gene gun, electroporation, particle bombardment, ultrasound utilization and magnetofection.

In some embodiments, the nucleic acids and expression cassettes of the invention are delivered as naked DNA, minicircles, transposons, of closed-ended linear duplex DNA.

In other embodiments, the nucleic acids, and expression cassettes of the invention are delivered or administered in AAV vector particles, or other viral particles, that are further encapsulated or complexed with liposomes, nanoparticles, lipid nanoparticles, polymers, microparticles, microcapsules, micelles, or extracellular vesicles.

A "lipid nanoparticle" or "LNP" refers to a lipid-based vesicle useful for delivery of AAV and having dimensions on the nanoscale, i.e., from about 10 nm to about 1000 nm, or from about 50 to about 500 nm, or from about 75 to about 127 nm. Without being bound by theory, the LNP is believed to provide the nucleic acid, expression cassette, or AAV vector with partial or complete shielding from the immune system. Shielding allows delivery of the nucleic acid, expression cassette, or AAV vector to a tissue or cell while avoiding inducing a substantial immune response against the nucleic acid, expression cassette, or AAV vector in vivo. Shielding may also allow repeated administration without inducing a substantial immune response against the nucleic acid, expression vector or AAV vector in vivo (e.g., in a subject such as a human). Shielding may also improve or increase nucleic acid, expression cassette, or AAV vector delivery efficiency in vivo.

The pI (isoelectric point) of AAV is in a range from about 6 to about 6.5. Thus, the AAV surface carries a slight negative charge. As such it may be beneficial for the LNP to comprise a cationic lipid such as, for example, an amino lipid. Exemplary amino lipids have been described in U.S. Pat. Nos. 9,352,042, 9,220,683, 9,186,325, 9,139,554, 9,126,966 9,018,187, 8,999,351, 8,722,082, 8,642,076, 8,569,256, 8,466,122, and 7,745,651 and U.S. Patent Publication Nos. 2016/0213785, 2016/0199485, 2015/0265708, 2014/0288146, 2013/0123338, 2013/0116307, 2013/0064894, 2012/0172411, and 2010/0117125.

The terms "cationic lipid" and "amino lipid" are used interchangeably herein to include those lipids and salts thereof having one, two, three, or more fatty acid or fatty alkyl chains and a pH-titratable amino group (e.g., an alkylamino or dialkylamino group). The cationic lipid is typically protonated (i.e., positively charged) at a pH below the pKa of the cationic lipid and is substantially neutral at a pH above the pKa. The cationic lipids may also be titratable cationic lipids. In some embodiments, the cationic lipids comprise: a protonatable tertiary amine (e.g., pH-titratable) group; C18 alkyl chains, wherein each alkyl chain independently has 0 to 3 (e.g., 0, 1, 2, or 3) double bonds; and ether, ester, or ketal linkages between the head group and alkyl chains.

Cationic lipids may include, without limitation, 1,2-dilinoleyloxy-N,N-dimethylaminopropane (DLinDMA), 1,2-dilinolenyloxy-N,N-dimethylaminopropane (DLenDMA), 1,2-di-γ-linolenyloxy-N,N-dimethylaminopropane (γ-DLenDMA), 2,2-dilinoleyl-4-(2-dimethylaminoethyl)-[1,3]-dioxolane (DLin-K-C2-DMA, also known as DLin-C2K-DMA, XTC2, and C2K), 2,2-dilinoleyl-4-dimethylaminomethyl-[1,3]-dioxolane (DLin-K-DMA), dilinoleylmethyl-3-dimethylaminopropionate (DLin-M-C2-DMA, also known as MC2), (6Z,9Z,28Z,31 Z)-heptatriaconta-6,9,28,31-tetraen-19-yl 4-(dimethylamino)butanoate (DLin-M-C3-DMA, also known as MC3), salts thereof, and mixtures thereof. Other cationic lipids also include, but are not limited to, 1,2-distearyloxy-N,N-dimethyl-3-aminopropane (DSDMA), 1,2-dioleyloxy-N,N-dimethyl-3-aminopropane (DODMA), 2,2-dilinoleyl-4-(3-dimethylaminopropyl)-[1,3]-dioxolane (DLin-K-C3-DMA), 2,2-dilinoleyl-4-(3-dimethylaminobutyl)-[1,3]-dioxolane (DLin-K-C4-DMA), DLen-C2K-DMA, γ-DLen-C2K-DMA, and (DLin-MP-DMA) (also known as 1-B11).

Still further cationic lipids may include, without limitation, 2,2-dilinoleyl-5-dimethylaminomethyl-[1,3]-dioxane (DLin-K6-DMA), 2,2-dilinoleyl-4-N-methylpepiazino-[1,3]-dioxolane (DLin-K-MPZ), 1,2-dilinoleylcarbamoyloxy-3-dimethylaminopropane (DLin-C-DAP), 1,2-dilinoleyoxy-3-(dimethylamino)acetoxypropane (DLin-DAC), 1,2-dilinoleyoxy-3-morpholinopropane (DLin-MA), 1,2-dilinoleoyl-3-dimethylaminopropane (DLinDAP), 1,2-dilinoleylthio-3-dimethylaminopropane (DLin-S-DMA), 1-linoleoyl-2-linoleyloxy-3-dimethylaminopropane (DLin-2-DMAP), 1,2-dilinoleyloxy-3-trimethylaminopropane chloride salt (DLin-TMA.Cl), 1,2-dilinoleoyl-3-trimethylaminopropane chloride salt (DLin-TAP.Cl), 1,2-dilinoleyloxy-3-(N-methylpiperazino)propane (DLin-MPZ), 3-(N,N-dilinoleylamino)-1,2-propanediol (DLinAP), 3-(N,N-dioleylamino)-1,2-propanedio (DOAP), 1,2-dilinoleyloxo-3-(2-N,N-dimethylamino)ethoxypropane (DLin-EG-DMA), N,N-dioleyl-N,N-dimethylammonium chloride (DODAC), N-(1-(2,3-dioleyloxy)propyl)-N,N,N-trimethylammonium chloride (DOTMA), N,N-distearyl-N,N-dimethylammonium bromide (DDAB), N-(1-(2,3-dioleoyloxy)propyl)-N,N,N-trimethylammonium chloride (DOTAP), 3-(N—(N',N'-dimethylaminoethane)-carbamoyl)cholesterol (DC-Chol), N-(1,2-dimyristyloxyprop-3-yl)-N,N-dimethyl-N-hydroxyethyl ammonium bromide (DMRIE), 2,3-dioleyloxy-N-[2(spermine-carboxamido)ethyl]-N,N-dimethyl-1-propanaminiumtrifluoroacetate (DOSPA), dioctadecylamidoglycyl spermine (DOGS), 3-dimethylamino-2-(cholest-5-en-3-beta-oxybutan-4-oxy)-1-(cis,cis-9,12-octadecadienoxy)propane (CLinDMA), 2-[5'-(cholest-5-en-3-beta-oxy)-3'-oxapentoxy)-3-dimethyl-1-(cis,cis-9',1-2'-octadecadienoxy) propane (CpLinDMA), N,N-dimethyl-3,4-dioleyloxybenzylamine (DMOBA), 1,2-N,N'-dioleylcarbamyl-3-dimethylaminopropane (DOcarbDAP), 1,2-N,N'-dilinoleylcarbamyl-3-dimethylaminopropane (DLincarbDAP), dexamethasone-sperimine (DS) and disubstituted spermine (D2S) or mixtures thereof.

A number of commercial preparations of cationic lipids can be used, such as, LIPOFECTIN® (including DOTMA and DOPE, available from GIBCO/BRL), and LIPOFECTAMINE® (comprising DOSPA and DOPE, available from GIBCO/BRL).

In certain embodiments, cationic lipid may be present in an amount from about 10% by weight of the LNP to about 85% by weight of the lipid nanoparticle, or from about 50% by weight of the LNP to about 75% by weight of the LNP.

Sterols may confer fluidity to the LNP. As used herein, "sterol" refers to any naturally occurring sterol of plant (phytosterols) or animal (zoosterols) origin as well as non-naturally occurring synthetic sterols, all of which are characterized by the presence of a hydroxyl group at the 3-position of the steroid A-ring. The sterol can be any sterol conventionally used in the field of liposome, lipid vesicle or lipid particle preparation, most commonly cholesterol. Phytosterols may include campesterol, sitosterol, and stigmasterol. Sterols also includes sterol-modified lipids, such as those described in U.S. Patent Application Publication 2011/0177156. In some embodiments, a sterol may be present in an amount from about 5% by weight of the LNP to about 50% by weight of the lipid nanoparticle or from about 10% by weight of the LNP to about 25% by weight of the LNP.

LNP can comprise a neutral lipid. Neutral lipids may comprise any lipid species which exists either in an uncharged or neutral zwitterionic form at physiological pH. Such lipids include, without limitation, diacylphosphatidylcholine, diacylphosphatidylethanolamine, ceramide, sphingomyelin, dihydrosphingomyelin, cephalin, and cerebrosides. The selection of neutral lipids is generally guided by consideration of, inter alia, particle size and the requisite stability. In some embodiments, the neutral lipid component may be a lipid having two acyl groups (e.g., diacylphosphatidylcholine and diacylphosphatidylethanolamine).

Lipids having a variety of acyl chain groups of varying chain length and degree of saturation are available or may be isolated or synthesized by well-known techniques. In some embodiments, lipids containing saturated fatty acids with carbon chain lengths in the range of C14 to C22 may be used. In another group of embodiments, lipids with mono or diunsaturated fatty acids with carbon chain lengths in the range of C14 to C22 are used. Additionally, lipids having mixtures of saturated and unsaturated fatty acid chains can be used. Exemplary neutral lipids include, without limitation, 1,2-dioleoyl-sn-glycero-3-phosphatidyl-ethanolamine (DOPE), 1,2-distearoyl-sn-glycero-3-phosphocholine (DSPC), 1-palmitoyl-2-oleoyl-sn-glycero-3-phosphocholine (POPC), or any related phosphatidylcholine. The neutral lipids may also be composed of sphingomyelin, dihydrosphingomyelin, or phospholipids with other head groups, such as serine and inositol.

In some embodiments, the neutral lipid may be present in an amount from about 0.1% by weight of the lipid nanoparticle to about 75% by weight of the LNP, or from about 5% by weight of the LNP to about 15% by weight of the LNP.

LNP encapsulated nucleic acids, expression cassettes and AAV vector can be incorporated into pharmaceutical compositions, e.g., a pharmaceutically acceptable carrier or excipient. Such pharmaceutical compositions are useful for, among other things, administration and delivery of LNP encapsulated acids, expression cassettes and AAV vector to a subject in vivo or ex vivo.

Preparations of LNP can be combined with additional components. Non-limiting examples include polyethylene glycol (PEG) and sterols.

The term "PEG" refers to a polyethylene glycol, a linear, water-soluble polymer of ethylene PEG repeating units with two terminal hydroxyl groups. PEGs are classified by their molecular weights; for example, PEG 2000 has an average molecular weight of about 2,000 daltons, and PEG 5000 has an average molecular weight of about 5,000 daltons. PEGs are commercially available from Sigma Chemical Co. and other companies and include, for example, the following functional PEGs: monomethoxypolyethylene glycol (MePEG-OH), monomethoxypolyethylene glycol-succinate (MePEG-S), monomethoxypolyethylene glycol-succinimidyl succinate (MePEG-S-NHS), monomethoxypolyethylene glycol-amine (MePEG-NH2), monomethoxypolyethylene glycol-tresylate (MePEG-TRES), and monomethoxypolyethylene glycol-imidazolyl-carbonyl (MePEG-IM).

In some embodiments, PEG may be a polyethylene glycol with an average molecular weight of about 550 to about 10,000 daltons and is optionally substituted by alkyl, alkoxy, acyl or aryl. In some embodiments, the PEG may be substituted with methyl at the terminal hydroxyl position. In another preferred embodiment, the PEG may have an average molecular weight from about 750 to about 5,000 daltons, or from about 1,000 to about 5,000 daltons, or from about 1,500 to about 3,000 daltons or from about 2,000 daltons or of about 750 daltons. The PEG can be optionally substituted with alkyl, alkoxy, acyl or aryl. In some embodiments, the terminal hydroxyl group may be substituted with a methoxy or methyl group.

PEG-modified lipids include the PEG-dialkyloxypropyl conjugates (PEG-DAA) described in U.S. Pat. Nos. 8,936,942 and 7,803,397. PEG-modified lipids (or lipid-polyoxyethylene conjugates) that are useful may have a variety of "anchoring" lipid portions to secure the PEG portion to the surface of the lipid vesicle. Examples of suitable PEG-modified lipids include PEG-modified phosphatidylethanolamine and phosphatidic acid, PEG-ceramide conjugates (e.g., PEG-CerC14 or PEG-CerC20) which are described in U.S. Pat. No. 5,820,873, PEG-modified dialkylamines and PEG-modified 1,2-diacyloxypropan-3-amines. In some embodiments, the PEG-modified lipid may be PEG-modified diacylglycerols and dialkylglycerols. In some embodiments, the PEG may be in an amount from about 0.5% by weight of the LNP to about 20% by weight of the LNP, or from about 5% by weight of the LNP to about 15% by weight of the LNP.

Furthermore, LNP can be a PEG-modified and a sterol-modified LNP. The LNPs, combined with additional components, can be the same or separate LNPs. In other words, the same LNP can be PEG modified and sterol modified or, alternatively, a first LNP can be PEG modified and a second LNP can be sterol modified. Optionally, the first and second modified LNPs can be combined.

In some embodiments, prior to encapsulating LNPs may have a size in a range from about 10 nm to 500 nm, or from about 50 nm to about 200 nm, or from 75 nm to about 125 nm. In some embodiments, LNP encapsulated nucleic acid, expression vector or AAV vector may have a size in a range from about 10 nm to 500 nm.

Recombinant cells capable of expressing the GAA sequences of the invention can be used for delivery or administration.

Naked DNA such as minicircles and transposons can be used for administration or delivery or lentiviral vectors. Additionally, gene editing technologies such as zinc finger nucleases, meganucleases, TALENs, and CRISPR can also be used to deliver the coding sequence of the invention.

A glycogen storage disease (GSD) results from absence of an enzyme that ultimately converts glycogen compounds to glucose. Enzyme deficiency results in glycogen accumulation in tissues. In many cases, the defect has systemic consequences, but, in some cases, the defect is limited to specific tissues. Most patients experience muscle symptoms, such as weakness and cramps, although certain GSDs manifest as specific syndromes, such as hypoglycemic seizures or cardiomegaly.

The following are non-limiting examples of GSDs:

0—Glycogen synthase deficiency; Ia—Glucose-6-phosphatase deficiency (von Gierke disease); II—Acid maltase deficiency (Pompe disease); III—Debranching enzyme deficiency (Forbes-Cori disease); IV—Transglucosidase deficiency (Andersen disease, amylopectinosis); V—Myophosphorylase deficiency (McArdle disease); VI—Phosphorylase deficiency (Hers disease); and VII—Phosphofructokinase deficiency (Tarui disease).

Various forms of GSD affect metabolic carbohydrate pathways. Although at least 14 unique GSDs are discussed in the literature, the 4 that cause clinically significant muscle weakness are Pompe disease (GSD type II, acid maltase deficiency), Cori disease (GSD type IIIa, debranching enzyme deficiency), McArdle disease (GSD type V, myophosphorylase deficiency), and Tarui disease (GSD type VII, phosphofructokinase deficiency). One form, Von Gierke disease (GSD type Ia, glucose-6-phosphatase deficiency), causes clinically significant end-organ disease with significant morbidity.

In general, GSDs are inherited as autosomal recessive conditions. These inherited enzyme defects usually present in childhood, although some, such as McArdle disease and Pompe disease, have separate adult-onset forms.

GSDs can be treated by enzyme replacement therapy (ERT), for example, with recombinantly produced GAA. Enzyme replacement therapy is an approved treatment for all patients with Pompe disease. It involves the intravenous administration of recombinant human acid α-glucosidase. This treatment, manufactured by Genzyme, a Sanofi Corporation, is Lumizyme (marketed as Myozyme outside the United States), and was first approved by the U.S. Food and Drug Administration (FDA) in 2006. It has been approved for all patients with Pompe disease. The benefits of ERT may be attenuated by antibody formation, so ERT can also be combined with immune expression.

GSDs can be treated by diet therapy, involving meticulous adherence to a dietary regimen, may reduce liver size, prevent hypoglycemia, allow for reduction in symptoms, and allow for growth and development.

Additional treatment of Pompe disease is symptomatic and supportive. Respiratory support may be required, as most patients have some degree of respiratory compromise and/or respiratory failure. Physical therapy may be helpful to strengthen respiratory muscles. Some patients may need respiratory assistance through mechanical ventilation (i.e., bipap or volume ventilators) during the night and/or periods of the day. In addition, it may be necessary for additional support during respiratory tract infections. Mechanical ventilation support can be through noninvasive or invasive techniques. The decision about the duration of respiratory support is best made by the family in careful consultation with the patient's physicians and other members of the healthcare team based upon the specifics of the patient. A high-protein diet may be beneficial in the noninfantile form of Pompe.

Physiotherapy is recommended to improve strength and physical ability. Occupational therapy, including the use of canes or walkers, may be necessary. Eventually, some individuals may require the use of a wheelchair. Speech therapy can be beneficial to improve articulation and speech for some patients.

Orthopedic devices including braces may be recommended for some patients. Surgery may be required for certain orthopedic symptoms such as contractures or spinal deformity.

Since Pompe disease can weaken muscles used for chewing and swallowing, measures may be required to ensure proper nutrition and weight gain. Some patients may need specialized, high-calorie diets and may need to learn techniques to change the size and texture of food to lower the risk of aspiration. Some infants may require the insertion of a feeding tube that is run through the nose, down the esophagus and into the stomach (nasogastric tube). In some children, a feeding tube may need to be inserted directly into the stomach through a small surgical opening in the abdominal wall. Some individuals with late onset Pompe disease may require a soft diet, but few require feeding tubes.

Subjects can be tested for one or more liver enzymes for an adverse response to treatment or to determine if such subjects, pretreatment, are appropriate for treatment according to a method of the invention. Candidate subjects can therefore be screened for amounts of one or more liver enzymes prior to or after treatment according to a method of the invention. Treated subjects can be monitored after treatment for elevated liver enzymes, periodically, e.g., every 1-4 weeks, 1-6 months, 6-12 months, or 1, 2, 3, 4, 5 or more years.

Exemplary liver enzymes include alanine aminotransferase (ALT), aspartate aminotransferase (AST), and lactate dehydrogenase (LDH), but other enzymes indicative of liver damage can also be monitored. A normal level of these enzymes in the circulation is typically defined as a range that has an upper level, above which the enzyme level is considered elevated, and therefore indicative of liver damage. A normal range depends in part on the standards used by the clinical laboratory conducting the assay.

The invention provides kits with packaging material and one or more components therein. A kit typically includes a label or packaging insert including a description of the components or instructions for use in vitro, in vivo, or ex vivo, of the components therein. A kit can contain a collection of such components, e.g., a rAAV particle and optionally a second active, such as another compound, agent, drug or composition.

A kit refers to a physical structure housing one or more components of the kit. Packaging material can maintain the components sterilely, and can be made of material commonly used for such purposes (e.g., paper, corrugated fiber, glass, plastic, foil, ampules, vials, tubes, etc.).

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer, lot numbers, manufacture location and date, expiration dates. Labels or inserts can include information identifying manufacturer information, lot numbers, manufacturer location and date. Labels or inserts can include information on a disease for which a kit component may be used. Labels or inserts can include instructions for the clinician or subject for using one or more of the kit components in a method, use, or treatment protocol or therapeutic regimen. Instructions can include dosage amounts, frequency or duration, and instructions for practicing any of the methods, uses, treatment protocols or prophylactic or therapeutic regimes described herein.

Labels or inserts can include information on any benefit that a component may provide, such as a prophylactic or therapeutic benefit. Labels or inserts can include information on potential adverse side effects, complications or reactions, such as warnings to the subject or clinician regarding situations where it would not be appropriate to use a particular composition. Adverse side effects or complications could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a bar-coded printed label, a disk, optical disk such as CD- or DVD-ROM/RAM, DVD, MP3, magnetic tape, or an electrical storage media such as RAM and ROM or hybrids of these such as magnetic/optical storage media, FLASH media or memory type cards.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All patents, patent applications, publications, and other references, GenBank citations and ATCC citations cited herein are incorporated by reference in their entirety. In case of conflict, the specification, including definitions, will control.

All of the features disclosed herein may be combined in any combination. Each feature disclosed in the specification may be replaced by an alternative feature serving a same, equivalent, or similar purpose. Thus, unless expressly stated otherwise, disclosed features (e.g., modified nucleic acids encoding GAA, expression cassettes comprising modified nucleic acids encoding GAA, and rAAV particles comprising the modified nucleic acids encoding GAA) are an example of a genus of equivalent or similar features.

As used herein, the singular forms "a", "and," and "the" include plural referents unless the context clearly indicates otherwise. Thus, for example, reference to "a nucleic acid" includes a plurality of such nucleic acids, reference to "a vector" includes a plurality of such vectors, and reference to "a virus" or "particle" includes a plurality of such viruses/particles.

As used herein, all numerical values or numerical ranges include integers within such ranges and fractions of the values or the integers within ranges unless the context clearly indicates otherwise. Thus, to illustrate, reference to 86% or more identity, includes 86%, 87%, 88%, 89%, 90%, 91%, 92%, 93%, 94%, 95%, 96%, 97%, 98%, 99%, 100% etc., as well as 86.1%, 86.2%, 86.3%, 86.4%, 86.5%, etc., 87.1%, 88.2%, 88.3%, 88.4%, 88.5%, etc., and so forth.

Reference to an integer with more (greater) or less than includes any number greater or less than the reference number, respectively. Thus, for example, a reference to less than 127, includes 126, 125, 124, 123, 122, 121, 120, 119, 118, 117, 116, 115, 114, 113, 112, 111, 110, etc. all the way down to zero (0); and less than 10, includes 9, 8, 7, etc. all the way down to zero (0).

As used herein, all numerical values or ranges include sub ranges and fractions of the values and integers within such ranges and sub ranges and the wrong 1 as well as the file okay thanks fractions of the integers within such ranges unless the context clearly indicates otherwise. Thus, to illustrate, reference to a numerical range, such as 1-10 includes 1-2, 1-3, 1-4, 1-5, 1-6, 1-7, 1-8, 1-9, 2-3, 2-4, 2-5, 2-6, 2-7, 2-8, 2-9, 2-10, 3-4, 3-5, 3-6, 3-7, 3-8, 3-9, 3-10, etc.; and 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth.

Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-850, includes ranges of 1-20, 1-30, 1-40, 1-50, 1-60, 10-30, 10-40, 10-50, 10-60, 10-70, 10-80, 20-40, 20-50, 20-60, 20-70, 20-80, 20-90, 50-75, 50-100, 50-150, 50-200, 50-250, 100-200, 100-250, 100-300, 100-350, 100-400, 100-500, 150-250, 150-300, 150-350, 150-400, 150-450, 150-500, etc.

The invention is generally disclosed herein using affirmative language to describe the numerous embodiments and aspects. The invention also specifically includes embodiments in which particular subject matter is excluded, in full or in part, such as substances or materials, method steps and conditions, protocols, or procedures. For example, in certain embodiments or aspects of the invention, materials and/or method steps are excluded. Thus, even though the invention is generally not expressed herein in terms of what the invention does not include aspects that are not expressly excluded in the invention are nevertheless disclosed herein.

A number of embodiments of the invention have been described. Nevertheless, one skilled in the art, without departing from the spirit and scope of the invention, can make various changes and modifications of the invention to adapt it to various usages and conditions. Accordingly, the following examples are intended to illustrate but not limit the scope of the invention claimed in any way.

Example 1

TABLE 1

GAA Expression Cassette Overview

| Expression Cassette (SEQ ID NOs: 16-24) | SEQ ID NO | Codon Optimized Variant | BGH PolyA Signal | Packaged into (SEQ ID NOs: 30-32) Vector |
|---|---|---|---|---|
| pAAV-ApoE/ hAAT.fixUTR.GAA13.BGH | 16 | GAA13 | CpG-reduced | SPK-AAV-01 |
| pAAV-ApoE/ hAAT.GAA13.BGH | 17 | GAA13 | CpG-reduced | SPK-AAV-02 |
| pAAV-ApoE/ hAAT.GAA7.BGH | 18 | GAA7 | CpG-reduced | SPK-AAV-03 |
| pAAV-ApoE/ hAAT.GAA8.BGH | 19 | GAA8 | CpG-reduced | SPK-AAV-04 |
| pAAV-ApoE/ hAAT.GAA2.wtBGH | 20 | GAA2 | wtBGH | SPK-AAV-05 |
| pAAV-ApoE/ hAAT.GAA5.wtBGH | 21 | GAA5 | wtBGH | SPK-AAV-06 |
| pAAV-ApoE/ hAAT.GAA7.wtBGH | 22 | GAA7 | wtBGH | SPK-AAV-07 |
| pAAV-ApoE/ hAAT.GAA8.wtBGH | 23 | GAA8 | wtBGH | SPK-AAV-08 |
| pAAV-ApoE/ hAAT.GAA13.wtBGH | 24 | GAA13 | wtBGH | SPK-AAV-09 |
| pAAV-ApoE/ hAAT.GAA13.BGH | 17 | GAA13 | CpG-reduced | SPK-AAV-10* |

*SPK-AAV-10 is packaged in AAV6 capsid and all the others are packaged in AAV-4-1 capsid variant, described in International Patent Application publication WO 2016/210170.

GAA expression cassettes are shown in FIGS. 1 through 9. All contain 5' and 3' flanking AAV inverted terminal repeats (ITRs), a liver-specific ApoE/hAAT enhancer/promoter sequence operably linked to an optimized GAA coding sequence, including a human hemoglobin subunit beta (HBB2) intron, followed by a wild type or CpG reduced bovine growth hormone (bGH) polyadenylation (poly A) sequence.

```
SEQ ID NO: 1: nucleic acid sequence for GAA2
ATGGCTTTCCTGTGGCTGCTGAGCTGCTGGGCTCTGCTGGGCACCACCTTTGGGCTGCTGGTGCCTAGGGAGCTG
TCTGGGTCTAGCCCTGTGCTGGAGGAGACTCACCCTGCCCATCAGCAGGGGGCTAGCAGGCCTGGCCCCAGGGAT
GCTCAGGCCCACCCTGGCAGGCCCAGGGCTGTGCCCACCCAGTGTGATGTGCCCCCCAACAGCAGGTTTGACTGT
GCCCCTGACAAGGCCATTACCCAGGAGCAGTGTGAGGCCAGGGGCTGCTGCTACATTCCAGCTAAGCAGGGCCTG
CAGGGGGCCCAGATGGGCCAGCCCTGGTGCTTCTTCCCCCCCAGCTATCCTAGCTATAAACTGGAGAACCTGAGC
AGCTCTGAGATGGGCTATACTGCCACCCTGACTAGGACTACTCCCACCTTTTTTCCTAAGGATATCCTGACCCTG
AGGCTGGATGTGATGATGGAGACTGAGAACAGGCTGCACTTCACTATTAAGGACCCTGCCAATAGGAGGTATGAA
GTGCCTCTGGAGACTCCTCATGTGCACTCTAGGGCCCCCAGCCCCCTGTATTCTGTGGAGTTCTCTGAGGAGCCC
TTTGGGGTGATTGTGAGGAGGCAGCTGGATGGCAGGGTGCTGCTGAACACCACTGTGGCCCCCCTGTTCTTTGCT
GACCAGTTCCTGCAGCTGAGCACCAGCCTGCCCAGCCAGTACATCACTGGGCTGGCTGAGCATCTGAGCCCTCTG
ATGCTGAGCACCTCTTGGACCAGGATCACCCTGTGGAATAGGGATCTGGCCCCCACCCCTGGGGCTAATCTGTAT
GGCTCTCATCCCTTTTACCTGGCCCTGGAGGATGGGGGCTCTGCCCATGGGGTGTTTCTGCTGAACAGCAATGCC
ATGGATGTGGTGCTGCAGCCCTCTCCTGCCCTGAGCTGGAGGAGCACTGGGGGCATCCTGGATGTGTACATCTTC
CTGGGCCCTGAGCCCAAGTCTGTGGTCCAGCAGTATCTGGATGTGGTGGGCTACCCCTTTATGCCCCCCTATTGG
GGCCTGGGCTTCCACCTGTGCAGGTGGGGGTATTCTTCTACTGCTATCACCAGGCAGGTGGTGGAGAACATGACC
AGGGCTCACTTCCCCCTGGATGTGCAGTGGAATGACCTGGACTATATGGACTCTAGGAGGGATTTCACCTTCAAC
AAGGATGGCTTCAGGGACTTCCCTGCTATGGTCCAGGAGCTGCATCAGGGGGGCAGGAGGTACATGATGATTGTG
GACCCTGCCATCAGCAGCTCTGGCCCTGCTGGCAGCTATAGGCCCTATGATGAGGGCCTGAGGAGGGGGGTGTTT
ATCACTAATGAAACTGGGCAGCCCCTGATTGGCAAGGTGTGGCCTGGCTCTACTGCCTTCCCTGACTTCACCAAC
CCCACTGCTCTGGCCTGGTGGGAGGACATGGTGGCTGAGTTCCATGACCAGGTGCCTTTTGATGGCATGTGGATT
GACATGAATGAGCCCAGCAACTTCATCAGGGGCTCTGAGGATGGGTGCCCCAATAATGAGCTGGAGAACCCCCCC
TATGTGCCTGGGGTGGTGGGGGGCACCCTGCAGGCTGCCACTATTTGTGCCAGCTCTCACCAGTTCCTGAGCACC
```

-continued

CACTACAACCTGCACAATCTGTATGGCCTGACTGAGGCCATTGCCAGCCACAGGGCCCTGGTGAAGGCCAGGGGC
ACTAGGCCCTTTGTGATCTCTAGAAGCACCTTTGCTGGCCATGGGAGGTATGCTGGCCACTGGACTGGGGATGTG
TGGAGCTCTTGGGAGCAGCTGGCCAGCTCTGTGCCTGAGATCCTGCAGTTCAACCTGCTGGGGGTGCCCCTGGTG
GGGGCTGATGTGTGTGGCTTCCTGGGCAACACCTCTGAAGAGCTGTGTGTGAGGTGGACCCAGCTGGGGGCCTTC
TACCCTTTCATGAGGAACCACAACAGCCTGCTGAGCCTGCCTCAGGAGCCTTACTCTTTCTCTGAGCCTGCCCAG
CAGGCCATGAGGAAGGCCCTGACCCTGAGGTATGCTCTGCTGCCCCACCTGTACACCCTGTTCCACCAGGCCCAT
GTGGCTGGGGAGACTGTGGCCAGGCCCCTGTTCCTGGAGTTTCCTAAGGATAGCAGCACCTGGACTGTGGACCAC
CAGCTGCTGTGGGGGGAGGCCCTGCTGATTACCCCTGTGCTGCAGGCTGGCAAGGCTGAGGTGACTGGCTACTTC
CCCCTGGGCACTTGGTATGACCTGCAGACTGTGCCTGTGGAAGCCCTGGGCAGCCTGCCTCCCCCCCCTGCTGCC
CCCAGGGAGCCTGCCATCCACTCTGAGGGCCAGTGGGTGACCCTGCCTGCCCCCCTGGACACCATTAATGTGCAT
CTGAGGGCTGGGTATATTATCCCCCTGCAGGGGCCTGGGCTGACTACCACTGAGAGCAGGCAGCAGCCTATGGCC
CTGGCTGTGGCTCTGACTAAGGGGGGGGAGGCCAGGGGGGAGCTGTTCTGGGATGATGGGGAGAGCCTGGAGGTG
CTGGAGAGGGGGGCCTACACCCAGGTGATTTTCCTGGCCAGGAACAACACCATTGTGAATGAGCTGGTGAGGGTG
ACCTCTGAGGGGGCTGGCCTGCAGCTGCAGAAAGTGACTGTGCTGGGGGTGGCCACTGCCCCCCAGCAGGTGCTG
AGCAATGGGGTGCCTGTGAGCAACTTCACCTACAGCCCTGACACCAAGGTGCTGGATATTTGTGTGAGCCTGCTG
ATGGGGGAGCAGTTCCTGGTGAGCTGGTGCTGA

SEQ ID NO: 2: nucleic acid sequence for GAA5

ATGGCTTTCCTGTGGCTGCTGTCTTGCTGGGCCCTGCTGGGGACTACCTTTGGCCTGCTGGTGCCCAGGGAACTG
TCTGGCTCTAGCCCAGTGCTGGAGGAGACCCACCCTGCCCACCAGCAGGGGGCTTCTAGGCCTGGCCCCAGGGAT
GCCCAGGCCCACCCTGGCAGGCCAAGGGCTGTGCCCACCCAGTGTGATGTGCCCCCCAACTCTAGATTTGATTGT
GCCCCTGATAAGGCCATCACCCAGGAGCAGTGTGAGGCTAGGGGCTGCTGCTACATCCCTGCTAAGCAGGGCCTG
CAGGGGGCTCAGATGGGCCAGCCCTGGTGCTTCTTCCCCCCCAGCTATCCCTCTTACAAGCTGGAGAATCTGAGC
AGCTCTGAGATGGGCTACACTGCCACCCTGACCAGGACTACTCCCACCTTCTTCCCCAAGGACATCCTGACCCTG
AGGCTGGATGTGATGATGGAGACTGAGAACAGGCTGCATTTCACCATCAAGGATCCTGCCAACAGGAGGTATGAG
GTGCCTCTGGAGACCCCCCATGTGCACAGCAGGGCTCCTTCTCCCCTGTACTCTGTGGAGTTCTCTGAGGAACCC
TTTGGGGTGATTGTGAGGAGGCAGCTGGATGGCAGGGTCCTGCTGAACACCACTGTGGCCCCCCTGTTCTTTGCT
GATCAGTTCCTGCAGCTGTCCACTTCTCTGCCTAGCCAGTACATCACTGGGCTGGCTGAGCACCTGAGCCCTCTG
ATGCTGAGCACCTCTTGGACTAGGATCACCCTGTGGAACAGGGACCTGGCCCCCACCCCTGGGGCCAACCTGTAT
GGCAGCCACCCCTTCTATCTGGCCCTGGAGGATGGGGGCTCTGCCCATGGGGTGTTCCTGCTGAATAGCAATGCT
ATGGATGTGGTGCTGCAGCCCAGCCCTGCCCTGTCTTGGAGGAGCACTGGGGGCATCCTGGATGTGTACATTTTC
CTGGGGCCTGAGCCCAAGTCTGTGGTGCAGCAGTACCTGGATGTGGTGGGCTACCCCTTCATGCCTCCCTACTGG
GGCCTGGGCTTCCACCTGTGCAGGTGGGGCTACAGCTCTACTGCCATCACCAGGCAGGTGGTGGAGAATATGACC
AGGGCCCACTTCCCCCTGGATGTGCAGTGGAATGACCTGGACTACATGGACTCTAGGAGGGACTTCACCTTCAAT
AAGGATGGCTTCAGAGACTTCCCTGCCATGGTGCAGGAGCTGCATCAGGGGGGCAGGAGGTACATGATGATTGTG
GACCCTGCCATCAGCTCTTCTGGCCCTGCTGGCTCTTACAGGCCCTATGATGAGGGCCTGAGGAGGGGGGTGTTC
ATCACCAATGAGACTGGGCAGCCCCTGATTGGGAAGGTGTGGCCTGGCTCTACTGCCTTCCCTGACTTCACCAAT
CCTACTGCCCTGGCCTGGTGGGAGGACATGGTGGCTGAGTTCCATGACCAGGTGCCCTTTGATGGCATGTGGATT
GACATGAATGAGCCCTCTAATTTCATCAGGGGCTCTGAGGATGGCTGCCCCAACAATGAGCTGGAGAACCCCCCC
TATGTGCCTGGGGTGGTGGGGGGCACCCTGCAGGCTGCCACCATCTGTGCTAGCTCTCACCAGTTCCTGAGCACC
CACTACAATCTGCATAACCTGTATGGCCTGACTGAGGCCATTGCCAGCCACAGGGCCCTGGTGAAGGCTAGGGGC
ACCAGGCCCTTTGTGATTTCTAGGAGCACTTTTGCTGGCCATGGCAGGTATGCTGGGCACTGGACTGGGGATGTG
TGGTCTAGCTGGGAGCAGCTGGCTTCTTCTGTGCCTGAGATCCTGCAGTTCAACCTGCTGGGGGTGCCTCTGGTG
GGGGCTGATGTGTGTGGGTTCCTGGGCAACACTTCTGAGGAGCTGTGTGTGAGGTGGACCCAGCTGGGGGCCTTC
TACCCTTTCATGAGGAACCACAACAGCCTGCTGAGCCTGCCCCAGGAGCCCTACAGCTTCTCTGAGCCTGCCCAG
CAGGCCATGAGGAAGGCCCTGACCCTGAGGTATGCCCTGCTGCCCCACCTGTACACCCTGTTCCACCAGGCCCAT
GTGGCTGGGGAGACTGTGGCTAGGCCTCTGTTCCTGGAGTTCCCCAAGGACTCTAGCACCTGGACTGTGGACCAC
CAGCTGCTGTGGGGGGAGGCCCTGCTGATCACTCCTGTGCTGCAGGCTGGGAAGGCTGAGGTGACTGGCTATTTC
CCCCTGGGCACCTGGTATGACCTGCAGACTGTGCCTGTGGAGGCCCTGGGGAGCCTGCCCCCCCCCCCTGCTGCC
CCCAGGGAGCCTGCCATCCACTCTGAGGGCCAGTGGGTGACCCTGCCTGCCCCTCTGGATACCATCAATGTGCAC
CTGAGGGCTGGCTACATCATTCCCCTGCAGGGCCCTGGCCTGACCACTACTGAGTCTAGGCAGCAGCCCATGGCC
CTGGCTGTGGCCCTGACCAAGGGGGGGGAGGCTAGGGGGGAGCTGTTTTGGGATGATGGGGAGAGCCTGGAGGTG
CTGGAGAGGGGGGCCTACACTCAGGTGATCTTCCTGGCCAGGAACAATACCATTGTGAATGAGCTGGTGAGGGTG
ACCTCTGAGGGGGCTGGCCTGCAGCTGCAGAAGGTGACTGTGCTGGGGGTGGCCACTGCCCCCCAGCAGGTGCTG
AGCAATGGGGTGCCTGTGAGCAACTTCACCTATAGCCCTGATACCAAGGTGCTGGATATTTGTGTGAGCCTGCTG
ATGGGGGAGCAGTTCCTGGTGAGCTGGTGCTGA

SEQ ID NO: 3: nucleic acid sequence for GAA7

ATGGCTTTCCTGTGGCTGCTGTCTTGTTGGGCTCTGCTGGGCACCACCTTTGGCCTGCTGGTGCCCAGGGAGCTG
TCTGGCAGCAGCCCTGTGCTGGAGGAGACCCACCCTGCTCATCAGCAGGGGGCTAGCAGGCCTGGCCCCAGGGAT
GCCCAGGCTCACCCTGGGAGACCCAGGGCTGTGCCCACTCAGTGTGATGTGCCCCCCAACAGCAGGTTTGACTGT
GCTCCTGACAAGGCTATCACCCAGGAGCAGTGTGAGGCCAGGGGGTGCTGCTACATTCCTGCTAAGCAGGGCCTG
CAGGGGGCCCAGATGGGCCAGCCCTGGTGCTTCTTCCCCCCCTCTTATCCCAGCTATAAGCTGGAGAACCTGAGC
AGCTCTGAGATGGGCTACACTGCCACCCTGACCAGGACCACTCCCACCTTCTTTCCCAAGGATATTCTGACTCTG
AGGCTGGATGTGATGATGGAGACTGAGAACAGGCTGCACTTCACTATCAAGGACCCTGCCAATAGGAGGTATGAG
GTGCCCCTGGAGACTCCTCATGTGCATAGCAGGGCCCCTTCTCCTCTGTATTCTGTGGAGTTCTCTGAGGAGCCC
TTTGGGGTGATTGTGAGGAGGCAGCTGGATGGCAGGGTGCTGCTGAACACCACTGTGGCCCCCCTGTTCTTTGCT
GACCAGTTCCTGCAGCTGAGCACTTCTCTGCCCAGCCAGTACATTACTGGGCTGGCTGAGCATCTGAGCCCCCTG
ATGCTGAGCACCTCTTGGACCAGGATCACCCTGTGGAACAGGGACCTGGCCCCCACTCCTGGGGCTAACCTGTAT
GGCTCTCACCCCTTTTACCTGGCCCTGGAGGATGGGGGCTCTGCCCATGGGGTGTTTCTGCTGAACAGCAATGCT
ATGGATGTGGTGCTGCAGCCCTCTCCAGCCCTGTCTTGGAGGAGCACTGGGGGCATTCTGGATGTGTACATTTTC
CTGGGGCCTGAACCCAAGTCTGTGGTGCAGCAGTACCTGGATGTGGTGGGCTACCCCTTCATGCCCCCCTATTGG
GGGCTGGGGTTTCACCTGTGCAGGTGGGGCTACAGCAGCACTGCCATCACCAGGCAGGTGGTGGAGAACATGACC
AGGGCCCATTTCCCCCTGGATGTGCAGTGGAATGACCTGGACTACATGGATAGCAGGAGGGATTTCACCTTCAAC
AAGGATGGCTTCAGGGACTTTCCTGCCATGGTGCAGGAGCTGCACCAGGGGGGCAGGAGGTATATGATGATTGTG
GACCCTGCTATCAGCAGCTCTGGCCCTGCTGGCTCTTACAGGCCCTATGATGAGGGCCTGAGGAGGGGGGTGTTT
ATCACTAATGAAACTGGCCAGCCTCTGATTGGCAAGGTCTGGCCTGGCTCTACTGCCTTCCCTGATTTTACTAAC
CCCACTGCCCTGGCCTGGTGGGAGGACATGGTGGCTGAGTTCCATGATCAGGTGCCTTTTGATGGCATGTGGATT
GATATGAATGAACCAAGCAACTTCATCAGAGGCTCTGAGGATGGCTGCCCCAACAATGAGCTGGAGAACCCCCCC
TATGTGCCTGGGGTGGTGGGGGGCACTCTGCAGGCTGCCACCATTTGTGCTAGCAGCCACCAGTTCCTGAGCACC
CACTACAATCTGCACAACCTGTATGGCCTGACTGAAGCCATTGCCAGCCATAGGGCCCTGGTGAAGGCCAGGGGC

-continued

ACTAGGCCTTTTGTGATCAGCAGGAGCACTTTTGCTGGCCATGGCAGGTATGCTGGCCACTGGACTGGGGATGTG
TGGAGCAGCTGGGAGCAGCTGGCCAGCTCTGTGCCTGAGATTCTGCAGTTTAACCTGCTGGGGGTGCCCCTGGTG
GGGGCTGATGTGTGTGGCTTCCTGGGCAACACCTCTGAGGAGCTGTGTGTGAGGTGGACCCAGCTGGGGGCCTTT
TATCCCTTCATGAGGAACCACAACAGCCTGCTGAGCCTGCCTCAGGAGCCCTACTCTTTCTCTGAGCCTGCCCAG
CAGGCCATGAGGAAGGCCCTGACCCTGAGGTATGCCCTGCTGCCCCACCTGTATACCCTGTTCCACCAGGCCCAT
GTGGCTGGGGAGACTGTGGCCAGGCCCCTGTTCCTGGAGTTCCCCAAGGACAGCAGCACCTGGACTGTGGATCAT
CAGCTGCTGTGGGGGGAGGCCCTGCTGATCACCCCTGTGCTGCAGGCTGGCAAGGCTGAGGTCACTGGCTACTTC
CCTCTGGGCACCTGGTATGACCTGCAGACTGTGCCTGTGGAGGCTCTGGGCAGCCTGCCCCCCCCCCCTGCTGCT
CCCAGGGAGCCTGCCATCCACTCTGAGGGCCAGTGGGTGACCCTGCCTGCTCCCCTGGACACCATCAATGTGCAC
CTGAGGGCTGGCTACATTATCCCCCTGCAGGGCCCAGGGCTGACTACCACTGAGAGCAGACAGCAGCCCATGGCT
CTGGCTGTGGCCCTGACCAAGGGGGGGGAAGCTAGGGGGGAGCTGTTCTGGGATGATGGGGAGAGCCTGGAGGTG
CTGGAGAGGGGGGCCTATACCCAGGTGATCTTCCTGGCTAGGAACAACACCATTGTCAATGAGCTGGTGAGGGTG
ACTTCTGAGGGGGCTGGGCTGCAGCTGCAGAAGGTGACTGTGCTGGGGGTGGCCACTGCTCCCCAGCAGGTGCTG
AGCAATGGGGTGCCTGTGAGCAACTTCACCTACAGCCCTGACACCAAGGTGCTGGACATCTGTGTGTCTCTGCTG
ATGGGGGAGCAGTTCCTGGTGAGCTGGTGCTGA

SEQ ID NO: 4: nucleic acid sequence for GAA8
ATGGCCTTCCTGTGGCTGCTGTCTTGCTGGGCTCTGCTGGGGACCACCTTTGGCCTGCTGGTCCCCAGGGAGCTG
TCTGGCTCTTCTCCTGTCCTGGAGGAGACCCACCCTGCCCACCAGCAGGGGGCTAGCAGGCCTGGCCCCAGGGAT
GCCCAGGCCCACCCTGGCAGGCCCAGGGCTGTGCCCACCCAGTGTGATGTGCCTCCCAACAGCAGGTTTGACTGT
GCCCCTGACAAGGCCATCACCCAGGAGCAGTGTGAGGCCAGGGGCTGCTGCTATATCCCTGCCAAGCAGGGCCTG
CAGGGGGCTCAGATGGGCCAGCCCTGGTGCTTCTTTCCCCCCTCTTATCCTAGCTATAAGCTGGAGAACCTGAGC
AGCTCTGAGATGGGGTACACTGCCACCCTGACCAGGACCACCCCCACTTTCTTCCCTAAGGACATCCTGACCCTG
AGGCTGGATGTGATGATGGAGACTGAGAATAGGCTGCACTTTACTATCAAGGACCCTGCCAACAGGAGGTATGAG
GTGCCTCTGGAGACCCCCCATGTGCATTCTAGGGCCCCCAGCCCCCTGTACTCTGTGGAGTTCTCTGAGGAGCCC
TTTGGGGTGATTGTGAGGAGACAGCTGGATGGCAGGGTCCTGCTGAACACCACTGTGGCTCCCCTGTTTTTTGCT
GACCAGTTCCTGCAGCTGAGCACCAGCCTGCCCAGCCAGTACATCACTGGGCTGGCTGAGCACCTGAGCCCCCTG
ATGCTGAGCACCAGCTGGACCAGGATCACCCTGTGGAACAGGGATCTGGCTCCTACCCCTGGGGCCAACCTGTAT
GGCTCTCACCCCTTTTACCTGGCCCTGGAGGATGGGGGCTCTGCCCATGGGGTGTTCCTGCTGAACAGCAATGCT
ATGGATGTGGTGCTGCAGCCCAGCCCTGCCCTGAGCTGGAGGTCTACTGGGGGCATCCTGGATGTGTACATCTTT
CTGGGGCCTGAGCCCAAGTCTGTGGTGCAGCAGTACCTGGATGTGGTGGGCTATCCTTTTATGCCCCCCTATTGG
GGCCTGGGCTTCCACCTGTGCAGGTGGGGCTACAGCAGCACTGCCATCACCAGACAGGTGGTGGAGAACATGACC
AGGGCCCACTTCCCCCTGGATGTGCAGTGGAATGACCTGGACTACATGGACAGCAGGAGGGACTTCACCTTTAAC
AAGGATGGCTTTAGGGACTTCCCTGCCATGGTGCAGGAGCTGCATCAGGGGGGCAGGAGGTACATGATGATTGTG
GACCCAGCCATCAGCAGCTCTGGGCCTGCTGGGTCTTACAGGCCCTATGATGAGGGCCTGAGGAGGGGGGTGTTC
ATCACCAATGAGACTGGCCAGCCCCTGATTGGCAAGGTGTGGCCTGGGAGCACTGCCTTCCCTGATTTTACCAAC
CCCACTGCCCTGGCCTGGTGGGAGGATATGGTGGCTGAGTTTCATGACCAGGTGCCCTTTGATGGCATGTGGATT
GACATGAATGAGCCCAGCAATTTCATCAGGGGCTCTGAGGATGGCTGCCCCAACAATGAGCTGGAGAATCCTCCC
TATGTGCCTGGGGTGGTGGGGGGCACCCTGCAGGCTGCCACCATCTGTGCCTCTAGCCACCAGTTCCTGAGCACC
CACTATAACCTGCATAACCTGTATGGCCTGACTGAGGCCATTGCCAGCCATAGAGCCCTGGTGAAGGCCAGAGGG
ACCAGGCCCTTTGTGATCTCTAGGAGCACCTTTGCTGGCCATGGCAGGTATGCTGGCCACTGGACTGGGGATGTG
TGGAGCTCTTGGGAGCAGCTGGCCAGCTCTGTGCCAGAGATCCTGCAGTTCAACCTGCTGGGGGTGCCTCTGGTG
GGGGCTGATGTGTGTGGCTTCCTGGGCAATACCTCTGAAGAGCTGTGTGTGAGGTGGACTCAGCTGGGGGCCTTC
TATCCCTTCATGAGGAACCACAACAGCCTGCTGTCTCTGCCCCAGGAGCCCTACAGCTTCTCTGAGCCTGCTCAG
CAGGCTATGAGGAAGGCCCTGACCCTGAGGTATGCCCTGCTGCCCCATCTGTACACCCTGTTCCACCAGGCCCAT
GTGGCTGGGGAGACTGTGGCCAGGCCCCTGTTTCTGGAGTTTCCCAAGGACAGCAGCACCTGGACTGTGGACCAT
CAGCTGCTGTGGGGGGAGGCTCTGCTGATTACCCCTGTGCTGCAGGCTGGCAAGGCTGAGGTGACTGGGTACTTC
CCCCTGGGGACTTGGTATGACCTGCAGACTGTGCCTGTGGAAGCTCTGGGCAGCCTGCCCCCACCCCCTGCTGCC
CCTAGGGAGCCTGCCATCCACTCTGAGGGCCAGTGGGTGACCCTGCCTGCCCCTCTGGACACCATCAATGTGCAC
CTGAGGGCTGGCTATATCATCCCCCTGCAGGGCCCTGGGCTGACCACCACTGAGAGCAGGCAGCAGCCCATGGCC
CTGGCTGTGGCCCTGACTAAGGGGGGGGAGGCCAGGGGGGAGCTGTTCTGGGATGATGGGGAGAGCCTGGAGGTG
CTGGAGAGAGGGGCCTACACCCAGGTGATCTTTCTGGCCAGGAACAACACCATTGTGAATGAGCTGGTGAGGGTG
ACTTCTGAGGGGGCTGGCCTGCAGCTGCAGAAGGTGACTGTGCTGGGGGTGGCCACTGCCCCCCAGCAGGTGCTG
AGCAATGGGGTGCCTGTGTCTAACTTCACCTACAGCCCTGATACTAAGGTGCTGGATATCTGTGTGAGCCTGCTG
ATGGGGGAGCAGTTTCTGGTGAGCTGGTGCTGA SEQ ID NO: 5: nucleic acid sequence for GAA13
ATGGCCTTTCTGTGGCTGCTGTCCTGCTGGGCCCTGCTGGGGACCACCTTTGGCCTGCTGGTGCCCAGGGAGCTG
TCTGGGAGCAGCCCAGTGCTGGAGGAGACCCACCCTGCCCACCAGCAGGGGGCCAGCAGGCCTGGCCCTAGGGAT
GCCCAGGCCCACCCTGGCAGGCCCAGGGCTGTGCCTACCCAGTGTGATGTGCCACCCAATTCTAGGTTTGACTGT
GCTCCTGACAAGGCCATCACTCAGGAGCAGTGTGAAGCTAGGGGGTGCTGCTACATCCCAGCCAAGCAGGGCCTG
CAGGGGGCCCAGATGGGCCAGCCCTGGTGCTTCTTCCCCCCCAGCTACCCTAGCTACAAGCTGGAGAATCTGAGC
AGCTCTGAGATGGGCTACACTGCTACCCTGACCAGGACCACTCCTACCTTCTTCCCCAAGGACATCCTGACTCTG
AGGCTGGATGTCATGATGGAGACTGAAAATAGGCTGCACTTCACCATCAAGGACCCTGCCAATAGGAGGTATGAG
GTGCCTCTGGAGACCCCCCATGTGCATAGCAGGGCTCCCAGCCCCCTGTATTCTGTGGAGTTCTCTGAGGAGCCC
TTTGGGGTCATTGTGAGGAGACAGCTGGATGGGAGGGTGCTGCTGAACACTACTGTGGCTCCCCTGTTCTTTGCT
GACCAGTTCCTGCAGCTGTCTACCAGCCTGCCCAGCCAGTACATCACTGGGCTGGCTGAGCATCTGAGCCCCCTG
ATGCTGAGCACCAGCTGGACCAGGATCACTCTGTGGAACAGGGATCTGGCCCCCACTCCTGGGGCCAACCTGTAT
GGGAGCCATCCCTTCTACCTGGCCCTGGAGGATGGGGGCTCTGCCCATGGGGTGTTCCTGCTGAACAGCAATGCC
ATGGATGTGGTGCTGCAGCCTAGCCCTGCCCTGAGCTGGAGGAGCACTGGGGGCATCCTGGATGTCTACATCTTC
CTGGGGCCTGAGCCCAAGTCTGTGGTGCAGCAGTATCTGGATGTGGTGGGGTATCCCTTCATGCCCCCCTACTGG
GGCCTGGGCTTTCACCTGTGCAGGTGGGGCTACAGCAGCACTGCCATCACCAGGCAGGTGGTGGAGAACATGACC
AGGGCCCACTTCCCTCTGGATGTGCAGTGGAATGACCTGGACTATATGGATTCTAGGAGAGACTTTACTTTTAAC
AAGGATGGCTTCAGGGATTTCCCTGCCATGGTGCAGGAGCTGCACCAGGGGGGCAGGAGGTACATGATGATTGTG
GACCCTGCTATTAGCAGCTCTGGCCCTGCTGGGTCTTACAGGCCTTATGATGAGGGCCTGAGGAGGGGGGTGTTC
ATCACCAATGAGACTGGCCAGCCCCTGATTGGCAAGGTGTGGCCTGGCAGCACTGCCTTCCCTGACTTCACCAAC
CCCACTGCCCTGGCCTGGTGGGAGGACATGGTGGCTGAGTTCCATGACCAGGTGCCCTTTGATGGGATGTGGATT
GACATGAATGAGCCCTCTAACTTCATCAGGGGGTCTGAGGATGGCTGCCCCAACAATGAGCTGGAGAACCCCCCC
TATGTGCCTGGGGTGGTGGGGGGCACTCTGCAGGCTGCCACTATCTGTGCTTCTTCTCACCAGTTTCTGAGCACC
CACTATAATCTGCACAACCTGTATGGCCTGACTGAGGCCATTGCCAGCCATAGGGCCCTGGTGAAGGCCAGGGGC
ACCAGGCCCTTTGTGATCAGCAGGTCTACCTTTGCTGGCCATGGCAGGTATGCTGGCCACTGGACTGGGGATGTG -continued TGGTCTTCTTGGGAGCAGCTGGCCAGCTCTGTGCCTGAGATCCTGCAGTTCAACCTGCTGGGGGTGCCTCTGGTG
GGGGCTGATGTGTGTGGCTTTCTGGGCAACACCTCTGAGGAGCTGTGTGTGAGGTGGACCCAGCTGGGGGCCTTT
TACCCCTTCATGAGGAACCACAATAGCCTGCTGAGCCTGCCCCAGGAGCCTTACTCTTTCTCTGAGCCTGCCCAG
CAGGCCATGAGGAAGGCCCTGACTCTGAGGTATGCCCTGCTGCCCCATCTGTATACCCTGTTTCACCAGGCCCAT
GTGGCTGGGGAGACTGTGGCTAGGCCTCTGTTTCTGGAGTTCCCTAAGGACTCTAGCACCTGGACTGTGGACCAC
CAGCTGCTGTGGGGGGAGGCCCTGCTGATCACCCCTGTGCTGCAGGCTGGCAAGGCTGAGGTGACTGGCTACTTC
CCCCTGGGCACCTGGTATGACCTGCAGACTGTGCCTGTGGAGGCCCTGGGGAGCCTGCCTCCCCCCCCTGCTGCC
CCCAGGGAGCCTGCCATTCATTCTGAGGGCCAGTGGGTGACCCTGCCTGCCCCTCTGGACACCATCAATGTGCAC
CTGAGGGCTGGGTACATCATCCCCCTGCAGGGCCCTGGCCTGACCACCACTGAGAGCAGGCAGCAGCCCATGGCC
CTGGCTGTGGCTCTGACCAAGGGGGGGGAGGCCAGGGGGGAGCTGTTCTGGGATGATGGGGAGTCTCTGGAGGTG
CTGGAGAGGGGGGCCTACACCCAGGTGATCTTTCTGGCCAGGAACAATACTATTGTGAATGAGCTGGTGAGGGTG
ACCTCTGAGGGGGCTGGCCTGCAGCTGCAGAAGGTGACTGTGCTGGGGGTGGCCACTGCCCCCCAGCAGGTCCTG
AGCAATGGGGTGCCTGTGAGCAACTTCACCTACTCTCCTGACACCAAGGTGCTGGACATTTGTGTGTCTCTGCTG
ATGGGGGAGCAGTTCCTGGTGAGCTGGTGCTGA SEQ ID NO: 6: nucleic acid sequence for GAA2 plus WT BGH poly A
ATGGCTTTCCTGTGGCTGCTGAGCTGCTGGGCTCTGCTGGGCACCACCTTTGGGCTGCTGGTGCCTAGGGAGCTG
TCTGGGTCTAGCCCTGTGCTGGAGGAGACTCACCCTGCCCATCAGCAGGGGGCTAGCAGGCCTGGCCCCAGGGAT
GCTCAGGCCCACCCTGGCAGGCCCAGGGCTGTGCCCACCCAGTGTGATGTGCCCCCCAACAGCAGGTTTGACTGT
GCCCCTGACAAGGCCATTACCCAGGAGCAGTGTGAGGCCAGGGGCTGCTGCTACATTCCAGCTAAGCAGGGCCTG
CAGGGGGCCCAGATGGGCCAGCCCTGGTGCTTCTTCCCCCCCAGCTATCCTAGCTATAAACTGGAGAACCTGAGC
AGCTCTGAGATGGGCTATACTGCCACCCTGACTAGGACTACTCCCACCTTTTTTCCTAAGGATATCCTGACCCTG
AGGCTGGATGTGATGATGGAGACTGAGAACAGGCTGCACTTCACTATTAAGGACCCTGCCAATAGGAGGTATGAA
GTGCCTCTGGAGACTCCTCATGTGCACTCTAGGGCCCCCAGCCCCCTGTATTCTGTGGAGTTCTCTGAGGAGCCC
TTTGGGGTGATTGTGAGGAGGCAGCTGGATGGCAGGGTGCTGCTGAACACCACTGTGGCCCCCCTGTTCTTTGCT
GACCAGTTCCTGCAGCTGAGCACCAGCCTGCCCAGCCAGTACATCACTGGGCTGGCTGAGCATCTGAGCCCTCTG
ATGCTGAGCACCTCTTGGACCAGGATCACCCTGTGGAATAGGGATCTGGCCCCCACCCCTGGGGCTAATCTGTAT
GGCTCTCATCCCTTTTACCTGGCCCTGGAGGATGGGGGCTCTGCCCATGGGGTGTTTCTGCTGAACAGCAATGCC
ATGGATGTGGTGCTGCAGCCCTCTCCTGCCCTGAGCTGGAGGAGCACTGGGGGCATCCTGGATGTGTACATCTTC
CTGGGCCCTGAGCCCAAGTCTGTGGTCCAGCAGTATCTGGATGTGGTGGGCTACCCCTTTATGCCCCCCTATTGG
GGCCTGGGCTTCCACCTGTGCAGGTGGGGGTATTCTTCTACTGCTATCACCAGGCAGGTGGTGGAGAACATGACC
AGGGCTCACTTCCCCCTGGATGTGCAGTGGAATGACCTGGACTATATGGACTCTAGGAGGGATTTCACCTTCAAC
AAGGATGGCTTCAGGGACTTCCCTGCTATGGTCCAGGAGCTGCATCAGGGGGGCAGGAGGTACATGATGATTGTG
GACCCTGCCATCAGCAGCTCTGGCCCTGCTGGCAGCTATAGGCCCTATGATGAGGGCCTGAGGAGGGGGGTGTTT
ATCACTAATGAAACTGGGCAGCCCCTGATTGGCAAGGTGTGGCCTGGCTCTACTGCCTTCCCTGACTTCACCAAC
CCCACTGCTCTGGCCTGGTGGGAGGACATGGTGGCTGAGTTCCATGACCAGGTGCCTTTTGATGGCATGTGGATT
GACATGAATGAGCCCAGCAACTTCATCAGGGGCTCTGAGGATGGGTGCCCCAATAATGAGCTGGAGAACCCCCCC
TATGTGCCTGGGGTGGTGGGGGGCACCCTGCAGGCTGCCACTATTTGTGCCAGCTCTCACCAGTTCCTGAGCACC
CACTACAACCTGCACAATCTGTATGGCCTGACTGAGGCCATTGCCAGCCACAGGGCCCTGGTGAAGGCCAGGGGC
ACTAGGCCCTTTGTGATCTCTAGAAGCACCTTTGCTGGCCATGGGAGGTATGCTGGCCACTGGACTGGGGATGTG
TGGAGCTCTTGGGAGCAGCTGGCCAGCTCTGTGCCTGAGATCCTGCAGTTCAACCTGCTGGGGGTGCCCCTGGTG
GGGGCTGATGTGTGTGGCTTCCTGGGCAACACCTCTGAAGAGCTGTGTGTGAGGTGGACCCAGCTGGGGGCCTTC
TACCCTTTCATGAGGAACCACAACAGCCTGCTGAGCCTGCCTCAGGAGCCTTACTCTTTCTCTGAGCCTGCCCAG
CAGGCCATGAGGAAGGCCCTGACCCTGAGGTATGCTCTGCTGCCCCACCTGTACACCCTGTTCCACCAGGCCCAT
GTGGCTGGGGAGACTGTGGCCAGGCCCCTGTTCCTGGAGTTTCCTAAGGATAGCAGCACCTGGACTGTGGACCAC
CAGCTGCTGTGGGGGGAGGCCCTGCTGATTACCCCTGTGCTGCAGGCTGGCAAGGCTGAGGTGACTGGCTACTTC
CCCCTGGGCACTTGGTATGACCTGCAGACTGTGCCTGTGGAAGCCCTGGGCAGCCTGCCTCCCCCCCCTGCTGCC
CCCAGGGAGCCTGCCATCCACTCTGAGGGCCAGTGGGTGACCCTGCCTGCCCCCCTGGACACCATTAATGTGCAT
CTGAGGGCTGGGTATATTATCCCCCTGCAGGGGCCTGGGCTGACTACCACTGAGAGCAGGCAGCAGCCTATGGCC
CTGGCTGTGGCTCTGACTAAGGGGGGGGAGGCCAGGGGGGAGCTGTTCTGGGATGATGGGGAGAGCCTGGAGGTG
CTGGAGAGGGGGGCCTACACCCAGGTGATTTTCCTGGCCAGGAACAACACCATTGTGAATGAGCTGGTGAGGGTG
ACCTCTGAGGGGGCTGGCCTGCAGCTGCAGAAAGTGACTGTGCTGGGGGTGGCCACTGCCCCCCAGCAGGTGCTG
AGCAATGGGGTGCCTGTGAGCAACTTCACCTACAGCCCTGACACCAAGGTGCTGGATATTTGTGTGAGCCTGCTG
ATGGGGGAGCAGTTCCTGGTGAGCTGGTGCTGACTCGAGAGATCTACCGGTGAATTCACCGCGGGTTTAAACTGT
GCCTTCTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGTGGGGT
GGGGGCTAGCTCTAGA SEQ ID NO: 7: nucleic acid sequence for GAA5 plus WT BGH poly A
ATGGCTTTCCTGTGGCTGCTGTCTTGCTGGGCCCTGCTGGGGACTACCTTTGGCCTGCTGGTGCCCAGGGAACTG
TCTGGCTCTAGCCCAGTGCTGGAGGAGACCCACCCTGCCCACCAGCAGGGGGCTTCTAGGCCTGGCCCCAGGGAT
GCCCAGGCCCACCCTGGCAGGCCAAGGGCTGTGCCCACCCAGTGTGATGTGCCCCCCAACTCTAGATTTGATTGT
GCCCCTGATAAGGCCATCACCCAGGAGCAGTGTGAGGCTAGGGGCTGCTGCTACATCCCTGCTAAGCAGGGCCTG
CAGGGGGCTCAGATGGGCCAGCCCTGGTGCTTCTTCCCCCCCAGCTATCCCTCTTACAAGCTGGAGAATCTGAGC
AGCTCTGAGATGGGCTACACTGCCACCCTGACCAGGACTACTCCCACCTTCTTCCCCAAGGACATCCTGACCCTG
AGGCTGGATGTGATGATGGAGACTGAGAACAGGCTGCATTTCACCATCAAGGATCCTGCCAACAGGAGGTATGAG
GTGCCTCTGGAGACCCCCCATGTGCACAGCAGGGCTCCTTCTCCCCTGTACTCTGTGGAGTTCTCTGAGGAACCC
TTTGGGGTGATTGTGAGGAGGCAGCTGGATGGCAGGGTCCTGCTGAACACCACTGTGGCCCCCCTGTTCTTTGCT
GATCAGTTCCTGCAGCTGTCCACTTCTCTGCCTAGCCAGTACATCACTGGGCTGGCTGAGCACCTGAGCCCTCTG
ATGCTGAGCACCTCTTGGACTAGGATCACCCTGTGGAACAGGGACCTGGCCCCCACCCCTGGGGCCAACCTGTAT
GGCAGCCACCCCTTCTATCTGGCCCTGGAGGATGGGGGCTCTGCCCATGGGGTGTTCCTGCTGAATAGCAATGCT
ATGGATGTGGTGCTGCAGCCCAGCCCTGCCCTGTCTTGGAGGAGCACTGGGGGCATCCTGGATGTGTACATTTTC
CTGGGGCCTGAGCCCAAGTCTGTGGTGCAGCAGTACCTGGATGTGGTGGGCTACCCCTTCATGCCTCCCTACTGG
GGCCTGGGCTTCCACCTGTGCAGGTGGGGCTACAGCTCTACTGCCATCACCAGGCAGGTGGTGGAGAATATGACC
AGGGCCCACTTCCCCCTGGATGTGCAGTGGAATGACCTGGACTACATGGACTCTAGGAGGGACTTCACCTTCAAT
AAGGATGGCTTCAGAGACTTCCCTGCCATGGTGCAGGAGCTGCATCAGGGGGGCAGGAGGTACATGATGATTGTG
GACCCTGCCATCAGCTCTTCTGGCCCTGCTGGCTCTTACAGGCCCTATGATGAGGGCCTGAGGAGGGGGGTGTTC
ATCACCAATGAGACTGGGCAGCCCCTGATTGGGAAGGTGTGGCCTGGCTCTACTGCCTTCCCTGACTTCACCAAT
CCTACTGCCCTGGCCTGGTGGGAGGACATGGTGGCTGAGTTCCATGACCAGGTGCCCTTTGATGGCATGTGGATT
GACATGAATGAGCCCTCTAATTTCATCAGGGGCTCTGAGGATGGCTGCCCCAACAATGAGCTGGAGAACCCCCCC
TATGTGCCTGGGGTGGTGGGGGGCACCCTGCAGGCTGCCACCATCTGTGCTAGCTCTCACCAGTTCCTGAGCACC -continued CACTACAATCTGCATAACCTGTATGGCCTGACTGAGGCCATTGCCAGCCACAGGGCCCTGGTGAAGGCTAGGGGC
ACCAGGCCCTTTGTGATTTCTAGGAGCACTTTTGCTGGCCATGGCAGGTATGCTGGGCACTGGACTGGGGATGTG
TGGTCTAGCTGGGAGCAGCTGGCTTCTTCTGTGCCTGAGATCCTGCAGTTCAACCTGCTGGGGGTGCCTCTGGTG
GGGGCTGATGTGTGTGGGTTCCTGGGCAACACTTCTGAGGAGCTGTGTGTGAGGTGGACCCAGCTGGGGGCCTTC
TACCCTTTCATGAGGAACCACAACAGCCTGCTGAGCCTGCCCCAGGAGCCCTACAGCTTCTCTGAGCCTGCCCAG
CAGGCCATGAGGAAGGCCCTGACCCTGAGGTATGCCCTGCTGCCCCACCTGTACACCCTGTTCCACCAGGCCCAT
GTGGCTGGGGAGACTGTGGCTAGGCCTCTGTTCCTGGAGTTCCCCAAGGACTCTAGCACCTGGACTGTGGACCAC
CAGCTGCTGTGGGGGGAGGCCCTGCTGATCACTCCTGTGCTGCAGGCTGGGAAGGCTGAGGTGACTGGCTATTTC
CCCCTGGGCACCTGGTATGACCTGCAGACTGTGCCTGTGGAGGCCCTGGGGAGCCTGCCCCCCCCCCCTGCTGCC
CCCAGGGAGCCTGCCATCCACTCTGAGGGCCAGTGGGTGACCCTGCCTGCCCCTCTGGATACCATCAATGTGCAC
CTGAGGGCTGGCTACATCATTCCCCTGCAGGGCCCTGGCCTGACCACTACTGAGTCTAGGCAGCAGCCCATGGCC
CTGGCTGTGGCCCTGACCAAGGGGGGGGAGGCTAGGGGGGAGCTGTTTGGGATGATGGGGAGAGCCTGGAGGTG
CTGGAGAGGGGGGCCTACACTCAGGTGATCTTCCTGGCCAGGAACAATACCATTGTGAATGAGCTGGTGAGGGTG
ACCTCTGAGGGGGCTGGCCTGCAGCTGCAGAAGGTGACTGTGCTGGGGGTGGCCACTGCCCCCCAGCAGGTGCTG
AGCAATGGGGTGCCTGTGAGCAACTTCACCTATAGCCCTGATACCAAGGTGCTGGATATTTGTGTGAGCCTGCTG
ATGGGGGAGCAGTTCCTGGTGAGCTGGTGCTGACTCGAGAGATCTACCGGTGAATTCACCGCGGGTTTAAACTGT
GCCTTCTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGTGGGGT
GGGGGCTAGCTCTAGA SEQ ID NO: 8: nucleic acid sequence for GAA7 plus WT BGH poly A
ATGGCTTTCCTGTGGCTGCTGTCTTGTTGGGCTCTGCTGGGCACCACCTTTGGCCTGCTGGTGCCCAGGGAGCTG
TCTGGCAGCAGCCCTGTGCTGGAGGAGACCCACCCTGCTCATCAGCAGGGGGCTAGCAGGCCTGGCCCCAGGGAT
GCCCAGGCTCACCCTGGGAGACCCAGGGCTGTGCCCACTCAGTGTGATGTGCCCCCCAACAGCAGGTTTGACTGT
GCTCCTGACAAGGCTATCACCCAGGAGCAGTGTGAGGCCAGGGGGTGCTGCTACATTCCTGCTAAGCAGGGCCTG
CAGGGGGCCCAGATGGGCCAGCCCTGGTGCTTCTTCCCCCCCTCTTATCCCAGCTATAAGCTGGAGAACCTGAGC
AGCTCTGAGATGGGCTACACTGCCACCCTGACCAGGACCACTCCCACCTTCTTTCCCAAGGATATTCTGACTCTG
AGGCTGGATGTGATGATGGAGACTGAGAACAGGCTGCACTTCACTATCAAGGACCCTGCCAATAGGAGGTATGAG
GTGCCCCTGGAGACTCCTCATGTGCATAGCAGGGCCCCTTCTCCTCTGTATTCTGTGGAGTTCTCTGAGGAGCCC
TTTGGGGTGATTGTGAGGAGGCAGCTGGATGGCAGGGTGCTGCTGAACACCACTGTGGCCCCCCTGTTCTTTGCT
GACCAGTTCCTGCAGCTGAGCACTTCTCTGCCCAGCCAGTACATTACTGGGCTGGCTGAGCATCTGAGCCCCCTG
ATGCTGAGCACCTCTTGGACCAGGATCACCCTGTGGAACAGGGACCTGGCCCCCACTCCTGGGGCTAACCTGTAT
GGCTCTCACCCCTTTTACCTGGCCCTGGAGGATGGGGGCTCTGCCCATGGGGTGTTTCTGCTGAACAGCAATGCT
ATGGATGTGGTGCTGCAGCCCTCTCCAGCCCTGTCTTGGAGGAGCACTGGGGGCATTCTGGATGTGTACATTTTC
CTGGGGCCTGAACCCAAGTCTGTGGTGCAGCAGTACCTGGATGTGGTGGGCTACCCCTTCATGCCCCCCTATTGG
GGGCTGGGGTTTCACCTGTGCAGGTGGGGCTACAGCAGCACTGCCATCACCAGGCAGGTGGTGGAGAACATGACC
AGGGCCCATTTCCCCCTGGATGTGCAGTGGAATGACCTGGACTACATGGATAGCAGGAGGGATTTCACCTTCAAC
AAGGATGGCTTCAGGGACTTTCCTGCCATGGTGCAGGAGCTGCACCAGGGGGGCAGGAGGTATATGATGATTGTG
GACCCTGCTATCAGCAGCTCTGGCCCTGCTGGCTCTTACAGGCCCTATGATGAGGGCCTGAGGAGGGGGGTGTTT
ATCACTAATGAAACTGGCCAGCCTCTGATTGGCAAGGTCTGGCCTGGCTCTACTGCCTTCCCTGATTTTACTAAC
CCCACTGCCCTGGCCTGGTGGGAGGACATGGTGGCTGAGTTCCATGATCAGGTGCCTTTTGATGGCATGTGGATT
GATATGAATGAACCAAGCAACTTCATCAGAGGCTCTGAGGATGGCTGCCCCAACAATGAGCTGGAGAACCCCCCC
TATGTGCCTGGGGTGGTGGGGGGCACTCTGCAGGCTGCCACCATTIGTGCTAGCAGCCACCAGTTCCTGAGCACC
CACTACAATCTGCACAACCTGTATGGCCTGACTGAAGCCATTGCCAGCCATAGGGCCCTGGTGAAGGCCAGGGGC
ACTAGGCCTTTTGTGATCAGCAGGAGCACTTTTGCTGGCCATGGCAGGTATGCTGGCCACTGGACTGGGGATGTG
TGGAGCAGCTGGGAGCAGCTGGCCAGCTCTGTGCCTGAGATTCTGCAGTTTAACCTGCTGGGGGTGCCCCTGGTG
GGGGCTGATGTGTGTGGCTTCCTGGGCAACACCTCTGAGGAGCTGTGTGTGAGGTGGACCCAGCTGGGGGCCTTT
TATCCCTTCATGAGGAACCACAACAGCCTGCTGAGCCTGCCTCAGGAGCCCTACTCTTTCTCTGAGCCTGCCCAG
CAGGCCATGAGGAAGGCCCTGACCCTGAGGTATGCCCTGCTGCCCCACCTGTATACCCTGTTCCACCAGGCCCAT
GTGGCTGGGGAGACTGTGGCCAGGCCCCTGTTCCTGGAGTTCCCCAAGGACAGCAGCACCTGGACTGTGGATCAT
CAGCTGCTGTGGGGGGAGGCCCTGCTGATCACCCCTGTGCTGCAGGCTGGCAAGGCTGAGGTCACTGGCTACTTC
CCTCTGGGCACCTGGTATGACCTGCAGACTGTGCCTGTGGAGGCTCTGGGCAGCCTGCCCCCCCCCCCTGCTGCT
CCCAGGGAGCCTGCCATCCACTCTGAGGGCCAGTGGGTGACCCTGCCTGCTCCCCTGGACACCATCAATGTGCAC
CTGAGGGCTGGCTACATTATCCCCCTGCAGGGCCCAGGGCTGACTACCACTGAGAGCAGACAGCAGCCCATGGCT
CTGGCTGTGGCCCTGACCAAGGGGGGGGAAGCTAGGGGGGAGCTGTTCTGGGATGATGGGGAGAGCCTGGAGGTG
CTGGAGAGGGGGGCCTATACCCAGGTGATCTTCCTGGCTAGGAACAACACCATTGTCAATGAGCTGGTGAGGGTG
ACTTCTGAGGGGGCTGGGCTGCAGCTGCAGAAGGTGACTGTGCTGGGGGTGGCCACTGCTCCCCAGCAGGTGCTG
AGCAATGGGGTGCCTGTGAGCAACTTCACCTACAGCCCTGACACCAAGGTGCTGGACATCTGTGTGTCTCTGCTG
ATGGGGGAGCAGTTCCTGGTGAGCTGGTGCTGACTCGAGAGATCTACCGGTGAATTCACCGCGGGTTTAAACTGT
GCCTTCTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGTGGGGT
GGGGGCTAGCTCTAGA SEQ ID NO: 9: nucleic acid sequence for GAA8 plus WT BGH poly A
ATGGCCTTCCTGTGGCTGCTGTCTTGCTGGGCTCTGCTGGGGACCACCTTTGGCCTGCTGGTCCCCAGGGAGCTG
TCTGGCTCTTCTCCTGTCCTGGAGGAGACCCACCCTGCCCACCAGCAGGGGGCTAGCAGGCCTGGCCCCAGGGAT
GCCCAGGCCCACCCTGGCAGGCCCAGGGCTGTGCCCACCCAGTGTGATGTGCCTCCCAACAGCAGGTTTGACTGT
GCCCCTGACAAGGCCATCACCCAGGAGCAGTGTGAGGCCAGGGGCTGCTGCTATATCCCTGCCAAGCAGGGCCTG
CAGGGGGCTCAGATGGGCCAGCCCTGGTGCTTCTTTCCCCCCTCTTATCCTAGCTATAAGCTGGAGAACCTGAGC
AGCTCTGAGATGGGGTACACTGCCACCCTGACCAGGACCACCCCCACTTTCTTCCCTAAGGACATCCTGACCCTG
AGGCTGGATGTGATGATGGAGACTGAGAATAGGCTGCACTTTACTATCAAGGACCCTGCCAACAGGAGGTATGAG
GTGCCTCTGGAGACCCCCCATGTGCATTCTAGGGCCCCCAGCCCCCTGTACTCTGTGGAGTTCTCTGAGGAGCCC
TTTGGGGTGATTGTGAGGAGACAGCTGGATGGCAGGGTCCTGCTGAACACCACTGTGGCTCCCCTGTTTTTTGCT
GACCAGTTCCTGCAGCTGAGCACCAGCCTGCCCAGCCAGTACATCACTGGGCTGGCTGAGCACCTGAGCCCCCTG
ATGCTGAGCACCAGCTGGACCAGGATCACCCTGTGGAACAGGGATCTGGCTCCTACCCCTGGGGCCAACCTGTAT
GGCTCTCACCCCTTTTACCTGGCCCTGGAGGATGGGGGCTCTGCCCATGGGGTGTTCCTGCTGAACAGCAATGCT
ATGGATGTGGTGCTGCAGCCCAGCCCTGCCCTGAGCTGGAGGTCTACTGGGGGCATCCTGGATGTGTACATCTTT
CTGGGGCCTGAGCCCAAGTCTGTGGTGCAGCAGTACCTGGATGTGGTGGGCTATCCTTTTATGCCCCCCTATTGG
GGCCTGGGCTTCCACCTGTGCAGGTGGGGCTACAGCAGCACTGCCATCACCAGACAGGTGGTGGAGAACATGACC
AGGGCCCACTTCCCCCTGGATGTGCAGTGGAATGACCTGGACTACATGGACAGCAGGAGGGACTTCACCTTTAAC
AAGGATGGCTTTAGGGACTTCCCTGCCATGGTGCAGGAGCTGCATCAGGGGGGCAGGAGGTACATGATGATTGTG -continued GACCCAGCCATCAGCAGCTCTGGGCCTGCTGGGTCTTACAGGCCCTATGATGAGGGCCTGAGGAGGGGGGTGTTC
ATCACCAATGAGACTGGCCAGCCCCTGATTGGCAAGGTGTGGCCTGGGAGCACTGCCTTCCCTGATTTTACCAAC
CCCACTGCCCTGGCCTGGTGGGAGGATATGGTGGCTGAGTTTCATGACCAGGTGCCCTTTGATGGCATGTGGATT
GACATGAATGAGCCCAGCAATTTCATCAGGGGCTCTGAGGATGGCTGCCCCAACAATGAGCTGGAGAATCCTCCC
TATGTGCCTGGGGTGGTGGGGGGCACCCTGCAGGCTGCCACCATCTGTGCCTCTAGCCACCAGTTCCTGAGCACC
CACTATAACCTGCATAACCTGTATGGCCTGACTGAGGCCATTGCCAGCCATAGAGCCCTGGTGAAGGCCAGAGGG
ACCAGGCCCTTTGTGATCTCTAGGAGCACCTTTGCTGGCCATGGCAGGTATGCTGGCCACTGGACTGGGGATGTG
TGGAGCTCTTGGGAGCAGCTGGCCAGCTCTGTGCCAGAGATCCTGCAGTTCAACCTGCTGGGGGTGCCTCTGGTG
GGGGCTGATGTGTGTGGCTTCCTGGGCAATACCTCTGAAGAGCTGTGTGTGAGGTGGACTCAGCTGGGGGCCTTC
TATCCCTTCATGAGGAACCACAACAGCCTGCTGTCTCTGCCCCAGGAGCCCTACAGCTTCTCTGAGCCTGCTCAG
CAGGCTATGAGGAAGGCCCTGACCCTGAGGTATGCCCTGCTGCCCCATCTGTACACCCTGTTCCACCAGGCCCAT
GTGGCTGGGGAGACTGTGGCCAGGCCCCTGTTTCTGGAGTTTCCCAAGGACAGCAGCACCTGGACTGTGGACCAT
CAGCTGCTGTGGGGGGAGGCTCTGCTGATTACCCCTGTGCTGCAGGCTGGCAAGGCTGAGGTGACTGGGTACTTC
CCCCTGGGGACTTGGTATGACCTGCAGACTGTGCCTGTGGAAGCTCTGGGCAGCCTGCCCCCACCCCCTGCTGCC
CCTAGGGAGCCTGCCATCCACTCTGAGGGCCAGTGGGTGACCCTGCCTGCCCCTCTGGACACCATCAATGTGCAC
CTGAGGGCTGGCTATATCATCCCCCTGCAGGGCCCTGGGCTGACCACCACTGAGAGCAGGCAGCAGCCCATGGCC
CTGGCTGTGGCCCTGACTAAGGGGGGGGAGGCCAGGGGGGAGCTGTTCTGGGATGATGGGGAGAGCCTGGAGGTG
CTGGAGAGAGGGGCCTACACCCAGGTGATCTTTCTGGCCAGGAACAACACCATTGTGAATGAGCTGGTGAGGGTG
ACTTCTGAGGGGGCTGGCCTGCAGCTGCAGAAGGTGACTGTGCTGGGGGTGGCCACTGCCCCCCAGCAGGTGCTG
AGCAATGGGGTGCCTGTGTCTAACTTCACCTACAGCCCTGATACTAAGGTGCTGGATATCTGTGTGAGCCTGCTG
ATGGGGGAGCAGTTTCTGGTGAGCTGGTGCTGACTCGAGAGATCTACCGGTGAATTCACCGCGGGTTTAAACTGT
GCCTTCTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGTGGGGT
GGGGGCTAGCTCTAGA SEQ ID NO: 10: nucleic acid sequence for GAA13 plus WT BGH poly A
ATGGCCTTTCTGTGGCTGCTGTCCTGCTGGGCCCTGCTGGGGACCACCTTTGGCCTGCTGGTGCCCAGGGAGCTG
TCTGGGAGCAGCCCAGTGCTGGAGGAGACCCACCCTGCCCACCAGCAGGGGGCCAGCAGGCCTGGCCCTAGGGAT
GCCCAGGCCCACCCTGGCAGGCCCAGGGCTGTGCCTACCCAGTGTGATGTGCCACCCAATTCTAGGTTTGACTGT
GCTCCTGACAAGGCCATCACTCAGGAGCAGTGTGAAGCTAGGGGGTGCTGCTACATCCCAGCCAAGCAGGGCCTG
CAGGGGGCCCAGATGGGCCAGCCCTGGTGCTTCTTCCCCCCCAGCTACCCTAGCTACAAGCTGGAGAATCTGAGC
AGCTCTGAGATGGGCTACACTGCTACCCTGACCAGGACCACTCCTACCTTCTTCCCCAAGGACATCCTGACTCTG
AGGCTGGATGTCATGATGGAGACTGAAAATAGGCTGCACTTCACCATCAAGGACCCTGCCAATAGGAGGTATGAG
GTGCCTCTGGAGACCCCCCATGTGCATAGCAGGGCTCCCAGCCCCCTGTATTCTGTGGAGTTCTCTGAGGAGCCC
TTTGGGGTCATTGTGAGGAGACAGCTGGATGGGAGGGTGCTGCTGAACACTACTGTGGCTCCCCTGTTCTTTGCT
GACCAGTTCCTGCAGCTGTCTACCAGCCTGCCCAGCCAGTACATCACTGGGCTGGCTGAGCATCTGAGCCCCCTG
ATGCTGAGCACCAGCTGGACCAGGATCACTCTGTGGAACAGGGATCTGGCCCCCACTCCTGGGGCCAACCTGTAT
GGGAGCCATCCCTTCTACCTGGCCCTGGAGGATGGGGGCTCTGCCCATGGGGTGTTCCTGCTGAACAGCAATGCC
ATGGATGTGGTGCTGCAGCCTAGCCCTGCCCTGAGCTGGAGGAGCACTGGGGGCATCCTGGATGTCTACATCTTC
CTGGGGCCTGAGCCCAAGTCTGTGGTGCAGCAGTATCTGGATGTGGTGGGGTATCCCTTCATGCCCCCCTACTGG
GGCCTGGGCTTTCACCTGTGCAGGTGGGGCTACAGCAGCACTGCCATCACCAGGCAGGTGGTGGAGAACATGACC
AGGGCCCACTTCCCTCTGGATGTGCAGTGGAATGACCTGGACTATATGGATTCTAGGAGAGACTTTACTTTTAAC
AAGGATGGCTTCAGGGATTTCCCTGCCATGGTGCAGGAGCTGCACCAGGGGGGCAGGAGGTACATGATGATTGTG
GACCCTGCTATTAGCAGCTCTGGCCCTGCTGGGTCTTACAGGCCTTATGATGAGGGCCTGAGGAGGGGGGTGTTC
ATCACCAATGAGACTGGCCAGCCCCTGATTGGCAAGGTGTGGCCTGGCAGCACTGCCTTCCCTGACTTCACCAAC
CCCACTGCCCTGGCCTGGTGGGAGGACATGGTGGCTGAGTTCCATGACCAGGTGCCCTTTGATGGGATGTGGATT
GACATGAATGAGCCCTCTAACTTCATCAGGGGGTCTGAGGATGGCTGCCCCAACAATGAGCTGGAGAACCCCCCC
TATGTGCCTGGGGTGGTGGGGGGCACTCTGCAGGCTGCCACTATCTGTGCTTCTTCTCACCAGTTTCTGAGCACC
CACTATAATCTGCACAACCTGTATGGCCTGACTGAGGCCATTGCCAGCCATAGGGCCCTGGTGAAGGCCAGGGGC
ACCAGGCCCTTTGTGATCAGCAGGTCTACCTTTGCTGGCCATGGCAGGTATGCTGGCCACTGGACTGGGGATGTG
TGGTCTTCTTGGGAGCAGCTGGCCAGCTCTGTGCCTGAGATCCTGCAGTTCAACCTGCTGGGGGTGCCTCTGGTG
GGGGCTGATGTGTGTGGCTTTCTGGGCAACACCTCTGAGGAGCTGTGTGTGAGGTGGACCCAGCTGGGGGCCTTT
TACCCCTTCATGAGGAACCACAATAGCCTGCTGAGCCTGCCCCAGGAGCCTTACTCTTTCTCTGAGCCTGCCCAG
CAGGCCATGAGGAAGGCCCTGACTCTGAGGTATGCCCTGCTGCCCCATCTGTATACCCTGTTTCACCAGGCCCAT
GTGGCTGGGGAGACTGTGGCTAGGCCTCTGTTTCTGGAGTTCCCTAAGGACTCTAGCACCTGGACTGTGGACCAC
CAGCTGCTGTGGGGGGAGGCCCTGCTGATCACCCCTGTGCTGCAGGCTGGCAAGGCTGAGGTGACTGGCTACTTC
CCCCTGGGCACCTGGTATGACCTGCAGACTGTGCCTGTGGAGGCCCTGGGGAGCCTGCCTCCCCCCCCTGCTGCC
CCCAGGGAGCCTGCCATTCATTCTGAGGGCCAGTGGGTGACCCTGCCTGCCCCTCTGGACACCATCAATGTGCAC
CTGAGGGCTGGGTACATCATCCCCCTGCAGGGCCCTGGCCTGACCACCACTGAGAGCAGGCAGCAGCCCATGGCC
CTGGCTGTGGCTCTGACCAAGGGGGGGGAGGCCAGGGGGGAGCTGTTCTGGGATGATGGGGAGTCTCTGGAGGTG
CTGGAGAGGGGGGCCTACACCCAGGTGATCTTTCTGGCCAGGAACAATACTATTGTGAATGAGCTGGTGAGGGTG
ACCTCTGAGGGGGCTGGCCTGCAGCTGCAGAAGGTGACTGTGCTGGGGGTGGCCACTGCCCCCCAGCAGGTCCTG
AGCAATGGGGTGCCTGTGAGCAACTTCACCTACTCTCCTGACACCAAGGTGCTGGACATTTGTGTGTCTCTGCTG
ATGGGGGAGCAGTTCCTGGTGAGCTGGTGCTGACTCGAGAGATCTACCGGTGAATTCACCGCGGGTTTAAACTGT
GCCTTCTAGTTGCCAGCCATCTGTTGTTTGCCCCTCCCCCGTGCCTTCCTTGACCCTGGAAGGTGCCACTCCCAC
TGTCCTTTCCTAATAAAATGAGGAAATTGCATCGCATTGTCTGAGTAGGTGTCATTCTATTCTGGGGGGTGGGGT
GGGGGCTAGCTCTAGA SEQ ID NO: 11: nucleic acid sequence for GAA2 plus CpG-reduced BGH poly A
ATGGCTTTCCTGTGGCTGCTGAGCTGCTGGGCTCTGCTGGGCACCACCTTTGGGCTGCTGGTGCCTAGGGAGCTG
TCTGGGTCTAGCCCTGTGCTGGAGGAGACTCACCCTGCCCATCAGCAGGGGGCTAGCAGGCCTGGCCCCAGGGAT
GCTCAGGCCCACCCTGGCAGGCCCAGGGCTGTGCCCACCCAGTGTGATGTGCCCCCCAACAGCAGGTTTGACTGT
GCCCCTGACAAGGCCATTACCCAGGAGCAGTGTGAGGCCAGGGGCTGCTGCTACATTCCAGCTAAGCAGGGCCTG
CAGGGGGCCCAGATGGGCCAGCCCTGGTGCTTCTTCCCCCCCAGCTATCCTAGCTATAAACTGGAGAACCTGAGC
AGCTCTGAGATGGGCTATACTGCCACCCTGACTAGGACTACTCCCACCTTTTTCCTAAGGATATCCTGACCCTG
AGGCTGGATGTGATGATGGAGACTGAGAACAGGCTGCACTTCACTATTAAGGACCCTGCCAATAGGAGGTATGAA
GTGCCTCTGGAGACTCCTCATGTGCACTCTAGGGCCCCCAGCCCCCTGTATTCTGTGGAGTTCTCTGAGGAGCCC
TTTGGGGTGATTGTGAGGAGGCAGCTGGATGGCAGGGTGCTGCTGAACACCACTGTGGCCCCCCTGTTCTTTGCT
GACCAGTTCCTGCAGCTGAGCACCAGCCTGCCCAGCCAGTACATCACTGGGCTGGCTGAGCATCTGAGCCCTCTG
ATGCTGAGCACCTCTTGGACCAGGATCACCCTGTGGAATAGGGATCTGGCCCCCACCCCTGGGGCTAATCTGTAT
GGCTCTCATCCCTTTTACCTGGCCCTGGAGGATGGGGGCTCTGCCCATGGGGTGTTTCTGCTGAACAGCAATGCC -continued ATGGATGTGGTGCTGCAGCCCTCTCCTGCCCTGAGCTGGAGGAGCACTGGGGGCATCCTGGATGTGTACATCTTC
CTGGGCCCTGAGCCCAAGTCTGTGGTCCAGCAGTATCTGGATGTGGTGGGCTACCCCTTTATGCCCCCCTATTGG
GGCCTGGGCTTCCACCTGTGCAGGTGGGGGTATTCTTCTACTGCTATCACCAGGCAGGTGGTGGAGAACATGACC
AGGGCTCACTTCCCCCTGGATGTGCAGTGGAATGACCTGGACTATATGGACTCTAGGAGGGATTTCACCTTCAAC
AAGGATGGCTTCAGGGACTTCCCTGCTATGGTCCAGGAGCTGCATCAGGGGGGCAGGAGGTACATGATGATTGTG
GACCCTGCCATCAGCAGCTCTGGCCCTGCTGGCAGCTATAGGCCCTATGATGAGGGCCTGAGGAGGGGGGTGTTT
ATCACTAATGAAACTGGGCAGCCCCTGATTGGCAAGGTGTGGCCTGGCTCTACTGCCTTCCCTGACTTCACCAAC
CCCACTGCTCTGGCCTGGTGGGAGGACATGGTGGCTGAGTTCCATGACCAGGTGCCTTTTGATGGCATGTGGATT
GACATGAATGAGCCCAGCAACTTCATCAGGGGCTCTGAGGATGGGTGCCCCAATAATGAGCTGGAGAACCCCCCC
TATGTGCCTGGGGTGGTGGGGGGCACCCTGCAGGCTGCCACTATTTGTGCCAGCTCTCACCAGTTCCTGAGCACC
CACTACAACCTGCACAATCTGTATGGCCTGACTGAGGCCATTGCCAGCCACAGGGCCCTGGTGAAGGCCAGGGGC
ACTAGGCCCTTTGTGATCTCTAGAAGCACCTTTGCTGGCCATGGGAGGTATGCTGGCCACTGGACTGGGGATGTG
TGGAGCTCTTGGGAGCAGCTGGCCAGCTCTGTGCCTGAGATCCTGCAGTTCAACCTGCTGGGGGTGCCCCTGGTG
GGGGCTGATGTGTGTGGCTTCCTGGGCAACACCTCTGAAGAGCTGTGTGTGAGGTGGACCCAGCTGGGGGCCTTC
TACCCTTTCATGAGGAACCACAACAGCCTGCTGAGCCTGCCTCAGGAGCCTTACTCTTTCTCTGAGCCTGCCCAG
CAGGCCATGAGGAAGGCCCTGACCCTGAGGTATGCTCTGCTGCCCCACCTGTACACCCTGTTCCACCAGGCCCAT
GTGGCTGGGGAGACTGTGGCCAGGCCCCTGTTCCTGGAGTTTCCTAAGGATAGCAGCACCTGGACTGTGGACCAC
CAGCTGCTGTGGGGGGAGGCCCTGCTGATTACCCCTGTGCTGCAGGCTGGCAAGGCTGAGGTGACTGGCTACTTC
CCCCTGGGCACTTGGTATGACCTGCAGACTGTGCCTGTGGAAGCCCTGGGCAGCCTGCCTCCCCCCCCTGCTGCC
CCCAGGGAGCCTGCCATCCACTCTGAGGGCCAGTGGGTGACCCTGCCTGCCCCCCTGGACACCATTAATGTGCAT
CTGAGGGCTGGGTATATTATCCCCCTGCAGGGGCCTGGGCTGACTACCACTGAGAGCAGGCAGCAGCCTATGGCC
CTGGCTGTGGCTCTGACTAAGGGGGGGGAGGCCAGGGGGGAGCTGTTCTGGGATGATGGGGAGAGCCTGGAGGTG
CTGGAGAGGGGGGCCTACACCCAGGTGATTTTCCTGGCCAGGAACAACACCATTGTGAATGAGCTGGTGAGGGTG
ACCTCTGAGGGGGCTGGCCTGCAGCTGCAGAAAGTGACTGTGCTGGGGGTGGCCACTGCCCCCCAGCAGGTGCTG
AGCAATGGGGTGCCTGTGAGCAACTTCACCTACAGCCCTGACACCAAGGTGCTGGATATTTGTGTGAGCCTGCTG
ATGGGGGAGCAGTTCCTGGTGAGCTGGTGCTGAAGATCTAGAGCTGAATTCCTGCAGCCAGGGGGATCAGCCTCT
ACTGTGCCTTCTAGTTGCCAGCCATCTGTTGTTTGCCCCTCCCCCTTGCCTTCCTTGACCCTGGAAGGTGCCACT
CCCACTGTCCTTTCCTAATAAAATGAGGAAATTGCATCACATTGTCTGAGTAGGTGTCATTCTATTCTGGGGGGT
GGGGTGGGGCAGGACAGCAAGGGGGAGGATTGGGAAGACAATAGCAGGCATGCTGGGGATGCAGTGGGCTCTATG
G SEQ ID NO: 12: nucleic acid sequence for GAA5 plus CpG-reduced BGH poly A ATGGCTTTCCTGTGGCTGCTGTCTTGCTGGGCCCTGCTGGGGACTACCTTTGGCCTGCTGGTGCCCAGGGAACTG
TCTGGCTCTAGCCCAGTGCTGGAGGAGACCCACCCTGCCCACCAGCAGGGGGCTTCTAGGCCTGGCCCCAGGGAT
GCCCAGGCCCACCCTGGCAGGCCAAGGGCTGTGCCCACCCAGTGTGATGTGCCCCCCAACTCTAGATTTGATTGT
GCCCCTGATAAGGCCATCACCCAGGAGCAGTGTGAGGCTAGGGGCTGCTGCTACATCCCTGCTAAGCAGGGCCTG
CAGGGGGCTCAGATGGGCCAGCCCTGGTGCTTCTTCCCCCCCAGCTATCCCTCTTACAAGCTGGAGAATCTGAGC
AGCTCTGAGATGGGCTACACTGCCACCCTGACCAGGACTACTCCCACCTTCTTCCCCAAGGACATCCTGACCCTG
AGGCTGGATGTGATGATGGAGACTGAGAACAGGCTGCATTTCACCATCAAGGATCCTGCCAACAGGAGGTATGAG
GTGCCTCTGGAGACCCCCCATGTGCACAGCAGGGCTCCTTCTCCCCTGTACTCTGTGGAGTTCTCTGAGGAACCC
TTTGGGGTGATTGTGAGGAGGCAGCTGGATGGCAGGGTCCTGCTGAACACCACTGTGGCCCCCCTGTTCTTTGCT
GATCAGTTCCTGCAGCTGTCCACTTCTCTGCCTAGCCAGTACATCACTGGGCTGGCTGAGCACCTGAGCCCTCTG
ATGCTGAGCACCTCTTGGACTAGGATCACCCTGTGGAACAGGGACCTGGCCCCCACCCCTGGGGCCAACCTGTAT
GGCAGCCACCCCTTCTATCTGGCCCTGGAGGATGGGGGCTCTGCCCATGGGGTGTTCCTGCTGAATAGCAATGCT
ATGGATGTGGTGCTGCAGCCCAGCCCTGCCCTGTCTTGGAGGAGCACTGGGGGCATCCTGGATGTGTACATTTTC
CTGGGGCCTGAGCCCAAGTCTGTGGTGCAGCAGTACCTGGATGTGGTGGGCTACCCCTTCATGCCTCCCTACTGG
GGCCTGGGCTTCCACCTGTGCAGGTGGGGCTACAGCTCTACTGCCATCACCAGGCAGGTGGTGGAGAATATGACC
AGGGCCCACTTCCCCCTGGATGTGCAGTGGAATGACCTGGACTACATGGACTCTAGGAGGGACTTCACCTTCAAT
AAGGATGGCTTCAGAGACTTCCCTGCCATGGTGCAGGAGCTGCATCAGGGGGGCAGGAGGTACATGATGATTGTG
GACCCTGCCATCAGCTCTTCTGGCCCTGCTGGCTCTTACAGGCCCTATGATGAGGGCCTGAGGAGGGGGGTGTTC
ATCACCAATGAGACTGGGCAGCCCCTGATTGGGAAGGTGTGGCCTGGCTCTACTGCCTTCCCTGACTTCACCAAT
CCTACTGCCCTGGCCTGGTGGGAGGACATGGTGGCTGAGTTCCATGACCAGGTGCCCTTTGATGGCATGTGGATT
GACATGAATGAGCCCTCTAATTTCATCAGGGGCTCTGAGGATGGCTGCCCCAACAATGAGCTGGAGAACCCCCCC
TATGTGCCTGGGGTGGTGGGGGGCACCCTGCAGGCTGCCACCATCTGTGCTAGCTCTCACCAGTTCCTGAGCACC
CACTACAATCTGCATAACCTGTATGGCCTGACTGAGGCCATTGCCAGCCACAGGGCCCTGGTGAAGGCTAGGGGC
ACCAGGCCCTTTGTGATTTCTAGGAGCACTTTTGCTGGCCATGGCAGGTATGCTGGGCACTGGACTGGGGATGTG
TGGTCTAGCTGGGAGCAGCTGGCTTCTTCTGTGCCTGAGATCCTGCAGTTCAACCTGCTGGGGGTGCCTCTGGTG
GGGGCTGATGTGTGTGGGTTCCTGGGCAACACTTCTGAGGAGCTGTGTGTGAGGTGGACCCAGCTGGGGGCCTTC
TACCCTTTCATGAGGAACCACAACAGCCTGCTGAGCCTGCCCCAGGAGCCCTACAGCTTCTCTGAGCCTGCCCAG
CAGGCCATGAGGAAGGCCCTGACCCTGAGGTATGCCCTGCTGCCCCACCTGTACACCCTGTTCCACCAGGCCCAT
GTGGCTGGGGAGACTGTGGCTAGGCCTCTGTTCCTGGAGTTCCCCAAGGACTCTAGCACCTGGACTGTGGACCAC
CAGCTGCTGTGGGGGGAGGCCCTGCTGATCACTCCTGTGCTGCAGGCTGGGAAGGCTGAGGTGACTGGCTATTTC
CCCCTGGGCACCTGGTATGACCTGCAGACTGTGCCTGTGGAGGCCCTGGGGAGCCTGCCCCCCCCCCCTGCTGCC
CCCAGGGAGCCTGCCATCCACTCTGAGGGCCAGTGGGTGACCCTGCCTGCCCCTCTGGATACCATCAATGTGCAC
CTGAGGGCTGGCTACATCATTCCCCTGCAGGGCCCTGGCCTGACCACTACTGAGTCTAGGCAGCAGCCCATGGCC
CTGGCTGTGGCCCTGACCAAGGGGGGGGAGGCTAGGGGGGAGCTGTTTTGGGATGATGGGGAGAGCCTGGAGGTG
CTGGAGAGGGGGGCCTACACTCAGGTGATCTTCCTGGCCAGGAACAATACCATTGTGAATGAGCTGGTGAGGGTG
ACCTCTGAGGGGGCTGGCCTGCAGCTGCAGAAGGTGACTGTGCTGGGGGTGGCCACTGCCCCCCAGCAGGTGCTG
AGCAATGGGGTGCCTGTGAGCAACTTCACCTATAGCCCTGATACCAAGGTGCTGGATATTTGTGTGAGCCTGCTG
ATGGGGGAGCAGTTCCTGGTGAGCTGGTGCTGAAGATCTAGAGCTGAATTCCTGCAGCCAGGGGGATCAGCCTCT
ACTGTGCCTTCTAGTTGCCAGCCATCTGTTGTTTGCCCCTCCCCCTTGCCTTCCTTGACCCTGGAAGGTGCCACT
CCCACTGTCCTTTCCTAATAAAATGAGGAAATTGCATCACATTGTCTGAGTAGGTGTCATTCTATTCTGGGGGGT
GGGGTGGGGCAGGACAGCAAGGGGGAGGATTGGGAAGACAATAGCAGGCATGCTGGGGATGCAGTGGGCTCTATG SEQ ID NO: 13: nucleic acid sequence for GAA7 plus CpG-reduced BGH poly A ATGGCTTTCCTGTGGCTGCTGTCTTGTTGGGCTCTGCTGGGCACCACCTTTGGCCTGCTGGTGCCCAGGGAGCTG
TCTGGCAGCAGCCCTGTGCTGGAGGAGACCCACCCTGCTCATCAGCAGGGGGCTAGCAGGCCTGGCCCCAGGGAT
GCCCAGGCTCACCCTGGGAGACCCAGGGCTGTGCCCACTCAGTGTGATGTGCCCCCCAACAGCAGGTTTGACTGT
GCTCCTGACAAGGCTATCACCCAGGAGCAGTGTGAGGCCAGGGGGTGCTGCTACATTCCTGCTAAGCAGGGCCTG
CAGGGGGCCCAGATGGGCCAGCCCTGGTGCTTCTTCCCCCCCTCTTATCCCAGCTATAAGCTGGAGAACCTGAGC
AGCTCTGAGATGGGCTACACTGCCACCCTGACCAGGACCACTCCCACCTTCTTTCCCAAGGATATTCTGACTCTG -continued AGGCTGGATGTGATGATGGAGACTGAGAACAGGCTGCACTTCACTATCAAGGACCCTGCCAATAGGAGGTATGAG
GTGCCCCTGGAGACTCCTCATGTGCATAGCAGGGCCCCTTCTCCTCTGTATTCTGTGGAGTTCTCTGAGGAGCCC
TTTGGGGTGATTGTGAGGAGGCAGCTGGATGGCAGGGTGCTGCTGAACACCACTGTGGCCCCCCTGTTCTTTGCT
GACCAGTTCCTGCAGCTGAGCACTTCTCTGCCCAGCCAGTACATTACTGGGCTGGCTGAGCATCTGAGCCCCCTG
ATGCTGAGCACCTCTTGGACCAGGATCACCCTGTGGAACAGGGACCTGGCCCCCACTCCTGGGGCTAACCTGTAT
GGCTCTCACCCCTTTTACCTGGCCCTGGAGGATGGGGGCTCTGCCCATGGGGTGTTTCTGCTGAACAGCAATGCT
ATGGATGTGGTGCTGCAGCCCTCTCCAGCCCTGTCTTGGAGGAGCACTGGGGGCATTCTGGATGTGTACATTTTC
CTGGGGCCTGAACCCAAGTCTGTGGTGCAGCAGTACCTGGATGTGGTGGGCTACCCCTTCATGCCCCCCTATTGG
GGGCTGGGGTTTCACCTGTGCAGGTGGGGCTACAGCAGCACTGCCATCACCAGGCAGGTGGTGGAGAACATGACC
AGGGCCCATTTCCCCCTGGATGTGCAGTGGAATGACCTGGACTACATGGATAGCAGGAGGGATTTCACCTTCAAC
AAGGATGGCTTCAGGGACTTTCCTGCCATGGTGCAGGAGCTGCACCAGGGGGGCAGGAGGTATATGATGATTGTG
GACCCTGCTATCAGCAGCTCTGGCCCTGCTGGCTCTTACAGGCCCTATGATGAGGGCCTGAGGAGGGGGGTGTTT
ATCACTAATGAAACTGGCCAGCCTCTGATTGGCAAGGTCTGGCCTGGCTCTACTGCCTTCCCTGATTTTACTAAC
CCCACTGCCCTGGCCTGGTGGGAGGACATGGTGGCTGAGTTCCATGATCAGGTGCCTTTTGATGGCATGTGGATT
GATATGAATGAACCAAGCAACTTCATCAGAGGCTCTGAGGATGGCTGCCCCAACAATGAGCTGGAGAACCCCCCC
TATGTGCCTGGGGTGGTGGGGGGCACTCTGCAGGCTGCCACCATTTGTGCTAGCAGCCACCAGTTCCTGAGCACC
CACTACAATCTGCACAACCTGTATGGCCTGACTGAAGCCATTGCCAGCCATAGGGCCCTGGTGAAGGCCAGGGGC
ACTAGGCCTTTTGTGATCAGCAGGAGCACTTTTGCTGGCCATGGCAGGTATGCTGGCCACTGGACTGGGGATGTG
TGGAGCAGCTGGGAGCAGCTGGCCAGCTCTGTGCCTGAGATTCTGCAGTTTAACCTGCTGGGGGTGCCCCTGGTG
GGGGCTGATGTGTGTGGCTTCCTGGGCAACACCTCTGAGGAGCTGTGTGTGAGGTGGACCCAGCTGGGGGCCTTT
TATCCCTTCATGAGGAACCACAACAGCCTGCTGAGCCTGCCTCAGGAGCCCTACTCTTTCTCTGAGCCTGCCCAG
CAGGCCATGAGGAAGGCCCTGACCCTGAGGTATGCCCTGCTGCCCCACCTGTATACCCTGTTCCACCAGGCCCAT
GTGGCTGGGGAGACTGTGGCCAGGCCCCTGTTCCTGGAGTTCCCCAAGGACAGCAGCACCTGGACTGTGGATCAT
CAGCTGCTGTGGGGGGAGGCCCTGCTGATCACCCCTGTGCTGCAGGCTGGCAAGGCTGAGGTCACTGGCTACTTC
CCTCTGGGCACCTGGTATGACCTGCAGACTGTGCCTGTGGAGGCTCTGGGCAGCCTGCCCCCCCCCCCTGCTGCT
CCCAGGGAGCCTGCCATCCACTCTGAGGGCCAGTGGGTGACCCTGCCTGCTCCCCTGGACACCATCAATGTGCAC
CTGAGGGCTGGCTACATTATCCCCCTGCAGGGCCCAGGGCTGACTACCACTGAGAGCAGACAGCAGCCCATGGCT
CTGGCTGTGGCCCTGACCAAGGGGGGGGAAGCTAGGGGGGAGCTGTTCTGGGATGATGGGGAGAGCCTGGAGGTG
CTGGAGAGGGGGGCCTATACCCAGGTGATCTTCCTGGCTAGGAACAACACCATTGTCAATGAGCTGGTGAGGGTG
ACTTCTGAGGGGGCTGGGCTGCAGCTGCAGAAGGTGACTGTGCTGGGGGTGGCCACTGCTCCCCAGCAGGTGCTG
AGCAATGGGGTGCCTGTGAGCAACTTCACCTACAGCCCTGACACCAAGGTGCTGGACATCTGTGTGTCTCTGCTG
ATGGGGGAGCAGTTCCTGGTGAGCTGGTGCTGAAGATCTAGAGCTGAATTCCTGCAGCCAGGGGGATCAGCCTCT
ACTGTGCCTTCTAGTTGCCAGCCATCTGTTGTTTGCCCCTCCCCCTTGCCTTCCTTGACCCTGGAAGGTGCCACT
CCCACTGTCCTTTCCTAATAAAATGAGGAAATTGCATCACATTGTCTGAGTAGGTGTCATTCTATTCTGGGGGGT
GGGGTGGGGCAGGACAGCAAGGGGGAGGATTGGGAAGACAATAGCAGGCATGCTGGGGATGCAGTGGGCTCTATG
G SEQ ID NO: 14: nucleic acid sequence for GAA8 plus CpG-reduced BGH poly A
ATGGCCTTCCTGTGGCTGCTGTCTTGCTGGGCTCTGCTGGGGACCACCTTTGGCCTGCTGGTCCCCAGGGAGCTG
TCTGGCTCTTCTCCTGTCCTGGAGGAGACCCACCCTGCCCACCAGCAGGGGGCTAGCAGGCCTGGCCCCAGGGAT
GCCCAGGCCCACCCTGGCAGGCCCAGGGCTGTGCCCACCCAGTGTGATGTGCCTCCCAACAGCAGGTTTGACTGT
GCCCCTGACAAGGCCATCACCCAGGAGCAGTGTGAGGCCAGGGGCTGCTGCTATATCCCTGCCAAGCAGGGCCTG
CAGGGGGCTCAGATGGGCCAGCCCTGGTGCTTCTTTCCCCCCTCTTATCCTAGCTATAAGCTGGAGAACCTGAGC
AGCTCTGAGATGGGGTACACTGCCACCCTGACCAGGACCACCCCCACTTTCTTCCCTAAGGACATCCTGACCCTG
AGGCTGGATGTGATGATGGAGACTGAGAATAGGCTGCACTTTACTATCAAGGACCCTGCCAACAGGAGGTATGAG
GTGCCTCTGGAGACCCCCCATGTGCATTCTAGGGCCCCCAGCCCCCTGTACTCTGTGGAGTTCTCTGAGGAGCCC
TTTGGGGTGATTGTGAGGAGACAGCTGGATGGCAGGGTCCTGCTGAACACCACTGTGGCTCCCCTGTTTTTTGCT
GACCAGTTCCTGCAGCTGAGCACCAGCCTGCCCAGCCAGTACATCACTGGGCTGGCTGAGCACCTGAGCCCCCTG
ATGCTGAGCACCAGCTGGACCAGGATCACCCTGTGGAACAGGGATCTGGCTCCTACCCCTGGGGCCAACCTGTAT
GGCTCTCACCCCTTTTACCTGGCCCTGGAGGATGGGGGCTCTGCCCATGGGGTGTTCCTGCTGAACAGCAATGCT
ATGGATGTGGTGCTGCAGCCCAGCCCTGCCCTGAGCTGGAGGTCTACTGGGGGCATCCTGGATGTGTACATCTTT
CTGGGGCCTGAGCCCAAGTCTGTGGTGCAGCAGTACCTGGATGTGGTGGGCTATCCTTTTATGCCCCCCTATTGG
GGCCTGGGCTTCCACCTGTGCAGGTGGGGCTACAGCAGCACTGCCATCACCAGACAGGTGGTGGAGAACATGACC
AGGGCCCACTTCCCCCTGGATGTGCAGTGGAATGACCTGGACTACATGGACAGCAGGAGGGACTTCACCTTTAAC
AAGGATGGCTTTAGGGACTTCCCTGCCATGGTGCAGGAGCTGCATCAGGGGGGCAGGAGGTACATGATGATTGTG
GACCCAGCCATCAGCAGCTCTGGGCCTGCTGGGTCTTACAGGCCCTATGATGAGGGCCTGAGGAGGGGGGTGTTC
ATCACCAATGAGACTGGCCAGCCCCTGATTGGCAAGGTGTGGCCTGGGAGCACTGCCTTCCCTGATTTTACCAAC
CCCACTGCCCTGGCCTGGTGGGAGGATATGGTGGCTGAGTTTCATGACCAGGTGCCCTTTGATGGCATGTGGATT
GACATGAATGAGCCCAGCAATTTCATCAGGGGCTCTGAGGATGGCTGCCCCAACAATGAGCTGGAGAATCCTCCC
TATGTGCCTGGGGTGGTGGGGGGCACCCTGCAGGCTGCCACCATCTGTGCCTCTAGCCACCAGTTCCTGAGCACC
CACTATAACCTGCATAACCTGTATGGCCTGACTGAGGCCATTGCCAGCCATAGAGCCCTGGTGAAGGCCAGAGGG
ACCAGGCCCTTTGTGATCTCTAGGAGCACCTTTGCTGGCCATGGCAGGTATGCTGGCCACTGGACTGGGGATGTG
TGGAGCTCTTGGGAGCAGCTGGCCAGCTCTGTGCCAGAGATCCTGCAGTTCAACCTGCTGGGGGTGCCTCTGGTG
GGGGCTGATGTGTGTGGCTTCCTGGGCAATACCTCTGAAGAGCTGTGTGTGAGGTGGACTCAGCTGGGGGCCTTC
TATCCCTTCATGAGGAACCACAACAGCCTGCTGTCTCTGCCCCAGGAGCCCTACAGCTTCTCTGAGCCTGCTCAG
CAGGCTATGAGGAAGGCCCTGACCCTGAGGTATGCCCTGCTGCCCCATCTGTACACCCTGTTCCACCAGGCCCAT
GTGGCTGGGGAGACTGTGGCCAGGCCCCTGTTTCTGGAGTTTCCCAAGGACAGCAGCACCTGGACTGTGGACCAT
CAGCTGCTGTGGGGGGAGGCTCTGCTGATTACCCCTGTGCTGCAGGCTGGCAAGGCTGAGGTGACTGGGTACTTC
CCCCTGGGGACTTGGTATGACCTGCAGACTGTGCCTGTGGAAGCTCTGGGCAGCCTGCCCCCACCCCCTGCTGCC
CCTAGGGAGCCTGCCATCCACTCTGAGGGCCAGTGGGTGACCCTGCCTGCCCCTCTGGACACCATCAATGTGCAC
CTGAGGGCTGGCTATATCATCCCCCTGCAGGGCCCTGGGCTGACCACCACTGAGAGCAGGCAGCAGCCCATGGCC
CTGGCTGTGGCCCTGACTAAGGGGGGGGAGGCCAGGGGGGAGCTGTTCTGGGATGATGGGGAGAGCCTGGAGGTG
CTGGAGAGAGGGGCCTACACCCAGGTGATCTTTCTGGCCAGGAACAACACCATTGTGAATGAGCTGGTGAGGGTG
ACTTCTGAGGGGGCTGGCCTGCAGCTGCAGAAGGTGACTGTGCTGGGGGTGGCCACTGCCCCCCAGCAGGTGCTG
AGCAATGGGGTGCCTGTGTCTAACTTCACCTACAGCCCTGATACTAAGGTGCTGGATATCTGTGTGAGCCTGCTG
ATGGGGGAGCAGTTTCTGGTGAGCTGGTGCTGAAGATCTAGAGCTGAATTCCTGCAGCCAGGGGGATCAGCCTCT
ACTGTGCCTTCTAGTTGCCAGCCATCTGTTGTTTGCCCCTCCCCCTTGCCTTCCTTGACCCTGGAAGGTGCCACT
CCCACTGTCCTTTCCTAATAAAATGAGGAAATTGCATCACATTGTCTGAGTAGGTGTCATTCTATTCTGGGGGGT
GGGGTGGGGCAGGACAGCAAGGGGGAGGATTGGGAAGACAATAGCAGGCATGCTGGGGATGCAGTGGGCTCTATG
G -continued SEQ ID NO: 15: nucleic acid sequence for GAA13 plus CpG-reduced BGH poly A
ATGGCCTTTCTGTGGCTGCTGTCCTGCTGGGCCCTGCTGGGGACCACCTTTGGCCTGCTGGTGCCCAGGGAGCTG
TCTGGGAGCAGCCCAGTGCTGGAGGAGACCCACCCTGCCCACCAGCAGGGGGCCAGCAGGCCTGGCCCTAGGGAT
GCCCAGGCCCACCCTGGCAGGCCCAGGGCTGTGCCTACCCAGTGTGATGTGCCACCCAATTCTAGGTTTGACTGT
GCTCCTGACAAGGCCATCACTCAGGAGCAGTGTGAAGCTAGGGGGTGCTGCTACATCCCAGCCAAGCAGGGCCTG
CAGGGGGCCCAGATGGGCCAGCCCTGGTGCTTCTTCCCCCCCAGCTACCCTAGCTACAAGCTGGAGAATCTGAGC
AGCTCTGAGATGGGCTACACTGCTACCCTGACCAGGACCACTCCTACCTTCTTCCCCAAGGACATCCTGACTCTG
AGGCTGGATGTCATGATGGAGACTGAAAATAGGCTGCACTTCACCATCAAGGACCCTGCCAATAGGAGGTATGAG
GTGCCTCTGGAGACCCCCCATGTGCATAGCAGGGCTCCCAGCCCCCTGTATTCTGTGGAGTTCTCTGAGGAGCCC
TTTGGGGTCATTGTGAGGAGACAGCTGGATGGGAGGGTGCTGCTGAACACTACTGTGGCTCCCCTGTTCTTTGCT
GACCAGTTCCTGCAGCTGTCTACCAGCCTGCCCAGCCAGTACATCACTGGGCTGGCTGAGCATCTGAGCCCCCTG
ATGCTGAGCACCAGCTGGACCAGGATCACTCTGTGGAACAGGGATCTGGCCCCCACTCCTGGGGCCAACCTGTAT
GGGAGCCATCCCTTCTACCTGGCCCTGGAGGATGGGGGCTCTGCCCATGGGGTGTTCCTGCTGAACAGCAATGCC
ATGGATGTGGTGCTGCAGCCTAGCCCTGCCCTGAGCTGGAGGAGCACTGGGGGCATCCTGGATGTCTACATCTTC
CTGGGGCCTGAGCCCAAGTCTGTGGTGCAGCAGTATCTGGATGTGGTGGGGTATCCCTTCATGCCCCCCTACTGG
GGCCTGGGCTTTCACCTGTGCAGGTGGGGCTACAGCAGCACTGCCATCACCAGGCAGGTGGTGGAGAACATGACC
AGGGCCCACTTCCCTCTGGATGTGCAGTGGAATGACCTGGACTATATGGATTCTAGGAGAGACTTTACTTTTAAC
AAGGATGGCTTCAGGGATTTCCCTGCCATGGTGCAGGAGCTGCACCAGGGGGGCAGGAGGTACATGATGATTGTG
GACCCTGCTATTAGCAGCTCTGGCCCTGCTGGGTCTTACAGGCCTTATGATGAGGGCCTGAGGAGGGGGGTGTTC
ATCACCAATGAGACTGGCCAGCCCCTGATTGGCAAGGTGTGGCCTGGCAGCACTGCCTTCCCTGACTTCACCAAC
CCCACTGCCCTGGCCTGGTGGGAGGACATGGTGGCTGAGTTCCATGACCAGGTGCCCTTTGATGGGATGTGGATT
GACATGAATGAGCCCTCTAACTTCATCAGGGGGTCTGAGGATGGCTGCCCCAACAATGAGCTGGAGAACCCCCCC
TATGTGCCTGGGGTGGTGGGGGGCACTCTGCAGGCTGCCACTATCTGTGCTTCTTCTCACCAGTTTCTGAGCACC
CACTATAATCTGCACAACCTGTATGGCCTGACTGAGGCCATTGCCAGCCATAGGGCCCTGGTGAAGGCCAGGGGC
ACCAGGCCCTTTGTGATCAGCAGGTCTACCTTTGCTGGCCATGGCAGGTATGCTGGCCACTGGACTGGGGATGTG
TGGTCTTCTTGGGAGCAGCTGGCCAGCTCTGTGCCTGAGATCCTGCAGTTCAACCTGCTGGGGGTGCCTCTGGTG
GGGGCTGATGTGTGTGGCTTTCTGGGCAACACCTCTGAGGAGCTGTGTGTGAGGTGGACCCAGCTGGGGGCCTTT
TACCCCTTCATGAGGAACCACAATAGCCTGCTGAGCCTGCCCCAGGAGCCTTACTCTTTCTCTGAGCCTGCCCAG
CAGGCCATGAGGAAGGCCCTGACTCTGAGGTATGCCCTGCTGCCCCATCTGTATACCCTGTTTCACCAGGCCCAT
GTGGCTGGGGAGACTGTGGCTAGGCCTCTGTTTCTGGAGTTCCCTAAGGACTCTAGCACCTGGACTGTGGACCAC
CAGCTGCTGTGGGGGGAGGCCCTGCTGATCACCCCTGTGCTGCAGGCTGGCAAGGCTGAGGTGACTGGCTACTTC
CCCCTGGGCACCTGGTATGACCTGCAGACTGTGCCTGTGGAGGCCCTGGGGAGCCTGCCTCCCCCCCCTGCTGCC
CCCAGGGAGCCTGCCATTCATTCTGAGGGCCAGTGGGTGACCCTGCCTGCCCCTCTGGACACCATCAATGTGCAC
CTGAGGGCTGGGTACATCATCCCCCTGCAGGGCCCTGGCCTGACCACCACTGAGAGCAGGCAGCAGCCCATGGCC
CTGGCTGTGGCTCTGACCAAGGGGGGGGAGGCCAGGGGGGAGCTGTTCTGGGATGATGGGGAGTCTCTGGAGGTG
CTGGAGAGGGGGGCCTACACCCAGGTGATCTTTCTGGCCAGGAACAATACTATTGTGAATGAGCTGGTGAGGGTG
ACCTCTGAGGGGGCTGGCCTGCAGCTGCAGAAGGTGACTGTGCTGGGGGTGGCCACTGCCCCCCAGCAGGTCCTG
AGCAATGGGGTGCCTGTGAGCAACTTCACCTACTCTCCTGACACCAAGGTGCTGGACATTTGTGTGTCTCTGCTG
ATGGGGGAGCAGTTCCTGGTGAGCTGGTGCTGAAGATCTAGAGCTGAATTCCTGCAGCCAGGGGGATCAGCCTCT
ACTGTGCCTTCTAGTTGCCAGCCATCTGTTGTTTGCCCCTCCCCCTTGCCTTCCTTGACCCTGGAAGGTGCCACT
CCCACTGTCCTTTCCTAATAAAATGAGGAAATTGCATCACATTGTCTGAGTAGGTGTCATTCTATTCTGGGGGGT
GGGGTGGGGCAGGACAGCAAGGGGGAGGATTGGGAAGACAATAGCAGGCATGCTGGGGATGCAGTGGGCTCTATG
G >pAAV-ApoE/hAAT.fixUTR.GAA13.BGH (SEQ ID NO: 16)
CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCTAG
TAGGCTCAGAGGCACACAGGAGTTTCTGGGCTCACCCTGCCCCCTTCCAACCCCTCAGTTCCCATCCTCCAGCAG
CTGTTTGTGTGCTGCCTCTGAAGTCCACACTGAACAAACTTCAGCCTACTCATGTCCCTAAAATGGGCAAACATT
GCAAGCAGCAAACAGCAAACACACAGCCCTCCCTGCCTGCTGACCTTGGAGCTGGGGCAGAGGTCAGAGACCTCT
CTGGGCCCATGCCACCTCCAACATCCACTCGACCCCTTGGAATTTCGGTGGAGAGGAGCAGAGGTTGTCCTGGCG
TGGTTTAGGTAGTGTGAGAGGGGTACCCGGGGATCTTGCTACCAGTGGAACAGCCACTAAGGATTCTGCAGTGAG
AGCAGAGGGCCAGCTAAGTGGTACTCTCCCAGAGACTGTCTGACTCACGCCACCCCCTCCACCTTGGACACAGGA
CGCTGTGGTTTCTGAGCCAGGTACAATGACTCCTTTCGGTAAGTGCAGTGGAAGCTGTACACTGCCCAGGCAAAG
CGTCCGGGCAGCGTAGGCGGGCGACTCAGATCCCAGCCAGTGGACTTAGCCCCTGTTTGCTCCTCCGATAACTGG
GGTGACCTTGGTTAATATTCACCAGCAGCCTCCCCCGTTGCCCCTCTGGATCCACTGCTTAAATACGGACGAGGA
CAGGGCCCTGTCTCCTCAGCTTCAGGCACCACCACTGACCTGGGACAGTGAATACCACTTTCACAATCTGCTAGC
GTTTAAACGATCCTGAGAACTTCAGGGTGAGTCTATGGGACCCTTGATGTTTTCTTTCCCCTTCTTTTCTATGGT
TAAGTTCATGTCATAGGAAGGGGAGAAGTAACAGGGTACACATATTGACCAAATCAGGGTAATTTTGCATTTGTA
ATTTTAAAAAATGCTTTCTTCTTTTAATATACTTTTTTGTTTATCTTATTTCTAATACTTTCCCTAATCTCTTTC
TTTCAGGGCAATAATGATACAATGTATCATGCCTCTTTGCACCATTCTAAAGAATAACAGTGATAATTTCTGGGT
TAAGGCAATAGCAATATTTCTGCATATAAATATTTCTGCATATAAATTGTAACTGATGTAAGAGGTTTCATATTG
CTAATAGCAGCTACAATCCAGCTACCATTCTGCTTTTATTTTCTGGTTGGGATAAGGCTGGATTATTCTGAGTCC
AAGCTAGGCCCTTTTGCTAATCTTGTTCATACCTCTTATCTTCCTCCCACAGCTCCTGGGCAACCTGCTGGTCTC
TCTGCTGGCCCATCACTTTGGCAAAGCACGCGTGCCACCATGGCCTTTCTGTGGCTGCTGTCCTGCTGGGCCCTG
CTGGGGACCACCTTTGGCCTGCTGGTGCCCAGGGAGCTGTCTGGGAGCAGCCCAGTGCTGGAGGAGACCCACCCT
GCCCACCAGCAGGGGGCCAGCAGGCCTGGCCCTAGGGATGCCCAGGCCCACCCTGGCAGGCCCAGGGCTGTGCCT
ACCCAGTGTGATGTGCCACCCAATTCTAGGTTTGACTGTGCTCCTGACAAGGCCATCACTCAGGAGCAGTGTGAA
GCTAGGGGGTGCTGCTACATCCCAGCCAAGCAGGGCCTGCAGGGGGCCCAGATGGGCCAGCCCTGGTGCTTCTTC
CCCCCCAGCTACCCTAGCTACAAGCTGGAGAATCTGAGCAGCTCTGAGATGGGCTACACTGCTACCCTGACCAGG
ACCACTCCTACCTTCTTCCCCAAGGACATCCTGACTCTGAGGCTGGATGTCATGATGGAGACTGAAAATAGGCTG
CACTTCACCATCAAGGACCCTGCCAATAGGAGGTATGAGGTGCCTCTGGAGACCCCCCATGTGCATAGCAGGGCT
CCCAGCCCCCTGTATTCTGTGGAGTTCTCTGAGGAGCCCTTTGGGGTCATTGTGAGGAGACAGCTGGATGGGAGG
GTGCTGCTGAACACTACTGTGGCTCCCCTGTTCTTTGCTGACCAGTTCCTGCAGCTGTCTACCAGCCTGCCCAGC
CAGTACATCACTGGGCTGGCTGAGCATCTGAGCCCCCTGATGCTGAGCACCAGCTGGACCAGGATCACTCTGTGG
AACAGGGATCTGGCCCCCACTCCTGGGGCCAACCTGTATGGGAGCCATCCCTTCTACCTGGCCCTGGAGGATGGG
GGCTCTGCCCATGGGGTGTTCCTGCTGAACAGCAATGCCATGGATGTGGTGCTGCAGCCTAGCCCTGCCCTGAGC
TGGAGGAGCACTGGGGGCATCCTGGATGTCTACATCTTCCTGGGGCCTGAGCCCAAGTCTGTGGTGCAGCAGTAT
CTGGATGTGGTGGGGTATCCCTTCATGCCCCCCTACTGGGGCCTGGGCTTTCACCTGTGCAGGTGGGGCTACAGC
AGCACTGCCATCACCAGGCAGGTGGTGGAGAACATGACCAGGGCCCACTTCCCTCTGGATGTGCAGTGGAATGAC -continued CTGGACTATATGGATTCTAGGAGAGACTTTACTTTTAACAAGGATGGCTTCAGGGATTTCCCTGCCATGGTGCAG
GAGCTGCACCAGGGGGGCAGGAGGTACATGATGATTGTGGACCCTGCTATTAGCAGCTCTGGCCCTGCTGGGTCT
TACAGGCCTTATGATGAGGGCCTGAGGAGGGGGGTGTTCATCACCAATGAGACTGGCCAGCCCCTGATTGGCAAG
GTGTGGCCTGGCAGCACTGCCTTCCCTGACTTCACCAACCCCACTGCCCTGGCCTGGTGGGAGGACATGGTGGCT
GAGTTCCATGACCAGGTGCCCTTTGATGGGATGTGGATTGACATGAATGAGCCCTCTAACTTCATCAGGGGGTCT
GAGGATGGCTGCCCCAACAATGAGCTGGAGAACCCCCCCTATGTGCCTGGGGTGGTGGGGGGCACTCTGCAGGCT
GCCACTATCTGTGCTTCTTCTCACCAGTTTCTGAGCACCCACTATAATCTGCACAACCTGTATGGCCTGACTGAG
GCCATTGCCAGCCATAGGGCCCTGGTGAAGGCCAGGGGCACCAGGCCCTTTGTGATCAGCAGGTCTACCTTTGCT
GGCCATGGCAGGTATGCTGGCCACTGGACTGGGGATGTGTGGTCTTCTTGGGAGCAGCTGGCCAGCTCTGTGCCT
GAGATCCTGCAGTTCAACCTGCTGGGGGTGCCTCTGGTGGGGGCTGATGTGTGTGGCTTTCTGGGCAACACCTCT
GAGGAGCTGTGTGTGAGGTGGACCCAGCTGGGGGCCTTTTACCCCTTCATGAGGAACCACAATAGCCTGCTGAGC
CTGCCCCAGGAGCCTTACTCTTTCTCTGAGCCTGCCCAGCAGGCCATGAGGAAGGCCCTGACTCTGAGGTATGCC
CTGCTGCCCCATCTGTATACCCTGTTTCACCAGGCCCATGTGGCTGGGGAGACTGTGGCTAGGCCTCTGTTTCTG
GAGTTCCCTAAGGACTCTAGCACCTGGACTGTGGACCACCAGCTGCTGTGGGGGGAGGCCCTGCTGATCACCCCT
GTGCTGCAGGCTGGCAAGGCTGAGGTGACTGGCTACTTCCCCCTGGGCACCTGGTATGACCTGCAGACTGTGCCT
GTGGAGGCCCTGGGGAGCCTGCCTCCCCCCCCTGCTGCCCCCAGGGAGCCTGCCATTCATTCTGAGGGCCAGTGG
GTGACCCTGCCTGCCCCTCTGGACACCATCAATGTGCACCTGAGGGCTGGGTACATCATCCCCCTGCAGGGCCCT
GGCCTGACCACCACTGAGAGCAGGCAGCAGCCCATGGCCCTGGCTGTGGCTCTGACCAAGGGGGGGGAGGCCAGG
GGGGAGCTGTTCTGGGATGATGGGGAGTCTCTGGAGGTGCTGGAGAGGGGGGCCTACACCCAGGTGATCTTTCTG
GCCAGGAACAATACTATTGTGAATGAGCTGGTGAGGGTGACCTCTGAGGGGGGCTGGCCTGCAGCTGCAGAAGGTG
ACTGTGCTGGGGGTGGCCACTGCCCCCCAGCAGGTCCTGAGCAATGGGGTGCCTGTGAGCAACTTCACCTACTCT
CCTGACACCAAGGTGCTGGACATTTGTGTGTCTCTGCTGATGGGGGAGCAGTTCCTGGTGAGCTGGTGCTGAAGA
TCTAGAGCTGAATTCCTGCAGCCAGGGGGATCAGCCTCTACTGTGCCTTCTAGTTGCCAGCCATCTGTTGTTTGC
CCCTCCCCCTTGCCTTCCTTGACCCTGGAAGGTGCCACTCCCACTGTCCTTTCCTAATAAAATGAGGAAATTGCA
TCACATTGTCTGAGTAGGTGTCATTCTATTCTGGGGGGTGGGGTGGGGCAGGACAGCAAGGGGGAGGATTGGGAA
GACAATAGCAGGCATGCTGGGGATGCAGTGGGCTCTATGGCTTCTGAGGCAGAAAGAACCAGCTGGGGCTCGAGA
TCCACTAGGGCCGCAGGAACCCCTAGTGATGGAGTTGGCCACTCCCTCTCTGCGCGCTCGCTCGCTCACTGAGGC
CGGGCGACCAAAGGTCGCCCGACGCCCGGGCTTTGCCCGGGCGGCCTCAGTGAGCGAGCGAGCGCGCAGCTGCCT
GCAGG >pAAV-ApoE/hAAT.GAA13.BGH (SEQ ID NO: 17)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCTAG
TAGGCTCAGAGGCACACAGGAGTTTCTGGGCTCACCCTGCCCCCTTCCAACCCCTCAGTTCCCATCCTCCAGCAG
CTGTTTGTGTGCTGCCTCTGAAGTCCACACTGAACAAACTTCAGCCTACTCATGTCCCTAAAATGGGCAAACATT
GCAAGCAGCAAACAGCAAACACACAGCCCTCCCTGCCTGCTGACCTTGGAGCTGGGGCAGAGGTCAGAGACCTCT
CTGGGCCCATGCCACCTCCAACATCCACTCGACCCCTTGGAATTTCGGTGGAGAGGAGCAGAGGTTGTCCTGGCG
TGGTTTAGGTAGTGTGAGAGGGGTACCCGGGGATCTTGCTACCAGTGGAACAGCCACTAAGGATTCTGCAGTGAG
AGCAGAGGGCCAGCTAAGTGGTACTCTCCCAGAGACTGTCTGACTCACGCCACCCCCTCCACCTTGGACACAGGA
CGCTGTGGTTTCTGAGCCAGGTACAATGACTCCTTTCGGTAAGTGCAGTGGAAGCTGTACACTGCCCAGGCAAAG
CGTCCGGGCAGCGTAGGCGGGCGACTCAGATCCCAGCCAGTGGACTTAGCCCCTGTTTGCTCCTCCGATAACTGG
GGTGACCTTGGTTAATATTCACCAGCAGCCTCCCCCGTTGCCCCTCTGGATCCACTGCTTAAATACGGACGAGGA
CAGGGCCCTGTCTCCTCAGCTTCAGGCACCACCACTGACCTGGGACAGTGAATAGATCCTGAGAACTTCAGGGTG
AGTCTATGGGACCCTTGATGTTTTCTTTCCCCTTCTTTTCTATGGTTAAGTTCATGTCATAGGAAGGGGAGAAGT
AACAGGGTACACATATTGACCAAATCAGGGTAATTTTGCATTTGTAATTTTAAAAAATGCTTTCTTCTTTTAATA
TACTTTTTTGTTTATCTTATTTCTAATACTTTCCCTAATCTCTTTCTTTCAGGGCAATAATGATACAATGTATCA
TGCCTCTTTGCACCATTCTAAAGAATAACAGTGATAATTTCTGGGTTAAGGCAATAGCAATATTTCTGCATATAA
ATATTTCTGCATATAAATTGTAACTGATGTAAGAGGTTTCATATTGCTAATAGCAGCTACAATCCAGCTACCATT
CTGCTTTTATTTTCTGGTTGGGATAAGGCTGGATTATTCTGAGTCCAAGCTAGGCCCTTTTGCTAATCTTGTTCA
TACCTCTTATCTTCCTCCCACAGCTCCTGGGCAACCTGCTGGTCTCTCTGCTGGCCCATCACTTTGGCAAAGCAC
GCGTGCCACCATGGCCTTTCTGTGGCTGCTGTCCTGCTGGGCCCTGCTGGGGACCACCTTTGGCCTGCTGGTGCC
CAGGGAGCTGTCTGGGAGCAGCCCAGTGCTGGAGGAGACCCACCCTGCCCACCAGCAGGGGGCCAGCAGGCCTGG
CCCTAGGGATGCCCAGGCCCACCCTGGCAGGCCCAGGGCTGTGCCTACCCAGTGTGATGTGCCACCCAATTCTAG
GTTTGACTGTGCTCCTGACAAGGCCATCACTCAGGAGCAGTGTGAAGCTAGGGGGTGCTGCTACATCCCAGCCAA
GCAGGGCCTGCAGGGGGCCCAGATGGGCCAGCCCTGGTGCTTCTTCCCCCCCAGCTACCCTAGCTACAAGCTGGA
GAATCTGAGCAGCTCTGAGATGGGCTACACTGCTACCCTGACCAGGACCACTCCTACCTTCTTCCCCAAGGACAT
CCTGACTCTGAGGCTGGATGTCATGATGGAGACTGAAAATAGGCTGCACTTCACCATCAAGGACCCTGCCAATAG
GAGGTATGAGGTGCCTCTGGAGACCCCCCATGTGCATAGCAGGGCTCCCAGCCCCCTGTATTCTGTGGAGTTCTC
TGAGGAGCCCTTTGGGGTCATTGTGAGGAGACAGCTGGATGGGAGGGTGCTGCTGAACACTACTGTGGCTCCCCT
GTTCTTTGCTGACCAGTTCCTGCAGCTGTCTACCAGCCTGCCCAGCCAGTACATCACTGGGCTGGCTGAGCATCT
GAGCCCCCTGATGCTGAGCACCAGCTGGACCAGGATCACTCTGTGGAACAGGGATCTGGCCCCCACTCCTGGGGC
CAACCTGTATGGGAGCCATCCCTTCTACCTGGCCCTGGAGGATGGGGGCTCTGCCCATGGGGTGTTCCTGCTGAA
CAGCAATGCCATGGATGTGGTGCTGCAGCCTAGCCCTGCCCTGAGCTGGAGGAGCACTGGGGGCATCCTGGATGT
CTACATCTTCCTGGGGCCTGAGCCCAAGTCTGTGGTGCAGCAGTATCTGGATGTGGTGGGGTATCCCTTCATGCC
CCCCTACTGGGGCCTGGGCTTTCACCTGTGCAGGTGGGGCTACAGCAGCACTGCCATCACCAGGCAGGTGGTGGA
GAACATGACCAGGGCCCACTTCCCTCTGGATGTGCAGTGGAATGACCTGGACTATATGGATTCTAGGAGAGACTT
TACTTTTAACAAGGATGGCTTCAGGGATTTCCCTGCCATGGTGCAGGAGCTGCACCAGGGGGGCAGGAGGTACAT
GATGATTGTGGACCCTGCTATTAGCAGCTCTGGCCCTGCTGGGTCTTACAGGCCTTATGATGAGGGCCTGAGGAG
GGGGGTGTTCATCACCAATGAGACTGGCCAGCCCCTGATTGGCAAGGTGTGGCCTGGCAGCACTGCCTTCCCTGA
CTTCACCAACCCCACTGCCCTGGCCTGGTGGGAGGACATGGTGGCTGAGTTCCATGACCAGGTGCCCTTTGATGG
GATGTGGATTGACATGAATGAGCCCTCTAACTTCATCAGGGGGTCTGAGGATGGCTGCCCCAACAATGAGCTGGA
GAACCCCCCCTATGTGCCTGGGGTGGTGGGGGGCACTCTGCAGGCTGCCACTATCTGTGCTTCTTCTCACCAGTT
TCTGAGCACCCACTATAATCTGCACAACCTGTATGGCCTGACTGAGGCCATTGCCAGCCATAGGGCCCTGGTGAA
GGCCAGGGGCACCAGGCCCTTTGTGATCAGCAGGTCTACCTTTGCTGGCCATGGCAGGTATGCTGGCCACTGGAC
TGGGGATGTGTGGTCTTCTTGGGAGCAGCTGGCCAGCTCTGTGCCTGAGATCCTGCAGTTCAACCTGCTGGGGGT
GCCTCTGGTGGGGGCTGATGTGTGTGGCTTTCTGGGCAACACCTCTGAGGAGCTGTGTGTGAGGTGGACCCAGCT
GGGGGCCTTTTACCCCTTCATGAGGAACCACAATAGCCTGCTGAGCCTGCCCCAGGAGCCTTACTCTTTCTCTGA
GCCTGCCCAGCAGGCCATGAGGAAGGCCCTGACTCTGAGGTATGCCCTGCTGCCCCATCTGTATACCCTGTTTCA
CCAGGCCCATGTGGCTGGGGAGACTGTGGCTAGGCCTCTGTTTCTGGAGTTCCCTAAGGACTCTAGCACCTGGAC
TGTGGACCACCAGCTGCTGTGGGGGGAGGCCCTGCTGATCACCCCTGTGCTGCAGGCTGGCAAGGCTGAGGTGAC

-continued

TGGCTACTTCCCCCTGGGCACCTGGTATGACCTGCAGACTGTGCCTGTGGAGGCCCTGGGGAGCCTGCCTCCCCC
CCCTGCTGCCCCCAGGGAGCCTGCCATTCATTCTGAGGGCCAGTGGGTGACCCTGCCTGCCCCTCTGGACACCAT
CAATGTGCACCTGAGGGCTGGGTACATCATCCCCCTGCAGGGCCCTGGCCTGACCACCACTGAGAGCAGGCAGCA
GCCCATGGCCCTGGCTGTGGCTCTGACCAAGGGGGGGGAGGCCAGGGGGGAGCTGTTCTGGGATGATGGGGAGTC
TCTGGAGGTGCTGGAGAGGGGGGCCTACACCCAGGTGATCTTTCTGGCCAGGAACAATACTATTGTGAATGAGCT
GGTGAGGGTGACCTCTGAGGGGGCTGGCCTGCAGCTGCAGAAGGTGACTGTGCTGGGGGTGGCCACTGCCCCCCA
GCAGGTCCTGAGCAATGGGGTGCCTGTGAGCAACTTCACCTACTCTCCTGACACCAAGGTGCTGGACATTTGTGT
GTCTCTGCTGATGGGGGAGCAGTTCCTGGTGAGCTGGTGCTGAAGATCTAGAGCTGAATTCCTGCAGCCAGGGGG
ATCAGCCTCTACTGTGCCTTCTAGTTGCCAGCCATCTGTTGTTTGCCCCTCCCCCTTGCCTTCCTTGACCCTGGA
AGGTGCCACTCCCACTGTCCTTTCCTAATAAAATGAGGAAATTGCATCACATTGTCTGAGTAGGTGTCATTCTAT
TCTGGGGGGTGGGGTGGGGCAGGACAGCAAGGGGGAGGATTGGGAAGACAATAGCAGGCATGCTGGGGATGCAGT
GGGCTCTATGGCTTCTGAGGCAGAAAGAACCAGCTGGGGCTCGAGATCCACTAGGGCCGCAGGAACCCCTAGTGA
TGGAGTTGGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGG

>pAAV-ApoE/hAAT.GAA7.BGH (SEQ ID NO: 18)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCTAG
TAGGCTCAGAGGCACACAGGAGTTTCTGGGCTCACCCTGCCCCCTTCCAACCCCTCAGTTCCCATCCTCCAGCAG
CTGTTTGTGTGCTGCCTCTGAAGTCCACACTGAACAAACTTCAGCCTACTCATGTCCCTAAAATGGGCAAACATT
GCAAGCAGCAAACAGCAAACACACAGCCCTCCCTGCCTGCTGACCTTGGAGCTGGGGCAGAGGTCAGAGACCTCT
CTGGGCCCATGCCACCTCCAACATCCACTCGACCCCTTGGAATTTCGGTGGAGAGGAGCAGAGGTTGTCCTGGCG
TGGTTTAGGTAGTGTGAGAGGGGTACCCGGGGATCTTGCTACCAGTGGAACAGCCACTAAGGATTCTGCAGTGAG
AGCAGAGGGCCAGCTAAGTGGTACTCTCCCAGAGACTGTCTGACTCACGCCACCCCCTCCACCTTGGACACAGGA
CGCTGTGGTTTCTGAGCCAGGTACAATGACTCCTTTCGGTAAGTGCAGTGGAAGCTGTACACTGCCCAGGCAAAG
CGTCCGGGCAGCGTAGGCGGGCGACTCAGATCCCAGCCAGTGGACTTAGCCCCTGTTTGCTCCTCCGATAACTGG
GGTGACCTTGGTTAATATTCACCAGCAGCCTCCCCCGTTGCCCCTCTGGATCCACTGCTTAAATACGGACGAGGA
CAGGGCCCTGTCTCCTCAGCTTCAGGCACCACCACTGACCTGGGACAGTGAATAGATCCTGAGAACTTCAGGGTG
AGTCTATGGGACCCTTGATGTTTTCTTTCCCCTTCTTTTCTATGGTTAAGTTCATGTCATAGGAAGGGGAGAAGT
AACAGGGTACACATATTGACCAAATCAGGGTAATTTTGCATTTGTAATTTTAAAAAATGCTTTCTTCTTTTAATA
TACTTTTTTGTTTATCTTATTTCTAATACTTTCCCTAATCTCTTTCTTTCAGGGCAATAATGATACAATGTATCA
TGCCTCTTTGCACCATTCTAAAGAATAACAGTGATAATTTCTGGGTTAAGGCAATAGCAATATTTCTGCATATAA
ATATTTCTGCATATAAATTGTAACTGATGTAAGAGGTTTCATATTGCTAATAGCAGCTACAATCCAGCTACCATT
CTGCTTTTATTTTCTGGTTGGGATAAGGCTGGATTATTCTGAGTCCAAGCTAGGCCCTTTTGCTAATCTTGTTCA
TACCTCTTATCTTCCTCCCACAGCTCCTGGGCAACCTGCTGGTCTCTCTGCTGGCCCATCACTTTGGCAAAGCAC
GCGTGCCACCATGGCTTTCCTGTGGCTGCTGTCTTGTTGGGCTCTGCTGGGCACCACCTTTGGCCTGCTGGTGCC
CAGGGAGCTGTCTGGCAGCAGCCCTGTGCTGGAGGAGACCCACCCTGCTCATCAGCAGGGGGCTAGCAGGCCTGG
CCCCAGGGATGCCCAGGCTCACCCTGGGAGACCCAGGGCTGTGCCCACTCAGTGTGATGTGCCCCCCAACAGCAG
GTTTGACTGTGCTCCTGACAAGGCTATCACCCAGGAGCAGTGTGAGGCCAGGGGGTGCTGCTACATTCCTGCTAA
GCAGGGCCTGCAGGGGGCCCAGATGGGCCAGCCCTGGTGCTTCTTCCCCCCCTCTTATCCCAGCTATAAGCTGGA
GAACCTGAGCAGCTCTGAGATGGGCTACACTGCCACCCTGACCAGGACCACTCCCACCTTCTTTCCCAAGGATAT
TCTGACTCTGAGGCTGGATGTGATGATGGAGACTGAGAACAGGCTGCACTTCACTATCAAGGACCCTGCCAATAG
GAGGTATGAGGTGCCCCTGGAGACTCCTCATGTGCATAGCAGGGCCCCTTCTCCTCTGTATTCTGTGGAGTTCTC
TGAGGAGCCCTTTGGGGTGATTGTGAGGAGGCAGCTGGATGGCAGGGTGCTGCTGAACACCACTGTGGCCCCCCT
GTTCTTTGCTGACCAGTTCCTGCAGCTGAGCACTTCTCTGCCCAGCCAGTACATTACTGGGCTGGCTGAGCATCT
GAGCCCCCTGATGCTGAGCACCTCTTGGACCAGGATCACCCTGTGGAACAGGGACCTGGCCCCCACTCCTGGGGC
TAACCTGTATGGCTCTCACCCCTTTTACCTGGCCCTGGAGGATGGGGGCTCTGCCCATGGGGTGTTTCTGCTGAA
CAGCAATGCTATGGATGTGGTGCTGCAGCCCTCTCCAGCCCTGTCTTGGAGGAGCACTGGGGGCATTCTGGATGT
GTACATTTTCCTGGGGCCTGAACCCAAGTCTGTGGTGCAGCAGTACCTGGATGTGGTGGGCTACCCCTTCATGCC
CCCCTATTGGGGGCTGGGGTTTCACCTGTGCAGGTGGGGCTACAGCAGCACTGCCATCACCAGGCAGGTGGTGGA
GAACATGACCAGGGCCCATTTCCCCCTGGATGTGCAGTGGAATGACCTGGACTACATGGATAGCAGGAGGGATTT
CACCTTCAACAAGGATGGCTTCAGGGACTTTCCTGCCATGGTGCAGGAGCTGCACCAGGGGGGCAGGAGGTATAT
GATGATTGTGGACCCTGCTATCAGCAGCTCTGGCCCTGCTGGCTCTTACAGGCCCTATGATGAGGGCCTGAGGAG
GGGGGTGTTTATCACTAATGAAACTGGCCAGCCTCTGATTGGCAAGGTCTGGCCTGGCTCTACTGCCTTCCCTGA
TTTTACTAACCCCACTGCCCTGGCCTGGTGGGAGGACATGGTGGCTGAGTTCCATGATCAGGTGCCTTTTGATGG
CATGTGGATTGATATGAATGAACCAAGCAACTTCATCAGAGGCTCTGAGGATGGCTGCCCCAACAATGAGCTGGA
GAACCCCCCCTATGTGCCTGGGGTGGTGGGGGGCACTCTGCAGGCTGCCACCATTTGTGCTAGCAGCCACCAGTT
CCTGAGCACCCACTACAATCTGCACAACCTGTATGGCCTGACTGAAGCCATTGCCAGCCATAGGGCCCTGGTGAA
GGCCAGGGGCACTAGGCCTTTTGTGATCAGCAGGAGCACTTTTGCTGGCCATGGCAGGTATGCTGGCCACTGGAC
TGGGGATGTGTGGAGCAGCTGGGAGCAGCTGGCCAGCTCTGTGCCTGAGATTCTGCAGTTTAACCTGCTGGGGGT
GCCCCTGGTGGGGGCTGATGTGTGTGGCTTCCTGGGCAACACCTCTGAGGAGCTGTGTGTGAGGTGGACCCAGCT
GGGGGCCTTTTATCCCTTCATGAGGAACCACAACAGCCTGCTGAGCCTGCCTCAGGAGCCCTACTCTTTCTCTGA
GCCTGCCCAGCAGGCCATGAGGAAGGCCCTGACCCTGAGGTATGCCCTGCTGCCCCACCTGTATACCCTGTTCCA
CCAGGCCCATGTGGCTGGGGAGACTGTGGCCAGGCCCCTGTTCCTGGAGTTCCCCAAGGACAGCAGCACCTGGAC
TGTGGATCATCAGCTGCTGTGGGGGGAGGCCCTGCTGATCACCCCTGTGCTGCAGGCTGGCAAGGCTGAGGTCAC
TGGCTACTTCCCTCTGGGCACCTGGTATGACCTGCAGACTGTGCCTGTGGAGGCTCTGGGCAGCCTGCCCCCCCC
CCCTGCTGCTCCCAGGGAGCCTGCCATCCACTCTGAGGGCCAGTGGGTGACCCTGCCTGCTCCCCTGGACACCAT
CAATGTGCACCTGAGGGCTGGCTACATTATCCCCCTGCAGGGCCCAGGGCTGACTACCACTGAGAGCAGACAGCA
GCCCATGGCTCTGGCTGTGGCCCTGACCAAGGGGGGGGAAGCTAGGGGGGAGCTGTTCTGGGATGATGGGGAGAG
CCTGGAGGTGCTGGAGAGGGGGGCCTATACCCAGGTGATCTTCCTGGCTAGGAACAACACCATTGTCAATGAGCT
GGTGAGGGTGACTTCTGAGGGGGCTGGGCTGCAGCTGCAGAAGGTGACTGTGCTGGGGGTGGCCACTGCTCCCCA
GCAGGTGCTGAGCAATGGGGTGCCTGTGAGCAACTTCACCTACAGCCCTGACACCAAGGTGCTGGACATCTGTGT
GTCTCTGCTGATGGGGGAGCAGTTCCTGGTGAGCTGGTGCTGAAGATCTAGAGCTGAATTCCTGCAGCCAGGGGG
ATCAGCCTCTACTGTGCCTTCTAGTTGCCAGCCATCTGTTGTTTGCCCCTCCCCCTTGCCTTCCTTGACCCTGGA
AGGTGCCACTCCCACTGTCCTTTCCTAATAAAATGAGGAAATTGCATCACATTGTCTGAGTAGGTGTCATTCTAT
TCTGGGGGGTGGGGTGGGGCAGGACAGCAAGGGGGAGGATTGGGAAGACAATAGCAGGCATGCTGGGGATGCAGT
GGGCTCTATGGCTTCTGAGGCAGAAAGAACCAGCTGGGGCTCGAGATCCACTAGGGCCGCAGGAACCCCTAGTGA
TGGAGTTGGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGG

-continued

>pAAV-ApoE/hAAT.GAA8.BGH (SEQ ID NO: 19)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCTAG
TAGGCTCAGAGGCACACAGGAGTTTCTGGGCTCACCCTGCCCCCTTCCAACCCCTCAGTTCCCATCCTCCAGCAG
CTGTTTGTGTGCTGCCTCTGAAGTCCACACTGAACAAACTTCAGCCTACTCATGTCCCTAAAATGGGCAAACATT
GCAAGCAGCAAACAGCAAACACACAGCCCTCCCTGCCTGCTGACCTTGGAGCTGGGGCAGAGGTCAGAGACCTCT
CTGGGCCCATGCCACCTCCAACATCCACTCGACCCCTTGGAATTTCGGTGGAGAGGAGCAGAGGTTGTCCTGGCG
TGGTTTAGGTAGTGTGAGAGGGGTACCCGGGGATCTTGCTACCAGTGGAACAGCCACTAAGGATTCTGCAGTGAG
AGCAGAGGGCCAGCTAAGTGGTACTCTCCCAGAGACTGTCTGACTCACGCCACCCCCTCCACCTTGGACACAGGA
CGCTGTGGTTTCTGAGCCAGGTACAATGACTCCTTTCGGTAAGTGCAGTGGAAGCTGTACACTGCCCAGGCAAAG
CGTCCGGGCAGCGTAGGCGGGCGACTCAGATCCCAGCCAGTGGACTTAGCCCCTGTTTGCTCCTCCGATAACTGG
GGTGACCTTGGTTAATATTCACCAGCAGCCTCCCCCGTTGCCCCTCTGGATCCACTGCTTAAATACGGACGAGGA
CAGGGCCCTGTCTCCTCAGCTTCAGGCACCACCACTGACCTGGGACAGTGAATAGATCCTGAGAACTTCAGGGTG
AGTCTATGGGACCCTTGATGTTTTCTTTCCCCTTCTTTTCTATGGTTAAGTTCATGTCATAGGAAGGGGAGAAGT
AACAGGGTACACATATTGACCAAATCAGGGTAATTTTGCATTTGTAATTTTAAAAAATGCTTTCTTCTTTTAATA
TACTTTTTTGTTTATCTTATTTCTAATACTTTCCCTAATCTCTTTCTTTCAGGGCAATAATGATACAATGTATCA
TGCCTCTTTGCACCATTCTAAAGAATAACAGTGATAATTTCTGGGTTAAGGCAATAGCAATATTTCTGCATATAA
ATATTTCTGCATATAAATTGTAACTGATGTAAGAGGTTTCATATTGCTAATAGCAGCTACAATCCAGCTACCATT
CTGCTTTTATTTTCTGGTTGGGATAAGGCTGGATTATTCTGAGTCCAAGCTAGGCCCTTTTGCTAATCTTGTTCA
TACCTCTTATCTTCCTCCCACAGCTCCTGGGCAACCTGCTGGTCTCTCTGCTGGCCCATCACTTTGGCAAAGCAC
GCGTGCCACCATGGCCTTCCTGTGGCTGCTGTCTTGCTGGGCTCTGCTGGGGACCACCTTTGGCCTGCTGGTCCC
CAGGGAGCTGTCTGGCTCTTCTCCTGTCCTGGAGGAGACCCACCCTGCCCACCAGCAGGGGGCTAGCAGGCCTGG
CCCCAGGGATGCCCAGGCCCACCCTGGCAGGCCCAGGGCTGTGCCCACCCAGTGTGATGTGCCTCCCAACAGCAG
GTTTGACTGTGCCCCTGACAAGGCCATCACCCAGGAGCAGTGTGAGGCCAGGGGCTGCTGCTATATCCCTGCCAA
GCAGGGCCTGCAGGGGGCTCAGATGGGCCAGCCCTGGTGCTTCTTCCCCCCTCTTATCCTAGCTATAAGCTGGA
GAACCTGAGCAGCTCTGAGATGGGGTACACTGCCACCCTGACCAGGACCACCCCCACTTTCTTCCCTAAGGACAT
CCTGACCCTGAGGCTGGATGTGATGATGGAGACTGAGAATAGGCTGCACTTTACTATCAAGGACCCTGCCAACAG
GAGGTATGAGGTGCCTCTGGAGACCCCCCATGTGCATTCTAGGGCCCCCAGCCCCCTGTACTCTGTGGAGTTCTC
TGAGGAGCCCTTTGGGGTGATTGTGAGGAGACAGCTGGATGGCAGGGTCCTGCTGAACACCACTGTGGCTCCCCT
GTTTTTTGCTGACCAGTTCCTGCAGCTGAGCACCAGCCTGCCCAGCCAGTACATCACTGGGCTGGCTGAGCACCT
GAGCCCCCTGATGCTGAGCACCAGCTGGACCAGGATCACCCTGTGGAACAGGGATCTGGCTCCTACCCCTGGGGC
CAACCTGTATGGCTCTCACCCCTTTTACCTGGCCCTGGAGGATGGGGGCTCTGCCCATGGGGTGTTCCTGCTGAA
CAGCAATGCTATGGATGTGGTGCTGCAGCCCAGCCCTGCCCTGAGCTGGAGGTCTACTGGGGGCATCCTGGATGT
GTACATCTTTCTGGGGCCTGAGCCCAAGTCTGTGGTGCAGCAGTACCTGGATGTGGTGGGCTATCCCTTTATGCC
CCCCTATTGGGGCCTGGGCTTCCACCTGTGCAGGTGGGGCTACAGCAGCACTGCCATCACCAGACAGGTGGTGGA
GAACATGACCAGGGCCCACTTCCCCCTGGATGTGCAGTGGAATGACCTGGACTACATGGACAGCAGGAGGGACTT
CACCTTTAACAAGGATGGCTTTAGGGACTTCCCTGCCATGGTGCAGGAGCTGCATCAGGGGGGCAGGAGGTACAT
GATGATTGTGGACCCAGCCATCAGCAGCTCTGGGCCTGCTGGGTCTTACAGGCCCTATGATGAGGGCCTGAGGAG
GGGGGTGTTCATCACCAATGAGACTGGCCAGCCCCTGATTGGCAAGGTGTGGCCTGGGAGCACTGCCTTCCCTGA
TTTTACCAACCCCACTGCCCTGGCCTGGTGGGAGGATATGGTGGCTGAGTTTCATGACCAGGTGCCCTTTGATGG
CATGTGGATTGACATGAATGAGCCCAGCAATTTCATCAGGGGCTCTGAGGATGGCTGCCCCAACAATGAGCTGGA
GAATCCTCCCTATGTGCCTGGGGTGGTGGGGGGCACCCTGCAGGCTGCCACCATCTGTGCCTCTAGCCACCAGTT
CCTGAGCACCCACTATAACCTGCATAACCTGTATGGCCTGACTGAGGCCATTGCCAGCCATAGAGCCCTGGTGAA
GGCCAGAGGGACCAGGCCCTTTGTGATCTCTAGGAGCACCTTTGCTGGCCATGGCAGGTATGCTGGCCACTGGAC
TGGGGATGTGTGGAGCTCTTGGGAGCAGCTGGCCAGCTCTGTGCCAGAGATCCTGCAGTTCAACCTGCTGGGGGT
GCCTCTGGTGGGGGCTGATGTGTGTGGCTTCCTGGGCAATACCTCTGAAGAGCTGTGTGTGAGGTGGACTCAGCT
GGGGGCCTTCTATCCCTTCATGAGGAACCACAACAGCCTGCTGTCTCTGCCCCAGGAGCCCTACAGCTTCTCTGA
GCCTGCTCAGCAGGCTATGAGGAAGGCCCTGACCCTGAGGTATGCCCTGCTGCCCCATCTGTACACCCTGTTCCA
CCAGGCCCATGTGGCTGGGGAGACTGTGGCCAGGCCCCTGTTTCTGGAGTTTCCCAAGGACAGCAGCACCTGGAC
TGTGGACCATCAGCTGCTGTGGGGGGAGGCTCTGCTGATTACCCCTGTGCTGCAGGCTGGCAAGGCTGAGGTGAC
TGGGTACTTCCCCCTGGGGACTTGGTATGACCTGCAGACTGTGCCTGTGGAAGCTCTGGGCAGCCTGCCCCCACC
CCCTGCTGCCCCTAGGGAGCCTGCCATCCACTCTGAGGGCCAGTGGGTGACCCTGCCTGCCCCTCTGGACACCAT
CAATGTGCACCTGAGGGCTGGCTATATCATCCCCCTGCAGGGCCCTGGGCTGACCACCACTGAGAGCAGGCAGCA
GCCCATGGCCCTGGCTGTGGCCCTGACTAAGGGGGGGGAGGCCAGGGGGGAGCTGTTCTGGGATGATGGGGAGAG
CCTGGAGGTGCTGGAGAGAGGGGCCTACACCCAGGTGATCTTTCTGGCCAGGAACAACACCATTGTGAATGAGCT
GGTGAGGGTGACTTCTGAGGGGGCTGGCCTGCAGCTGCAGAAGGTGACTGTGCTGGGGGTGGCCACTGCCCCCCA
GCAGGTGCTGAGCAATGGGGTGCCTGTGTCTAACTTCACCTACAGCCCTGATACTAAGGTGCTGGATATCTGTGT
GAGCCTGCTGATGGGGGAGCAGTTTCTGGTGAGCTGGTGCTGAAGATCTAGAGCTGAATTCCTGCAGCCAGGGGG
ATCAGCCTCTACTGTGCCTTCTAGTTGCCAGCCATCTGTTGTTTGCCCCTCCCCCTTGCCTTCCTTGACCCTGGA
AGGTGCCACTCCCACTGTCCTTTCCTAATAAAATGAGGAAATTGCATCACATTGTCTGAGTAGGTGTCATTCTAT
TCTGGGGGGTGGGGTGGGGCAGGACAGCAAGGGGGAGGATTGGGAAGACAATAGCAGGCATGCTGGGGATGCAGT
GGGCTCTATGGCTTCTGAGGCAGAAAGAACCAGCTGGGGCTCGAGATCCACTAGGGCCGCAGGAACCCCTAGTGA
TGGAGTTGGCCACTCCCTCTCTGCGCGCTCGCTCGCTCACTGAGGCCGGGCGACCAAAGGTCGCCCGACGCCCGG
GCTTTGCCCGGGCGGCCTCAGTGAGCGAGCGAGCGCGCAGCTGCCTGCAGG

>pAAV-ApoE/hAAT.GAA2. wtBGH (SEQ ID NO: 20)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCGCA
GGCTCAGAGGCACACAGGAGTTTCTGGGCTCACCCTGCCCCCTTCCAACCCCTCAGTTCCCATCCTCCAGCAGCT
GTTTGTGTGCTGCCTCTGAAGTCCACACTGAACAAACTTCAGCCTACTCATGTCCCTAAAATGGGCAAACATTGC
AAGCAGCAAACAGCAAACACACAGCCCTCCCTGCCTGCTGACCTTGGAGCTGGGGCAGAGGTCAGAGACCTCTCT
GGGCCCATGCCACCTCCAACATCCACTCGACCCCTTGGAATTTCGGTGGAGAGGAGCAGAGGTTGTCCTGGCGTG
GTTTAGGTAGTGTGAGAGGGGTACCCGGGGATCTTGCTACCAGTGGAACAGCCACTAAGGATTCTGCAGTGAGAG
CAGAGGGCCAGCTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCCCAGGCAAAGCG
TCCGGGCAGCGTAGGCGGGCGACTCAGATCCCAGCCAGTGGACTTAGCCCCTGTTTGCTCCTCCGATAACTGGGG
TGACCTTGGTTAATATTCACCAGCAGCCTCCCCCGTTGCCCCTCTGGATCCACTGCTTAAATACGGACGAGGACA
GGGCCCTGTCTCCTCAGCTTCAGGCACCACCACTGACCTGGGACAGTGAATAGATCCTGAGAACTTCAGGGTGAG
TCTATGGGACCCTTGATGTTTTCTTTCCCCTTCTTTTCTATGGTTAAGTTCATGTCATAGGAAGGGGAGAAGTAA

-continued

CAGGGTACACATATTGACCAAATCAGGGTAATTTTGCATTTGTAATTTTAAAAAATGCTTTCTTCTTTTAATATA
CTTTTTTGTTTATCTTATTTCTAATACTTTCCCTAATCTCTTTCTTTCAGGGCAATAATGATACAATGTATCATG
CCTCTTTGCACCATTCTAAAGAATAACAGTGATAATTTCTGGGTTAAGGCAATAGCAATATTTCTGCATATAAAT
ATTTCTGCATATAAATTGTAACTGATGTAAGAGGTTTCATATTGCTAATAGCAGCTACAATCCAGCTACCATTCT
GCTTTTATTTTCTGGTTGGGATAAGGCTGGATTATTCTGAGTCCAAGCTAGGCCCTTTTGCTAATCTTGTTCATA
CCTCTTATCTTCCTCCCACAGCTCCTGGGCAACCTGCTGGTCTCTCTGCTGGCCCATCACTTTGGCAAAGCACGC
GTGCCACCATGGCTTTCCTGTGGCTGCTGAGCTGCTGGGCTCTGCTGGGCACCACCTTTGGCTGCTGGTGCCTA
GGGAGCTGTCTGGGTCTAGCCCTGTGCTGGAGGAGACTCACCCTGCCCATCAGCAGGGGGCTAGCAGGCCTGGCC
CCAGGGATGCTCAGGCCCACCCTGGCAGGCCCAGGGCTGTGCCCACCCAGTGTGATGTGCCCCCCAACAGCAGGT
TTGACTGTGCCCCTGACAAGGCCATTACCCAGGAGCAGTGTGAGGCCAGGGGCTGCTGCTACATTCCAGCTAAGC
AGGGCCTGCAGGGGGCCCAGATGGGCCAGCCCTGGTGCTTCTTCCCCCCCAGCTATCCTAGCTATAAACTGGAGA
ACCTGAGCAGCTCTGAGATGGGCTATACTGCCACCCTGACTAGGACTACTCCCACCTTTTTTCCTAAGGATATCC
TGACCCTGAGGCTGGATGTGATGATGGAGACTGAGAACAGGCTGCACTTCACTATTAAGGACCCTGCCAATAGGA
GGTATGAAGTGCCTCTGGAGACTCCTCATGTGCACTCTAGGGCCCCCAGCCCCCTGTATTCTGTGGAGTTCTCTG
AGGAGCCCTTTGGGGTGATTGTGAGGAGGCAGCTGGATGGCAGGGTGCTGCTGAACACCACTGTGGCCCCCCTGT
TCTTTGCTGACCAGTTCCTGCAGCTGAGCACCAGCCTGCCCAGCCAGTACATCACTGGGCTGGCTGAGCATCTGA
GCCCTCTGATGCTGAGCACCTCTTGGACCAGGATCACCCTGTGGAATAGGGATCTGGCCCCCACCCCTGGGGCTA
ATCTGTATGGCTCTCATCCCTTTTACCTGGCCCTGGAGGATGGGGGCTCTGCCCATGGGGTGTTTCTGCTGAACA
GCAATGCCATGGATGTGGTGCTGCAGCCCTCTCCTGCCCTGAGCTGGAGGAGCACTGGGGGCATCCTGGATGTGT
ACATCTTCCTGGGCCCTGAGCCCAAGTCTGTGGTCCAGCAGTATCTGGATGTGGTGGGCTACCCCTTTATGCCCC
CCTATTGGGGCCTGGGCTTCCACCTGTGCAGGTGGGGGTATTCTTCTACTGCTATCACCAGGCAGGTGGTGGAGA
ACATGACCAGGGCTCACTTCCCCCTGGATGTGCAGTGGAATGACCTGGACTATATGGACTCTAGGAGGGATTTCA
CCTTCAACAAGGATGGCTTCAGGGACTTCCCTGCTATGGTCCAGGAGCTGCATCAGGGGGGCAGGAGGTACATGA
TGATTGTGGACCCTGCCATCAGCAGCTCTGGCCCTGCTGGCAGCTATAGGCCCTATGATGAGGGCCTGAGGAGGG
GGGTGTTTATCACTAATGAAACTGGGCAGCCCCTGATTGGCAAGGTGTGGCCTGGCTCTACTGCCTTCCCTGACT
TCACCAACCCCACTGCTCTGGCCTGGTGGGAGGACATGGTGGCTGAGTTCCATGACCAGGTGCCTTTTGATGGCA
TGTGGATTGACATGAATGAGCCCAGCAACTTCATCAGGGGCTCTGAGGATGGGTGCCCCAATAATGAGCTGGAGA
ACCCCCCCTATGTGCCTGGGGTGGTGGGGGGCACCCTGCAGGCTGCCACTATTTGTGCCAGCTCTCACCAGTTCC
TGAGCACCCACTACAACCTGCACAATCTGTATGGCCTGACTGAGGCCATTGCCAGCCACAGGGCCCTGGTGAAGG
CCAGGGGCACTAGGCCCTTTGTGATCTCTAGAAGCACCTTTGCTGGCCATGGGAGGTATGCTGGCCACTGGACTG
GGGATGTGTGGAGCTCTTGGGAGCAGCTGGCCAGCTCTGTGCCTGAGATCCTGCAGTTCAACCTGCTGGGGGTGC
CCCTGGTGGGGGCTGATGTGTGTGGCTTCCTGGGCAACACCTCTGAAGAGCTGTGTGTGAGGTGGACCCAGCTGG
GGGCCTTCTACCCTTTCATGAGGAACCACAACAGCCTGCTGAGCCTGCCTCAGGAGCCTTACTCTTTCTCTGAGC
CTGCCCAGCAGGCCATGAGGAAGGCCCTGACCCTGAGGTATGCTCTGCTGCCCCACCTGTACACCCTGTTCCACC
AGGCCCATGTGGCTGGGGAGACTGTGGCCAGGCCCCTGTTCCTGGAGTTTCCTAAGGATAGCAGCACCTGGACTG
TGGACCACCAGCTGCTGTGGGGGGAGGCCCTGCTGATTACCCCTGTGCTGCAGGCTGGCAAGGCTGAGGTGACTG
GCTACTTCCCCCTGGGCACTTGGTATGACCTGCAGACTGTGCCTGTGGAAGCCCTGGGCAGCCTGCCTCCCCCCC
CTGCTGCCCCCAGGGAGCCTGCCATCCACTCTGAGGGCCAGTGGGTGACCCTGCCTGCCCCCCTGGACACCATTA
ATGTGCATCTGAGGGCTGGGTATATTATCCCCCTGCAGGGGCCTGGGCTGACTACCACTGAGAGCAGGCAGCAGC
CTATGGCCCTGGCTGTGGCTCTGACTAAGGGGGGGGAGGCCAGGGGGGAGCTGTTCTGGGATGATGGGGAGAGCC
TGGAGGTGCTGGAGAGGGGGGCCTACACCCAGGTGATTTTCCTGGCCAGGAACAACACCATTGTGAATGAGCTGG
TGAGGGTGACCTCTGAGGGGGCTGGCCTGCAGCTGCAGAAAGTGACTGTGCTGGGGGTGGCCACTGCCCCCCAGC
AGGTGCTGAGCAATGGGGTGCCTGTGAGCAACTTCACCTACAGCCCTGACACCAAGGTGCTGGATATTTGTGTGA
GCCTGCTGATGGGGGAGCAGTTCCTGGTGAGCTGGTGCTGACTCGAGAGATCTACCGGTGAATTCACCGCGGGTT
TAAACTGTGCCTTCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGG
GGTGGGGTGGGGCTAGCTCTAGACTCGAGATCCACTAGGGCCGCAGGAACCCCTAGTGATGGAGTTGGCCACTC
CCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGG

>pAAV-ApoE/hAAT.GAA5.wtBGH (SEQ ID NO: 21)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCGCA
GGCTCAGAGGCACACAGGAGTTTCTGGGCTCACCCTGCCCCCTTCCAACCCCTCAGTTCCCATCCTCCAGCAGCT
GTTTGTGTGCTGCCTCTGAAGTCCACACTGAACAAACTTCAGCCTACTCATGTCCCTAAAATGGGCAAACATTGC
AAGCAGCAAACAGCAAACACACAGCCCTCCCTGCCTGCTGACCTTGGAGCTGGGGCAGAGGTCAGAGACCTCTCT
GGGCCCATGCCACCTCCAACATCCACTCGACCCCTTGGAATTTCGGTGGAGAGGAGCAGAGGTTGTCCTGGCGTG
GTTTAGGTAGTGTGAGAGGGGTACCCGGGGATCTTGCTACCAGTGGAACAGCCACTAAGGATTCTGCAGTGAGAG
CAGAGGGCCAGCTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCCCAGGCAAAGCG
TCCGGGCAGCGTAGGCGGGCGACTCAGATCCCAGCCAGTGGACTTAGCCCCTGTTTGCTCCTCCGATAACTGGGG
TGACCTTGGTTAATATTCACCAGCAGCCTCCCCCGTTGCCCCTCTGGATCCACTGCTTAAATACGGACGAGGACA
GGGCCCTGTCTCCTCAGCTTCAGGCACCACCACTGACCTGGGACAGTGAATAGATCCTGAGAACTTCAGGGTGAG
TCTATGGGACCCTTGATGTTTTCTTTCCCCTTCTTTTCTATGGTTAAGTTCATGTCATAGGAAGGGGAGAAGTAA
CAGGGTACACATATTGACCAAATCAGGGTAATTTTGCATTTGTAATTTTAAAAAATGCTTTCTTCTTTTAATATA
CTTTTTTGTTTATCTTATTTCTAATACTTTCCCTAATCTCTTTCTTTCAGGGCAATAATGATACAATGTATCATG
CCTCTTTGCACCATTCTAAAGAATAACAGTGATAATTTCTGGGTTAAGGCAATAGCAATATTTCTGCATATAAAT
ATTTCTGCATATAAATTGTAACTGATGTAAGAGGTTTCATATTGCTAATAGCAGCTACAATCCAGCTACCATTCT
GCTTTTATTTTCTGGTTGGGATAAGGCTGGATTATTCTGAGTCCAAGCTAGGCCCTTTTGCTAATCTTGTTCATA
CCTCTTATCTTCCTCCCACAGCTCCTGGGCAACCTGCTGGTCTCTCTGCTGGCCCATCACTTTGGCAAAGCACGC
GTGCCACCATGGCTTTCCTGTGGCTGCTGTCTTGCTGGGCCCTGCTGGGGACTACCTTTGGCCTGCTGGTGCCCA
GGGAACTGTCTGGCTCTAGCCCAGTGCTGGAGGAGACCCACCCTGCCCACCAGCAGGGGGCTTCTAGGCCTGGCC
CCAGGGATGCCCAGGCCCACCCTGGCAGGCCAAGGGCTGTGCCCACCCAGTGTGATGTGCCCCCCAACTCTAGAT
TTGATTGTGCCCCTGATAAGGCCATCACCCAGGAGCAGTGTGAGGCTAGGGGCTGCTGCTACATCCCTGCTAAGC
AGGGCCTGCAGGGGGCTCAGATGGGCCAGCCCTGGTGCTTCTTCCCCCCCAGCTATCCCTCTTACAAGCTGGAGA
ATCTGAGCAGCTCTGAGATGGGCTACACTGCCACCCTGACCAGGACTACTCCCACCTTCTTCCCCAAGGACATCC
TGACCCTGAGGCTGGATGTGATGATGGAGACTGAGAACAGGCTGCATTTCACCATCAAGGATCCTGCCAACAGGA
GGTATGAGGTGCCTCTGGAGACCCCCCATGTGCACAGCAGGGCTCCTTCTCCCCTGTACTCTGTGGAGTTCTCTG
AGGAACCCTTTGGGGTGATTGTGAGGAGGCAGCTGGATGGCAGGGTCCTGCTGAACACCACTGTGGCCCCCCTGT
TCTTTGCTGATCAGTTCCTGCAGCTGTCCACTTCTCTGCCTAGCCAGTACATCACTGGGCTGGCTGAGCACCTGA

-continued

GCCCTCTGATGCTGAGCACCTCTTGGACTAGGATCACCCTGTGGAACAGGGACCTGGCCCCCACCCCTGGGGCCA
ACCTGTATGGCAGCCACCCCTTCTATCTGGCCCTGGAGGATGGGGGCTCTGCCCATGGGGTGTTCCTGCTGAATA
GCAATGCTATGGATGTGGTGCTGCAGCCCAGCCCTGCCCTGTCTTGGAGGAGCACTGGGGGCATCCTGGATGTGT
ACATTTTCCTGGGGCCTGAGCCCAAGTCTGTGGTGCAGCAGTACCTGGATGTGGTGGGCTACCCCTTCATGCCTC
CCTACTGGGGCCTGGGCTTCCACCTGTGCAGGTGGGGCTACAGCTCTACTGCCATCACCAGGCAGGTGGTGGAGA
ATATGACCAGGGCCCACTTCCCCCTGGATGTGCAGTGGAATGACCTGGACTACATGGACTCTAGGAGGGACTTCA
CCTTCAATAAGGATGGCTTCAGAGACTTCCCTGCCATGGTGCAGGAGCTGCATCAGGGGGGCAGGAGGTACATGA
TGATTGTGGACCCTGCCATCAGCTCTTCTGGCCCTGCTGGCTCTTACAGGCCCTATGATGAGGGCCTGAGGAGGG
GGGTGTTCATCACCAATGAGACTGGGCAGCCCCTGATTGGGAAGGTGTGGCCTGGCTCTACTGCCTTCCCTGACT
TCACCAATCCTACTGCCCTGGCCTGGTGGGAGGACATGGTGGCTGAGTTCCATGACCAGGTGCCCTTTGATGGCA
TGTGGATTGACATGAATGAGCCCTCTAATTTCATCAGGGGCTCTGAGGATGGCTGCCCCAACAATGAGCTGGAGA
ACCCCCCCTATGTGCCTGGGGTGGTGGGGGGCACCCTGCAGGCTGCCACCATCTGTGCTAGCTCTCACCAGTTCC
TGAGCACCCACTACAATCTGCATAACCTGTATGGCCTGACTGAGGCCATTGCCAGCCACAGGGCCCTGGTGAAGG
CTAGGGGCACCAGGCCCTTTGTGATTTCTAGGAGCACTTTTGCTGGCCATGGCAGGTATGCTGGGCACTGGACTG
GGGATGTGTGGTCTAGCTGGGAGCAGCTGGCTTCTTCTGTGCCTGAGATCCTGCAGTTCAACCTGCTGGGGGTGC
CTCTGGTGGGGGCTGATGTGTGTGGGTTCCTGGGCAACACTTCTGAGGAGCTGTGTGTGAGGTGGACCCAGCTGG
GGGCCTTCTACCCTTTCATGAGGAACCACAACAGCCTGCTGAGCCTGCCCCAGGAGCCCTACAGCTTCTCTGAGC
CTGCCCAGCAGGCCATGAGGAAGGCCCTGACCCTGAGGTATGCCCTGCTGCCCCACCTGTACACCCTGTTCCACC
AGGCCCATGTGGCTGGGGAGACTGTGGCTAGGCCTCTGTTCCTGGAGTTCCCCAAGGACTCTAGCACCIGGACTG
TGGACCACCAGCTGCTGTGGGGGGAGGCCCTGCTGATCACTCCTGTGCTGCAGGCTGGGAAGGCTGAGGTGACTG
GCTATTTCCCCCTGGGCACCTGGTATGACCTGCAGACTGTGCCTGTGGAGGCCCTGGGGAGCCTGCCCCCCCCCC
CTGCTGCCCCCAGGGAGCCTGCCATCCACTCTGAGGGCCAGTGGGTGACCCTGCCTGCCCCTCTGGATACCATCA
ATGTGCACCTGAGGGCTGGCTACATCATTCCCCTGCAGGGCCCTGGCCTGACCACTACTGAGTCTAGGCAGCAGC
CCATGGCCCTGGCTGTGGCCCTGACCAAGGGGGGGGAGGCTAGGGGGGAGCTGTTTTGGGATGATGGGGAGAGCC
TGGAGGTGCTGGAGAGGGGGGCCTACACTCAGGTGATCTTCCTGGCCAGGAACAATACCATTGTGAATGAGCTGG
TGAGGGTGACCTCTGAGGGGGCTGGCCTGCAGCTGCAGAAGGTGACTGTGCTGGGGGTGGCCACTGCCCCCCAGC
AGGTGCTGAGCAATGGGGTGCCTGTGAGCAACTTCACCTATAGCCCTGATACCAAGGTGCTGGATATTTGTGTGA
GCCTGCTGATGGGGGAGCAGTTCCTGGTGAGCTGGTGCTGACTCGAGAGATCTACCGGTGAATTCACCGCGGGTT
TAAACTGTGCCTTCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGG
GGTGGGGTGGGGCTAGCTCTAGACTCGAGATCCACTAGGGCCGCAGGAACCCCTAGTGATGGAGTTGGCCACTC
CCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGG

>pAAV-ApoE/hAAT.GAA7.wtBGH (SEQ ID NO: 22)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCGCA
GGCTCAGAGGCACACAGGAGTTTCTGGGCTCACCCTGCCCCCTTCCAACCCCTCAGTTCCCATCCTCCAGCAGCT
GTTTGTGTGCTGCCTCTGAAGTCCACACTGAACAAACTTCAGCCTACTCATGTCCCTAAAATGGGCAAACATTGC
AAGCAGCAAACAGCAAACACACAGCCCTCCCTGCCTGCTGACCTTGGAGCTGGGGCAGAGGTCAGAGACCTCTCT
GGGCCCATGCCACCTCCAACATCCACTCGACCCCTTGGAATTTCGGTGGAGAGGAGCAGAGGTTGTCCTGGCGTG
GTTTAGGTAGTGTGAGAGGGGTACCCGGGGATCTTGCTACCAGTGGAACAGCCACTAAGGATTCTGCAGTGAGAG
CAGAGGGCCAGCTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCCCAGGCAAAGCG
TCCGGGCAGCGTAGGCGGGCGACTCAGATCCCAGCCAGTGGACTTAGCCCCTGTTTGCTCCTCCGATAACTGGGG
TGACCTTGGTTAATATTCACCAGCAGCCTCCCCCGTTGCCCCTCTGGATCCACTGCTTAAATACGGACGAGGACA
GGGCCCTGTCTCCTCAGCTTCAGGCACCACCACTGACCTGGGACAGTGAATAGATCCTGAGAACTTCAGGGTGAG
TCTATGGGACCCTTGATGTTTTCTTTCCCCTTCTTTTCTATGGTTAAGTTCATGTCATAGGAAGGGGAGAAGTAA
CAGGGTACACATATTGACCAAATCAGGGTAATTTTGCATTTGTAATTTTAAAAAATGCTTTCTTCTTTTAATATA
CTTTTTTGTTTATCTTATTTCTAATACTTTCCCTAATCTCTTTCTTTCAGGGCAATAATGATACAATGTATCATG
CCTCTTTGCACCATTCTAAAGAATAACAGTGATAATTTCTGGGTTAAGGCAATAGCAATATTTCTGCATATAAAT
ATTTCTGCATATAAATTGTAACTGATGTAAGAGGTTTCATATTGCTAATAGCAGCTACAATCCAGCTACCATTCT
GCTTTTATTTTCTGGTTGGGATAAGGCTGGATTATTCTGAGTCCAAGCTAGGCCCTTTTGCTAATCTTGTTCATA
CCTCTTATCTTCCTCCCACAGCTCCTGGGCAACCTGCTGGTCTCTCTGCTGGCCCATCACTTTGGCAAAGCACGC
GTGCCACCATGGCTTTCCTGTGGCTGCTGTCTTGTTGGGCTCTGCTGGGCACCACCTTTGGCCTGCTGGTGCCCA
GGGAGCTGTCTGGCAGCAGCCCTGTGCTGGAGGAGACCCACCCTGCTCATCAGCAGGGGGCTAGCAGGCCTGGCC
CCAGGGATGCCCAGGCTCACCCTGGGAGACCCAGGGCTGTGCCCACTCAGTGTGATGTGCCCCCCAACAGCAGGT
TTGACTGTGCTCCTGACAAGGCTATCACCCAGGAGCAGTGTGAGGCCAGGGGGTGCTGCTACATTCCTGCTAAGC
AGGGCCTGCAGGGGGCCCAGATGGGCCAGCCCTGGTGCTTCTTCCCCCCCTCTTATCCCAGCTATAAGCTGGAGA
ACCTGAGCAGCTCTGAGATGGGCTACACTGCCACCCTGACCAGGACCACTCCCACCTTCTTTCCCAAGGATATTC
TGACTCTGAGGCTGGATGTGATGATGGAGACTGAGAACAGGCTGCACTTCACTATCAAGGACCCTGCCAATAGGA
GGTATGAGGTGCCCCTGGAGACTCCTCATGTGCATAGCAGGGCCCCTTCTCCTCTGTATTCTGTGGAGTTCTCTG
AGGAGCCCTTTGGGGTGATTGTGAGGAGGCAGCTGGATGGCAGGGTGCTGCTGAACACCACTGTGGCCCCCCTGT
TCTTTGCTGACCAGTTCCTGCAGCTGAGCACTTCTCTGCCCAGCCAGTACATTACTGGGCTGGCTGAGCATCTGA
GCCCCCTGATGCTGAGCACCTCTTGGACCAGGATCACCCTGTGGAACAGGGACCTGGCCCCCACTCCTGGGGCTA
ACCTGTATGGCTCTCACCCCTTTTACCTGGCCCTGGAGGATGGGGGCTCTGCCCATGGGGTGTTTCTGCTGAACA
GCAATGCTATGGATGTGGTGCTGCAGCCCTCTCCAGCCCTGTCTTGGAGGAGCACTGGGGGCATTCTGGATGTGT
ACATTTTCCTGGGGCCTGAACCCAAGTCTGTGGTGCAGCAGTACCTGGATGTGGTGGGCTACCCCTTCATGCCCC
CCTATTGGGGGCTGGGGTTTCACCTGTGCAGGTGGGGCTACAGCAGCACTGCCATCACCAGGCAGGTGGTGGAGA
ACATGACCAGGGCCCATTTCCCCCTGGATGTGCAGTGGAATGACCTGGACTACATGGATAGCAGGAGGGATTTCA
CCTTCAACAAGGATGGCTTCAGGGACTTTCCTGCCATGGTGCAGGAGCTGCACCAGGGGGGCAGGAGGTATATGA
TGATTGTGGACCCTGCTATCAGCAGCTCTGGCCCTGCTGGCTCTTACAGGCCCTATGATGAGGGCCTGAGGAGGG
GGGTGTTTATCACTAATGAAACTGGCCAGCCTCTGATTGGCAAGGTCTGGCCTGGCTCTACTGCCTTCCCTGATT
TTACTAACCCCACTGCCCTGGCCTGGTGGGAGGACATGGTGGCTGAGTTCCATGATCAGGTGCCTTTTGATGGCA
TGTGGATTGATATGAATGAACCAAGCAACTTCATCAGAGGCTCTGAGGATGGCTGCCCCAACAATGAGCTGGAGA
ACCCCCCCTATGTGCCTGGGGTGGTGGGGGGCACTCTGCAGGCTGCCACCATTIGTGCTAGCAGCCACCAGTTCC
TGAGCACCCACTACAATCTGCACAACCTGTATGGCCTGACTGAAGCCATTGCCAGCCATAGGGCCCTGGTGAAGG
CCAGGGGCACTAGGCCTTTTGTGATCAGCAGGAGCACTTTTGCTGGCCATGGCAGGTATGCTGGCCACTGGACTG
GGGATGTGTGGAGCAGCTGGGAGCAGCTGGCCAGCTCTGTGCCTGAGATTCTGCAGTTTAACCTGCTGGGGGTGC
CCCTGGTGGGGGCTGATGTGTGTGGCTTCCTGGGCAACACCTCTGAGGAGCTGTGTGTGAGGTGGACCCAGCTGG

-continued

GGGCCTTTTATCCCTTCATGAGGAACCACAACAGCCTGCTGAGCCTGCCTCAGGAGCCCCTACTCTTTCTCTGAGC
CTGCCCAGCAGGCCATGAGGAAGGCCCTGACCCTGAGGTATGCCCTGCTGCCCCACCTGTATACCCTGTTCCACC
AGGCCCATGTGGCTGGGGAGACTGTGGCCAGGCCCCTGTTCCTGGAGTTCCCCAAGGACAGCAGCACCTGGACTG
TGGATCATCAGCTGCTGTGGGGGGAGGCCCTGCTGATCACCCCTGTGCTGCAGGCTGGCAAGGCTGAGGTCACTG
GCTACTTCCCTCTGGGCACCTGGTATGACCTGCAGACTGTGCCTGTGGAGGCTCTGGGCAGCCTGCCCCCCCCCC
CTGCTGCTCCCAGGGAGCCTGCCATCCACTCTGAGGGCCAGTGGGTGACCCTGCCTGCTCCCCTGGACACCATCA
ATGTGCACCTGAGGGCTGGCTACATTATCCCCCTGCAGGGCCCAGGGCTGACTACCACTGAGAGCAGACAGCAGC
CCATGGCTCTGGCTGTGGCCCTGACCAAGGGGGGGGAAGCTAGGGGGGAGCTGTTCTGGGATGATGGGGAGAGCC
TGGAGGTGCTGGAGAGGGGGGCCTATACCCAGGTGATCTTCCTGGCTAGGAACAACACCATTGTCAATGAGCTGG
TGAGGGTGACTTCTGAGGGGGCTGGGCTGCAGCTGCAGAAGGTGACTGTGCTGGGGGTGGCCACTGCTCCCCAGC
AGGTGCTGAGCAATGGGGTGCCTGTGAGCAACTTCACCTACAGCCCTGACACCAAGGTGCTGGACATCTGTGTGT
CTCTGCTGATGGGGGAGCAGTTCCTGGTGAGCTGGTGCTGACTCGAGAGATCTACCGGTGAATTCACCGCGGGTT
TAAACTGTGCCTTCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGG
GGTGGGGTGGGGGCTAGCTCTAGACTCGAGATCCACTAGGGCCGCAGGAACCCCTAGTGATGGAGTTGGCCACTC
CCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGG

>pAAV-ApoE/hAAT.GAA8.wtBGH (SEQ ID NO: 23)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCGCA
GGCTCAGAGGCACACAGGAGTTTCTGGGCTCACCCTGCCCCCTTCCAACCCCTCAGTTCCCATCCTCCAGCAGCT
GTTTGTGTGCTGCCTCTGAAGTCCACACTGAACAAACTTCAGCCTACTCATGTCCCTAAAATGGGCAAACATTGC
AAGCAGCAAACAGCAAACACACAGCCCTCCCTGCCTGCTGACCTTGGAGCTGGGGCAGAGGTCAGAGACCTCTCT
GGGCCCATGCCACCTCCAACATCCACTCGACCCCTTGGAATTTCGGTGGAGAGGAGCAGAGGTTGTCCTGGCGTG
GTTTAGGTAGTGTGAGAGGGGTACCCGGGGATCTTGCTACCAGTGGAACAGCCACTAAGGATTCTGCAGTGAGAG
CAGAGGGCCAGCTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCCCAGGCAAAGCG
TCCGGGCAGCGTAGGCGGGCGACTCAGATCCCAGCCAGTGGACTTAGCCCCTGTTTGCTCCTCCGATAACTGGGG
TGACCTTGGTTAATATTCACCAGCAGCCTCCCCCGTTGCCCCTCTGGATCCACTGCTTAAATACGGACGAGGACA
GGGCCCTGTCTCCTCAGCTTCAGGCACCACCACTGACCTGGGACAGTGAATAGATCCTGAGAACTTCAGGGTGAG
TCTATGGGACCCTTGATGTTTTCTTTCCCCTTCTTTTCTATGGTTAAGTTCATGTCATAGGAAGGGGAGAAGTAA
CAGGGTACACATATTGACCAAATCAGGGTAATTTTGCATTTGTAATTTTAAAAAATGCTTTCTTCTTTTAATATA
CTTTTTTGTTTATCTTATTTCTAATACTTTCCCTAATCTCTTTCTTTCAGGGCAATAATGATACAATGTATCATG
CCTCTTTGCACCATTCTAAAGAATAACAGTGATAATTTCTGGGTTAAGGCAATAGCAATATTTCTGCATATAAAT
ATTTCTGCATATAAATTGTAACTGATGTAAGAGGTTTCATATTGCTAATAGCAGCTACAATCCAGCTACCATTCT
GCTTTTATTTTCTGGTTGGGATAAGGCTGGATTATTCTGAGTCCAAGCTAGGCCCTTTTGCTAATCTTGTTCATA
CCTCTTATCTTCCTCCCACAGCTCCTGGGCAACCTGCTGGTCTCTCTGCTGGCCCATCACTTTGGCAAAGCACGC
GTGCCACCATGGCCTTCCTGTGGCTGCTGTCTTGCTGGGCTCTGCTGGGGACCACCTTTGGCCTGCTGGTCCCCA
GGGAGCTGTCTGGCTCTTCTCCTGTCCTGGAGGAGACCCACCCTGCCCACCAGCAGGGGGCTAGCAGGCCTGGCC
CCAGGGATGCCCAGGCCCACCCTGGCAGGCCCAGGGCTGTGCCCACCCAGTGTGATGTGCCTCCCAACAGCAGGT
TTGACTGTGCCCCTGACAAGGCCATCACCCAGGAGCAGTGTGAGGCCAGGGGCTGCTGCTATATCCCTGCCAAGC
AGGGCCTGCAGGGGGCTCAGATGGGCCAGCCCTGGTGCTTCTTTCCCCCCTCTTATCCTAGCTATAAGCTGGAGA
ACCTGAGCAGCTCTGAGATGGGGTACACTGCCACCCTGACCAGGACCACCCCCACTTTCTTCCCTAAGGACATCC
TGACCCTGAGGCTGGATGTGATGATGGAGACTGAGAATAGGCTGCACTTTACTATCAAGGACCCTGCCAACAGGA
GGTATGAGGTGCCTCTGGAGACCCCCCATGTGCATTCTAGGGCCCCCAGCCCCCTGTACTCTGTGGAGTTCTCTG
AGGAGCCCTTTGGGGTGATTGTGAGGAGACAGCTGGATGGCAGGGTCCTGCTGAACACCACTGTGGCTCCCCTGT
TTTTTGCTGACCAGTTCCTGCAGCTGAGCACCAGCCTGCCCAGCCAGTACATCACTGGGCTGGCTGAGCACCTGA
GCCCCCTGATGCTGAGCACCAGCTGGACCAGGATCACCCTGTGGAACAGGGATCTGGCTCCTACCCCTGGGGCCA
ACCTGTATGGCTCTCACCCCTTTTACCTGGCCCTGGAGGATGGGGGCTCTGCCCATGGGGTGTTCCTGCTGAACA
GCAATGCTATGGATGTGGTGCTGCAGCCCAGCCCTGCCCTGAGCTGGAGGTCTACTGGGGGCATCCTGGATGTGT
ACATCTTTCTGGGGCCTGAGCCCAAGTCTGTGGTGCAGCAGTACCTGGATGTGGTGGGCTATCCTTTTATGCCCC
CCTATTGGGGCCTGGGCTTCCACCTGTGCAGGTGGGGCTACAGCAGCACTGCCATCACCAGACAGGTGGTGGAGA
ACATGACCAGGGCCCACTTCCCCCTGGATGTGCAGTGGAATGACCTGGACTACATGGACAGCAGGAGGGACTTCA
CCTTTAACAAGGATGGCTTTAGGGACTTCCCTGCCATGGTGCAGGAGCTGCATCAGGGGGGCAGGAGGTACATGA
TGATTGTGGACCCAGCCATCAGCAGCTCTGGGCCTGCTGGGTCTTACAGGCCCTATGATGAGGGCCTGAGGAGGG
GGGTGTTCATCACCAATGAGACTGGCCAGCCCCTGATTGGCAAGGTGTGGCCTGGGAGCACTGCCTTCCCTGATT
TTACCAACCCCACTGCCCTGGCCTGGTGGAGGATATGGTGGCTGAGTTTCATGACCAGGTGCCCTTTGATGGCA
TGTGGATTGACATGAATGAGCCCAGCAATTTCATCAGGGGCTCTGAGGATGGCTGCCCCAACAATGAGCTGGAGA
ATCCTCCCTATGTGCCTGGGGTGGTGGGGGGCACCCTGCAGGCTGCCACCATCTGTGCCTCTAGCCACCAGTTCC
TGAGCACCCACTATAACCTGCATAACCTGTATGGCCTGACTGAGGCCATTGCCAGCCATAGAGCCCTGGTGAAGG
CCAGAGGGACCAGGCCCTTTGTGATCTCTAGGAGCACCTTTGCTGGCCATGGCAGGTATGCTGGCCACTGGACTG
GGGATGTGTGGAGCTCTTGGGAGCAGCTGGCCAGCTCTGTGCCAGAGATCCTGCAGTTCAACCTGCTGGGGGTGC
CTCTGGTGGGGGCTGATGTGTGTGGCTTCCTGGGCAATACCTCTGAAGAGCTGTGTGTGAGGTGGACTCAGCTGG
GGGCCTTCTATCCCTTCATGAGGAACCACAACAGCCTGCTGTCTCTGCCCCAGGAGCCCTACAGCTTCTCTGAGC
CTGCTCAGCAGGCTATGAGGAAGGCCCTGACCCTGAGGTATGCCCTGCTGCCCCATCTGTACACCCTGTTCCACC
AGGCCCATGTGGCTGGGGAGACTGTGGCCAGGCCCCTGTTTCTGGAGTTTCCCAAGGACAGCAGCACCTGGACTG
TGGACCATCAGCTGCTGTGGGGGGAGGCTCTGCTGATTACCCCTGTGCTGCAGGCTGGCAAGGCTGAGGTGACTG
GGTACTTCCCCCTGGGGACTTGGTATGACCTGCAGACTGTGCCTGTGGAAGCTCTGGGCAGCCTGCCCCCACCCC
CTGCTGCCCCTAGGGAGCCTGCCATCCACTCTGAGGGCCAGTGGGTGACCCTGCCTGCCCCTCTGGACACCATCA
ATGTGCACCTGAGGGCTGGCTATATCATCCCCCTGCAGGGCCCTGGGCTGACCACCACTGAGAGCAGGCAGCAGC
CCATGGCCCTGGCTGTGGCCCTGACTAAGGGGGGGGAGGCCAGGGGGGAGCTGTTCTGGGATGATGGGGAGAGCC
TGGAGGTGCTGGAGAGAGGGGCCTACACCCAGGTGATCTTTCTGGCCAGGAACAACACCATTGTGAATGAGCTGG
TGAGGGTGACTTCTGAGGGGGCTGGCCTGCAGCTGCAGAAGGTGACTGTGCTGGGGGTGGCCACTGCCCCCCAGC
AGGTGCTGAGCAATGGGGTGCCTGTGTCTAACTTCACCTACAGCCCTGATACTAAGGTGCTGGATATCTGTGTGA

-continued

GCCTGCTGATGGGGGAGCAGTTTCTGGTGAGCTGGTGCTGACTCGAGAGATCTACCGGTGAATTCACCGCGGGTT
TAAACTGTGCCTTCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGG
GGTGGGGTGGGGCTAGCTCTAGACTCGAGATCCACTAGGGCCGCAGGAACCCCTAGTGATGGAGTTGGCCACTC
CCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGG

>pAAV-ApoE/hAAT.GAA13.wtBGH (SEQ ID NO: 24)

CCTGCAGGCAGCTGCGCGCTCGCTCGCTCACTGAGGCCGCCCGGGCAAAGCCCGGGCGTCGGGCGACCTTTGGTC
GCCCGGCCTCAGTGAGCGAGCGAGCGCGCAGAGAGGGAGTGGCCAACTCCATCACTAGGGGTTCCTGCGGCCGCA
GGCTCAGAGGCACACAGGAGTTTCTGGGCTCACCCTGCCCCCTTCCAACCCCTCAGTTCCCATCCTCCAGCAGCT
GTTTGTGTGCTGCCTCTGAAGTCCACACTGAACAAACTTCAGCCTACTCATGTCCCTAAAATGGGCAAACATTGC
AAGCAGCAAACAGCAAACACACAGCCCTCCCTGCCTGCTGACCTTGGAGCTGGGGCAGAGGTCAGAGACCTCTCT
GGGCCCATGCCACCTCCAACATCCACTCGACCCCTTGGAATTTCGGTGGAGAGGAGCAGAGGTTGTCCTGGCGTG
GTTTAGGTAGTGTGAGAGGGGTACCCGGGGATCTTGCTACCAGTGGAACAGCCACTAAGGATTCTGCAGTGAGAG
CAGAGGGCCAGCTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCCCAGGCAAAGCG
TCCGGGCAGCGTAGGCGGGCGACTCAGATCCCAGCCAGTGGACTTAGCCCCTGTTTGCTCCTCCGATAACTGGGG
TGACCTTGGTTAATATTCACCAGCAGCCTCCCCCGTTGCCCCTCTGGATCCACTGCTTAAATACGGACGAGGACA
GGGCCCTGTCTCCTCAGCTTCAGGCACCACCACTGACCTGGGACAGTGAATAGATCCTGAGAACTTCAGGGTGAG
TCTATGGGACCCTTGATGTTTTCTTTCCCCTTCTTTTCTATGGTTAAGTTCATGTCATAGGAAGGGGAGAAGTAA
CAGGGTACACATATTGACCAAATCAGGGTAATTTTGCATTTGTAATTTTAAAAAATGCTTTCTTCTTTTAATATA
CTTTTTTGTTTATCTTATTTCTAATACTTTCCCTAATCTCTTTCTTTCAGGGCAATAATGATACAATGTATCATG
CCTCTTTGCACCATTCTAAAGAATAACAGTGATAATTTCTGGGTTAAGGCAATAGCAATATTTCTGCATATAAAT
ATTTCTGCATATAAATTGTAACTGATGTAAGAGGTTTCATATTGCTAATAGCAGCTACAATCCAGCTACCATTCT
GCTTTTATTTTCTGGTTGGGATAAGGCTGGATTATTCTGAGTCCAAGCTAGGCCCTTTTGCTAATCTTGTTCATA
CCTCTTATCTTCCTCCCACAGCTCCTGGGCAACCTGCTGGTCTCTCTGCTGGCCCATCACTTTGGCAAAGCACGC
GTGCCACCATGGCCTTTCTGTGGCTGCTGTCCTGCTGGGCCCTGCTGGGGACCACCTTTGGCCTGCTGGTGCCCA
GGGAGCTGTCTGGGAGCAGCCCAGTGCTGGAGGAGACCCACCCTGCCCACCAGCAGGGGGCCAGCAGGCCTGGCC
CTAGGGATGCCCAGGCCCACCCTGGCAGGCCCAGGGCTGTGCCTACCCAGTGTGATGTGCCACCCAATTCTAGGT
TTGACTGTGCTCCTGACAAGGCCATCACTCAGGAGCAGTGTGAAGCTAGGGGGTGCTGCTACATCCCAGCCAAGC
AGGGCCTGCAGGGGGCCCAGATGGGCCAGCCCTGGTGCTTCTTCCCCCCCAGCTACCCTAGCTACAAGCTGGAGA
ATCTGAGCAGCTCTGAGATGGGCTACACTGCTACCCTGACCAGGACCACTCCTACCTTCTTCCCCAAGGACATCC
TGACTCTGAGGCTGGATGTCATGATGGAGACTGAAAATAGGCTGCACTTCACCATCAAGGACCCTGCCAATAGGA
GGTATGAGGTGCCTCTGGAGACCCCCCATGTGCATAGCAGGGCTCCCAGCCCCCTGTATTCTGTGGAGTTCTCTG
AGGAGCCCTTTGGGGTCATTGTGAGGAGACAGCTGGATGGGAGGGTGCTGCTGAACACTACTGTGGCTCCCCTGT
TCTTTGCTGACCAGTTCCTGCAGCTGTCTACCAGCCTGCCCAGCCAGTACATCACTGGGCTGGCTGAGCATCTGA
GCCCCCTGATGCTGAGCACCAGCTGGACCAGGATCACTCTGTGGAACAGGGATCTGGCCCCCACTCCTGGGGCCA
ACCTGTATGGGAGCCATCCCTTCTACCTGGCCCTGGAGGATGGGGGCTCTGCCCATGGGGTGTTCCTGCTGAACA
GCAATGCCATGGATGTGGTGCTGCAGCCTAGCCCTGCCCTGAGCTGGAGGAGCACTGGGGGCATCCTGGATGTCT
ACATCTTCCTGGGGCCTGAGCCCAAGTCTGTGGTGCAGCAGTATCTGGATGTGGTGGGGTATCCCTTCATGCCCC
CCTACTGGGGCCTGGGCTTTCACCTGTGCAGGTGGGGCTACAGCAGCACTGCCATCACCAGGCAGGTGGTGGAGA
ACATGACCAGGGCCCACTTCCCTCTGGATGTGCAGTGGAATGACCTGGACTATATGGATTCTAGGAGAGACTTTA
CTTTTAACAAGGATGGCTTCAGGGATTTCCCTGCCATGGTGCAGGAGCTGCACCAGGGGGGCAGGAGGTACATGA
TGATTGTGGACCCTGCTATTAGCAGCTCTGGCCCTGCTGGGTCTTACAGGCCTTATGATGAGGGCCTGAGGAGGG
GGGTGTTCATCACCAATGAGACTGGCCAGCCCCTGATTGGCAAGGTGTGGCCTGGCAGCACTGCCTTCCCTGACT
TCACCAACCCCACTGCCCTGGCCTGGTGGGAGGACATGGTGGCTGAGTTCCATGACCAGGTGCCCTTTGATGGGA
TGTGGATTGACATGAATGAGCCCTCTAACTTCATCAGGGGGTCTGAGGATGGCTGCCCCAACAATGAGCTGGAGA
ACCCCCCCTATGTGCCTGGGGTGGTGGGGGGCACTCTGCAGGCTGCCACTATCTGTGCTTCTTCTCACCAGTTTC
TGAGCACCCACTATAATCTGCACAACCTGTATGGCCTGACTGAGGCCATTGCCAGCCATAGGGCCCTGGTGAAGG
CCAGGGGCACCAGGCCCTTTGTGATCAGCAGGTCTACCTTTGCTGGCCATGGCAGGTATGCTGGCCACTGGACTG
GGGATGTGTGGTCTTCTTGGGAGCAGCTGGCCAGCTCTGTGCCTGAGATCCTGCAGTTCAACCTGCTGGGGGTGC
CTCTGGTGGGGGCTGATGTGTGTGGCTTTCTGGGCAACACCTCTGAGGAGCTGTGTGTGAGGTGGACCCAGCTGG
GGGCCTTTTACCCCTTCATGAGGAACCACAATAGCCTGCTGAGCCTGCCCCAGGAGCCTTACTCTTTCTCTGAGC
CTGCCCAGCAGGCCATGAGGAAGGCCCTGACTCTGAGGTATGCCCTGCTGCCCCATCTGTATACCCTGTTTCACC
AGGCCCATGTGGCTGGGGAGACTGTGGCTAGGCCTCTGTTTCTGGAGTTCCCTAAGGACTCTAGCACCTGGACTG
TGGACCACCAGCTGCTGTGGGGGGAGGCCCTGCTGATCACCCCTGTGCTGCAGGCTGGCAAGGCTGAGGTGACTG
GCTACTTCCCCCTGGGCACCTGGTATGACCTGCAGACTGTGCCTGTGGAGGCCCTGGGGAGCCTGCCTCCCCCCC
CTGCTGCCCCCAGGGAGCCTGCCATTCATTCTGAGGGCCAGTGGGTGACCCTGCCTGCCCCTCTGGACACCATCA
ATGTGCACCTGAGGGCTGGGTACATCATCCCCCTGCAGGGCCCTGGCCTGACCACCACTGAGAGCAGGCAGCAGC
CCATGGCCCTGGCTGTGGCTCTGACCAAGGGGGGGGAGGCCAGGGGGGAGCTGTTCTGGGATGATGGGGAGTCTC
TGGAGGTGCTGGAGAGGGGGGCCTACACCCAGGTGATCTTTCTGGCCAGGAACAATACTATTGTGAATGAGCTGG
TGAGGGTGACCTCTGAGGGGGGCTGGCCTGCAGCTGCAGAAGGTGACTGTGCTGGGGGTGGCCACTGCCCCCCAGC
AGGTCCTGAGCAATGGGGTGCCTGTGAGCAACTTCACCTACTCTCCTGACACCAAGGTGCTGGACATTTGTGTGT
CTCTGCTGATGGGGGAGCAGTTCCTGGTGAGCTGGTGCTGACTCGAGAGATCTACCGGTGAATTCACCGCGGGTT
TAAACTGTGCCTTCTAGTTGCCAGCCATCTGTTGTTTGCCCCTCCCCCGTGCCTTCCTTGACCCTGGAAGGTGCC
ACTCCCACTGTCCTTTCCTAATAAAATGAGGAAATTGCATCGCATTGTCTGAGTAGGTGTCATTCTATTCTGGGG
GGTGGGGTGGGGCTAGCTCTAGACTCGAGATCCACTAGGGCCGCAGGAACCCCTAGTGATGGAGTTGGCCACTC
CCTCTCTGCGCGCTCGCTCGCTCACTGAGGCCGGGCGACCAAAGGTCGCCCGACGCCCGGGCTTTGCCCGGGCGG
CCTCAGTGAGCGAGCGAGCGCGCAGCTGCCTGCAGG

SEQ ID NO: 25: amino acid sequence for a secretable GAA protein

MAFLWLLSCWALLGTTFGLLVPRELSGSSPVLEETHPAHQQGASRPGPRDAQAHPGRPRAVPTQCDVPPNSREDC
APDKAITQEQCEARGCCYIPAKQGLQGAQMGQPWCFFPPSYPSYKLENLSSSEMGYTATLTRTTPTFFPKDILTL
RLDVMMETENRLHFTIKDPANRRYEVPLETPHVHSRAPSPLYSVEFSEEPFGVIVRRQLDGRVLLNTTVAPLFFA
DQFLQLSTSLPSQYITGLAEHLSPLMLSTSWTRITLWNRDLAPTPGANLYGSHPFYLALEDGGSAHGVFLLNSNA
MDVVLQPSPALSWRSTGGILDVYIFLGPEPKSVVQQYLDVVGYPFMPPYWGLGFHLCRWGYSSTAITRQVVENMT
RAHFPLDVQWNDLDYMDSRRDFTENKDGFRDFPAMVQELHQGGRRYMMIVDPAISSSGPAGSYRPYDEGLRRGVF
ITNETGQPLIGKVWPGSTAFPDFTNPTALAWWEDMVAEFHDQVPFDGMWIDMNEPSNFIRGSEDGCPNNELENPP
YVPGVVGGTLQAATICASSHQFLSTHYNLHNLYGLTEAIASHRALVKARGTRPFVISRSTFAGHGRYAGHWTGDV

-continued

WSSWEQLASSVPEILQFNLLGVPLVGADVCGFLGNTSEELCVRWTQLGAFYPFMRNHNSLLSLPQEPYSFSEPAQ
QAMRKALTLRYALLPHLYTLFHQAHVAGETVARPLFLEFPKDSSTWTVDHQLLWGEALLITPVLQAGKAEVTGYF
PLGTWYDLQTVPVEALGSLPPPPAAPREPAIHSEGQWVTLPAPLDTINVHLRAGYIIPLQGPGLTTTESRQQPMA
LAVALTKGGEARGELFWDDGESLEVLERGAYTQVIFLARNNTIVNELVRVTSEGAGLQLQKVTVLGVATAPQQVL
SNGVPVSNFTYSPDTKVLDICVSLLMGEQFLVSWC

SEQ ID NO: 26: CpG reduced BGH poly A nucleic acid sequence
AGATCTAGAGCTGAATTCCTGCAGCCAGGGGGATCAGCCTCTACTGTGCCTTCTAGTTGCCAGCCATCTGTTGTT
TGCCCCTCCCCCTTGCCTTCCTTGACCCTGGAAGGTGCCACTCCCACTGTCCTTTCCTAATAAAATGAGGAAATT
GCATCACATTGTCTGAGTAGGTGTCATTCTATTCTGGGGGGGGGGTGGGGCAGGACAGCAAGGGGGAGGATTGG
GAAGACAATAGCAGGCATGCTGGGGATGCAGTGGGCTCTATGG SEQ ID NO: 27: wtBGH poly A nucleic acid sequence
AGATCTACCGGTGAATTCACCGCGGGTTTAAACTGTGCCTTCTAGTTGCCAGCCATCTGTTGTTTGCCCCTCCCC
CGTGCCTTCCTTGACCCTGGAAGGTGCCACTCCCACTGTCCTTTCCTAATAAAATGAGGAAATTGCATCGCATTG
TCTGAGTAGGTGTCATTCTATTCTGGGGGGTGGGGTGGGGGCTAGCTCTAGA SEQ ID NO: 28: ApoE/hAAT sequence bordered by Apal restriction sites (underlined).
GGGCCCATGCCACCTCCAACATCCACTCGACCCCTTGGAATTTCGGTGGAGAGGAGCAGAGGTTGTCCTGGCGTG
GTTTAGGTAGTGTGAGAGGGGTACCCGGGGATCTTGCTACCAGTGGAACAGCCACTAAGGATTCTGCAGTGAGAG
CAGAGGGCCAGCTAAGTGGTACTCTCCCAGAGACTGTCTGACTCACGCCACCCCCTCCACCTTGGACACAGGACG
CTGTGGTTTCTGAGCCAGGTACAATGACTCCTTTCGGTAAGTGCAGTGGAAGCTGTACACTGCCCAGGCAAAGCG
TCCGGGCAGCGTAGGCGGGCGACTCAGATCCCAGCCAGTGGACTTAGCCCCTGTTTGCTCCTCCGATAACTGGGG
TGACCTTGGTTAATATTCACCAGCAGCCTCCCCCGTTGCCCCTCTGGATCCACTGCTTAAATACGGACGAGGACA
GGGCCC SEQ ID NO: 29: ApoE/hAAT sequence.
ATGCCACCTCCAACATCCACTCGACCCCTTGGAATTTCGGTGGAGAGGAGCAGAGGTTGTCCTGGCGTGGTTTAG
GTAGTGTGAGAGGGGTACCCGGGGATCTTGCTACCAGTGGAACAGCCACTAAGGATTCTGCAGTGAGAGCAGAGG
GCCAGCTAAGTGGTACTCTCCCAGAGACTGTCTGACTCACGCCACCCCCTCCACCTTGGACACAGGACGCTGTGG
TTTCTGAGCCAGGTACAATGACTCCTTTCGGTAAGTGCAGTGGAAGCTGTACACTGCCCAGGCAAAGCGTCCGGG
CAGCGTAGGCGGGCGACTCAGATCCCAGCCAGTGGACTTAGCCCCTGTTTGCTCCTCCGATAACTGGGGTGACCT
TGGTTAATATTCACCAGCAGCCTCCCCCGTTGCCCCTCTGGATCCACTGCTTAAATACGGACGAGGACA AAV vector capsids:
VP1

(SEQ ID NO: 30)

MAADGYLPDWLEDNLSEGIREWWDLKPGAPKPKANQQKQDNGRGLVLPGYKYLGPENGLD
KGEPVNAADAAALEHDKAYDQQLQAGDNPYLRYNHADAEFQERLQEDTSEGGNLGRAVFQ
AKKRVLEPLGLVESPVKTAPGKKRPVEPSPQRSPDSSTGIGKKGQQPAKKRLNFGQTGDS
ESVPDPQPIGEPPAAPSGVGPNTMAAGGGAPMADNNEGADGVGSSSGNWHCDSTWLGDRV
ITTSTRTWALPTYNNHLYKQISNGTSGGSTNDNTYFGYSTPWGYFDFNRFHCHFSPRDWQ
RLINNNWGFRPKRLNFKLFNIQVKEVTQNEGTKTIANNLTSTIQVFTDSEYQLPYVLGSA
HQGCLPPFPADVEMIPQYGYLTLNNGSQAVGRSSFYCLEYFPSQMLRTGNNFEFSYNFED
VPFHSSYAHSQSLDRLMNPLIDQYLYYLSRTQSTGGTAGTQQLLFSQAGPNNMSAQAKNW
LPGPCYRQQRVSTTLSQNNNSNFAWTGATKYHLNGRDSLVNPGVAMATHKDDEERFFPSS
GVLMFGKQGAGKDNVDYSSVMLTSEEEIKTTNPVATEQYGVVADNLQQQNAAPIVGAVNS
QGALPGMVWQNRDVYLQGPIWAKIPHTDGNFHPSPLMGGFGLKHPPPQILIKNTPVPADP
PTTFNQAKLASFITQYSTGQVSVEIEWELQKENSKRWNPEIQYTSNYYKSTNVDFAVNTE
GTYSEPRPIGTRYLTRNL

VP2

(SEQ ID NO: 31)

TAPGKKRPVEPSPQRSPDSSTGIGKKGQQPAKKRLNFGQTGDSESVPDPQPIGEPPAGPS
GLGSGTMAAGGGAPMADNNEGADGVGSSSGNWHCDSTWLGDRVITTSTRTWALPTYNNHL
YKQISNGTSGGSTNDNTYFGYSTPWGYFDFNRFHCHFSPRDWQRLINNNWGFRPKRLNEK
LFNIQVKEVTQNEGTKTIANNLTSTIQVFTDSEYQLPYVLGSAHQGCLPPFPADVFMIPQ
YGYLTLNNGSQAVGRSSFYCLEYFPSQMLRTGNNFEFSYNFEDVPFHSSYAHSQSLDRLM
NPLIDQYLYYLSRTQSTGGTAGTQQLLFSQAGPNNMSAQAKNWLPGPCYRQQRVSTTLSQ
NNNSNFAWTGATKYHLNGRDSLVNPGVAMATHKDDEERFFPSSGVLMFGKQGAGKDNVDY
SSVMLTSEEEIKTTNPVATEQYGVVADNLQQQNAAPIVGAVNSQGALPGMVWQNRDVYLQ
GPIWAKIPHTDGNFHPSPLMGGFGLKHPPPQILIKNTPVPADPPTTENQAKLASFITQYS
TGQVSVEIEWELQKENSKRWNPEIQYTSNYYKSTNVDFAVNTEGTYSEPRPIGTRYLTRN
L

VP3

(SEQ ID NO: 32)

MAAGGGAPMADNNEGADGVGSSSGNWHCDSTWLGDRVITTSTRTWALPTYNNHLYKQISN
GTSGGSINDNTYFGYSTPWGYFDFNRFHCHFSPRDWQRLINNNWGFRPKRLNFKLFNIQV
KEVTQNEGTKTIANNLTSTIQVFTDSEYQLPYVLGSAHQGCLPPFPADVFMIPQYGYLTL
NNGSQAVGRSSFYCLEYFPSQMLRIGNNFEFSYNFEDVPFHSSYAHSQSLDRLMNPLIDQ
YLYYLSRTQSTGGTAGTQQLLFSQAGPNNMSAQAKNWLPGPCYRQQRVSTTLSQNNNSNF
AWTGATKYHLNGRDSLVNPGVAMATHKDDEERFFPSSGVLMFGKQGAGKDNVDYSSVMLT
SEEEIKTTNPVATEQYGVVADNLQQQNAAPIVGAVNSQGALPGMVWQNRDVYLQGPIWAK
IPHTDGNFHPSPLMGGFGLKHPPPQILIKNTPVPADPPTTFNQAKLASFITQYSTGQVSV
EIEWELQKENSKRWNPEIQYTSNYYKSTNVDFAVNTEGTYSEPRPIGTRYLTRNL

-continued

LK03-AAV VP1

(SEQ ID NO: 33)

```
MAADGYLPDWLEDNLSEGIREWWALQPGAPKPKANQQHQDNARGLVLPGYKYLGPGNGLDKGEPVNAADAAALEH
DKAYDQQLKAGDNPYLKYNHADAEFQERLKEDTSFGGNLGRAVFQAKKRLLEPLGLVEEAAKTAPGKKRPVDQSP
QEPDSSSGVGKSGKQPARKRLNFGQTGDSESVPDPQPLGEPPAAPTSLGSNTMASGGGAPMADNNEGADGVGNSS
GNWHCDSQWLGDRVITTSTRTWALPTYNNHLYKQISSQSGASNDNHYFGYSTPWGYFDFNRFHCHFSPRDWQRLI
NNNWGFRPKKLSFKLFNIQVKEVTQNDGTTTIANNLTSTVQVFTDSEYQLPYVLGSAHQGCLPPFPADVEMVPQY
GYLTLNNGSQAVGRSSFYCLEYFPSQMLRTGNNFQFSYTFEDVPFHSSYAHSQSLDRLMNPLIDQYLYYLNRTQG
TTSGTTNQSRLLFSQAGPQSMSLQARNWLPGPCYRQQRLSKTANDNNNSNFPWTAASKYHLNGRDSLVNPGPAMA
SHKDDEEKFFPMHGNLIFGKEGTTASNAELDNVMITDEEEIRTTNPVATEQYGTVANNLQSSNTAPTTRTVNDQG
ALPGMVWQDRDVYLQGPIWAKIPHTDGHFHPSPLMGGFGLKHPPPQIMIKNTPVPANPPTTFSPAKFASFITQYS
TGQVSVEIEWELQKENSKRWNPEIQYTSNYNKSVNVDFTVDINGVYSEPRPIGTRYLTRPL
```

Example 2

Study Design—Potency In Vitro (Huh7 Cells)

To evaluate potency of the GAA expression cassettes, 200 ng of plasmid DNA corresponding to each cassette was transfected into a human hepatocellular carcinoma cell line (Huh7) using Lipofectamine® 2000 (ThermoFisher). Following 48 hours of incubation, samples of culture medium from cells transfected with plasmids bearing each expression cassette were assessed for the levels of GAA by GAA activity assay and normalized to the intracellular protein content.

Results

Figure 10:
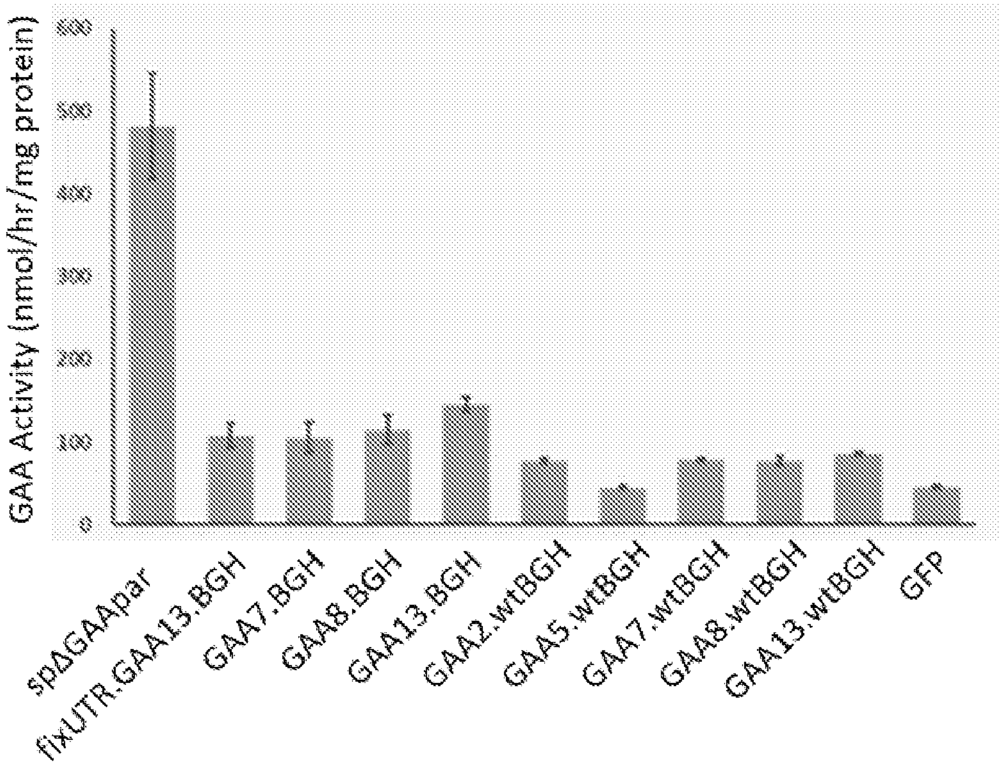
FIG. 10 shows evaluation of GAA activity levels in Huh7 cell supernatants by GAA activity assay.

FIG. 10 shows evaluation of different GAA expression plasmids in vitro in Huh7 cells by GAA activity assay. Results are the average of biological replicates n=3. Error bars represent standard deviation.

With the exception of GAA5.wtBGH, all plasmids demonstrated increased expression levels of secreted GAA compared to a green fluorescent protein (GFP) control plasmid, indicating that these plasmids resulted in expression of the GAA protein product (FIG. 10). In general, "BGH" plasmids (harboring a CpG-reduced poly A sequence) outperformed "wtBGH" plasmids (with a wild-type bGH poly A). In addition, codon optimized sequences GAA2, GAA7, GAA 8, and GAA13 appeared to be relatively similar, with a trend towards higher expression from GAA13 plasmids. An overall decrease in expression levels was observed when compared with parental spAGAApar plasmid.

Example 3

Study Design—Cassette Potency by Hydrodynamic Injection in Mice

To evaluate the potency of different GAA expression cassettes in mammals, 25 micrograms of plasmid DNA corresponding to each cassette was introduced into male C57BU6 mice (approximately 8 weeks of age) intravenously in the lateral tail vein by hydrodynamic injection. Plasma was collected at 72 hours post-injection and assessed for circulating GAA enzyme presence by GAA activity assay and western blot.

Results

Figure 11:
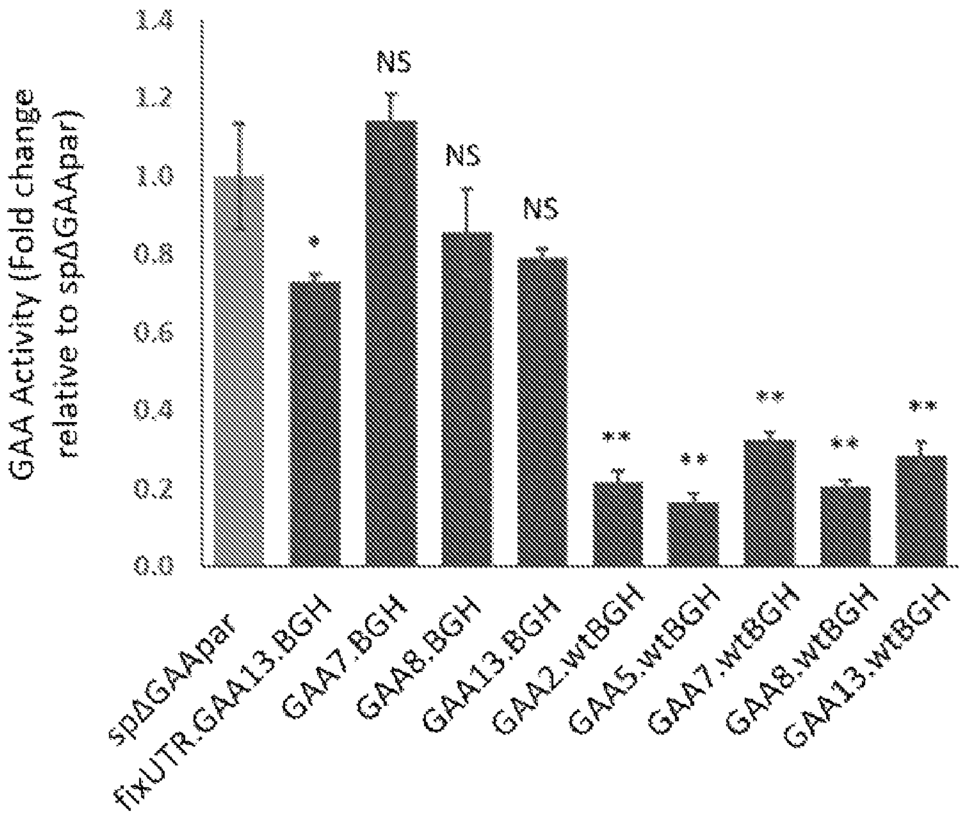
FIG. 11 shows evaluation of GAA activity levels in mouse plasma by GAA activity assay.
Figure 12:
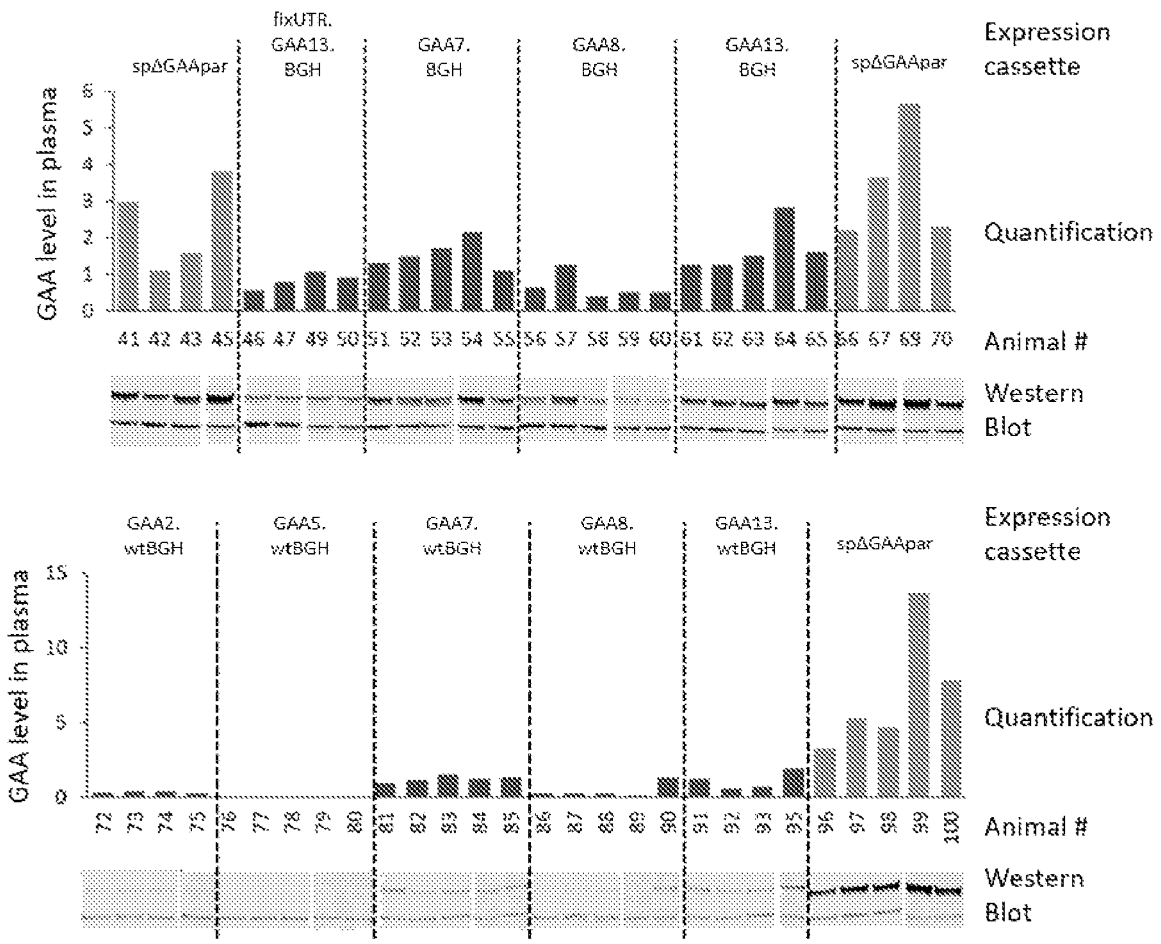
FIG. 12 shows evaluation of GAA levels in mouse plasma by GAA western blot.

FIGS. 11 and 12 show evaluation of different GAA expression cassettes by hydrodynamic injection in male C57BU6 mice by GAA activity assay and western blot, respectively, in plasma. For FIG. 11, plasma levels of GAA are normalized to the parental construct (spAGAApar). Results are the average of biological replicates n=4-5. Error bars represent standard deviation. NS, not significant. * $p<0.05$, ** $p<0.01$.

For FIG. 12, the GAA western blot analysis of plasma, the bar graph represents quantification of the upper band normalized to the bottom, non-specific band. Each of the biological replicates (n=4-5 per group) is shown.

Evaluation of codon-optimized GAA expression cassettes in mice by hydrodynamic injection revealed that these cassettes were capable of expression and secretion of the GAA transgene product from mouse liver, with levels similar to those observed with the parental GAA construct, spAGAApar (FIG. 11). As in the in vitro studies in Huh7 cells (Example 2), GAA expression cassettes harboring the CpG-reduced BGH poly A sequence outperformed those with a wild-type BGH poly A. Unexpectedly, in comparison to the results of Example 2, some of the codon-optimized GAA constructs performed as well as or better than the parental spAGAApar plasmid.

Example 4

Study Design—Vector Potency in Mice

To evaluate the potency of the codon-optimized GAA cassettes of the invention compared with parental cassette spAGAApar, spAGAApar and 9 codon-optimized cassettes were packaged into an AAV vector comprising SEQ ID NOs:30-32 capsids (Table 1). Five male C57BU6 mice per group were injected intravenously via the tail vein with 1 of 2 vector doses ($5\times10^{11}$ vg/kg or $2\times10^{12}$ vg/kg). Circulating GAA activity was longitudinally measured following AAV vector administration to the mice. Plasma were tested biweekly for GAA activity. At day 70, 7 of the 10 test animal groups were sacrificed, and the remaining three groups (SPK-AAV-01, SPK-AAV-02, and the parental vector) were sacrificed at day 147.

Results

Figure 13:
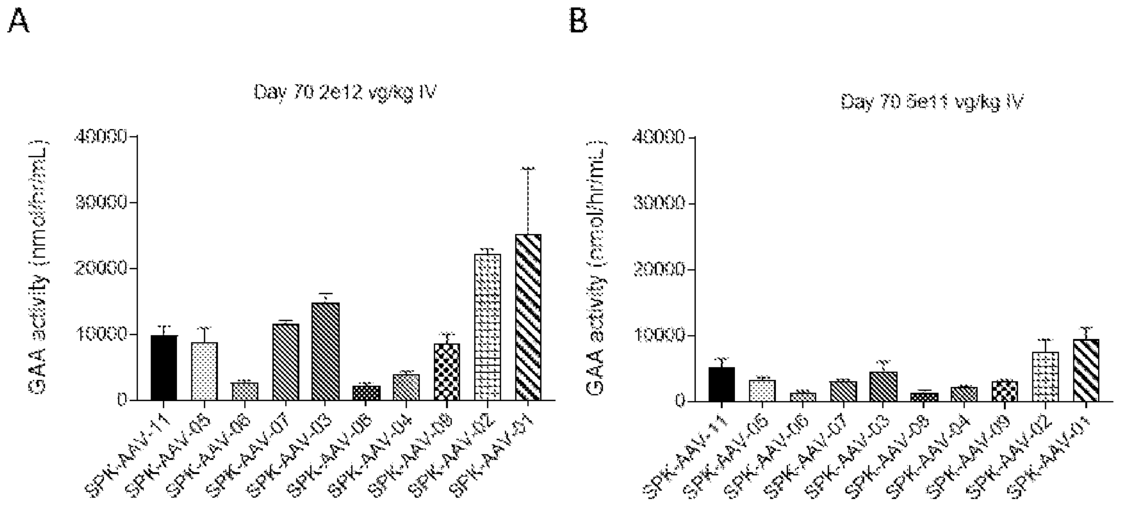
FIG. 13 shows evaluation of GAA activity levels in mouse plasma by GAA activity assay.

FIG. 13 shows evaluation of different codon-optimized GAA expression cassettes packaged into AAV (SEQ ID NOs:30-32) vector in male C57BL/6 mice by GAA activity assay in plasma 70 days post vector infusion. Results are the average of biological replicates n=4-5. Error bars represent standard deviation. NS, not significant. * $p<0.05$, ** $p<0.01$.

Two vectors, SPK-AAV-01 and SPK-AAV-02, consistently showed significantly higher GAA activity in the plasma (approximately 2- to 3-fold higher in the high dose) when compared to the parental vector (designated herein as SPK-AAV-11).

Figure 14:
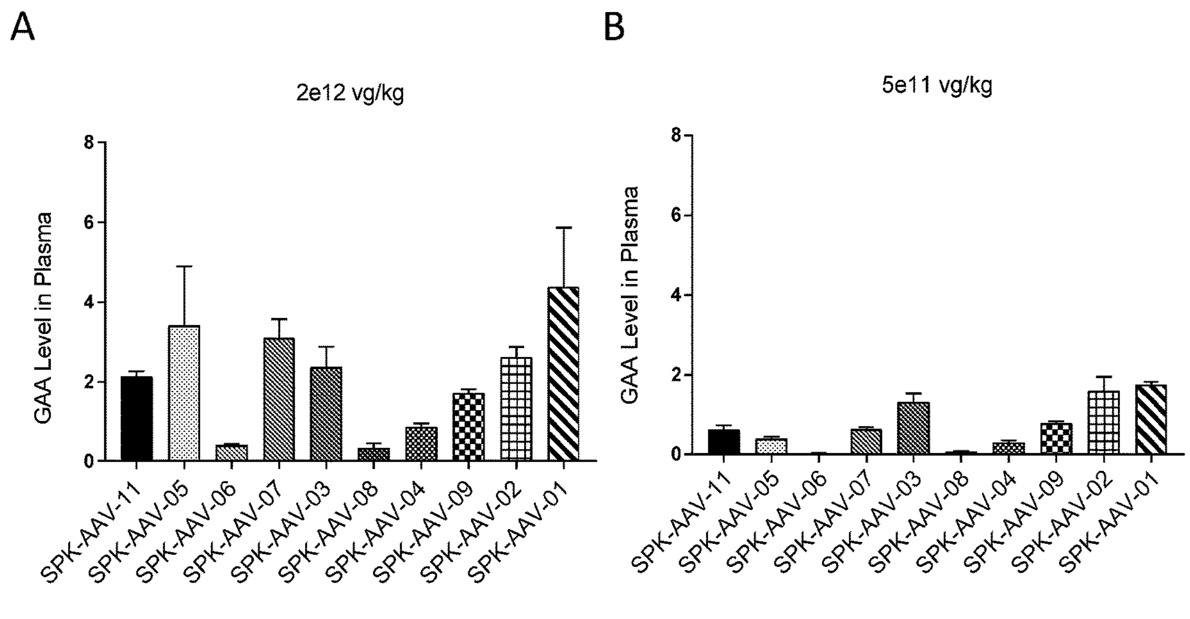
FIG. 14 shows evaluation of GAA levels in mouse plasma by GAA western blot.

FIG. 14 shows evaluation of different codon-optimized GAA expression cassettes packaged into AAV (SEQ ID NOs:30-32) vector in male C57BL/6 mice by GAA western blot in plasma 7 days post vector infusion. Results are the average of biological replicates n=4-5. Error bars represent standard deviation. NS, not significant. * $p<0.05$, ** $p<0.01$.

Figure 15:
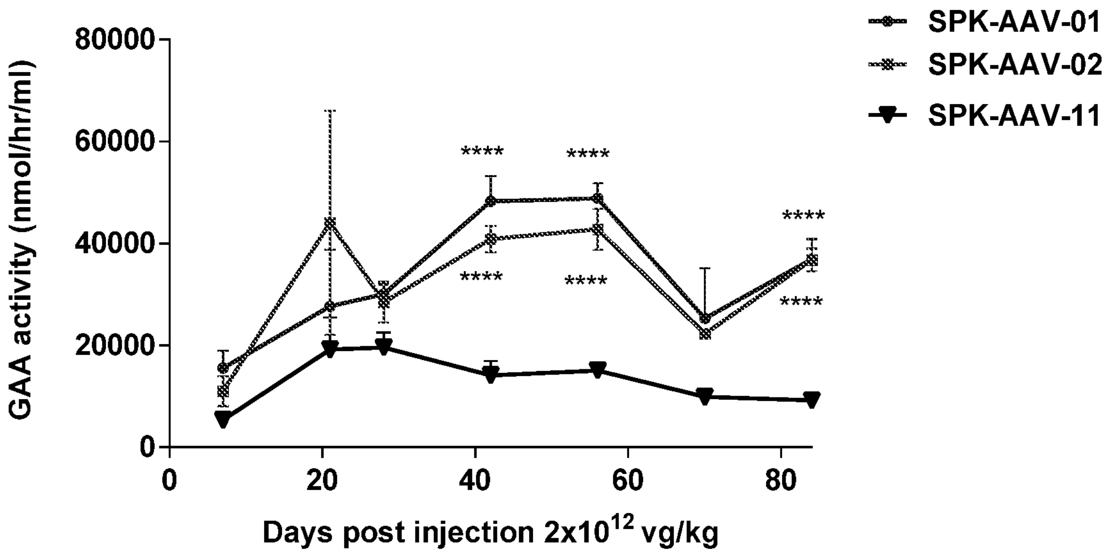
FIG. 15 shows evaluation of GAA activity levels in mouse plasma by GAA activity assay.
Figure 15:
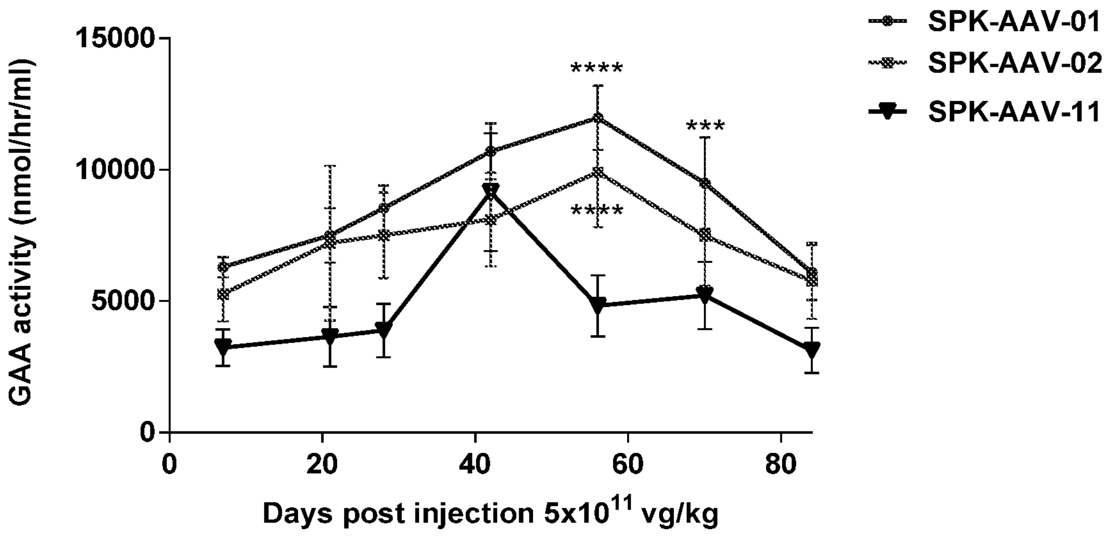

FIG. 15 shows GAA activity levels measured in plasma following administration of codon-optimized GAA expression cassettes packaged into AAV (SEQ ID NOs:30-32) vector to mice. Male C57BL/6 mice were injected with a dose of $5\times10^{11}$ (upper panel) or $2\times10^{12}$ vg/kg (lower panel)

of either of the two best performing GAA-expressing AAV (SEQ ID NOs:30-32) vectors (n=5 animals/group). GAA activity measured in the plasma of mice that received SPK-AAV-11 vector (parental spAGAApar construct) is shown for comparison. Starting at day 42, GAA activity in plasma was significantly higher for SPK-AAV-01 and SPK-AAV-02 vectors than that for SPK-AAV-11 vector (*p=<0.001,**p=<0.0001 Tukey multiple comparisons test).

Example 5

Study Design—Potency in Rats

The purpose of this study was to evaluate the potency of SPK-AAV-02 in two different rat strains. Circulating GAA activity was measured in plasma following vector administration to Wistar Hanover (n=4) and Sprague Dawley (n=5) rats. Male rats were injected intravenously via the tail vein with $2\times10^{13}$ vg/kg of vector.

Results

Figure 16:
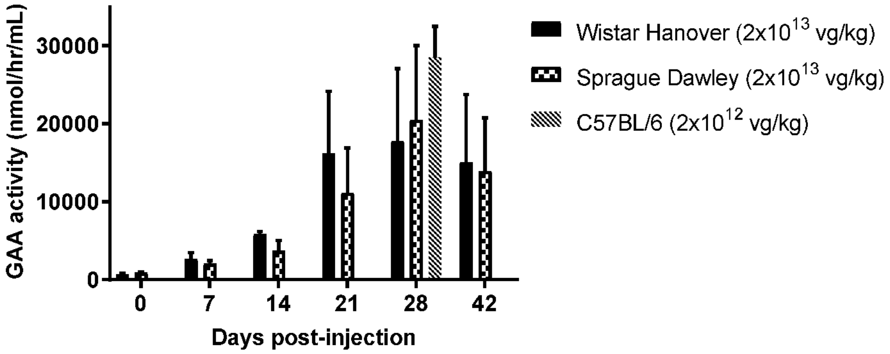
FIG. 16 shows evaluation of GAA activity levels in rat and mouse plasma by GAA activity assay.

FIG. 16 shows evaluation of SPK-AAV-02 (pAAV-ApoE/hAAT.GAA13.BGH packaged into AAV (SEQ ID NOs:30-32)) vector in male Wistar Hanover and Sprague Dawley rats compared to C57BL/6 mice by GAA activity assay in plasma. Results are the average of biological replicates n=4-5. Error bars represent standard deviation.

The levels of GAA activity started to plateau at day 28 with GAA activity measured around 15,000 nmol/hr/mL. Mice were injected with SPK-AAV-02 at a 10-fold lower dose ($2\times10^{12}$ vg/kg of vector) than the rats.

Example 6

Study Design—Potency in Non-Human Primates (NHPs), Part 1

To evaluate the long-term effects of secretable GAA expression, a single dose of SPK-AAV-01, SPK-AAV-02 or SPK-AAV-10 vector was administered to a species phylogenetically close to human, rhesus macaques (*Macaca mulatta*), and animals were evaluated for GAA activity levels in plasma.

Male rhesus macaques (n=3/dose cohort) received a 30-minute IV infusion in the saphenous vein of a single dose of $6\times10^{12}$ vg/kg of SPK-AAV-01, SPK-AAV-02 or SPK-AAV-10 vector. Following AAV vector administration, animals were monitored daily for clinical observations, and blood was collected weekly.

Results

Figure 17:
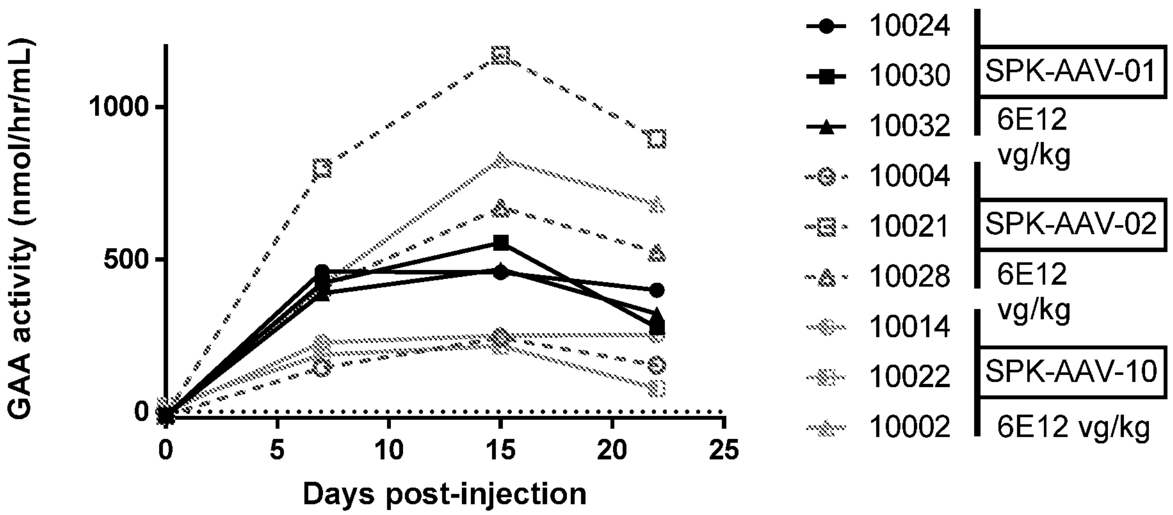
FIG. 17 shows evaluation of GAA activity levels in plasma of non-human primates (male rhesus macaque) by GAA activity assay.

Rhesus macaques were injected with a dose of $6\times10^{12}$ vg/kg of GAA-expressing AAV (SEQ ID NOs:30-32) vectors (n=3 animals/group). FIG. 17 shows GAA activity levels measured in plasma following administration of GAA expression cassettes packaged into AAV (SEQ ID NOs:30-32) vector to male rhesus macaques. No significant differences were observed among the plasma GAA activity levels of SPK-AAV-01, SPK-AAV-02 and SPK-AAV-10 vector injected NHPs.

Preliminary data in the NHP study confirm the results observed in the mouse studies, and show that plasma GAA activity levels resulting from administration of SPK-AAV-01 and SPK-AAV-02 are similar (FIG. 17).

Example 7

Study Design—Potency in Non-Human Primates, Part 2

The main objective of this study was to evaluate the transduction profile of SPK-AAV-01 and SPK-AAV-02 in African green monkeys (AGM; *Chlorocebus sabaeus*). Male AGM (n=4/dose cohort) received a 30-minute IV infusion in the saphenous vein of a single dose of $6\times10^{12}$ vg/kg of SPK-AAV-01 or SPK-AAV-02 vector. Following AAV vector administration, animals were monitored daily for clinical observations, and blood was collected weekly.

Results

Figure 18:
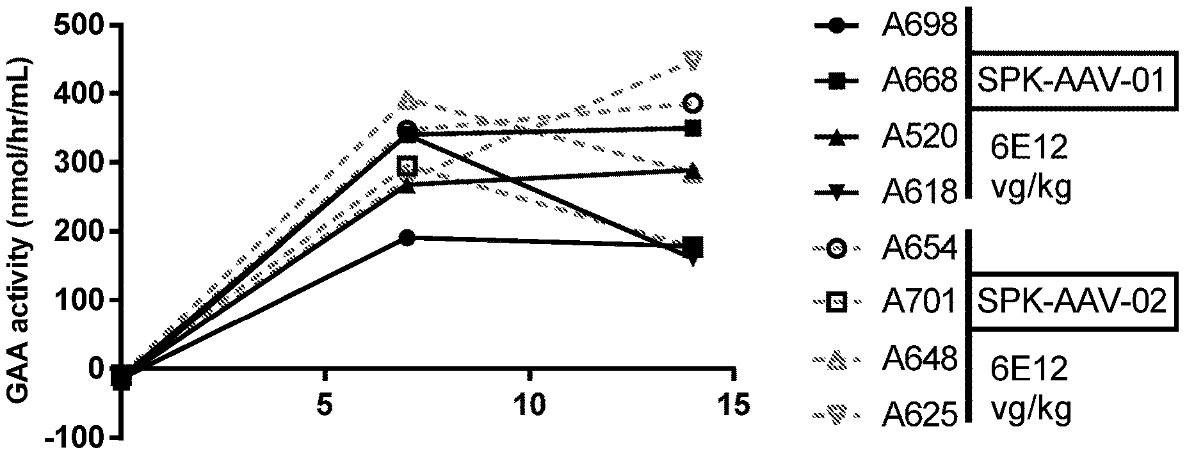
FIG. 18 shows evaluation of GAA activity levels in plasma of non-human primates (African green monkey) by GAA activity assay. The X-axis is days post injection.
Figure 19:
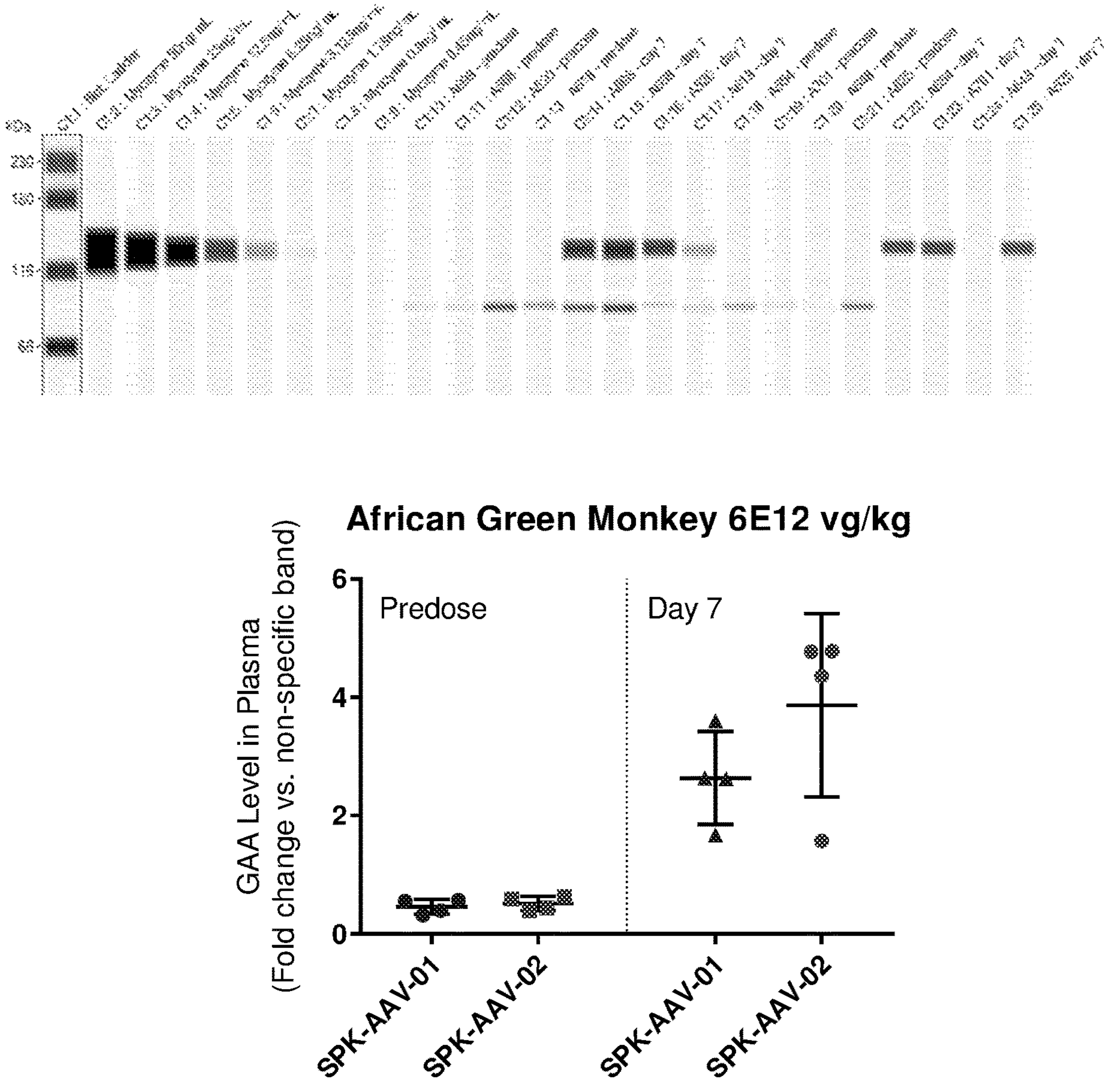
FIG. 19 shows evaluation of GAA levels in plasma of non-human primates (African green monkey) by western blot, with graphical presentation of certain data.
Figure 20:
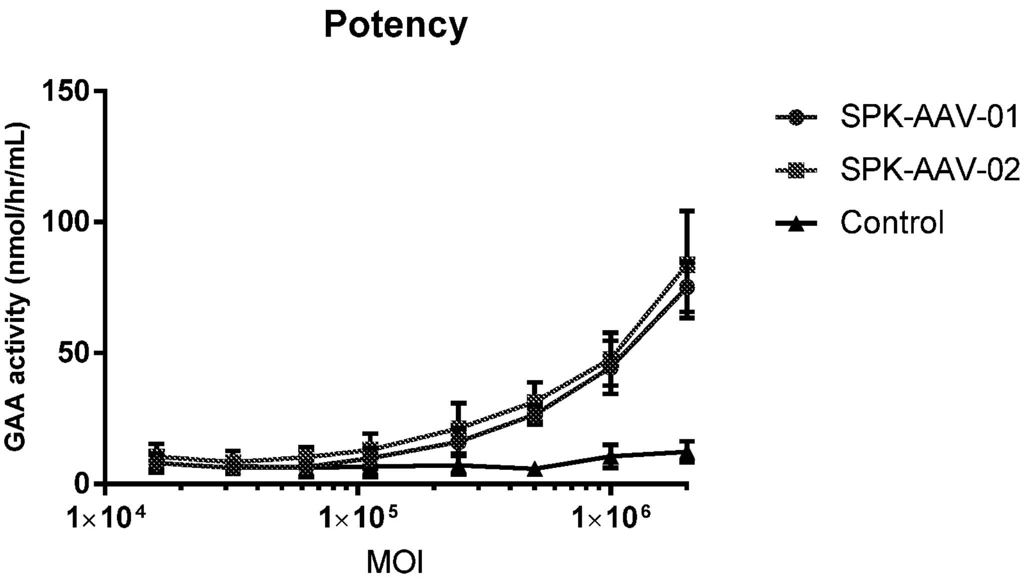
FIG. 20 shows evaluation of GAA activity in supernatants of Huh7 cells transduced with SPK-AAV-01, SPK-AAV-02 or a negative control (rAAV with non-GAA transgene packaged into AAV SEQ ID NOs:30-32 vector).

Preliminary data in African green monkeys confirm the results observed in mouse studies that plasma GAA activity levels resulting from administration of SPK-AAV-01 and SPK-AAV-02 are similar (FIG. 18).

Example 8

Conclusions

The codon-optimized GAA cassettes that express secretable human GAA represent a significant improvement over the parental spAGAApar construct. In particular, SPK-AAV-01 and SPK-AAV-02 exhibit excellent potency and expression of secretable human GAA in cell culture, rodent, and two non-human primate models.

Example 9

Study Design—Dose Ranging in NHPs

To evaluate the dose response of secretable GAA expression, three doses of SPK-AAV-02 vector were administered to a primate species phylogenetically close to humans, rhesus macaques (*Macaca mulatta*), and animals were evaluated for GAA activity levels over the course of one month.

Male rhesus macaques (n=4/dose cohort) received a 30-minute intravenous (IV) infusion in the saphenous vein of a dose of either $2\times10^{12}$, $6\times10^{12}$, $2\times10^{13}$ vg/kg of SPK-AAV-02 vector. Female rhesus macaques (n=4/dose cohort) received a 30-minute IV infusion in the saphenous vein of a dose of $2\times10^{13}$ vg/kg of SPK-AAV-02 vector. Following AAV vector administration, animals were monitored daily for clinical observations. Blood was collected weekly for 4 weeks to measure GAA activity, GAA antigen levels, anti-GAA IgG formation, hematology and clinical chemistries, including glucose levels to monitor potential alterations of glycemia.

Results

Figure 21:
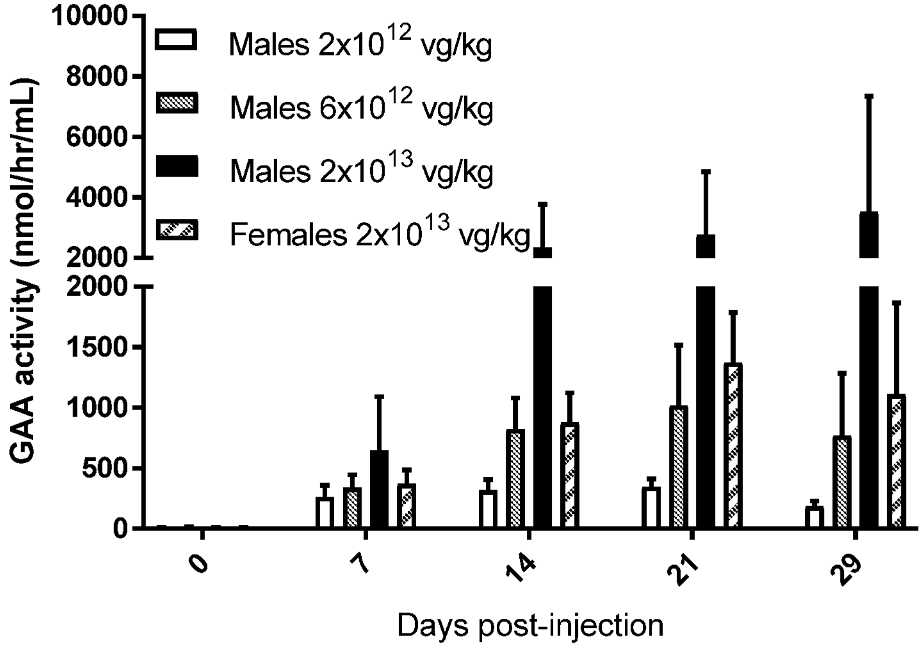
FIG. 21 shows evaluation of GAA activity in plasma from rhesus macaques following a single intravenous administration of SPK-AAV-02 at doses of $2\times10^{12}$, $6\times10^{12}$, $2\times10^{13}$ vg/kg.

FIG. 21 shows GAA activity levels measured in plasma following administration SPK-AAV-02 vector to male and female rhesus macaques. Results of GAA activity measured in plasma 7, 14, 21 and 28 days post vector injection show a correlation between vector dose and plasma GAA activity level. The levels of GAA activity in the plasma of female NHPs injected at a dose of $2\times10^{13}$ vg/kg were about 0.5-fold lower (49.6%) than those measured in male NHPs injected at an equal dose.

The data in this NHP study confirm the results observed in the mouse studies, namely that plasma GAA activity levels derived from AAV vectors for secretable GAA expression result in a dose dependent GAA activity in plasma following vector administration (FIG. 21). A single infusion of SPK-AAV-02 in NHPs at three ascending doses demonstrated dose-dependent expression of GAA in NHP plasma.

Example 10

Nine-Month NHP Study

Each of SPK-AAV-01, SPK-AAV-02 and SPK-AAV-10 were administered at a single dose ($6\times10^{12}$ vg/kg) via intravenous infusion to male Rhesus macaques (*Macaca*

*mulatta*). During the course of the study, a decrease in active GAA protein in plasma and concomitant rise in anti-GAA IgG antibody levels was observed in a portion of animals dosed with secretable GAA expressing vectors. Loss of GAA activity and antigen level in plasma was likely due to the development of an IgG-mediated humoral immune clearance of the human transgene protein product. In an effort to reduce the humoral immune response and possibly regain detectable circulating GAA enzyme levels, starting on day 183, certain animals were given an immunosuppression regimen of monthly rituximab in combination with daily cyclosporine A.

Results

Levels of secreted and active GAA in plasma were detected in all animals, exhibiting peak mean activity levels on day 15 of 482.07±47.90, 664.43±417.55 and 427.833±307.94 nmol/mL/hr for SPK-AAV-01, SPK-AAV-02 and SPK-AAV-10, respectively. Detectable levels of circulating GAA antigen were observed with mean peak levels of 14.84±2.21, 19.11±23.23, 14.64±16.96 ng/mL for animals administered with SPK-AAV-01, SPK-AAV-02 and SPK-AAV-10, respectively. Concomitant with the observed decrease in circulating GAA, starting at day 15, an increase in circulating anti-GAA IgG levels was observed. Analysis of vector genomes, by qPCR of liver tissue, confirmed presence of vector in the liver, exhibiting mean vector genome copies of 6.39±2.72, 11.43±4.23 and 19.01±13.93 per haploid genome, for animals administered SPK-AAV-01, SPK-AAV-02 and SPK-AAV-10, respectively.

Liver samples were analyzed for both full length GAA and cleaved GAA (lysosomal form) protein levels. Study samples were compared to vector-naïve Rhesus liver samples serving as a negative control, which did not display detectable levels of either cleaved or intact GAA at the levels of protein loaded (n=3). The amount of full-length protein in study animal liver was 4.0±7.0, 5.4±9.1, 11.0±11.3 ng of GAA/mg of total protein in animals administered SPK-AAV-01, SPK-AAV-02 and SPK-AAV-10, respectively. Each cohort contained higher levels of cleaved GAA than full length GAA, exhibiting levels of 41.6±57.6, 44.4±74.5, 49.0±40.3 ng of GAA/mg of total protein in animals administered SPK-AAV-01, SPK-AAV-02 and SPK-AAV-10, respectively. Regardless of GAA processing, differences between groups were not significant (P=0.72 for the full-length (intact) form; P=0.83 for the lysosomal (cleaved) form by Kruskal-Wallis). At terminus, all groups administered AAV vectors of the invention displayed average detectable levels of GAA above baseline in the liver.

Conclusion

Administration of each of SPK-AAV-01, SPK-AAV-02 and SPK-AAV-10 resulted in detectable and increasing plasma levels of GAA antigen, peaking over weeks 2-3 and correlating linearly with GAA activity, exhibiting similar kinetics regardless of vector genome. Both GAA activity and GAA antigen levels in plasma declined consecutively over the following timepoints in all but one animal. As previously observed in NHPs treated with AAV vectors, a humoral response to the human transgene product was observed beginning on day 43, which inversely correlated with GAA antigen levels in plasma in all animals that developed a GAA-specific IgG response. Suppression of anti-GAA IgG levels, via administration of an immunosuppressive agent targeting B-cell mediated IgG response (rituximab), resulted in a restoration of detectable GAA levels in plasma in a subset of animals. For all groups, vector genome copies were detectable in the liver at the end of the study, even in the absence of measurable circulating plasma levels of GAA. Correspondingly, GAA protein was detected in all liver tissues treated with vector at the end of the study, while GAA antigen was below the limit of detection in treatment-naïve liver tissue. Taken together, these results indicate that AAV vectors of the invention are able to mediate durable expression of secretable human GAA in the liver over 9 months, regardless of the development of an antibody response to the human transgene product.

Example 11

Nine-Week Rodent Immunosuppression Study

Expression levels of the GAA transgene product were measured for nine weeks following intravenous administration of a single dose of $2\times10^{12}$ vg/kg of SPK-AAV-02 particles, in the presence or absence of rapamycin and/or prednisolone, in male and female C57BL/6 mice. Mice were tested in 5 groups, as shown in Table 2.

TABLE 2

Group Designations and Dose Levels

| Group | No. of Animals Male | No. of Animals Female | SPK-AAV-02 (vg/kg) | Rapamycin (2-3 mg/kg)* | Prednisolone (1-0.25 mg/kg)** |
|---|---|---|---|---|---|
| 1 | 5 | 5 | Vehicle | | |
| 2 | 10 | 10 | $2\times10^{12}$ | | |
| 3 | 10 | 10 | | X | |
| 4 | 10 | 10 | | | X |
| 5 | 10 | 10 | | X | X |

vg = vector genomes, X = administered treatment

*Rapamycin was delivered daily at 2 mg/kg from day (−)7 through day 5. Starting at day 6, delivery was changed to 3 mg/kg every other day.

**Prednisolone was delivered at a concentration of 1 mg/kg from day (−)1 through day 15, 0.5 mg/kg from day 16 through day 22, and 0.25 mg/kg from day 23 through day 28.

In groups receiving immunosuppressive agent(s), agent(s) were administered prior to AAV particle dosing, and for the first 5 weeks of the study. Following completion of AAV dosing, animals were monitored for clinical observations and body weight for 9 weeks. At the end of the study, clinical chemistry and hematology was performed on blood samples, and histopathology was performed on select tissues. IgG antibodies against the rAAV capsid and plasma GAA activity were assessed weekly throughout the study.

Results

Levels of GAA activity in plasma were detected above background in all animals administered vector. Vehicle-administered males in Group 1 showed background levels approximately between 300-400 nmol/ml/hr. Circulating levels of GAA activity rose following vector administration with slightly different kinetics depending on the immunosuppressive treatment group but exhibited equivalent peak mean levels of GAA activity. In particular, the peak mean levels of GAA activity were 16114±5411, 14875±6882, 14890±6882, and 21480±6340 nmol/mL/hr for males in Group 2 (SPK-AAV-02 alone), Group 3 (SPK-AAV-02, 2-3 mg/kg rapamycin), Group 4 (SPK-AAV-02, 1-0.25 mg/kg prednisolone), and Group 5 (SPK-AAV-02, 2-3 mg/kg rapamycin, 1-0.25 mg/kg prednisolone), respectively. No statistically significant differences were observed in peak GAA activity levels between any of the AAV treatment groups.

In female mice, peak mean levels of GAA activity were 7380±4034, 5912±3259, 6096±3249, and 9955±3104 nmol/mL/hr for Group 2, Group 3, Group 4, and Group 5, respectively. These levels of GAA activity were significantly above the background detected in vehicle-administered female animals. As seen with the male mice, peak levels of GAA activity in the female mice were not statistically significantly different between any of the AAV treatment groups. The observed differences in plasma levels of GAA activity between males and females are consistent with the well-documented phenomenon of decreased AAV transduction of hepatocytes in female mice (Davidoff et al., 2003, Blood, 102:480-488; DOI: 10.1182/blood-2002-09-2889).

Anti-rAAV capsid IgG in plasma was detected in all animals administered SPK-AAV-02, exhibiting peak mean levels of 86527±92140, 6695±3555, 64368±29635, and 11374±6053 ng/mL for males in Group 2, Group 3, Group 4, and Group 5, respectively, and peak mean levels of 182009±148148, 66141±77925, 182654±90161, and 57752±59192 ng/ml for females in Groups 2, 3, 4 and 5, respectively. Group 1 (vehicle) for both males and females had levels of anti-rAAV capsid IgG that were below the quantitative limit of the assay for all timepoints.

Conclusion

Administration of SPK-AAV-02 resulted in detectable GAA activity levels in all animals. The combined treatment with rapamycin and prednisolone caused levels of GAA activity to be statistically increased (vs. rAAV vector alone) at days 22, 36, and 42 in male mice, and at day 43 in female animals. Of note, the difference in peak levels of GAA activity, regardless of when maximum expression was reached, was not statistically significant between any of the AAV treatment groups within sexes.

A humoral IgG response raised against the rAAV capsid was observed in all groups administered SPK-AAV-02. In both sexes, the presence of rapamycin (Groups 3 and 5) significantly reduced the formation of anti-capsid IgG when compared to vector alone. Treatment with prednisolone had more modest effects on anti-capsid IgG formation, with significant reduction at days 15, 43 and 60 in males and days 43 and 60 in females in Group 4.

Immunosuppression with rapamycin and/or prednisolone in mice, resulted in decreased humoral responses to the rAAV capsid, and did not significantly affect peak levels of GAA activity in plasma.

Example 12

4-Week Single Dose Co-Administered with Rapamycin in NHP

This study evaluated circulating GAA activity (levels of GAA activity in plasma) over a period of four weeks following administration of a single dose of SPK-AAV-02 at $5.5\times10^{13}$ vg/kg, in the presence of rapamycin, in three male African green monkeys (*Chlorocebus sabaeus*).

Animals were administered rapamycin (2 mg/kg daily) beginning 5 days prior to AAV dosing, and continuing throughout the four-week study. A single dose of $5.5\times10^{13}$ vg/kg of SPK-AAV-02 was administered intravenously via the saphenous vein. Following completion of AAV dosing, animals were monitored for clinical observations and body weight for 4 weeks. At the conclusion of the study, clinical chemistry and hematology was performed on blood samples, and histopathology was performed on select tissues. Plasma GAA activity was measured weekly throughout the study.

Results

Levels of GAA activity in plasma were above background in all animals following administration of SPK-AAV-02, with peak activity levels for each of the three animals reaching 1158.1, 711.9, and 623.8 nmol/mL/hr, at the final point measured (Table 3).

TABLE 3

Plasma GAA Activity for Individual NHPs Administered Rapamycin. GAA Activity in Plasma (nmol/ml/hr)

| | Individual NHP Number | | | |
|---|---|---|---|---|
| | 1 | 2 | 3 | Mean + SD |
| Baseline | 2.1 | 4.9 | 3.7 | 3.6 + 1.4 |
| Day 7 | 777.2 | 331.3 | 187.4 | 432.0 + 307.5 |
| Day 14 | 924.0 | 349.9 | 368.0 | 547.3 + 326.4 |
| Day 21 | 973.2 | 289.6 | 490.0 | 584.3 + 351.4 |
| Day 28 | 1158.1 | 711.9 | 623.8 | 831.3 + 286.5 |

Conclusion

Administration of SPK-AAV-02 resulted in detectable plasma GAA activity in all three NHPs. The combination of SPK-AAV-02 and rapamycin was well tolerated and had a favorable safety profile in all tests measured.

Example 13

Therapeutic Efficacy in $Gaa^{-/-}$ Mouse Pompe Model

A 10-month follow-up study of 4-month old $Gaa^{-/-}$ mice (an established mouse model of Pompe disease) administered SPK-AAV-02 at three doses ($1.25\times10^{11}$, $5\times10^{11}$ and $2\times10^{12}$ vg/kg) was carried out. The study demonstrated: (1) dose-dependent increases in circulating GAA enzyme activity, (2) significant improvement of muscle strength, and (3) no significant anti-GAA humoral immune responses.

Example 14

Methods

Cell-Based Assay to Measure the Protein Expression Efficiency of Plasmids Encoding Secretable Human GAA Transgenes Huh7 cells were plated in 48-well dishes at $5\times10^4$ cells per well overnight in DMEM+10% FBS+penicillin/streptomycin/L-glutamine. Plasmids prepared using Plasmid Giga Kit (Qiagen) were transfected into cells at 250 ng per well using Lipofectamine® 2000. Cells were maintained at 37 degrees Celsius and 5% $CO_2$ for 48-72 hours and supernatants were harvested and stored in low retention microtiter plates at −80 degrees Celsius until assayed for GAA activity. Supernatants were diluted 1:10 and incubated with 3 mM of fluorescent substrate 4-methylumbelliferyl α-D-glucopyranoside for 1 hour at 37 degrees Celsius. The reaction was stopped after 1 hour with carbonate buffer (pH 10.5) and compared to a standard curve generated by diluting 4-methylumbelliferone (4-MU) in the stop buffer, creating a 12-point standard curve starting at 250 pmol/μL and ending at 0 pmol/μL. The plate was read at λex 360 nm; λem 449 nm.

Hydrodynamic Injection of Plasmid DNA to Assess Potency of Plasmids Encoding Secretable Human GAA Transgenes Plasmids prepared using Plasmid Giga Kit (Qiagen) were diluted in PBS180+0.001% Pluronic. 25 micrograms of plasmid DNA corresponding to each cassette to be tested was introduced into male C57BU6 mice of approximately 8 weeks of age intravenously in the lateral tail vein by hydrodynamic injection. 72 hours post injection, whole blood was collected into sodium citrate tubes via lancing the submandibular vein. The first drop of blood was discarded and 200 μL of blood was collected into sodium citrate, and the tube was inverted to avoid hemolysis and clotting. The sample was spun down at 10,000 RPM for 10 minutes at 4 degrees Celsius. Plasma was aliquoted into tubes and stored in a −80 degrees Celsius freezer until analyzed for GAA activity. Plasma samples were diluted to varying degrees and incubated with 3 mM of fluorescent substrate 4-methylumbelliferyl α-D-glucopyranoside for 1 hour at 37 degrees Celsius. The reaction was stopped after 1 hour with carbonate buffer (pH 10.5) and compared to a standard curve generated by diluting 4-MU in the stop buffer, creating a 12-point standard curve starting at 250 pmol/μL and ending at 0 pmol/μL. The plate was read at λex 360 nm; λem 449 nm.

Cell-Based Assay to Measure the Potency of AAV Vectors Encoding Secretable Human GAA Transgenes Huh7 cells were plated in 48-well dishes at $5\times10^4$ cells per well overnight. SPK-AAV-01 and SPK-AAV-02 from stock vector were prepared in a dose curve (multiplicity of infection, MOI, range from $2\times10^6$-$1\times10^4$) in Opti-MEM™ or DMEM+10% FBS+penicillin/streptomycin/L-glutamine. Existing medium was removed from Huh7 cells and replaced with virus particle containing medium. Cells were maintained at 37 degrees Celsius and 5% $CO_2$ for 72 hours, and supernatants were harvested and stored in low retention microtiter plates at −80 degrees Celsius until assayed for GAA activity. Supernatants were diluted 1:10 and incubated with 3 mM of fluorescent substrate 4-methylumbelliferyl α-D-glucopyranoside for 1 hour at 37 degrees Celsius. The reaction was stopped after 1 hour with carbonate buffer (pH 10.5) and compared to a standard curve generated by diluting 4-MU in the stop buffer, creating a 12-point standard curve starting at 250 pmol/μL and ending at 0 pmol/μL. The plate was read at λex 360 nm; λem 449 nm.

GAA Activity Assay in Mouse/Rat Plasma

Whole blood was collected into sodium citrate tubes via lancing the submandibular vein. The first drop of blood was discarded and 200 μL of blood was collected into sodium citrate; the tube was inverted to avoid hemolysis and clotting. The sample was spun down at 10,000 rpm for 10 minutes at 4 degrees Celsius. Plasma was aliquoted into tubes and stored in a −80 degrees Celsius freezer until analyzed for GAA activity. Plasma samples were diluted to varying degrees and incubated with 3 mM of fluorescent substrate 4-methylumbelliferyl α-D-glucopyranoside for 1 hour at 37 degrees Celsius. The reaction is stopped after 1 hour with carbonate buffer (pH 10.5) and compared to a standard curve generated by diluting 4-MU in the stop buffer, creating a 12-point standard curve starting at 250 pmol/μL and ending at 0 pmol/μL. The plate was read at λex 360 nm; λem 449 nm.

GAA Activity Assay in NHP (Rhesus/AGM) Plasma

Male rhesus macaques/African green monkeys were injected intravenously via the saphenous vein, and whole blood was collected into sodium citrate tubes, which were inverted to avoid hemolysis and clotting. The sample was spun down at 10,000 RPM for 10 minutes at 4 degrees Celsius. Plasma was aliquoted into tubes and stored in a −80 degrees Celsius freezer until analyzed for GAA activity. Plasma samples were diluted to varying degrees and incubated with 3 mM of fluorescent substrate 4-methylumbelliferyl α-D-glucopyranoside for 1 hour at 37 degrees Celsius. The reaction was stopped after 1 hour with carbonate buffer (pH 10.5) and compared to a standard curve generated by diluting 4-MU in the stop buffer, creating a 12-point standard curve starting at 250 pmol/μL and ending at 0 pmol/μL, or an 11-point standard curve (5 μM/mL-0.49 nM/mL). The plate is read at λex 360 nm; λem 449 nm. GAA activity for tested samples were interpolated from the 4-MU standard curve and expressed as velocity (nanomole/milliliter/hour (nmol/mL/hr)).

Protein Level Assessment of GAA in Huh7 Supernatants by Western Blot

Huh7 cells were plated in 48-well dishes at $5\times10^4$ cells per well overnight. SPK-AAV-01 and SPK-AAV-02 from stock vector were prepared in a dose curve (multiplicity of infection, MOI, range from $2\times10^6$-$1\times10^4$) in Opti-MEM™ or DMEM+10% FBS+penicillin/streptomycin/L-glutamine. Existing medium was removed from Huh7 cells and replaced with virus particle containing medium. Cells were maintained at 37 degrees Celsius and 5% $CO_2$ for 72 hours, and supernatants were harvested and stored in low retention microtiter plates at −80 degrees Celsius until assayed for GAA protein level. Supernatants were diluted 1:20 with RIPA buffer incubated at 95 degrees Celsius for 5 minutes and run on a 4-12% Bis-Tris NuPage gel with MOPS running buffer. The protein was transferred to polyvinylidene difluoride (pvdf) membrane using the iBlot® system (ThermoFisher), and blocked for 1 hour at room temperature in Odyssey© TBS buffer. The membrane was incubated overnight at 4 degrees Celsius with the primary antibody, rabbit anti-human GAA (Abcam) diluted 1:1000. The membrane was washed and incubated at room temperature for 2 hours with the fluorescent secondary anti-rabbit antibody diluted 1:10,000. The membrane was washed and imaged using the Li-Core® imaging system. The bands were compared to 10 ng of Myozyme® and the marker. Densitometry analysis was conducted using Li-Core® software and bands were normalized to the Myozyme® control.

Protein Level Assessment of GAA in Mouse Plasma by Western Blot

Male and female C57BL/6 mice were injected intravenously via the tail vein, and whole blood was collected into sodium citrate tubes via lancing the submandibular vein. The first drop of blood was discarded and 200 μL of blood was collected into sodium citrate; the tube was inverted to avoid hemolysis and clotting. The sample was spun down at 10,000 RPM for 10 minutes at 4 degrees Celsius. Plasma was aliquoted into tubes and stored in a −80 degrees Celsius freezer until analyzed for GAA protein level. Plasma was diluted 1:20 with RIPA buffer, incubated at 95 degrees Celsius for 5 minutes, and run on a 4-12% Bis-Tris NuPage gel with MOPS running buffer. The protein was transferred to pvdf membrane using the iBlot® system (ThermoFisher), and blocked for 1 hour at room temperature in Odyssey® TBS buffer. The membrane was incubated overnight at 4 degrees Celsius with the primary antibody, rabbit anti-human GAA (Abcam) diluted 1:1000. The membrane was washed and incubated at room temperature for 2 hours with the fluorescent secondary anti-rabbit antibody diluted 1:10,000. The membrane was washed and imaged using the Li-Core® imaging system. The bands were compared to 10 ng of Myozyme® and the marker. Densitometry analysis was conducted using Li-Core® software and bands were normalized to the Myozyme® control.

Protein Level Assessment of GAA in NHP Plasma by WES

Male rhesus macaques/African green monkeys were injected intravenously via the saphenous vein, and whole blood was collected into sodium citrate tubes, which were inverted to avoid hemolysis and clotting. The sample was spun down at 10,000 rpm for 10 minutes at 4 degrees Celsius. Plasma was aliquoted into tubes and stored in a −80 degrees Celsius freezer until analyzed for GAA protein levels. Plasma samples were diluted 1:6000 in sample diluent. An 8-point, two-fold standard curve was added to each chip with the Myozyme® starting at a concentration of 50 ng/mL. The samples were diluted in the buffer, denatured at 95 degrees Celsius for 5 minutes, and loaded into the WES™ chip (Protein Simple). The primary antibody was added at a 1:1000 dilution, and the secondary antibody was loaded at working dilution. The chip was run in accordance to the WES™ Protein Simple software, and the resulting bands are analyzed and compared to the Myozyme® standard curve and normalized to the non-specific second band.

Anti-AAV Capsid IgG Antibodies

Anti-AAV capsid total IgG formation was measured with an ELISA capture assay. ELISA plate wells were coated with 50 μL of a solution containing 1 μg/mL of rAAV particles. Total human IgG (Southern Biotech, 0150-01) was diluted to generate a 10-point standard curve ranging from 10,000 ng/mL to 0.5 ng/mL and added to the plate. The limit of quantitation of the assay was 460 ng/mL after back-calculation. Three levels of quality control samples were prepared and included on each plate to assess assay performance. Capsid particles, standards, and quality controls were incubated overnight at 4 degrees Celsius. After washing, wells were blocked with 2% BSA, 0.05% Tween-20 in PBS for 2 hours at room temperature. Serial dilutions of samples in blocking buffer were loaded on the plate and incubated at room temperature for 2 hours. An HRP-conjugated sheep anti-human IgG antibody (GE Healthcare, NA933V) diluted 1:5000 in blocking buffer was used as detecting antibody and incubated on the plate for 1 hour at room temperature. Following washing, peroxidase activity was developed during a 10-minute incubation at room temperature with 3,3',5,5'-tetramethylbenzidine substrate (TMB). The reaction was stopped with 1M sulfuric acid, and the plate was read by an absorbance plate reader for optical density (OD) at 450 nm. IgG concentration was determined against a standard curve made with serial dilution of purified human total IgG.

What is claimed:

1. A nucleic acid encoding an acid α-glucosidase (GAA) protein, wherein said nucleic acid has greater than 90% sequence identity to a sequence selected from the group consisting of any of the sequences set forth as SEQ ID NOs:1-5, and wherein the encoded GAA protein has α-glucosidase activity.

2. The nucleic acid of claim 1, wherein said nucleic acid has 91%-92% sequence identity to a sequence selected from the group consisting of any of the sequences set forth as SEQ ID NOs:1-5.

3. The nucleic acid of claim 1, wherein said nucleic acid contains from about 126-5 CpG dinucleotides.

4. The nucleic acid of claim 1, wherein said nucleic acid contains 0-5 CpG dinucleotides.

5. The nucleic acid of claim 1, wherein said nucleic acid has 92% sequence identity to greater than 99.5% sequence identity to a sequence selected from the group consisting of any of the sequences set forth as SEQ ID NOs:1-24.

6. A nucleic acid encoding a GAA selected from the group consisting of SEQ ID NOs:1-24.

7. An expression cassette comprising the nucleic acid of claim 1 operably linked to an expression control element.

8. The expression cassette of claim 7, wherein said expression control element is positioned 5' of said nucleic acid.

9. The expression cassette of claim 8, further comprising a poly-adenylation sequence positioned 3' of said nucleic acid.

10. The expression cassette of claim 8, wherein said expression control element or poly-adenylation sequence is CpG reduced compared to wild-type expression control element or polyadenylation sequence.

11. The expression cassette of claim 7, wherein said expression control element comprises an ApoE/hAAT enhancer/promoter sequence.

12. The expression cassette of claim 9, wherein said poly-adenylation sequence comprises a bovine growth hormone (bGH) polyadenylation sequence.

13. The expression cassette of claim 11, wherein said ApoE/hAAT enhancer/promoter sequence or bGH polyadenylation sequence is CpG reduced compared to wild-type ApoE/hAAT enhancer/promoter sequence or bGH polyadenylation sequence.

14. The expression cassette of claim 7, further comprising an intron positioned between the 3' end of said expression control element and the 5' end of said nucleic acid.

15. The nucleic acid of claim 1, wherein said GAA comprises the sequence set forth as SEQ ID NO:25.

16. An adenovirus-associated virus (AAV) vector comprising the nucleic acid of claim 1.

17. The AAV vector of claim 16, wherein said AAV vector comprises:

a) one or more of an AAV capsid, and b) one or more AAV inverted terminal repeats (ITRs), wherein said AAV ITR(s) flanks the 5' or 3' terminus of said nucleic acid.

18. The AAV vector of claim 17, further comprising an intron positioned 5' or 3' of said one or more ITRs.

19. The AAV vector of claim 17, wherein at least one or more of said ITRs or said intron is modified to have reduced CpGs.

20. The AAV vector of claim 16, wherein said AAV vector has a capsid serotype comprising a modified or variant AAV VP1, VP2 and/or VP3 capsid having 90% or more sequence identity to AAV1, AAV2, AAV3, AAV4, AAV5, AAV6, AAV7, AAV8, AAV9, AAV10, AAV11, Rh10, Rh74, AAV3B, AAV-2i8 or SEQ ID NO:30, 31 or 32 VP1, VP2 and/or VP3 sequences, or a capsid having 95% or more sequence identity to AAV1, AAV2, AAV3, AAV4, AAV5, AAV6, AAV7, AAV8, AAV9, AAV10, AAV11, AAV12, Rh10, Rh74, AAV3B, AAV-2i8, or SEQ ID NO:30, 31 or 32 VP1, VP2 and/or VP3 sequences, or a capsid having 100% sequence identity to AAV1, AAV2, AAV3, AAV4, AAV5, AAV6, AAV7, AAV8, AAV9, AAV10, AAV11, Rh10, Rh74, AAV3B, AAV-2i8, or SEQ ID NO:30, 31 or 32 VP1, VP2 and/or VP3 sequences.

21. The AAV vector of claim 17, wherein said ITRs comprise one or more ITRs of any of: AAV1, AAV2, AAV3, AAV4, AAV5, AAV6, AAV7, AAV8, AAV9, AAV10, AAV11, Rh10, Rh74 or AAV3B, AAV serotypes, or a combination thereof.

22. A pharmaceutical composition comprising a plurality of AAV vectors of claim 16 in a biologically compatible carrier or excipient.

23. The pharmaceutical composition of claim 22, further comprising empty AAV capsids.

24. The pharmaceutical composition of claim 23, wherein the ratio of said empty AAV capsids to said AAV vector is within or between about 100:1-50:1, from about 50:1-25:1, from about 25:1-10:1, from about 10:1-1:1, from about 1:1-1:10, from about 1:10-1:25, from about 1:25-1:50, or from about 1:50-1:100.

25. The pharmaceutical composition of claim 23, further comprising a surfactant.

26. An isolated cell comprising the nucleic acid of claim 1.

27. An isolated cell that produces the AAV vector of claim 16.

28. The isolated cell of claim 26, wherein said cell comprises mammalian cells.

29. The isolated cell of claim 26, wherein said cell provides AAV helper functions.

30. The isolated cell of claim 26, wherein said cell provides AAV Rep and/or Cap proteins.

31. The isolated cell of claim 26, wherein said cell comprises HEK-293 cells.

32. A method of producing the AAV vector of claim 16, comprising a. introducing an AAV vector genome comprising said nucleic acid, of claim 1 into a packaging helper cell; and b. culturing said helper cell under conditions to produce said AAV vector.

33. A method of treating a human in need of acid α-glucosidase (GAA), comprising:

(a) providing the nucleic acid of claim 1, or the AAV vector of claim 16, or the pharmaceutical composition of claim 22; and (b) administering an amount of said nucleic acid, AAV vector, or pharmaceutical composition to said human, wherein said GAA is expressed in said human.

34. The method of claim 33, wherein said human has Pompe disease.

35. The method of claim 33, wherein said human has infantile onset Pompe disease.

36. The method of claim 33, wherein said human has late onset Pompe disease.

37. The method of claim 33, wherein said human has a glycogen storage disease (GSD).

38. The method of claim 37, wherein said GSD is selected from: GSD type I (von Gierke's disease), GSD type III (Forbes-Cori disease), GSD type IV (Anderson disease, amylopectinosis), GSD type V (McArdle disease), GSD type VI (Hers disease), GSD type VII (Tarui disease), and a lethal congenital GSD of the heart.

39. The method of claim 33, wherein said AAV vector is administered to said human intravenously, intraarterially, intra-cavity, intramucosally, or via catheter.

40. The method of claim 33, wherein said AAV vector is administered in a range from about $1\times10^8$ to about $1\times10^{14}$ vector genomes per kilogram (vg/kg) of the weight of said human.

* * * * *